US008920776B2

(12) United States Patent
Gaiger et al.

(10) Patent No.: US 8,920,776 B2
(45) Date of Patent: Dec. 30, 2014

(54) COMPOSITIONS AND METHODS FOR THE DETECTION DIAGNOSIS AND THERAPY OF HEMATOLOGICAL MALIGNANCIES

(75) Inventors: Alexander Gaiger, Vienna (AT); Paul A. Algate, Issaquah, WA (US); Jane Mannion, Edmonds, WA (US); Jonathan David Clapper, Seattle, WA (US); Aijun Wang, Issaquah, WA (US); Nadia Ordonez, Seattle, WA (US); Lauren Carter, Seattle, WA (US); Patricia Dianne McNeill, Federal Way, WA (US)

(73) Assignee: Corixa Corporation, Wilmington, DE (US)

( * ) Notice: Subject to any disclaimer, the term of this patent is extended or adjusted under 35 U.S.C. 154(b) by 2042 days.

(21) Appl. No.: 10/501,841

(22) PCT Filed: Jan. 22, 2003

(86) PCT No.: PCT/US03/02353
§ 371 (c)(1),
(2), (4) Date: Aug. 31, 2005

(87) PCT Pub. No.: WO03/062401
PCT Pub. Date: Jul. 31, 2003

(65) Prior Publication Data
US 2006/0084055 A1    Apr. 20, 2006

(51) Int. Cl.
*A61K 51/10*    (2006.01)
*A61K 39/395*    (2006.01)
*C07K 16/30*    (2006.01)
*G01N 33/574*    (2006.01)
*A61K 39/00*    (2006.01)

(52) U.S. Cl.
CPC ....... *A61K 39/0011* (2013.01); *A61K 2039/505* (2013.01); *C07K 16/3061* (2013.01); *G01N 33/57426* (2013.01)
USPC .................. 424/1.49; 424/133.1; 424/135.1; 424/139.1; 424/144.1; 424/153.1; 424/155.1; 424/181.1

(58) Field of Classification Search
None
See application file for complete search history.

(56) References Cited

U.S. PATENT DOCUMENTS 5,968,753 A * 10/1999 Tseng-Law et al. ......... 435/7.21
6,962,702 B2 * 11/2005 Hansen et al. ............. 424/136.1
2002/0028178 A1 * 3/2002 Hanna et al. ................. 424/1.49

FOREIGN PATENT DOCUMENTS

| WO | WO 00/40716 | 7/2000 |
|----|-------------|--------|
| WO | WO/0040716 A2 | 7/2000 |
| WO | WO/0112812 A2 | 2/2001 |
| WO | WO 01/24811 | 4/2001 |
| WO | WO/0124811 A1 | 4/2001 |
| WO | WO 01/60397 | 8/2001 |
| WO | WO/0160397 A1 | 8/2001 |
| WO | WO02/066516 * | 8/2002 |

OTHER PUBLICATIONS

Brauner-Osborne et al (Biochimica et Biophysica Acta, 2001, vol. 1518, pp. 237-248).*
Campbell (Monoclonal Antibody Technology, 1984, pp. 1-32).*
Laabi et al (EMBO, 1992, vol. 11, pp. 3897-3904).*
Claudio et al (Blood, Sep. 15, 2002, vol. 100, pp. 2175-2186).*
Shadidi et al (BBRC, 2001, vol. 280, pp. 548-552).*
EMBL Database, Accession No. AAE00506, Jul. 31, 2001. Retrieved from EBI.
EMBL Database, Accession No. AAE09241, Nov. 19, 2001. Retrieved from EBI.
EMBL Database, Accession No. AAY94001, Oct. 20, 2000. Retrieved from EBI.
GenBank Database, Accession No. AF319438, Feb. 6, 2001.
Genbank Database, Accession No. AB027233, Jun. 21, 2001.
Claudio, et al., "A molecular compendium of genes expressed in multiple myeloma," Blood, vol. 100, No. 6, pp. 2175-2186, (2002).
Shu, et al., "B cell maturation protein is a receptor for the tumor necrosis factor family member TALL-1," PNAS, vol. 97, No. 16, pp. 9156-9161 (2000).
Wierda, et al., "Chronic Lymphocytic Leukaemia," Curr. Opin. Hem., vol. 6, No. 4, p. 253 (1999).
Opponents's arguments in EP opposition to European Patent No. 1975231, 13 pages.
Ruffini, et al., "Immunotherapy of Multiple Myeloma", Seminars in Hematology, vol. 38, No. 3, pp. 260-267 (2001).
Treon, et al., "Immunotherapeutic Strategies for the Treatmentof Plasma Cell Malignancies", Seminars in Oncology, vol. 27, No. 5, pp. 598-613 (2000).
Rennert, et al., " A Soluble Form of B Cell Maturation Antigen, a Receptor for the Tumor Necrosis Factor Family Member APRIL, Inhibits Tumor Cell Growth", J. Exp. Med., vol. 192, No. 11, pp. 1677-1683 (2000).
Thompson, et al., "BAFF Binds to the Tumor Necrosis Factor Receptor-like Molecule B Cell Maturation Antigen and Is Important for Maintaining the Peripheral B Cell Population", J. Exp. Med., vol. 192, No. 1, pp. 129-135 (2000).

* cited by examiner

Primary Examiner — Karen Canella
(74) Attorney, Agent, or Firm — Margaret M. Tomaska; Edward R. Gimmi

(57) ABSTRACT

Disclosed are methods and compositions for the detection, diagnosis, prognosis, and therapy of hematological malignancies, and in particular, B cell leukemias, lymphomas and multiple myelomas. Disclosed are compositions, methods and kits for eliciting immune and T cell responses to specific malignancy-related antigenic polypeptides and antigenic polypeptide fragments thereof in an animal. Also disclosed are compositions and methods for use in the identification of cells and biological samples containing one or more hematological malignancy-related compositions, and methods for the detection and diagnosis of such diseases and affected cell types. Also disclosed are diagnostic and therapeutic kits, as well as methods for the diagnosis, therapy and/or prevention of variety of leukemias and lymphomas.

12 Claims, 15 Drawing Sheets

LEUKEMIA/LYMPHOMA CHIP #3: PROBES USED IN ANALYSIS

| Cy3 Probe | | Cy5 Probe | |
|---|---|---|---|
| Tissue | RNA# | RNA# | Tissue |
| Lymphoma, T cell | 952 | SPACT74 | Kidney N |
| Lymphoma, B cell | 955 | SPACT81 | Liver N |
| Lymphoma, B cell | 953 | SPACT78 | Lung N |
| Lymphoma | 916 | SPACT42 | Brain N |
| Lymphoma, Hodgkins | 950 | 138598B | Skin N |
| Lymphoma, Hodgkins | 950 | SPACT49 | Bone Marrow N |
| Lymphoma, B cell | CL151 | 888 | PBMC resting |
| Lymphoma, T cell | 904B | SPACT55 | Stomach N |
| Lymphoma, Hodgkins see RNA 959 | CL153 | SPACT70 | Thymus N |
| Lymphoma, B cell | CL152 | SPACT75 | Skeletal Muscle N |
| Lymphoma, B cell see RNA 958 | CL155 | SPACT73 | Heart N |
| Lymphoma, B cell | 944 | 243502B | Esophagus N |
| Lymphoma, B cell | 958 | 1006 | Colon N |
| Lymphoma, B cell | 954 | SPACT65 | Small Intestine N |
| Lymphoma | 960 | 779B | Trachea N |
| Lymphoma, T cell | 957 | S9327328 | Bladder N |
| Lymphoma, B cell | 914B | | |
| Lymphoma, B cell | 913 | | |
| Lymphoma, B cell | 944B | | |
| Lymphoma, B cell/failed | 903 | | |

GREEN: Tumor probes where gene expression would be desired.
RED: Normal essential tissue probes where gene expression is to be avoided.
BLACK: Normal tissue probes where gene expression is acceptable.

FIG. 4 a. TMpred Report for Ly1484 Long

RDFQSEVLLSAMELFHMTSGGDAAMFRDGKEPQPSAEAAAAPSLANISCF
TQKLVEKLYSGMFSADPRHILLFILEHIMVVIETASSQRDTVLSTLYSSL
NKVILYCLSKPQQSLSECLGLLSILGFLQEHWDVVFATYNSNISFLLCLM
HCLLLLNERSYPEGFGLEPKPRMSTYHQVFLSPNEDVKEKREDLPSLSDV
QHNIQKTVQTLWQQLVAQRQQTLEDAFKIDLSVKPGEREVKIEEVTPLWE
ETMLKAWQHYLASEKKSLASRSNVAHHSKVTLWSGSLSSAMKLMPGRQAK
DPECKTEDFVSCIENYRRRGQELYASLYKDHVQRRKCGNIKAANAWARIQ
EQLFGELGLWSQGEETKPCSPWELDWREGPARMRKRIKRLSPLEALSSGR
HKESQDKNDHISQTNAENQDELTLREAEGEPDEVGVDCTQLTFFPALHES
LHSEDFLELCRERQVILQELLDKEKVTQKFSLVIVQGHLVSEGVLLFGHQ
HFYICENFTLSPTGDVYCTRHCLSNISDPFIFNLCSKDRSTDHYSCQCHS
YADMRELRQARFLLQDIALEIPFHNGYSKFLVFYNNDRSKAFKSFCSFQP
SLKGKATSEDTLNLRRYPGSDRIMLQKWQKRDISNFEYLMYLNTAAGRTC
NDYMQYPVFPWVLADYTSETLNLANPKIFRDLSKPMGAQTKERKLKFIQR
FKEVEKTEGDMTVQCHYYTHYSSAIIVASYLVRMPPFTQAFCALQGGSFD
VADRMFHSVKSTWESASRENMSDVRELTPEFFYLPEFLTNCNGVEFGCMQ
DGTVLGDVQLPPWADGDPRKFTSLHRKALESDFVSANLHHWIDLIFGYKQ
QGPAAVDAVNIFHPYFYGDRMDLSSITDPLIKSTILGFVSNFGQVPKQLF
TKPHPARTAAGKPLPGKDVSTPVSLPGHPQPFFYSLQSLRPSQVTVKDMY
LFSLGSESPKGAIGHIVSTEKTILAVERNKVLLPPLWNRTFSWCFDDFSC
CLCSYGSDKVLMTFENLAAWGRCLCAVCPSPTTIVTSGTSTVVCVWELSM
TKGRPRGLRLRQALYCHTQAVTCLAASVTFSLLVSGSQDCTCTLWDLDHL
THVTRLPAHREGTSAITTSDVSGTIVSCAGAHLSLWNVNGQPLASITTAW
GPEGAITCCCLMEGPAWDTSQTILTGSQDGMVRWKTEDVKMSVPGRPAG
EEPLAQPPSPRGHKWEKNLALSRELDVSTALTGKPSKTSPAVTALAVSRN
HTKLLVGDERGRIFCWSADG (SEQ ID NO: 120)

Black = INTRACELLULAR, Red = TRANSMEMBRANE,
Blue = EXTRACELLULAR

Ly1484 Long has 1269 amino acids and 5
Transmembrane Domains
Transmembrane Domain 1:  63 - 84     Score: 1.36675
Transmembrane Domain 2: 118 - 139    Score: 1.38695
Transmembrane Domain 3: 480 - 501    Score: 1.36185
Transmembrane Domain 4: 562 - 583    Score: 1.31785
Transmembrane Domain 5: 725 - 746    Score: 1.3521

FIG. 6 b. TMpred Report for Ly1484 (short)

MLQKWQKRDISNFEYLMYLNTAAGRTCNDYMQYPVFPWVLADYTSETLNL
ANPKIFRDLSKPMGAQTKERKLKFIQRFKEVEKTEGDMTVQCHYYTHYSS
AIIVASYLVRMPPFTQAFCALQGGSFDVADRMFHSVKSTWESASRENMSD
VRELTPEFFYLPEFLTNCNGVEFGCMQDGTVLGDVQLPPWADGDPRKFIS
LHRKALESDFVSANLHHWIDLIFGVKQQGPAAVDAVNIFHPYFYGDRMDL
SSITDPLIKSTILGFVSNFGQVPKQLFTKPHPARTAAGKPLPGKDVSTPV
SLPGHPQPFYSLQSLRPSQVTVKDMYLFSLGSESPKGAIGHIVSTEKTI
LAVERNKVLLPPLWNRTFSWGFDDFSCCLGSYGSDKVLMTFENLAAWGRC
LCAVCPSPTTIVTSGTSTVVCVWELSMTKGRPRGLRLRQALYGHTQAVTC
LAASVTFSLLVSGSQDCTCILWDLDHLTHVTRLPAHREGISAITTSDVSG
TIVSCAGAHLSLWNVNGQPLASITTAWGPEGAITCCCLMEGPAWDTSQII
ITGSQDGMVRVWKTEDVKMSVPGRPAGEEPLAQPPSPRGHKWEKNLALSR
ELDVSTALTGKPSKTSPAVTALAVSRNHTKLLVGDERGRIFCWSADG (SEQ ID NO: 121)

**Black = INTRACELLULAR, Red = TRANSMEMBRANE,
Blue = EXTRACELLULAR**

Ly1484 has 646 amino acids and 1 Transmembrane Domains

Transmembrane Domain 1: 102 - 123   Score: 1.3521

FIG. 6 (cont.)

ANALYSIS RESULTS OF THE PROGRAM TSITES.
*************************************************

These are the results of the analysis of the file--> LY1484~1.TXT
Beginning with residue: 1 and ending with residue: 1270
AMPHI Window size: 11

A-AMPHI mid points of blocks.
R-Residues matching the Rothbard/Taylor motif.
D-Residues matching the IAd motif.
d-Residues matching the IEd motif.

(SEQ ID NO: 120)

```
     5    10   15   20   25   30   35   40   45   50   55   60   65   70   75
     RDFQSEVLLSAMELFHMTSGGDAAMFRDGKEPQPSAEAAAAPSLANISCFTQKLVEKLYSGMFSADPRHILLFIL
     ....AAAAA......................................AAAA.AAA....AAAAAAAAAA....
     ....RRRRR.RRRRRRR.............................................RRRRRRRRRR.
     ..........................................DDDDDD........................
     .........................................................................

80   85   90   95  100  105  110  115  120  125  130  135  140  145  150
     EHIMVIETASSQRDTVLSTLYSSLNKVILYCLSKPQQSLSECLGLLSILGFLQEHWDVVFATYNSNISFLLCLM
     ...............AAAAAAA.........................AAAAAAAAAAAAAA...........
     ....RRRR..RRRRR....................................RRRR..RRRR...........
     ..DDDDD......DDDDDDD.....................................................
```

FIG. 7

```
      155       160       165       170       175       180       185       190       195       200       205       210       215       220       225
HCLLLLNERSYPEGFGLEPKPRMSTYHQVFLSPNEDVKEKREDLPSLSDVQHNIQKTVQTLWQQLVAQRQQTLED
..........................................................AAAAA.AAAAAAAAAAAA.................R
............................................................RRRR.............................

230       235       240       245       250       255       260       265       270       275       280       285       290       295       300
AFKIDLSVKPGEREVKIEEVTPLWEETMLKAWQHYLASEKKSLASRSNVAHHSKVTLWSGSLSSAMKLMPGRQAK
.........................AAAA..AAAAAAA.......................AAAAAAAA.........................
.RRR..............RRRRRRRRRRRR..................................RRRRR.........................
............................................dddd..............................................

305       310       315       320       325       330       335       340       345       350       355       360       365       370       375
DPECKTEDFVSCIENYRRRGQELYASLYKDHVQRRKCGNIKAANAWARIQEQLFGELGLWSQGEETKPCSPWELD
.AAAAAA........AAAAA.................AAAA...........AAAAAAAAAAA................AAA.............
..........RRRR..............RRRRR........................................RRRR..................

380       385       390       395       400       405       410       415       420       425       430       435       440       445       450
WREGPARMRKRIKRLSPLEALSSGRHKESQDKNDHISQTNAENQDELTLREAEGEPDEVGVDCTQLTFFPALHES
.AAAAAAAAAAAAAAA......................................................AAAA.AAAA................
.......RRRR.................................................RRRR..............................
.....dddd............DDDDDD.............................DDDDDD.................................
```

FIG. 7 (cont.)

```
              455  460  465  470  475  480  485  490  495  500  505  510  515  520  525
              LHSEDFLELCRERQVILQELLDKEKVTQKFSLVIVQGHLVSEGVLLFGHQHFYICENFTLSPTGDVYCTRHCLSN
              ..AAAAA.............................................................AAAA
              ....RRRR..RRRR...............................RRRR..........................

530  535  540  545  550  555  560  565  570  575  580  585  590  595  600
              ISDPFIFNLCSKDRSTDHYSCQCHSYADMRELRQARFLLQDIALEIFFHNGYSKFLVFYNNDRSKAFKSFCSFQP
              A.AAAAA.....AAAAAAAAAA.................................AAAAAA..............
              .........................RRRRRRRRRRRRR.............................RRR....

605  610  615  620  625  630  635  640  645  650  655  660  665  670  675
              SLKGKATSEDTLNLRRYPGSDRIMLQKWQKRDISNFEYLMYLNTAAGRTCNDYMQYPVFPWVLADYTSETLNLAN
              .....AAAAA..................AAA........................AAAAAAAAA...........
              ....RRRR..RRRR...............................RRRR..........RRRRRRR......
              .DDDDDD.....................................................................

680  685  690  695  700  705  710  715  720  725  730  735  740  745  750
              PKIFRDLSKPMGAQTKERKLKFIQRFKEVEKTEGDMTVQCHYYTHYSSAIIVASYLVRMPPFTQAFCALQGGSFD
              AAAAAAAAAAA.............AAAAAAAAAAA...............AAAAA...................A
              .RRRR................RRRR............RRRRR.RRRRR..........................R
```

FIG. 7 (cont.)

```
                                                    .dddd.............................DDDDDDDDD.................
          755  760  765  770  775  780  785  790  795  800  805  810  815  820  825
       VADRMFHSVKSTWESASRENMSDVRELTPEFFYLPEFLTNCNGVEFGCMQDGTVLGDVQLPPWADGDPRKFISLH
       AAAAAAAAAA..AA..AAAA..AAAAAA........AAAAAA............AAA.....
       RRRRRRR............................RRRRR..........................RRRR.

830  835  840  845  850  855  860  865  870  875  880  885  890  895  900
       RKALESDFVSANLHHWIDLIFGYKQQGPAAVDAVNIFHPYFYGDRMDLSSITDPLIKSTILGFVSNFGQVPKQLF
                                 AAAAAAAAA.....AAAAAAAAAAAAA..AAAAA..AAAAAAAAAAAAAAAAA
       RRRR.RRRR......RRRRRRRRR...........RRRR.......................RRRR......
                                                              ..DDDDD.............

905  910  915  920  925  930  935  940  945  950  955  960  965  970  975
       TKPHPARTAAGKPLPGKDVSTPVSLPGHPQPFFYSLQSLRPSQVTVKDMYLFSLGSESPKGAIGHIVSTEKTILA
                          AAAAAAAA.                              AAAAAA.............
       .RRRRR.............................................RRRRRRRR......
       ......DDDDDD..........................................DDDDDD
```

FIG. 7 (cont.)

```
       980  985  990  995 1000 1005 1010 1015 1020 1025 1030 1035 1040 1045 1050
VERNKVLLPPLMNRTFSWGFDDFSCCLGSYGSDKVLMTFENLAAWGRCLCAVCPSPTTIVTSGTSTVVCVWELSM
............................................AAAAAAAAAAAA.................
..................RRRR....................................................
.....................................................................DDD 1055 1060 1065 1070 1075 1080 1085 1090 1095 1100 1105 1110 1115 1120 1125
TKGRPRGLRLRQALYGHTQAVTCLAASVTFSLLVSGSQDCTCILWDLDHLTHVTRLPAHREGISAITISDVSGTI
.............................AAAAAAAAAAA..........AAA...AAAA...AAAA
...................................................RRRRRRRR.............RRR
DDD...DDDDD.........DDDDDDDDD..........................DDDDD..DDDDD
.dddddddd 1130 1135 1140 1145 1150 1155 1160 1165 1170 1175 1180 1185 1190 1195 1200
VSCAGAHLSLMNVNGQPLASITTAWGPEGAITCCCLMEGPAWDTSQIIITGSQDGMVRVWKTEDVKMSVPGRPAG
A...........................AAA..................................AAAAAAA
RR...................................RRRR...........................RRRRRRR..
D.............DDDDDD..................................DDDDDD..DDDDDD 1205 1210 1215 1220 1225 1230 1235 1240 1245 1250 1255 1260 1265 1270 1275
EEPLAQPPSPRGHKWEKNLALSRELDVSIALTGKPSKTSPAVTALAVSRNHTKLLVGDERGRIFCWSADG
..............................................................RRRRR
................................DDDDDDD......DDDDDD
..
```

ANALYSIS RESULTS OF THE PROGRAM TSITES.
**********************************************

These are the results of the analysis of the file--> LY1484~2.TXT
Beginning with residue: 1 and ending with residue: 647
AMPHI Window size: 11

A-AMPHI mid points of blocks.
R-Residues matching the Rothbard/Taylor motif.
D-Residues matching the IAd motif.
d-Residues matching the IEd motif.

(SEQ ID NO: 121)

```
         5        10        15        20        25        30        35        40        45        50        55        60        65        70        75
         MLQKWQKRDISNFEYLMYLNTAAGRTCNDYMQYPVFPWVLADYTSETLNLANPKIFRDLSKPMGAQTKERKLKFI
         ....AAA......................................AAAAAAAAA......AAAAAAAAA...AAA
         ....................................RRRR.....RRRRRRRR........RRRR.......RRR
         ............................................................................
         ............................................................................

80        85        90        95       100       105       110       115       120       125       130       135       140       145       150
         QRFKEVEKTEGDMTVQCHYYTHYSSAIIVASYLVRMPPFTQAFCALQGGSFDVADRMFHSVKSTWESASRENMSD
         AAAAAAAA.......AAAAA......................AAAAAAAAAA..AAAAAAAAAA..AAAA..AA
         R.........RRRRR.RRRRR...........................RRRRRRRRR..................
         ...............DDDDDDDDDDD..................................................
         ............................................................dddd..........

155       160       165       170       175       180       185       190       195       200       205       210       215       220       225
         VRELTPEFFYLPEFLTNCNGVEFGCMQDGTVLGDVQLPPWADGDPRKFISLHRKALESDFVSANLHHWIDLIFGY
         AAAA.......AAAAA.................AAA.........................AAAAAAAA.....
         RRRRR......RRRRR..............RRRR....RRRR..RRRR....RRRR.RRRR.....RRRRRRRRR
         ............................................................................
         ............................................................................
```

```
     230       235       240       245       250       255       260       265       270       275       280       285       290       295       300
KQQGPAAVDAVNIFHPYFYGDRMDLSSITDPLIKSTILGFVSNFGQVPKQLFTKPHPARTAAGKPLPGKDVSTPV
..AAAAAAAAAA..AAAA..AAAAAAAAAAAAAAA.............................AAAA
......................................................RRRRR.........
............................................DDDDD...........DDDDDD..

305       310       315       320       325       330       335       340       345       350       355       360       365       370       375
SLPGHPQPFFYSLQSLRPSQVTVKDMYLFSLGSESPKGAIGHIVSTEKTILAVERNKVLLPPLWNRTFSWGFDDF
AAAAA.......................................AAAAA....................
....................................RRRRRRRRR.....................RRRR.
D..................................DDDDDD...........................

380       385       390       395       400       405       410       415       420       425       430       435       440       445       450
SCCLGSYGSDKVLMTFENLAAWGRCLCAVCPSPTTIVTSGTSTVVCVWELSMTKGRPRGLRLRQALYGHTQAVTC
......................AAAAAAAAAAA........................................
....RRRRR.................................................................
..........DDDDDDDDD..............DDDDDDDDD...........DDDDDD...........DDD
                                               ddddddddd 455       460       465       470       475       480       485       490       495       500       505       510       515       520       525
LAASVTFSLLVSGSQDCTCILWDLDHLTHVTRLPAHREGISAITISDVSGTIVSCAGAHLSLWNVNGQPLASITT
AAAAAAAAA...................AAAAAAAAAA.........AAA..AAAAA.............AAA
........RRRRRRRR..........................RRRRRR.........................
DDDDDDDD....................DDDDDD..DDDDDD.........................DDDDDD
```

FIG. 8 (cont.)

```
         530       540       550       560       570       580       590       600
AWGPEGAITCCCLMEGPAWDTSQIIITGSQDGMVRVWKTEDVKMSVPGRPAGEEPLAQPPSPRGHKWEKNLALSR
                                  AAAAAAA...............................
.....RRRR.........................RRRRRRR..................................
.D.....................................DDDDDD..DDDDDD......................
.

610       620       630       640       650       660       670
ELDVSIALTGKPSKTSPAVTALAVSRNHTKLLVGDERGRIFCWSADG
................................RRRRR.........
.DDDDDDD..DDDDDDD.............................
..........ddddd...............................
```

COMPOSITIONS AND METHODS FOR THE DETECTION DIAGNOSIS AND THERAPY OF HEMATOLOGICAL MALIGNANCIES

CROSS-REFERENCES TO RELATED APPLICATIONS

This application is 371 application of PCT/US2003/02353 filed 22 Jan. 2003 which claims the benefit of U.S. application Ser. No. 10/057,475 filed 22 Jan. 2002. Both applications are incorporated herein in their entirety.

STATEMENT AS TO RIGHTS TO INVENTIONS MADE UNDER FEDERALLY SPONSORED RESEARCH AND DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

1. BACKGROUND OF THE INVENTION 1.1 Field of the Invention

The present invention relates generally to the fields of cancer diagnosis and therapy. More particularly, it concerns the surprising discovery of compositions and methods for the detection and immunotherapy of hematological malignancies, and particularly, B cell leukemias, and lymphomas and multiple myelomas. The invention provides new, effective methods, compositions and kits for eliciting immune and T-cell response to antigenic polypeptides, and antigenic peptide fragments isolated therefrom, and methods for the use of such compositions for diagnosis, detection, treatment, monitoring, and/or prevention of various types of human hematological malignancies. In particular, the invention provides polypeptide, peptide, antibody, antigen binding fragment, hybridoma, host cell, vector, and polynucleotide compounds and compositions for use in identification and discrimination between various types of hematological malignancies, and methods for the detection, diagnosis, prognosis, monitoring, and therapy of such conditions in an affected animal.

1.2 Description of Related Art 1.2.1 Hematological Malignancies

Hematological malignancies, such as leukemias and lymphomas, are conditions characterized by abnormal growth and maturation of hematopoietic cells. Leukemias are generally neoplastic disorders of hematopoietic stem cells, and include adult and pediatric acute myeloid leukemia (AML), chronic myeloid leukemia (CML), acute lymphocytic leukemia (ALL), chronic lymphocytic leukemia (CLL) and secondary leukemia. Among lymphomas, there are two distinct groups: non-Hodgkin's lymphoma (NHL) and Hodgkin's disease. NHLs are the result of a clonal expansion of B- or T-cells, but the molecular pathogenesis of Hodgkin's disease, including lineage derivation and clonality, remains obscure. Other hematological malignancies include myelodysplastic syndromes (MDS), myeloproliferative syndromes (MPS) and multiple myeloma. Hematological malignancies are generally serious disorders, resulting in a variety of symptoms, including bone marrow failure and organ failure.

NHLs are the sixth most common cause of cancer related deaths in the United States. Only prostate, breast, lung, colorectal and bladder cancer currently exceed lymphoma in annual incidence. In 1995, more than 45,000 new NHLs were diagnosed, and over 21,000 patients died of these diseases. The average age of lymphoma patients is relatively young (42 years), and the resulting number of years of life lost to these diseases renders NHLs fourth in economic impact among cancers in the United States. In the past 15 years, the American Cancer Society reported a 50% increase in the incidence of NHLs, one of the largest increases for any cancer group. Much of this increase has been attributed to the development of lymphomas in younger men who have acquired AIDS. Lymphomas are also the third most common childhood malignancy and account for approximately 10% of cancers in children. The survival rate (all ages) varies from 73% (low risk) to 26% (high risk).

1.3 Deficiencies in the Prior Art

Treatment for many hematological malignancies, including leukemias and lymphomas, remains difficult, and existing therapies are not universally effective. While treatments involving specific immunotherapy appear to have considerable potential, such treatments have been limited by the small number of known malignancy-associated antigens. Moreover the ability to detect such hematological malignancies in their early stages can be quite difficult depending upon the particular malady. The lack of a sufficient number of specific diagnostic and prognostic markers of the diseases, and identification of cells and tissues that can be affected, has significantly limited the field of oncology.

Accordingly, there remains a need in the art for improved methods for detecting, screening, diagnosis and treatment of hematological malignancies such as B cell leukemias and lymphomas and multiple myelomas. The present invention fulfills these and other inherent needs in the field, and provides significant advantages in the detection of cells, and cell types that express one or more polypeptides that have been shown to be over-expressed in one or more of such hematological malignancies.

2. SUMMARY OF THE INVENTION

The present invention addresses the foregoing long-felt need and other deficiencies in the art by identifying new and effective strategies for the identification, detection, screening, diagnosis, prognosis, prophylaxis, therapy, and immunomodulation of one or more hematological malignancies, and in particular, B cell leukemias and lymphomas, and multiple myelomas.

The present invention is based, in part, upon the surprising and unexpected discovery that certain previously unknown or unidentified human polypeptides, peptides, and antigenic fragments derived therefrom have now been identified that are overexpressed in one or more types of hematological malignancies. The genes encoding several of these polypeptides are now identified and obtained in isolated form, and have been characterized using a series of molecular biology methodologies including subtractive library analysis, microarray screening, polynucleotide sequencing, peptide and epitopic identification and characterization, as well as expression profiling, and in vitro whole gene cell priming. A set of these polynucleotides, and the polypeptides, peptides, and antigenic fragments they encode are now identified and implicated in the complex processes of hematological malignancy disease onset, progression, and/or outcome, and in particular, diseases such as leukemias and lymphomas.

The inventors have further demonstrated that a number of these polynucleotides, and their encoded polypeptides, as well as antibodies, antigen presenting cells, T cells, and the antigen binding fragments derived from such antibodies are useful in the development of particularly advantageous compositions and methods for the detection, diagnosis, prognosis, prophylaxis and/or therapy of one or more of these diseases, and particularly those conditions that are characterized by (a) an increased, altered, elevated, or sustained expression of one or more polynucleotides that comprise at least a first sequence region that comprises a nucleic acid sequence as disclosed in any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or (b) an increased, altered, elevated, or sustained biological activity of one or more polypeptides that comprise at least a first sequence region that comprises an amino acid sequence as encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121.

The present invention also provides methods and uses for one or more of the disclosed peptide, polypeptide, antibody, antigen binding fragment, and polynucleotide compositions of the present invention in generating an immune response or in generating a T-cell response in an animal, and in particular in a mammal such as a human. The invention also provides methods and uses for one or more of these compositions in the identification, detection, and quantitation of hematological malignancy compositions in clinical samples, isolated cells, whole tissues, and even affected individuals. The compositions and methods disclosed herein also may be used in the preparation of one or more diagnostic reagents, assays, medicaments, or therapeutics, for diagnosis and/or therapy of such diseases.

In a first important embodiment, there is provided a composition comprising at least a first isolated peptide or polypeptide that comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121. Exemplary preferred sequences are those that comprise at least a first coding region that comprises an amino acid sequence that is at least about 85%, about 86%, about 87%, about 88%, about 89%, about 90%, about 91%, about 92%, about 93%, or about 94% identical to the amino acid sequence as encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121, with those sequences that comprise at least a first coding region that comprises an amino acid sequence that is at least about 95%, about 96%, about 97%, about 98%, or about 99% identical to the amino acid sequence as encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121 being examples of particularly preferred sequences in the practice of the present invention. Likewise, peptide and polypeptide compounds and compositions are also provided that comprise, consist essentially of, or consist of the amino acid sequence as encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121.

In a similar fashion, there are also embodiments disclosed herein that provide compositions and methods for the detection, diagnosis, prognosis, prophylaxis, treatment, and therapy of B cell leukemia, lymphoma and multiple myeloma. Exemplary preferred peptide and polypeptide compounds and compositions relating to this aspect of the invention include, but are not limited to, those peptide and polypeptide compounds or compositions that comprise at least a first isolated peptide or polypeptide that comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the amino acid sequence as encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121, and those that comprise at least a first coding region that comprises an amino acid sequence that is at least about 85%, about 86%, about 87%, about 88%, about 89%, about 90%, about 91%, about 92%, about 93%, or about 94% identical to the amino acid sequence as encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121, and even those sequences that comprise at least a first coding region that comprises an amino acid sequence that is at least about 95%, about 96%, about 97%, about 98%, or about 99% identical to the amino acid sequence as encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121.

Exemplary peptides of the present invention may be of any suitable length, depending upon the particular application thereof, and encompass those peptides that are about 9, about 10, about 15, about 20, about 25, about 30, about 35, about 40, about 45, about 50, about 55, about 60, about 65, about 70, about 75, about 80, about 85, about 90, about 95, or about 100 or so amino acids in length. Of course, the peptides of the invention may also encompass any intermediate lengths or integers within the stated ranges.

Exemplary polypeptides and proteins of the present invention may be of any suitable length, depending upon the particular application thereof, and encompass those polypeptides and proteins that are about 100, about 150, about 200, about 250, about 300, about 350, or about 400 or so amino acids in length. Of course, the polypeptides and proteins of the invention may also encompass any intermediate lengths or integers within the stated ranges.

The peptides, polypeptides, proteins, antibodies, and antigen binding fragments of the present invention will preferably comprise a sequence of at least about 5, 10, 15, 20, 25, 30, 35, 40, 45, 50, 55, 60, 65, 70, 75, 80, 85, 90, 95 or 100 contiguous amino acids from any one of the peptides as encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121.

Furthermore, the polypeptides, proteins, antibodies, and antigen binding fragments of the present invention will even more preferably comprise at least a first isolated coding region that comprises a sequence of at least about 100, 110, 120, 130, 140, 150, 160, 170, 180, 190, or 200 contiguous amino acids from any one of the peptides as encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121.

Likewise, the polypeptides, proteins, antibodies, and antigen binding fragments of the present invention may comprise at least a first isolated coding region that comprises a substantially longer sequence, such as for example, one of at least about 200, 220, 240, 260, 280, or 300 or more contiguous amino acids from any one of the peptides as encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121.

In illustrative embodiments, and particularly in those embodiments concerning methods and compositions relating to B cell leukemias, lymphomas and multiple myelomas, the polypeptides of the invention comprise an amino acid sequence that (a) comprises, (b) consists essentially of, or (c) consists of, the amino acid sequence encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121.

The polypeptides and proteins of the invention preferably comprise an amino acid sequence that is encoded by at least a first nucleic acid segment that comprises an at least 21, 22, 23, 24, 25, 26, 27, 28, 29, or 30 contiguous nucleotide sequence of any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124.

The polypeptides and proteins of the invention may also preferably comprise an amino acid sequence encoded by at least a first nucleic acid segment that comprises an at least about 31, 32, 33, 34, 35, 36, 37, 38, 39, or 40 contiguous nucleotide sequence of any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124. The polypeptides and proteins of the invention may also preferably comprise one or more coding regions that comprise an amino acid sequence encoded by at least a first nucleic acid segment that comprises an at least about 41, 42, 43, 44, 45, 46, 47, 48, 49, or 50 contiguous nucleotide sequence of any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124. The polypeptides and proteins of the invention may also preferably comprise one or more coding regions that comprise an amino acid sequence encoded by at least a first nucleic acid segment that comprises an at least about 51, 52, 53, 54, 55, 56, 57, 58, 59, or 60 contiguous nucleotide sequence of any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124. The polypeptides and proteins of the invention may also preferably comprise one or more coding regions that comprise an amino acid sequence encoded by at least a first nucleic acid segment that comprises an at least about 70, 80, 90, 100, 110, 120, 130, 140 or 150 contiguous nucleotide sequence of any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124. The polypeptides and proteins of the invention may also preferably comprise one or more coding regions that comprise an amino acid sequence encoded by at least a first nucleic acid segment that comprises an at least about 175, 200, 225, 250, 275, 300, 325, 350, 375, or 400 contiguous nucleotide sequence of any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124. The polypeptides and proteins of the invention may also preferably comprise one or more coding regions that comprise an amino acid sequence encoded by at least a first nucleic acid segment that comprises an at least about 500, 600, 700, 800, 900, 1000, 1100, 1200, 1300, 1400, or 1500 contiguous nucleotide sequence of any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124.

In a second important embodiment, there is provided a composition comprising at least a first isolated polynucleotide that comprises a nucleic acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the nucleic acid sequence of any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124. Exemplary preferred sequences are those that comprise a nucleic acid sequence that is at least about 85%, about 86%, about 87%, about 88%, about 89%, about 90%, about 91%, about 92%, about 93%, or about 94% identical to the nucleic acid sequence of any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124, with those sequences that comprise at least a nucleic acid sequence that is at least about 95%, about 96%, about 97%, about 98%, or about 99% identical to the nucleic acid sequence of any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 being examples of particularly preferred sequences in the practice of the present invention.

In embodiments that relate particularly to compositions and methods for the detection, diagnosis, prognosis, prophylaxis, treatment, and therapy of B cell leukemias, lymphomas, and multiple myelomas exemplary preferred polynucleotide compositions include those compositions that comprise at least a first isolated nucleic acid segment that comprises a sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to the nucleic acid sequence of anyone of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124. Such polynucleotides will preferably comprise one or more isolated coding region, each of which may (a) comprise, (b) consist essentially of, or (c) consist of, the nucleic acid sequence of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124.

Exemplary polynucleotides of the present invention may be of any suitable length, depending upon the particular application thereof, and encompass those polynucleotides that (a) are at least about, or (b) comprise at least a first isolated nucleic acid segment that is at least about 27, 30, 40, 50, 60, 70, 80, 90, 100, 110, 120, 120, 140, 150, 160, 170, 180, 190, 200, 210, 220, 230, 240, 250, 260, 270, 280, 290, 300, 320, 340, 360, 380, 400, 420, 440, 460, 480, 500, 520, 540, 560, 580, 600, 625, 650, 675, 700, 750, 800, 850, 900, 950, or 1000 or so nucleic acids in length, as well as longer polynucleotides that (a) are at least about, or (b) comprise at least a first isolated nucleic acid segment that is at least about 1000, 1025, 1050, 1075, 1100, 150, 1200, 1250, 1300, 1350, 1400, 1450, 1500, 1550, 1600, 1650, 1700, 1750, 1800, 1850, 1900, 1950, 2000, 2100, 2200, 2300, 2400, 2500, 2600, 2700, 2800, 2900, or 3000 or so nucleic acids in length, as well as substantially larger polynucleotides. Of course, the polynucleotides and nucleic acid segments of the invention may also encompass any intermediate lengths or integers within the stated ranges.

The compositions of the present invention may comprise a single polypeptide or polynucleotide, or alternatively, may comprise two or more such hematological malignancy compounds, such as for example, two or more polypeptides, two or more polynucleotides, or even combinations of one or more peptides or polypeptides, along with one or more polynucleotides. When two or more polypeptides are contemplated for particular applications, the second and/or third and/or fourth, etc. isolated peptides and/or polypeptides will preferably comprise an amino acid sequence that is at least about 91%, 93%, 95%, 97%, or 99% identical to the amino acid sequence encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in anyone of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121. Alternatively, the polynucleotides of the invention may comprise one or more coding regions that encode a first fusion protein or peptide, such as an adjuvant-coding region fused in correct reading frame to one or more of the disclosed hematological malignancy peptides or polypeptides. Alternatively, the fusion protein may comprise a hematological malignancy polypeptide or peptide fused, in correct reading frame, to a detectable protein or peptide, or to an immunostimulant protein or peptide, or other such construct. Fusion proteins such as these are particularly useful in those embodiments relating to diagnosis, detection, and therapy of one or more of the hematological malignancies as discussed herein.

The invention also provides a composition comprising at least a first hybridoma cell line that produces a monoclonal antibody having immunospecificity for one or more of the peptides or polypeptides as disclosed herein, or at least a first monoclonal antibody, or an antigen-binding fragment thereof, that has immunospecificity for such a peptide or polypeptide. The antigen binding fragments may comprise a light chain variable region, a heavy-chain variable region, a Fab fragment, a F(ab)$_2$ fragment, an Fv fragment, an scFv fragment, or an antigen-binding fragment of such an antibody.

The invention also provides a composition comprising at least a first isolated antigen-presenting cell that expresses a peptide or polypeptide as disclosed herein, or a plurality of isolated T cells that specifically react with such a peptide or polypeptide. Such pluralities of isolated T cells may be stimulated or expanded by contacting the T cells with one or more peptides or polypeptides as described herein. The T cells may be cloned prior to expansion, and may be obtained from bone marrow, a bone marrow fraction, peripheral blood, or a peripheral blood fraction from a healthy mammal, or from a mammal that is afflicted with at least a first hematological malignancy such as leukemia or lymphoma.

As described above, the isolated polypeptides of the invention may be on the order of from 9 to about 1000 amino acids in length, or alternatively, may be on the order of from 50 to about 900 amino acids in length, from 75 to about 800 amino acids in length, from 100 to about 700 amino acids in length, or from 125 to about 600 amino acids in length, or any other such suitable range.

The isolated nucleic acid segments that encode such isolated polypeptides may be on the order of from 27 to about 10,000 nucleotides in length, from 150 to about 8000 nucleotides in length, from 250 to about 6000 nucleotides in length, from 350 to about 4000 nucleotides in length, or from 450 to about 2000 nucleotides in length, or any other such suitable range.

The nucleic acid segment may be operably positioned under the control of at least a first heterologous, recombinant promoter, such as a tissue-specific, cell-specific, inducible, or otherwise regulated promoter. Such promoters may be further controlled or regulated by the presence of one or more additional enhancers or regulatory regions depending upon the particular cell type in which expression of the polynucleotide is desired. The polynucleotides and nucleic acid segments of the invention may also be comprised within a vector, such as a plasmid, or viral vector. The polypeptides and polynucleotides of the invention may also be comprised within a host cell, such as a recombinant host cell, or a human host cell such as a blood or bone marrow cell.

The polynucleotides of the invention may comprise at least a first isolated nucleic acid segment operably attached, in frame, to at least a second isolated nucleic acid segment, such that the polynucleotide encodes a fusion protein in which the first peptide or polypeptide is linked to the second peptide or polypeptide.

The polypeptides of the present invention may comprise a contiguous amino acid of any suitable length, such as for example, those of about 2000, about 1900, about 1850, about 1800, about 1750, about 1700, about 1650, about 1600, about 1550, about 1500, about 1450, about 1400, about 1350, about 1300, about 1250, about 1200, about 1150, about 1100 amino acids, or about 1000 or so amino acids in length. Likewise, the polypeptides and peptides of the present invention may comprise slightly shorter contiguous amino acid coding regions, such as for example, those of about 950, about 900, about 850, about 800, about 750, about 700, about 650, about 600, about 550, about 500, about 450, about 400, about 350, about 300, about 250, about 200, about 150, or even about 100 amino acids or so in length.

In similar fashion, the polypeptides and peptides of the present invention may comprise even smaller contiguous amino acid coding regions, such as for example, those of about 95, about 90, about 85, about 80, about 75, about 70, about 65, about 60, about 55, about 50, about 45, about 40, about 35, about 30, about 25, about 20, about 15, or even about 9 amino acids or so in length.

In all such embodiments, those peptides and polypeptides having intermediate lengths including all integers within the preferred ranges (e.g., those peptides and polypeptides that comprise at least a first coding region of at least about 94, about 93, about 92, about 91, about 89, about 88, about 87, about 86, about 84, about 83, about 82, about 81, about 79, about 78, about 77, about 76, about 74, about 73, about 72, about 71, about 69, about 68, about 67, about 66 or so amino acids in length, etc.) are all contemplated to fall within the scope of the present invention.

In particular embodiments, the peptides and polypeptides of the present invention may comprise a sequence of at least about 9, or about 10, or about 11, or about 12, or about 13, or about 14, or about 15, or about 16, or about 17, or about 18, or about 19, or about 20, or about 21, or about 22, or about 23, or about 24, or about 25, or about 26, or about 27, or about 28, or about 29, or about 30, or about 31, or about 32, or about 33, or about 34, or about 35, or about 36, or about 37, or about 38, or about 39, or about 40, or about 41, or about 42, or about 43, or about 44, or about 45, or about 46, or about 47, or about 48, or about 49, or about 50 contiguous amino acids as disclosed in any one or more of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121 herein.

In other embodiments, the peptides and polypeptides of the present invention may comprise a sequence of at least about 51, or about 52, or about 53, or about 54, or about 55, or about 56, or about 57, or about 58, or about 59, or about 60, or about 61, or about 62, or about 63, or about 64, or about 65, or about 66, or about 67, or about 68, or about 69, or about 70, or about 71, or about 72, or about 73, or about 74, or about 75, or about 76, or about 77, or about 78, or about 79, or about 80, or about 81, or about 82, or about 83, or about 84, or about 85, or about 86, or about 87, or about 88, or about 89, or about 90, about 91, or about 92, or about 93, or about 94, or about 95, or about 96, or about 97, or about 98, or about 99, or 100 contiguous amino acids as disclosed in any one or more of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121 herein.

In still other embodiments, the preferred peptides and polypeptides of the present invention comprise a sequence of at least about 100, 125, 150, 175, 200, 225, 250, 275, 300, 325, 350, 375, or 400 or more contiguous amino acids as disclosed in any one or more of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121 herein.

The polypeptides of the invention typically will comprise at least a first contiguous amino acid sequence according to any one of the peptides encoded by any one of the above polynucleotides or disclosed in any one of SEQ ID NOS:10, 471-10,474; SEQ ID NO:10,481; SEQ ID NOS:10,599-10, 819; SEQ ID NOS:10,820-10,842; SEQ ID NOS:10,849-10, 908; and SEQ ID NOS:10,909-10,968, but may also, optionally comprise at least a second, at least a third, or even at least a fourth or greater contiguous amino acid sequence according to any one of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121. A single polypeptide may contain only a single coding region, or alternatively, a single polypeptide may comprise a plurality of identical or distinctly different contiguous amino acid sequences in accordance with any one of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121. In fact, the polypeptide may comprise a plurality of the same contiguous amino acid sequences, or they may comprise one or more different contiguous amino acid sequences of any of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121. For example, a single polypeptide can comprise a single contiguous amino acid sequence from one or more of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121, or alternatively, may comprise two or more distinctly different contiguous amino acid sequences from one or more of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121. In fact, the polypeptide may comprise 2, 3, 4, or even 5 distinct contiguous amino sequences of any one of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121. Alternatively, a single polypeptide may comprise 2, 3, 4, or even 5 distinct coding regions. For example, a polypeptide may comprise at least a first coding region that comprises a first contiguous amino acid sequence of any one of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121, and at least a second coding region that comprises a second contiguous amino acid sequence of any one of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in anyone of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121. In contrast, a polypeptide may comprise at least a first coding region that comprises a first contiguous amino acid sequence of any one of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121, and at least a second coding region that comprises a second distinctly different peptide or polypeptide, such as for example, an adjuvant or an immunostimulant peptide or polypeptide.

In such cases, the two coding regions may be separate on the same polypeptide, or the two coding regions may be operatively attached, each in the correct reading frame, such that a fusion polypeptide is produced, in which the first amino acid sequence of the first coding region is linked to the second amino acid sequence of the second coding region.

Throughout this disclosure, a phrase such as "a sequence as disclosed in SEQ ID NO:1 to SEQ ID NO:4" is intended to encompass any and all contiguous sequences disclosed by any one of these sequence identifiers. That is to say, "a sequence as disclosed in any of SEQ ID NO:1 through SEQ ID NO:4" means any sequence that is disclosed in any one of SEQ ID NO:1, SEQ ID NO:2, SEQ ID NO:3, or SEQ ID NO:4. Likewise, "a sequence as disclosed in any of SEQ ID NOS:25 to 37" means any sequence that is disclosed in any one of SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37, and so forth.

Likewise, a phrase such as "at least a first sequence from any one of SEQ ID NO:55 to SEQ ID NO:62" is intended to refer to a first sequence that is disclosed in any one of SEQ ID NO:55, SEQ ID NO:56, SEQ ID NO:57, SEQ ID NO:58, SEQ ID NO:59, SEQ ID NO:60, SEQ ID NO:61, or SEQ ID NO:62.

It will also be understood that the kits, and compositions of the present invention comprise in an overall and general sense at least one or more particular polynucleotides, polypeptides, and peptides that comprise one or more contiguous sequence regions from one or more of the nucleic acid sequences disclosed herein in SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or from one or more of the amino acid sequences encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or disclosed in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121, and that such peptide, polypeptide and polynucleotide compositions may be used in one or more of the particular methods and uses disclosed herein for the diagnosis, detection, prophylaxis, and therapy of one or more hematological cancers, and in particular, lymphomas of a variety of specific types. It will also be understood to the skilled artisan having benefit of the teachings of the present specification, that the peptide and polypeptide compositions may be used to generate a T cell or an immune response in an animal, and that such compositions may also be administered to an animal from which immunospecific antibodies and antigen binding fragments may be isolated or identified that specifically bind to such peptides or polypeptides. Such an artisan will also recognize that the polynucleotides identified by the present disclosure may be used to produce such peptides, polypeptides, antibodies, and antigen binding fragments, by recombinant protein production methodologies that are also within the capability of the skilled artisan having benefit of the specific amino acid and nucleic acid sequences provided herein.

Likewise, it will be understood by a skilled artisan in the field, that one or more of the disclosed compositions may used in one or more diagnostic or detection methodologies to identify certain antibodies, peptides, polynucleotides, or polypeptides in a biological sample, in a host cell, or even within the body or tissues of an animal. It will be understood by a skilled artisan in the field, that one or more of the disclosed nucleic acid or amino acid compositions may used in the preparation or manufacture of one or more medicaments for use in the diagnosis, detection, prognosis, prophylaxis, or therapy of one or more hematological malignancies in an animal, and particularly those malignant conditions disclosed and claimed herein.

It will also be readily apparent to those of skill in the art, that the methods, kits, and uses, of the present invention preferably employ one or more of the compounds and/or compositions disclosed herein that comprise one or more contiguous nucleotide sequences as may be presented in SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 of the attached sequence listing.

Likewise, it will also be readily apparent to those of skill in the art, that the methods, kits, and uses, of the present invention may also employ one or more of the compounds and compositions disclosed herein that comprise one or more contiguous amino acid sequences of any of the peptides encoded by any one of SEQ ID NOS: 1-3, 5, 7, 9, 11, 13-14, 16-17, 19-20, 22-25, 27-28, 30-31, 33-34, 36, 38-39, 41-42, 44, 46-47, 49, 51, 53, 55, 57, 59-60, 62, 64-65, 67-70, 72-73, 75, 77-81, 83, 85-86, 88-100, 102-103, 105-106, 108, 110-113, 115-116, 118, or 124 or presented in any one of SEQ ID NOS: 4, 6, 8, 10, 12, 15, 18, 21, 26, 29, 32, 35, 37, 40, 43, 45, 48, 50, 52, 54, 56, 58, 61, 63, 66, 71, 74, 76, 82, 84, 87, 101, 104, 107, 109, 114, 117, or 119-121 of the attached sequence listing.

3. BRIEF DESCRIPTION OF THE DRAWINGS AND SEQUENCES

The invention may be understood by reference to the following description taken in conjunction with the accompanying drawings, in which like reference numerals identify like elements, and in which:

FIG. 4 illustrates the panel of probes used to identify cDNAs that are overexpressed in lymphoma cells.

Figure 5:
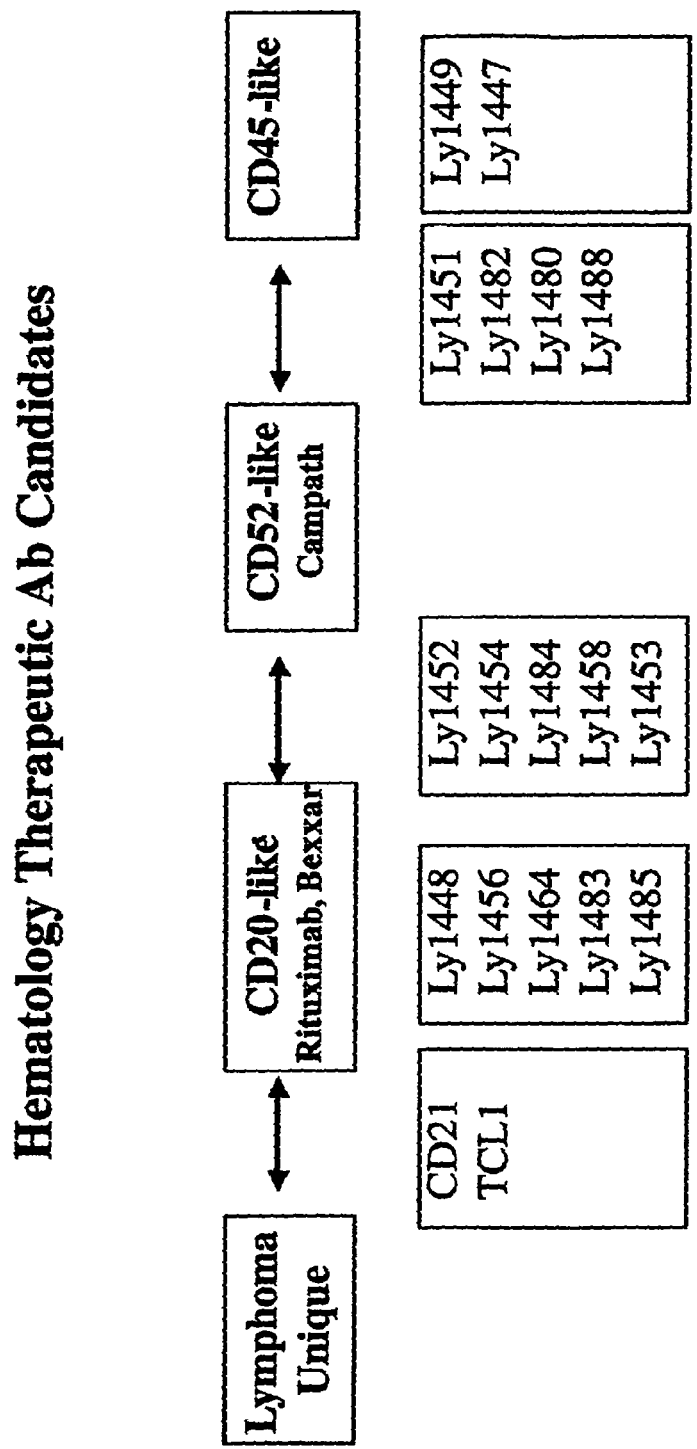

FIG. 5 lists the antigens that have similar tissue expression profiles as the known therapeutics, CD20 and CD52.

FIG. 6 illustrates the results of the TMpred report for Ly1484 long and Ly1484 short.

FIG. 7 illustrates the results of the TSITES analysis of Ly1484 long.

FIG. 8 illustrates the results of the TSITES analysis of Ly1484 short.

SEQ ID NO:1 is a full-length cDNA for Ly1728P.

SEQ ID NO:2 is a full-length protein sequence for Ly1728P.

SEQ ID NO:3 is a full-length cDNA sequence of Ly1732P.

SEQ ID NO:4 is a full-length protein of Ly1732P.

SEQ ID NO:5 is a full length cDNA sequence of Ly1888P.

SEQ ID NO:6 is a full length protein sequence of Ly1888P.

SEQ ID NO:7 is a full length cDNA sequence of Ly1452_His-tag-fusion.

SEQ ID NO:8 is a full length protein sequence of Ly1452_His-tag-fusion.

SEQ ID NO:9 is a full length cDNA sequence of Ly1452P, splice variant 1.

SEQ ID NO:10 is a full length protein sequence of Ly1452P, splice variant 1.

SEQ ID NO:11 is a full length cDNA sequence of Ly1452P, splice variant 2.

SEQ ID NO:12 is a full length protein sequence of Ly1452P, splice variant 2.

SEQ ID NO:13 is a partial cDNA sequence of Ly1462P.

SEQ ID NO:14 is a full length cDNA sequence of Ly1462P.

SEQ ID NO:15 is a full length protein sequence of Ly1462P.

SEQ ID NO:16 is a partial cDNA sequence of Ly1484P.

SEQ ID NO:17 is a full length cDNA sequence of Ly1484P.

SEQ ID NO:18 is a full length protein sequence of Ly1484P.

SEQ ID NO:19 is a partial cDNA sequence of Ly1486P.

SEQ ID NO:20 is a full length cDNA sequence of Ly1486P.

SEQ ID NO:21 is a full length protein sequence of Ly1486P.

SEQ ID NO:22 is a partial cDNA sequence of Ly1677P.

SEQ ID NO:23 is a partial cDNA sequence of Ly1682P.

SEQ ID NO:24 is a partial cDNA sequence of Ly1693P.

SEQ ID NO:25 is a full-length cDNA sequence of Ly1693P.

SEQ ID NO:26 is a full-length protein sequence of Ly1693P.

SEQ ID NO:27 is a partial cDNA sequence of Ly1697P.

SEQ ID NO:28 is a full-length cDNA sequence of Ly1715P.

SEQ ID NO:29 is a full-length protein sequence of Ly1715P.

SEQ ID NO:30 is a partial cDNA sequence of Ly1727P.

SEQ ID NO:31 is a full-length cDNA sequence of Ly1727P.

SEQ ID NO:32 is a full-length protein sequence of Ly1727P.

SEQ ID NO:33 is a partial cDNA sequence of Ly1885P.

SEQ ID NO:34 is a full-length cDNA sequence of Ly1885P.

SEQ ID NO:35 is a full-length protein sequence of Ly1885P.

SEQ ID NO:36 is a partial cDNA sequence of Ly1905P.
SEQ ID NO:37 is a partial protein sequence of Ly1905P.
SEQ ID NO:38 is a partial cDNA sequence of Ly1905P.
SEQ ID NO:39 is a full-length cDNA sequence of Ly1905P.
SEQ ID NO:40 is a full-length protein sequence of Ly1905P.
SEQ ID NO:41 is a partial cDNA sequence of Ly663S.
SEQ ID NO:42 is a full-length cDNA sequence of Ly663S.
SEQ ID NO:43 is a full-length protein sequence of Ly663S.
SEQ ID NO:44 is a full-length cDNA sequence of Ly664S.
SEQ ID NO:45 is a full-length protein sequence of Ly664S.
SEQ ID NO:46 is a partial cDNA sequence of Ly667S.
SEQ ID NO:47 is a full-length cDNA sequence of Ly667S.
SEQ ID NO:48 is a full-length protein sequence of Ly667S.
SEQ ID NO:49 is a partial cDNA sequence of Ly677S.
SEQ ID NO:50 is a partial protein sequence of Ly677S.
SEQ ID NO:51 is a partial cDNA sequence of Ly677S.
SEQ ID NO:52 is a partial protein sequence of Ly677S.
SEQ ID NO:53 is a full-length cDNA sequence of Ly677S.
SEQ ID NO:54 is a full-length protein sequence of Ly677S.
SEQ ID NO:55 is a full-length cDNA sequence of Ly1891P.
SEQ ID NO:56 is a full-length protein sequence of Ly1891P.
SEQ ID NO:57 is a full-length cDNA sequence of CD138.
SEQ ID NO:58 is a full-length protein sequence of CD138.
SEQ ID NO:59 is a partial cDNA sequence of CD22.
SEQ ID NO:60 is a full-length cDNA sequence of CD22.
SEQ ID NO:61 is a full-length protein sequence of CD22.
SEQ ID NO:62 is a partial cDNA sequence of CD79beta.
SEQ ID NO:63 is a partial protein sequence of CD79beta.
SEQ ID NO:64 is a partial cDNA sequence of CD79beta.
SEQ ID NO:65 is a full-length cDNA sequence of CD79beta.
SEQ ID NO:66 is a full-length protein sequence of CD79beta.
SEQ ID NO:67 is a partial cDNA sequence of Ly1450P.
SEQ ID NO:68 is a partial cDNA sequence of Ly1450P.
SEQ ID NO:69 is a partial cDNA sequence of Ly1451P.
SEQ ID NO:70 is a partial cDNA sequence of Ly1451P.
SEQ ID NO:71 is a partial protein sequence of Ly1451P.
SEQ ID NO:7272>Ly1454P, Old-SEQ-ID_3577, partial cDNA
SEQ ID NO:73 is a full-length cDNA sequence of Ly1454P.
SEQ ID NO:74 is a full-length protein sequence of Ly1454P.
SEQ ID NO:75 is a partial cDNA sequence of Ly1485P.
SEQ ID NO:76 is a partial protein sequence of Ly1485P.
SEQ ID NO:77 is a partial cDNA sequence of Ly1485P.
SEQ ID NO:78 is a partial cDNA sequence of Ly1500P.
SEQ ID NO:79 is a full-length cDNA sequence of Ly1500P, splice variant 1.
SEQ ID NO:80 is a full-length protein sequence of Ly1500P, splice variant 1.
SEQ ID NO:81 is a full-length cDNA sequence of Ly1500P, splice variant 2.
SEQ ID NO:82 is a full-length protein sequence of Ly1500P, splice variant 2.
SEQ ID NO:83 is a full-length cDNA sequence of Ly1500P, splice variant 3.
SEQ ID NO:84 is a full-length protein sequence of Ly1500P, splice variant 3.
SEQ ID NO:85 is a partial cDNA sequence of Ly1516P.
SEQ ID NO:86 is a full-length cDNA sequence of Ly1516P, splice variant 1.
SEQ ID NO:87 is a full-length protein sequence of Ly1516P, splice variant 1.
SEQ ID NO:88 is a partial cDNA sequence of Ly1516P, splice variant 2.
SEQ ID NO:89 is a partial cDNA sequence of Ly1516P, splice variant 3.
SEQ ID NO:90 is a partial cDNA sequence of Ly1678P.
SEQ ID NO:91 is a partial cDNA sequence of Ly1678P.
SEQ ID NO:92 is a partial cDNA sequence of Ly1678P.
SEQ ID NO:93 is a partial cDNA sequence of Ly1678P.
SEQ ID NO:94 is a partial cDNA sequence of Ly1680P.
SEQ ID NO:95 is a partial cDNA sequence of Ly1686P.
SEQ ID NO:96 is a partial cDNA sequence of Ly1687P.
SEQ ID NO:97 is a partial cDNA sequence of Ly1706P.
SEQ ID NO:98 is a partial cDNA sequence of Ly1712P.
SEQ ID NO:99 is a partial cDNA sequence of Ly1729P.
SEQ ID NO:100 is a full-length cDNA sequence of Ly1729P.
SEQ ID NO:101 is a full-length protein sequence of Ly1729P.
SEQ ID NO:102 is a partial cDNA sequence of Ly1848P.
SEQ ID NO:103 is a partial cDNA sequence of Ly1859P.
SEQ ID NO:104 is a partial protein sequence of Ly1859P.
SEQ ID NO:105 is a partial cDNA sequence of Ly1859P.
SEQ ID NO:106 is a full-length cDNA sequence of Ly1859P.
SEQ ID NO:107 is a full-length protein sequence of Ly1859P.
SEQ ID NO:108 is a full length cDNA sequence for Ly1866P.
SEQ ID NO:109 is a full length protein sequence for Ly1866P.
SEQ ID NO:110 is a partial cDNA sequence for Ly1867P.
SEQ ID NO:111 is a partial cDNA sequence for Ly1868P.
SEQ ID NO:112 is a partial cDNA sequence for Ly1886P.
SEQ ID NO:113 is a full length cDNA sequence for Ly669S.
SEQ ID NO:114 is a full length protein sequence for Ly669S.
SEQ ID NO:115 is a partial cDNA sequence for Ly672S.
SEQ ID NO:116 is a full length cDNA sequence for Ly672S.
SEQ ID NO:117 is a full length cDNA sequence for Ly672S.
SEQ ID NO:118 is a partial cDNA sequence of Ly675S.
SEQ ID NO:119 is a partial protein sequence of Ly675S.
SEQ ID NO:120 is a partial protein sequence of Ly1484P.
SEQ ID NO:121 is a partial protein sequence of Ly1484P.
SEQ ID NO:122 is a PCR primer sequence for His-Ly1452P.
SEQ ID NO:123 is a PCR primer sequence for His-Ly1452P.
SEQ ID NO:124 is an open reading frame sequence for Ly1451P.

4. DESCRIPTION OF ILLUSTRATIVE EMBODIMENTS

In order that the invention herein described may be more fully understood, the following description of various illustrative embodiments is set forth.

The present invention is generally directed to compositions and methods for the immunotherapy and diagnosis of Hematological malignancies, such as B cell leukemias and lymphomas and multiple myelomas.

4.1 Methods of Nucleic Acid Delivery and DNA Transfection

In certain embodiments, it is contemplated that one or more RNA or DNA and/or substituted polynucleotide compositions disclosed herein will be used to transfect an appropriate host cell. Technology for introduction of RNAs and DNAs, and vectors comprising them into suitable host cells is well known to those of skill in the art. In particular, such polynucleotides may be used to genetically transform one or more host cells, when therapeutic administration of one or more active peptides, compounds or vaccines is achieved through the expression of one or more polynucleotide constructs that encode one or more therapeutic compounds of interest.

A variety of means for introducing polynucleotides and/or polypeptides into suitable target cells is known to those of skill in the art. For example, when polynucleotides are contemplated for delivery to cells, several non-viral methods for the transfer of expression constructs into cultured mammalian cells are available to the skilled artisan for his use. These include, for example, calcium phosphate precipitation (Graham and Van Der Eb, 1973; Chen and Okayama, 1987; Rippe et al., 1990); DEAE-dextran precipitation (Gopal, 1985); electroporation (Wong and Neumann, 1982; Fromm et al., 1985; Tur-Kaspa et al., 1986; Potter et al., 1984; Suzuki et al., 1998; Vanbever et al., 1998), direct microinjection (Capecchi, 1980; Harland and Weintraub, 1985), DNA-loaded liposomes (Nicolau and Sene, 1982; Fraley et al., 1979; Takakura, 1998) and lipofectamine-DNA complexes, cell sonication (Fechheimer et al., 1987), gene bombardment using high velocity microprojectiles (Yang et al., 1990; Klein et al., 1992), and receptor-mediated transfection (Curiel et al., 1991; Wagner et al., 1992; Wu and Wu, 1987; Wu and Wu, 1988). Some of these techniques may be successfully adapted for in vivo or ex vivo use.

A bacterial cell, a yeast cell, or an animal cell transformed with one or more of the disclosed expression vectors represent an important aspect of the present invention. Such transformed host cells are often desirable for use in the expression of the various DNA gene constructs disclosed herein. In some aspects of the invention, it is often desirable to modulate, regulate, or otherwise control the expression of the gene segments disclosed herein. Such methods are routine to those of skill in the molecular genetic arts. Typically, when increased or over-expression of a particular gene is desired, various manipulations may be employed for enhancing the expression of the messenger RNA, particularly by using an active promoter, and in particular, a tissue-specific promoter such as those disclosed herein, as well as by employing sequences, which enhance the stability of the messenger RNA in the particular transformed host cell.

Typically, the initiation and translational termination region will involve stop codon(s), a terminator region, and optionally, a polyadenylation signal. In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism or eukaryotic host, but will usually be included with a DNA sequence involving a marker, where the second DNA sequence may be joined to the expression construct during introduction of the DNA into the host.

Where no functional replication system is present, the construct will also preferably include a sequence of at least about 30 or about 40 or about 50 base pairs (bp) or so, preferably at least about 60, about 70, about 80, or about 90 to about 100 or so bp, and usually not more than about 500 to about 1000 or so bp of a sequence homologous with a sequence in the host. In this way, the probability of legitimate recombination is enhanced, so that the gene will be integrated into the host and stably maintained by the host. Desirably, the regulatory regions of the expression construct will be in close proximity to (and also operably positioned relative to) the selected therapeutic gene providing for complementation as well as the gene providing for the competitive advantage. Therefore, in the event that the therapeutic gene is lost, the resulting organism will be likely to also lose the gene providing for the competitive advantage, so that it will be unable to compete in the environment with the gene retaining the intact construct.

The selected therapeutic gene can be introduced between the transcriptional and translational initiation region and the transcriptional and translational termination region, so as to be under the regulatory control of the initiation region. This construct may be included in a plasmid, which will include at least one replication system, but may include more than one, where one replication system is employed for cloning during the development of the plasmid and the second replication system is necessary for functioning in the ultimate host, in this case, a mammalian host cell. In addition, one or more markers may be present, which have been described previously. Where integration is desired, the plasmid will desirably include a sequence homologous with the host genome.

Genes or other nucleic acid segments, as disclosed herein, can be inserted into host cells using a variety of techniques that are well known in the art. Five general methods for delivering a nucleic segment into cells have been described: (1) chemical methods (Graham and Van Der Eb, 1973); (2) physical methods such as microinjection (Capecchi, 1980), electroporation (U.S. Pat. No. 5,472,869; Wong and Neumann, 1982; Fromm et al., 1985), microprojectiles bombardment (U.S. Pat. No. 5,874,265, specifically incorporated herein by reference in its entirety), "gene gun" (Yang et al., 1990); (3) viral vectors (Eglitis and Anderson, 1988); (4) receptor-mediated mechanisms (Curiel et al., 1991; Wagner et al., 1992); and (5) bacterial-mediated transformation.

4.2 Hematological Malignancy Related-Specific Antibodies and Antigen-Binding Fragments Thereof The present invention further provides antibodies and antigen-binding fragments thereof, that specifically bind to (or are immunospecific for) at least a first peptide or peptide variant as disclosed herein. As used herein, an antibody or an antigen-binding fragment is said to "specifically bind" to a peptide if it reacts at a detectable level (within, for example, an ELISA) with the peptide, and does not react detectably with unrelated peptides or proteins under similar conditions. As used herein, "binding" refers to a non-covalent association between two separate molecules such that a "complex" is formed. The ability to bind may be evaluated by, for example, determining a binding constant for the formation of the complex. The binding constant is the value obtained when the concentration of the complex is divided by the product of the component concentrations. In the context of the present invention, in general, two compounds are said to "bind" when the binding constant for complex formation exceeds about $10^3$ L/mol. The binding constant maybe determined using methods well known in the art.

Any agent that satisfies the above requirements may be a binding agent. In illustrative embodiments, a binding agent is an antibody or an antigen-binding fragment thereof. Such antibodies may be prepared by any of a variety of techniques known to those of ordinary skill in the art (Harlow and Lane, 1988). In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the peptide is initially injected into any of a wide variety of mammals (e.g., mice, rats, rabbits, sheep or goats). In this step, the peptides of this invention may serve as the immunogen without modification. Alternatively, particularly for relatively short peptides, a superior immune response may be elicited if the peptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the peptide may then be purified from such antisera by, for example, affinity chromatography using the peptide coupled to a suitable solid support.

"Antibody" refers to a polypeptide encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition, i.e., an antigen recognition domain. As used herein, "antigen recognition domain" means that part of the antibody, recombinant molecule, the fusion protein, or the immunoconjugate of the invention which recognizes the target or portions thereof. Typically the antigen recognition domain comprises the variable region of the antibody or a portion thereof, e.g., one, two, three, four, five, six, or more hypervariable regions. The terms "$V_H$" or "VH" refer to the variable region of an immunoglobulin heavy chain, including an Fv, scFv, dsFv or Fab. The terms "$V_L$" or "VL" refer to the variable region of an immunoglobulin light chain, including an Fv, scFv, dsFv or Fab.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). Thus, the term antibody, as used herein, also includes antibody fragments either produced by the modification of whole antibodies.

As used herein, "fragment" is defined as at least a portion of the variable region of the immunoglobulin molecule, which binds to its target, i.e. the antigen recognition domain or the antigen binding region. Some of the constant region of the immunoglobulin may be included. Examples of antibody functional fragments include, but are not limited to, complete antibody molecules, humanized antibodies, antibody fragments, such as Fv, single chain Fv (scFv), hypervariable regions or complementarity determining regions (CDRs), $V_L$ (light chain variable region), $V_H$ (heavy chain variable region), Fab, F(ab)2' and any combination of those or any other portion of an immunoglobulin peptide capable of binding to target antigen (see, e.g., Fundamental Immunology (Paul ed., 4th. 1999). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) Nature 348:552). The term antibody also includes bivalent or bispecific molecules, diabodies, triabodies, and tetrabodies. Bivalent and bispecific molecules are described in, e.g., Kostelny et al., *J. Immunol.* 148: 1547 (1992), Pack and Pluckthun, *Biochemistry* 31: 1579 (1992), Zhu et al. *Protein Sci.* 6: 781 (1997), Hu et al. *Cancer Res.* 56: 3055 (1996), Adams et al., *Cancer Res.* 53: 4026 (1993), and McCartney, et al., *Protein Eng.* 8: 301 (1995).

A "humanized antibody" refers to an antibody in which the antigen binding loops, i.e., complementarity determining regions (CDRs), comprised by the $V_H$ and $V_L$ regions are grafted to a human framework sequence. Typically, the humanized antibodies have the same binding specificity as the non-humanized antibodies described herein. Techniques for humanizing antibodies are well known in the art and are described in e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al., *Nature* 321: 522 (1986); and Verhoyen et al., *Science* 239: 1534 (1988). Humanized antibodies are further described in, e.g., Winter and Milstein, *Nature* 349: 293 (1991).

For preparation of monoclonal or polyclonal antibodies, any technique known in the art can be used (see, e.g., Kohler & Milstein, *Nature* 256: 495-497 (1975); Kozbor et al., *Immunology Today* 4: 72 (1983); Cole et al., pp. 77-96 in MONOCLONAL ANTIBODIES AND CANCER THERAPY, Alan R. Liss, Inc. (1985)).

Methods of producing of polyclonal antibodies are known to those of skill in the art. In an exemplary method, an inbred strain of mice (e.g., BALB/C mice) or rabbits is immunized with the chelate or a close structural analogue using a standard adjuvant, such as Freund's adjuvant, and a standard immunization protocol. Alternatively, or in addition to the use of an adjuvant, the chelate is coupled to a carrier that is itself immunogenic (e.g., keyhole limpit hemocyanin ("KLH"). The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired.

Monoclonal antibodies are obtained by various techniques familiar to those skilled in the art. Briefly, spleen cells from an animal immunized with a desired antigen are immortalized, commonly by fusion with a myeloma cell (see, for example, Kohler & Milstein, *Eur. J. Immunol.* 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246: 1275-1281 (1989).

Monoclonal antibodies and polyclonal sera are collected and titered against the immunogen in an immunoassay, for example, a solid phase immunoassay with the immunogen immobilized on a solid support. Typically, polyclonal antisera with a titer of $10^4$ or greater are selected and tested for cross reactivity against different chelates, using a competitive binding immunoassay. Specific polyclonal antisera and monoclonal antibodies will usually bind with a $K_d$ of at least about 0.1 mM, more usually at least about 1 µM, preferably, at least about 0.1 µM or better, and most preferably, 0.01 µM or better.

Techniques for the production of single chain antibodies (U.S. Pat. No. 4,946,778) can be adapted to produce antibodies to reactive chelates and other diagnostic, analytical and therapeutic agents. Also, transgenic mice, or other organisms such as other mammals, may be used to express humanized antibodies. Alternatively, phage display technology can be used to produce and identify antibodies and heteromeric Fab fragments that specifically bind to selected antigens (see, e.g., McCafferty et al., *Nature* 348: 552-554 (1990); Marks et al., *Biotechnology* 10: 779-783 (1992)).

In an exemplary embodiment, an animal, such as a rabbit or mouse is immunized with a chelate, or an immunogenic construct. The antibodies produced as a result of the immunization are preferably isolated using standard methods.

In a still further preferred embodiment, the antibody is a humanized antibody. "Humanized" refers to a non-human polypeptide sequence that has been modified to minimize immunoreactivity in humans, typically by altering the amino acid sequence to mimic existing human sequences, without substantially altering the function of the polypeptide sequence (see, e.g., Jones et al., *Nature* 321: 522-525 (1986), and published UK patent application No. 8707252).

In another preferred embodiment, the present invention provides an antibody, as described above, further comprising a member selected from detectable labels, biologically active agents and combinations thereof attached to the antibody.

When the antibody is conjugated to a detectable label, the label is preferably a member selected from the group consisting of radioactive isotopes, fluorescent agents, fluorescent agent precursors, chromophores, enzymes and combinations thereof. Methods for conjugating various groups to antibodies are well known in the art. For example, a detectable label that is frequently conjugated to an antibody is an enzyme, such as horseradish peroxidase, alkaline phosphatase, β-galactosidase, and glucose oxidase.

Methods of producing antibodies labeled with small molecules, for example, fluorescent agents, are well known in the art. Fluorescent labeled antibodies can be used in immunohistochemical staining (Osborn et al., *Methods Cell Biol.* 24: 97-132 (1990); in flow cytometry or cell sorting techniques (Ormerod, M. G. (ed.), FLOW CYTOMETRY. A PRACTICAL APPROACH, IRL Press, New York, 1990); for tracking and localization of antigens, and in various double-staining methods (Kawamura, A., Jr., FLUORESCENT ANTIBODY TECHNIQUES AND THEIR APPLICATION, Univ. Tokyo Press, Baltimore, 1977).

Many reactive fluorescent labels are available commercially (e.g., Molecular Probes, Eugene, Oreg.) or they can be synthesized using art-recognized techniques. In an exemplary embodiment, an antibody of the invention is labeled with an amine-reactive fluorescent agent, such as fluorescein isothiocyanate under mildly basic conditions. For other examples of antibody labeling techniques, see, Goding, *J. Immunol. Methods* 13: 215-226 (1976); and in, MONOCLONAL ANTIBODIES: PRINCIPLES AND PRACTICE, pp. 6-58, Academic Press, Orlando (1988).

Monoclonal antibodies specific for the antigenic peptide of interest may be prepared, for example, using the technique of Kohler and Milstein (1976) and improvements thereto. Briefly, these methods involve the preparation of immortal cell lines capable of producing antibodies having the desired specificity (i.e., reactivity with the peptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the peptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The peptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, 1988) and digested by papain to yield Fab and Fc fragments. The Fab and Fc fragments may be separated by affinity chromatography on Protein A bead columns.

Monoclonal antibodies and fragments thereof may be coupled to one or more therapeutic agents. Suitable agents in this regard include radioactive tracers and chemotherapeutic agents, which may be used, for example, to purge autologous bone marrow in vitro). Representative therapeutic agents include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein. For diagnostic purposes, coupling of radioactive agents may be used to facilitate tracing of metastases or to determine the location of hematological malignancy related-positive tumors.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be affected, for example, through amino groups, carboxyl groups, and sulfhydryl groups or oxidized carbohydrate residues. There are numerous references describing such methodology, e.g., U.S. Pat. No. 4,671,958.

Where a therapeutic agent is more potent when free from the antibody portion of the immunoconjugates of the present invention, it may be desirable to use a linker group that is cleavable during or upon internalization into a cell. A number of different cleavable linker groups have been described. The mechanisms for the intracellular release of an agent from these linker groups include cleavage by reduction of a disulfide bond (U.S. Pat. No. 4,489,710), by irradiation of a photolabile bond (U.S. Pat. No. 4,625,014), by hydrolysis of derivatized amino acid side chains (U.S. Pat. No. 4,638,045), by serum complement-mediated hydrolysis (U.S. Pat. No. 4,671,958), and acid-catalyzed hydrolysis (U.S. Pat. No. 4,569,789).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used. A carrier may bear the agents in a variety of ways, including covalent bonding either directly or via a linker group. Suitable carriers include proteins such as albumins (U.S. Pat. No. 4,507,234), peptides and polysaccharides such as aminodextran (U.S. Pat. No. 4,699,784). A carrier may also bear an agent by noncovalent bonding or by encapsulation, such as within a liposome vesicle (U.S. Pat. No. 4,429,008 and U.S. Pat. No. 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562 discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of hematological malignancy related. Such antibodies may be raised against an antibody, or an antigen-binding fragment thereof, that specifically binds to an immunogenic portion of hematological malignancy related, using well-known techniques. Anti-idiotypic antibodies that mimic an immunogenic portion of hematological malignancy related are those antibodies that bind to an antibody, or antigen-binding fragment thereof, that specifically binds to an immunogenic portion of hematological malignancy related, as described herein.

Irrespective of the source of the original hematological malignancy related peptide-specific antibody, the intact antibody, antibody multimers, or any one of a variety of functional, antigen-binding regions of the antibody may be used in the present invention. Exemplary functional regions include scFv, Fv, Fab', Fab and F(ab')2 fragments of the hematological malignancy related peptide-specific antibodies. Techniques for preparing such constructs are well known to those in the art and are further exemplified herein.

The choice of antibody construct may be influenced by various factors. For example, prolonged half-life can result from the active readsorption of intact antibodies within the kidney, a property of the Fc piece of immunoglobulin. IgG based antibodies, therefore, are expected to exhibit slower blood clearance than their Fab' counterparts. However, Fab' fragment-based compositions will generally exhibit better tissue penetrating capability.

Antibody fragments can be obtained by proteolysis of the whole immunoglobulin by the non-specific thiol protease, papain. Papain digestion yields two identical antigen-binding fragments, termed "Fab fragments," each with a single antigen-binding site, and a residual "Fc fragment."

Papain should first be activated by reducing the sulfhydryl group in the active site with cysteine, 2-mercaptoethanol or dithiothreitol. Heavy metals in the stock enzyme should be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by Protein A-Sepharose or ion exchange chromatography.

The usual procedure for preparation of F(ab')$_2$ fragments from IgG of rabbit and human origin is limited proteolysis by the enzyme pepsin. The conditions, 100× antibody excess wt./wt. in acetate buffer at pH 4.5, 37° C., suggest that antibody is cleaved at the C-terminal side of the inter-heavy-chain disulfide bond. Rates of digestion of mouse IgG may vary with subclass and it may be difficult to obtain high yields of active F(ab')$_2$ fragments without some undigested or completely degraded IgG. In particular, IgG$_{2b}$ is highly susceptible to complete degradation. The other subclasses require different incubation conditions to produce optimal results, all of which is known in the art.

Pepsin treatment of intact antibodies yields an F(ab')$_2$ fragment that has two antigen-combining sites and is still capable of cross-linking antigen. Digestion of rat IgG by pepsin requires conditions including dialysis in 0.1 M acetate buffer, pH 4.5, and then incubation for four hrs with 1% wt./wt. pepsin; IgG$_1$ and IgG$_{2a}$ digestion is improved if first dialyzed against 0.1 M formate buffer, pH 2.8, at 4° C., for 16 hrs followed by acetate buffer. IgG$_{2b}$ gives more consistent results with incubation in staphylococcal V8 protease (3% wt./wt.) in 0.1 M sodium phosphate buffer, pH 7.8, for four hrs at 37° C.

A Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. F(ab')$_2$ antibody fragments were originally produced as pairs of Fab' fragments that have hinge cysteines between them. Other chemical couplings of antibody fragments are also known.

The term "variable," as used herein in reference to antibodies, means that certain portions of the variable domains differ extensively in sequence among antibodies, and are used in the binding and specificity of each particular antibody to its particular antigen. However, the variability is not evenly distributed throughout the variable domains of antibodies. It is concentrated in three segments termed "hypervariable regions," both in the light chain and the heavy chain variable domains.

The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases, forming part of, the β-sheet structure.

The hypervariable regions in each chain are held together in close proximity by the FRs and, with the hypervariable regions from the other chain, contribute to the formation of the antigen-binding site of antibodies (Kabat et al., 1991, specifically incorporated herein by reference). The constant domains are not involved directly in binding an antibody to an antigen, but exhibit various effector functions, such as participation of the antibody in antibody-dependent cellular toxicity.

The term "hypervariable region," as used herein, refers to the amino acid residues of an antibody that are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-56 (H2) and 95-102 (H3) in the heavy chain variable domain (Kabat et al., 1991, specifically incorporated herein by reference) and/or those residues from a "hypervariable loop" (i.e., residues 26-32 (L1), 50-52(L2) and 91-96 (L3) in the light chain variable domain and 26-32 (H1), 53-55 (H2) and 96-101 (H3) in the heavy chain variable domain). "Framework" or "FR" residues are those variable domain residues other than the hypervariable region residues as herein defined.

An "Fv" fragment is the minimum antibody fragment that contains a complete antigen-recognition and binding site. This region consists of a dimer of one heavy chain and one light chain variable domain in tight, con-covalent association. It is in this configuration that three hypervariable regions of each variable domain interact to define an antigen-binding site on the surface of the $V_H$-$V_L$ dimer. Collectively, six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains that enables the sFv to form the desired structure for antigen binding.

"Diabodies" are small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described in European Pat. Appl. No. EP 404,097 and Intl. Pat. Appl. Publ. No. WO 93/11161, each specifically incorporated herein by reference. "Linear antibodies", which can be bispecific or monospecific, comprise a pair of tandem Fd segments ($V_H$-$C_H$1-$V_H$-$C_H$1) that form a pair of antigen binding regions, as described in Zapata et al. (1995), specifically incorporated herein by reference.

Other types of variants are antibodies with improved biological properties relative to the parent antibody from which they are generated. Such variants, or second-generation compounds, are typically substitutional variants involving one or more substituted hypervariable region residues of a parent antibody. A convenient way for generating such substitutional variants is affinity maturation using phage display.

In affinity maturation using phage display, several hypervariable region sites (e.g., 6 to 7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine-scanning mutagenesis can be performed on hypervariable region residues identified as contributing significantly to antigen binding.

Alternatively, or in addition, the crystal structure of the antigen-antibody complex be delineated and analyzed to identify contact points between the antibody and target. Such contact residues and neighboring residues are candidates for substitution. Once such variants are generated, the panel of variants is subjected to screening, and antibodies with analogues but different or even superior properties in one or more relevant assays are selected for further development.

In using a Fab' or antigen binding fragment of an antibody, with the attendant benefits on tissue penetration, one may derive additional advantages from modifying the fragment to increase its half-life. A variety of techniques may be employed, such as manipulation or modification of the antibody molecule itself, and also conjugation to inert carriers. Any conjugation for the sole purpose of increasing half-life, rather than to deliver an agent to a target, should be approached carefully in that Fab' and other fragments are chosen to penetrate tissues. Nonetheless, conjugation to non-protein polymers, such PEG and the like, is contemplated.

Modifications other than conjugation are therefore based upon modifying the structure of the antibody fragment to render it more stable, and/or to reduce the rate of catabolism in the body. One mechanism for such modifications is the use of D-amino acids in place of L-amino acids. Those of ordinary skill in the art will understand that the introduction of such modifications needs to be followed by rigorous testing of the resultant molecule to ensure that it still retains the desired biological properties. Further stabilizing modifications include the use of the addition of stabilizing moieties to either the N-terminal or the C-terminal, or both, which is generally used to prolong the half-life of biological molecules. By way of example only, one may wish to modify the termini by acylation or amination.

Moderate conjugation-type modifications for use with the present invention include incorporating a salvage receptor binding epitope into the antibody fragment. Techniques for achieving this include mutation of the appropriate region of the antibody fragment or incorporating the epitope as a peptide tag that is attached to the antibody fragment. Intl. Pat. Appl. Publ. No. WO 96/32478 is specifically incorporated herein by reference for the purposes of further exemplifying such technology. Salvage receptor binding epitopes are typically regions of three or more amino acids from one or two lops of the Fc domain that are transferred to the analogous position on the antibody fragment. The salvage receptor-binding epitopes disclosed in Intl. Pat. Appl. Publ. No. WO 98/45331 are incorporated herein by reference for use with the present invention.

4.3 T Cell Compositions Specific for Hematological Malignancy-Related Peptides

Immunotherapeutic compositions may also, or alternatively, comprise T cells specific for hematological malignancy related. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; Intl. Pat. Appl. Publ. No. WO 89/06280; Intl. Pat. Appl. Publ. No. WO 91/16116 and Intl. Pat. Appl. Publ. No. WO 92/07243). Alternatively, T cells may be derived from related or unrelated humans, non-human mammals, cell lines or cultures.

T cells may be stimulated with hematological malignancy related peptide, polynucleotide encoding a hematological malignancy related peptide and/or an antigen-presenting cell (APC) that expresses a hematological malignancy related peptide. Such stimulation is performed under conditions and for a time sufficient to permit the generation of T cells that are specific for the hematological malignancy related peptide. Preferably, a hematological malignancy related peptide or polynucleotide is present within a delivery vehicle, such as a microsphere, to facilitate the generation of antigen-specific T cells. Briefly, T cells, which may be isolated from a patient or a related or unrelated donor by routine techniques (such as by Ficoll/Hypaque® density gradient centrifugation of peripheral blood lymphocytes), are incubated with hematological malignancy related peptide. For example, T cells may be incubated in vitro for 2-9 days (typically 4 days) at 37° C. with hematological malignancy related peptide (e.g., 5 to 25 µg/ml) or cells synthesizing a comparable amount of hematological malignancy related peptide. It may be desirable to incubate a separate aliquot of a T cell sample in the absence of hematological malignancy related peptide to serve as a control.

T cells are considered to be specific for a hematological malignancy related peptide if the T cells kill target cells coated with a hematological malignancy related peptide or expressing a gene encoding such a peptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al. (1994). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a hematological malignancy related peptide may be quantified. Contact with a hematological malignancy related peptide (200 ng/ml-100 µg/ml, preferably 100 ng/ml-25 µg/ml) for 3-7 days should result in at least a two-fold increase in proliferation of the T cells and/or contact as described above for 2-3 hrs should result in activation of the T cells, as measured using standard cytokine assays in which a two-fold increase in the level of cytokine release (e.g., TNF or IFN-γ) is indicative of T cell activation (Coligan et al., 1998). hematological malignancy related specific T cells may be expanded using standard techniques. Within preferred embodiments, the T cells are derived from a patient or a related or unrelated donor and are administered to the patient following stimulation and expansion.

T cells that have been activated in response to a hematological malignancy related peptide, polynucleotide or hematological malignancy related-expressing APC may be $CD4^+$ and/or $CD8^+$. Specific activation of $CD4^+$ or $CD8^+$ T cells may be detected in a variety of ways. Methods for detecting specific T cell activation include detecting the proliferation of T cells, the production of cytokines (e.g., lymphokines), or the generation of cytolytic activity (i.e., generation of cytotoxic T cells specific for hematological malignancy related). For $CD4^+$ T cells, a preferred method for detecting specific T cell activation is the detection of the proliferation of T cells. For $CD8^+$ T cells, a preferred method for detecting specific T cell activation is the detection of the generation of cytolytic activity.

For therapeutic purposes, $CD4^+$ or $CD8^+$ T cells that proliferate in response to the hematological malignancy related peptide, polynucleotide or APC can be expanded in number either in vitro or in vivo. Proliferation of such T cells in vitro may be accomplished in a variety of ways. For example, the T cells can be re-exposed to hematological malignancy related peptide, with or without the addition of T cell growth factors, such as interleukin-2, and/or stimulator cells that synthesize a hematological malignancy related peptide. The addition of stimulator cells is preferred where generating $CD8^+$ T cell responses. T cells can be grown to large numbers in vitro with retention of specificity in response to intermittent restimulation with hematological malignancy related peptide. Briefly, for the primary in vitro stimulation (IVS), large numbers of lymphocytes (e.g., greater than $4 \times 10^7$) may be placed in flasks with media containing human serum. hematological malignancy related peptide (e.g., peptide at 10 µg/ml) may be added directly, along with tetanus toxoid (e.g., 5 µg/ml). The flasks may then be incubated (e.g. 37° C. for 7 days). For a second IVS, T cells are then harvested and placed in new flasks with 2-3×10$^7$ irradiated peripheral blood mononuclear cells. hematological malignancy related peptide (e.g., 10 μg/ml) is added directly. The flasks are incubated at 37° C. for 7 days. On day 2 and day 4 after the second IVS, 2-5 units of interleukin-2 (IL-2) may be added. For a third IVS, the T cells may be placed in wells and stimulated with the individual's own EBV transformed B cells coated with the peptide. IL-2 may be added on days 2 and 4 of each cycle. As soon as the cells are shown to be specific cytotoxic T cells, they may be expanded using a 10-day stimulation cycle with higher IL-2 (20 units) on days 2, 4 and 6.

Alternatively, one or more T cells that proliferate in the presence of hematological malignancy related peptide can be expanded in number by cloning. Methods for cloning cells are well known in the art, and include limiting dilution. Responder T cells may be purified from the peripheral blood of sensitized patients by density gradient centrifugation and sheep red cell rosetting and established in culture by stimulating with the nominal antigen in the presence of irradiated autologous filler cells. In order to generate CD4$^+$ T cell lines, hematological malignancy related peptide is used as the antigenic stimulus and autologous peripheral blood lymphocytes (PBL) or lymphoblastoid cell lines (LCL) immortalized by infection with Epstein Barr virus are used as antigen-presenting cells. In order to generate CD8$^+$ T cell lines, autologous antigen-presenting cells transfected with an expression vector that produces hematological malignancy related peptide may be used as stimulator cells. Established T cell lines may be cloned 2-4 days following antigen stimulation by plating stimulated T cells at a frequency of 0.5 cells per well in 96-well flat-bottom plates with 1×10$^6$ irradiated PBL or LCL cells and recombinant interleukin-2 (rIL2) (50 U/ml). Wells with established clonal growth may be identified at approximately 2-3 weeks after initial plating and restimulated with appropriate antigen in the presence of autologous antigen-presenting cells, then subsequently expanded by the addition of low doses of rIL2 (10 U/ml) 2-3 days following antigen stimulation. T cell clones may be maintained in 24-well plates by periodic restimulation with antigen and rIL2 approximately every two weeks. Cloned and/or expanded cells may be administered back to the patient as described, for example, by Chang et al., (1996).

Within certain embodiments, allogeneic T-cells may be primed (i.e., sensitized to hematological malignancy related) in vivo and/or in vitro. Such priming may be achieved by contacting T cells with a hematological malignancy related peptide, a polynucleotide encoding such a peptide or a cell producing such a peptide under conditions and for a time sufficient to permit the priming of T cells. In general, T cells are considered to be primed if, for example, contact with a hematological malignancy related peptide results in proliferation and/or activation of the T cells, as measured by standard proliferation, chromium release and/or cytokine release assays as described herein. A stimulation index of more than two fold increase in proliferation or lysis, and more than three fold increase in the level of cytokine, compared to negative controls indicates T-cell specificity. Cells primed in vitro may be employed, for example, within bone marrow transplantation or as donor lymphocyte infusion.

T cells specific for hematological malignancy related can kill cells that express hematological malignancy related protein. Introduction of genes encoding T-cell receptor (TCR) chains for hematological malignancy related are used as a means to quantitatively and qualitatively improve responses to hematological malignancy related bearing leukemia and cancer cells. Vaccines to increase the number of T cells that can react to hematological malignancy related positive cells are one method of targeting hematological malignancy related bearing cells. T cell therapy with T cells specific for hematological malignancy related is another method. An alternative method is to introduce the TCR chains specific for hematological malignancy related into T cells or other cells with lytic potential. In a suitable embodiment, the TCR alpha and beta chains are cloned out from a hematological malignancy related specific T cell line and used for adoptive T cell therapy, such as described in WO 96/30516, incorporated herein by reference.

4.4 Pharmaceutical Compositions and Vaccine Formulations

Within certain aspects, peptides, polynucleotides, antibodies and/or T cells may be incorporated into pharmaceutical compositions or immunogenic compositions (i.e., vaccines). Alternatively, a pharmaceutical composition may comprise an antigen-presenting cell (e.g., a dendritic cell) transfected with a hematological malignancy related polynucleotide such that the antigen-presenting cell expresses a hematological malignancy related peptide. Pharmaceutical compositions comprise one or more such compounds or cells and a physiologically acceptable carrier or excipient. Vaccines may comprise one or more such compounds or cells and an immunostimulant, such as an adjuvant or a liposome (into which the compound is incorporated). An immunostimulant may be any substance that enhances or potentiates an immune response (antibody- and/or cell-mediated) to an exogenous antigen. Examples of immunostimulants include adjuvants, biodegradable microspheres (e.g., polylactic galactide) and liposomes (into which the compound is incorporated) (U.S. Pat. No. 4,235,877). Vaccine preparation is generally described in, for example, Powell and Newman (1995). Pharmaceutical compositions and vaccines within the scope of the present invention may also contain other compounds, which may be biologically active or inactive. For example, one or more immunogenic portions of other tumor antigens may be present, either incorporated into a fusion peptide or as a separate compound, within the composition or vaccine.

Within certain embodiments, pharmaceutical compositions and vaccines are designed to elicit T cell responses specific for a hematological malignancy related peptide in a patient, such as a human. In general, T cell responses may be favored through the use of relatively short peptides (e.g., comprising less than 23 consecutive amino acid residues of a native hematological malignancy related peptide, preferably 4-16 consecutive residues, more preferably 8-16 consecutive residues and still more preferably 8-10 consecutive residues). Alternatively, or in addition, a vaccine may comprise an immunostimulant that preferentially enhances a T cell response. In other words, the immunostimulant may enhance the level of a T cell response to a hematological malignancy related peptide by an amount that is proportionally greater than the amount by which an antibody response is enhanced. For example, when compared to a standard oil based adjuvant, such as CFA, an immunostimulant that preferentially enhances a T cell response may enhance a proliferative T cell response by at least two fold, a lytic response by at least 10%, and/or T cell activation by at least two fold compared to hematological malignancy related-negative control cell lines, while not detectably enhancing an antibody response. The amount by which a T cell or antibody response to a hematological malignancy related peptide is enhanced may generally be determined using any representative technique known in the art, such as the techniques provided herein.

A pharmaceutical composition or vaccine may contain DNA encoding one or more of the peptides as described above, such that the peptide is generated in situ. As noted above, the DNA may be present within any of a variety of delivery systems known to those of ordinary skill in the art, including nucleic acid expression systems, bacterial and viral expression systems and mammalian expression systems. Numerous gene delivery techniques are well known in the art (Rolland, 1998, and references cited therein). Appropriate nucleic acid expression systems contain the necessary DNA, cDNA or RNA sequences for expression in the patient (such as a suitable promoter and terminating signal). Bacterial delivery systems involve the administration of a bacterium (such as Bacillus-Calmette-Guerrin) that expresses an immunogenic portion of the peptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus (Fisher-Hoch et al., 1989; Flexner et al., 1989; Flexner et al., 1990; U.S. Pat. No. 4,603,112, U.S. Pat. No. 4,769,330, U.S. Pat. No. 5,017,487; Intl. Pat. Appl. Publ. No. WO 89/01973; U.S. Pat. No. 4,777,127; Great Britain Patent No. GB 2,200,651; European Patent No. EP 0,345,242; Intl. Pat. Appl. Publ. No. WO 91/02805; Berkner, 1988; Rosenfeld et al., 1991; Kolls et al., 1994; Kass-Eisler et al., 1993; Guzman et al., 1993a; and Guzman et al., 1993). Techniques for incorporating DNA into such expression systems are well known to those of ordinary skill in the art. The DNA may also be "naked," as described, for example, in Ulmer et al. (1993) and reviewed by Cohen (1993). The uptake of naked DNA may be increased by coating the DNA onto biodegradable beads, which are efficiently transported into the cells. It will be apparent that a vaccine may comprise both a polynucleotide and a peptide component. Such vaccines may provide for an enhanced immune response.

As noted above, a pharmaceutical composition or vaccine may comprise an antigen-presenting cell that expresses a hematological malignancy related peptide. For therapeutic purposes, as described herein, the antigen-presenting cell is preferably an autologous dendritic cell. Such cells may be prepared and transfected using standard techniques (Reeves et al., 1996; Tuting et al., 1998; and Nair et al., 1998). Expression of a hematological malignancy related peptide on the surface of an antigen-presenting cell may be confirmed by in vitro stimulation and standard proliferation as well as chromium release assays, as described herein.

It will be apparent to those of ordinary skill in the art having the benefit of the present teachings that a vaccine may contain pharmaceutically acceptable salts of the polynucleotides and peptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts). The phrases "pharmaceutically or pharmacologically acceptable" refer to molecular entities and compositions that do not produce an adverse, allergic or other significant untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, and general safety and purity standards as required by the Food and Drug Administration Office of Biologics standards. Supplementary active ingredients can also be incorporated into the compositions.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. For certain topical applications, formulation as a cream or lotion, using well-known components, is preferred.

Such compositions may also comprise buffers (e.g., neutral buffered saline or phosphate buffered saline), carbohydrates (e.g., glucose, mannose, sucrose or dextrans), mannitol, proteins, peptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate, or formulated with one or more liposomes, microspheres, nanoparticles, or micronized delivery systems using well-known technology.

Any of a variety of immunostimulants, such as adjuvants, may be employed in the preparation of vaccine compositions of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, alum-based adjuvants (e.g., Alhydrogel, Rehydragel, aluminum phosphate, Algammulin, aluminum hydroxide); oil based adjuvants (Freund's Incomplete Adjuvant and Complete Adjuvant (Difco Laboratories, Detroit, Mich.), Specol, RIBI, Titer-Max, Montanide ISA50 or Seppic MONTANIDE ISA 720); nonionic block copolymer-based adjuvants, cytokines (e.g., GM-CSF or Flat3-ligand); Merck Adjuvant 65 (Merck and Company, Inc., Rahway, N.J.); AS-2 (SmithKline Beecham, Philadelphia, Pa.); salts of calcium, iron or zinc; an insoluble suspension of acylated tyrosine; acylated sugars; cationically or anionically derivatized polysaccharides; polyphosphazenes; biodegradable microspheres; monophosphoryl lipid A and Quil A. Cytokines, such as GM-CSF or interleukin-2, -7, or -12, may also be used as adjuvants.

Hemocyanins and hemoerythrins may also be used in the invention. The use of hemocyanin from keyhole limpet (KLH) is particularly preferred, although other molluscan and arthropod hemocyanins and hemoerythrins may be employed. Various polysaccharide adjuvants may also be used. Polyamine varieties of polysaccharides are particularly preferred, such as chitin and chitosan, including deacetylated chitin.

A further preferred group of adjuvants are the muramyl dipeptide (MDP, N-acetylmuramyl-$_L$-alanyl-$_D$-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide that is proposed for use in artificial liposomes formed from phosphatidyl choline and phosphatidyl glycerol. It is said to be effective in activating human monocytes and destroying tumor cells, but is non-toxic in generally high doses. The compounds of U.S. Pat. No. 4,950,645, and Intl. Pat Appl. Publ. No. WO 91/16347 are also proposed for use in achieving particular aspects of the present invention.

BCG and BCG-cell wall skeleton (CWS) may also be used as adjuvants in the invention, with or without trehalose dimycolate. Trehalose dimycolate may be used itself. Azuma et al. (1988) show that trehalose dimycolate administration correlates with augmented resistance to influenza virus infection in mice. Trehalose dimycolate may be prepared as described in U.S. Pat. No. 4,579,945.

Amphipathic and surface-active agents, e.g., saponin and derivatives such as QS21 (Cambridge Biotech), form yet another group of preferred adjuvants for use with the immunogens of the present invention. Nonionic block copolymer surfactants (Rabinovich et al., 1994; Hunter et al., 1991) may also be employed. Oligonucleotides, as described by Yamamoto et al. (1988) are another useful group of adjuvants. Quil A and lentinen are also preferred adjuvants.

Superantigens are also contemplated for use as adjuvants in the present invention. "Superantigens" are generally bacterial products that stimulate a greater proportion of T lymphocytes than peptide antigens without a requirement for antigen processing (Mooney et. al., 1994). Superantigens include *Staphylococcus* exoproteins, such as the α, β, γ and δ enterotoxins from *S. aureus* and *S. epidermidis*, and the α, β, γ and δ *E. coli* exotoxins.

Common *Staphylococcus* enterotoxins are known as staphylococcal enterotoxin A (SEA) and staphylococcal enterotoxin B (SEB), with enterotoxins through E (SEE) being described (Rott et. al., 1992). *Streptococcus pyogenes* B (SEB), *Clostridium perfringens* enterotoxin (Bowness et. al., 1992), cytoplasmic membrane-associated protein (CAP) from *S. pyogenes* (Sato et. al., 1994) and toxic shock syndrome toxin-1 (TSST-1) from *S. aureus* (Schwab et. al., 1993) are further useful superantigens.

One group of adjuvants particularly preferred for use in the invention are the detoxified endotoxins, such as the refined detoxified endotoxin of U.S. Pat. No. 4,866,034. These refined detoxified endotoxins are effective in producing adjuvant responses in mammals.

The detoxified endotoxins may be combined with other adjuvants. Combination of detoxified endotoxins with trehalose dimycolate is contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins are also envisioned to be useful, as described in U.S. Pat. No. 4,520,019.

MPL is currently one preferred immunopotentiating agent for use herein. References that concern the uses of MPL include Tomai et al. (1987), Chen et al. (1991) and Garg and Subbarao (1992), that each concern certain roles of MPL in the reactions of aging mice; Elliott et al. (1991), that concerns the D-galactosamine loaded mouse and its enhanced sensitivity to lipopolysaccharide and MPL; Chase et al. (1986), that relates to bacterial infections; and Masihi et al. (1988), that describes the effects of MPL and endotoxin on resistance of mice to *Toxoplasma gondii*. Fitzgerald (1991) also reported on the use of MPL to up-regulate the immunogenicty of a syphilis vaccine and to confer significant protection against challenge infection in rabbits.

Thus MPL is known to be safe for use, as shown in the above model systems. Phase-I clinical trials have also shown MPL to be safe for use (Vosika et al., 1984). Indeed, 100 µg/m$^2$ is known to be safe for human use, even on an outpatient basis (Vosika et al., 1984).

MPL generally induces polyclonal B cell activation (Baker et al., 1994), and has been shown to augment antibody production in many systems, for example, in immunologically immature mice (Baker et al., 1988); in aging mice (Tomai and Johnson, 1989); and in nude and Xid mice (Madonna and Vogel, 1986; Myers et al., 1995). Antibody production has been shown against erythrocytes (Hraba et al., 1993); T cell dependent and independent antigens; Pnu-immune vaccine (Garg and Subbarao, 1992); isolated tumor-associated antigens (U.S. Pat. No. 4,877,611); against syngeneic tumor cells (Livingston et al., 1985; Ravindranath et al., 1994a; b); and against tumor-associated gangliosides (Ravindranath et al., 1994a; b).

Another useful attribute of MPL is that is augments IgM responses, as shown by Baker et al. (1988a), who describe the ability of MPL to increase antibody responses in young mice. This is a particularly useful feature of an adjuvant for use in certain embodiments of the present invention. Myers et al. (1995) recently reported on the ability of MPL to induce IgM antibodies, by virtue T cell-independent antibody production.

In the Myers et al. (1995) studies, MPL was conjugated to the hapten, TNP. MPL was proposed for use as a carrier for other haptens, such as peptides.

MPL also activates and recruits macrophages (Verma et al., 1992). Tomai and Johnson (1989) showed that MPL-stimulated T cells enhance IL-1 secretion by macrophages. MPL is also known to activate superoxide production, lysozyme activity, phagocytosis, and killing of *Candida* in murine peritoneal macrophages (Chen et al., 1991).

The effects of MPL on T cells include the endogenous production of cytotoxic factors, such as TNF, in serum of BCG-primed mice by MPL (Bennett et al., 1988). Kovach et al. (1990) and Elliot et al. (1991) also show that MPL induces TNF activity. MPL is known to act with TNF-α to induce release of IFN-γ by NK cells. IFN-γ production by T cells in response to MPL was also documented by Tomai and Johnson (1989), and Odean et al. (1990).

MPL is also known to be a potent T cell adjuvant. For example, MPL stimulates proliferation of melanoma-antigen specific CTLs (Mitchell et al., 1988, 1993). Further, Baker et al. (1988b) showed that nontoxic MPL inactivated suppressor T cell activity. Naturally, in the physiological environment, the inactivation of T suppressor cells allows for increased benefit for the animal, as realized by, e.g. increased antibody production. Johnson and Tomai (1988) have reported on the possible cellular and molecular mediators of the adjuvant action of MPL.

MPL is also known to induce aggregation of platelets and to phosphorylate a platelet protein prior to induction of serotonin secretion (Grabarek et al., 1990). This study shows that MPL is involved in protein kinase C activation and signal transduction.

Many articles concern the structure and function of MPL include. These include Johnson et al. (1990), that describes the structural characterization of MPL homologs obtained from *Salmonella minnesota* Re595 lipopolysaccharide. The work of Johnson et al. (1990), in common with Grabarek et al. (1990), shows that the fatty acid moieties of MPL can vary, even in commercial species. In separating MPL into eight fractions by thin layer chromatography, Johnson et al. (1990) found that three were particularly active, as assessed using human platelet responses. The chemical components of the various MPL species were characterized by Johnson et al. (1990).

Baker et al. (1992) further analyzed the structural features that influence the ability of lipid A and its analogs to abolish expression of suppressor T cell activity. They reported that decreasing the number of phosphate groups in lipid A from two to one (i.e., creating monophosphoryl lipid A, MPL) as well as decreasing the fatty acyl content, primarily by removing the residue at the 3 position, resulted in a progressive reduction in toxicity; however, these structural modifications did not influence its ability to abolish the expression of Ts function (Baker et al., 1992). These types of MPL are ideal for use in the present invention.

Baker et al. (1992) also showed that reducing the fatty acyl content from five to four (lipid A precursor $IV_A$ or $I_a$) eliminated the capacity to influence Ts function but not to induce polyclonal activation of B cells. These studies show that in order to be able to abolish the expression of Ts function, lipid A must be a glucosamine disaccharide; may have either one or two phosphate groups; and must have at least five fatty acyl groups. Also, the chain length of the nonhydroxylated fatty acid, as well as the location of acyloxyacyl groups (2' versus 3' position), may play an important role (Baker et al., 1992).

In examining the relationship between chain length and position of fatty acyl groups on the ability of lipid A to abolish the expression of suppressor T-cell (Ts) activity, Baker et al. (1994) found that fatty acyl chain lengths of $C_{12}$ to $C_{14}$ appeared to be optimal for bioactivity. Therefore, although their use is still possible, lipid A preparations with fatty acyl groups of relatively short chain length ($C_{10}$ to $C_{12}$ from *Pseudomonas aeruginosa* and *Chromobacterium violaceum*) or predominantly long chain length ($C_{18}$ from *Helicobacter pylori*) are less preferred for use in this invention.

Baker et al. (1994) also showed that the lipid A proximal inner core region oligosaccharides of some bacterial lipopolysaccharides increase the expression of Ts activity; due mainly to the capacity of such oligosaccharides, which are relatively conserved in structure among gram-negative bacterial, to enlarge or expand upon the population of $CD8^+$ Ts generated during the course of a normal antibody response to unrelated microbial antigens. The minimal structure required for the expression of the added immuosuppression observed was reported to be a hexasaccharide containing one 2-keto-3-deoxyoctonate residue, two glucose residues, and three heptose residues to which are attached two pyrophosphorylethanolamine groups (Baker et al., 1994). This information may be considered in utilizing or even designing further adjuvants for use in the invention.

In a generally related line of work, Tanamoto et al. (1994a; b; 1995) described the dissociation of endotoxic activities in a chemically synthesized Lipid A precursor after acetylation or succinylation. Thus, compounds such as "acetyl 406" and "succinyl 516" (Tanamoto et al., 1994a; b; 1995) are also contemplated for use in the invention.

Synthetic MPLs form a particularly preferred group of antigens. For example, Brade et al. (1993) described an artificial glycoconjugate containing the bisphosphorylated glucosamine disaccharide backbone of lipid A that binds to anti-Lipid A MAbs. This is one candidate for use in certain aspects of the invention.

The MPL derivatives described in U.S. Pat. No. 4,987,237 are particularly contemplated for use in the present invention. U.S. Pat. No. 4,987,237 describes MPL derivatives that contain one or more free groups, such as amines, on a side chain attached to the primary hydroxyl groups of the monophosphoryl lipid A nucleus through an ester group. The derivatives provide a convenient method for coupling the lipid A through coupling agents to various biologically active materials. The immunostimulant properties of lipid A are maintained. All MPL derivatives in accordance with U.S. Pat. No. 4,987,237 are envisioned for use in the MPL adjuvant-incorporated cells of this invention.

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell-mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines see e.g., Mosmann and Coffman (1989).

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see e.g. U.S. Pat. Nos. 4,436,727; 4,877,611; 4,866,034 and 4,912,094, each of which is specifically incorporated herein by reference in its entirety). CpG-containing oligonucleotides (in which the CpG dinucleotide is unmethylated) also induce a predominantly Th1 response. Such oligonucleotides are well known and are described, for example, in Intl. Pat. Appl. Publ. No. WO 96/02555 and Intl. Pat. Appl. Publ. No. WO 99/33488. Immunostimulatory DNA sequences are also described, for example, by Sato et al. (1996). Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL (see e.g., Intl. Pat. Appl. Publ. No. WO 94/00153), or a less reactogenic composition where the QS21 is quenched with cholesterol (see e.g., Intl. Pat. Appl. Publ. No. WO 96/33739). Other preferred formulations comprise an oil-in-water emulsion and tocopherol. A particularly potent adjuvant formulation involving QS21, 3D-MPL and tocopherol in an oil-in-water emulsion has also been described (see e.g., Intl. Pat. Appl. Publ. No. WO 95/17210).

Other preferred adjuvants include Montanide ISA 720 (Seppic), SAF (Chiron), ISCOMS (CSL), MF-59 (Chiron), the SBAS series of adjuvants (e.g., SBAS-2 or SBAS-4, available from SmithKline Beecham, Rixensart, Belgium), Detox (Corixa Corporation), RC-529 (Corixa Corporation) and aminoalkyl glucosaminide 4-phosphates (AGPs).

Any vaccine provided herein may be prepared using well-known methods that result in a combination of one or more antigens, one or more immunostimulants or adjuvants and one or more suitable carriers, excipients, or pharmaceutically acceptable buffers. The compositions described herein may be administered as part of a sustained release formulation (i.e., a formulation such as a capsule, sponge or gel [composed of polysaccharides, for example] that effects a slow release of compound following administration). Such formulations may generally be prepared using well-known technology (Coombes et al., 1996) and administered by, for example, oral, rectal or subcutaneous implantation, or by implantation at the desired target site. Sustained-release formulations may contain a peptide, polynucleotide or antibody dispersed in a carrier matrix and/or contained within a reservoir surrounded by a rate-controlling membrane.

Carriers for use within such formulations are preferably biocompatible, and may also be biodegradable; preferably the formulation provides a relatively constant level of active component release. Such carriers include microparticles of poly (lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (U.S. Pat. No. 5,151,254; Intl. Pat. Appl. Publ. No. WO 94/20078; Intl. Pat Appl. Publ. No. WO/94/23701; and Intl. Pat. Appl. Publ. No. WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen-presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, 1998) and have been shown to be effective as a physiological adjuvant for eliciting prophylactic or therapeutic antitumor immunity (Timmerman and Levy, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (Zitvogel et al., 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a hematological malignancy related peptide, such that the peptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen-presenting cell may be administered to a patient, resulting in transfection that occurs in vivo. In vivo and ex vivo transfection of dendritic cells, for example, may generally be performed using any methods known in the art, such as those described in Intl. Pat. Appl. Publ. No. WO 97/24447, or the gene gun approach described by Mahvi et al. (1997). Antigen loading of dendritic cells may be achieved by incubating dendritic cells or progenitor cells with the hematological malignancy related peptide, DNA (naked or within a plasmid vector) or RNA; or with antigen-expressing recombinant bacterium or viruses (e.g., vaccinia, fowlpox, adenovirus or lentivirus vectors). Prior to loading, the peptide may be covalently conjugated to an immunological partner that provides T cell help (e.g., a carrier molecule). Alternatively, a dendritic cell may be pulsed with a non-conjugated immunological partner, separately or in the presence of the peptide.

Combined therapeutics is also contemplated, and the same type of underlying pharmaceutical compositions may be employed for both single and combined medicaments. Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

4.5 Diagnostic and Prognostic Methods for Hematological Malignancy Diseases

The present invention further provides methods for detecting a malignant disease associated with one or more of the polypeptide or polynucleotide compositions disclosed herein, and for monitoring the effectiveness of an immunization or therapy for such a disease. To determine the presence or absence of a malignant disease associated with one or more of the polypeptide or polynucleotide compositions disclosed herein, a patient may be tested for the level of T cells specific for one or more of such compositions. Within certain methods, a biological sample comprising $CD4^+$ and/or $CD8^+$ T cells isolated from a patient is incubated with one or more of the polypeptide or polynucleotide compositions disclosed herein, and/or an APC that expresses one or more of such peptides or polypeptides, and the presence or absence of specific activation of the T cells is detected, as described herein. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37° C. with one or more of the disclosed peptide, polypeptide or polynucleotide compositions (e.g., 5-25 µg/ml). It may be desirable to incubate another aliquot of a T cell sample in the absence of the composition to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a malignant disease associated with expression or one or more of the disclosed polypeptide or polynucleotide compositions. Further correlation may be made, using methods well known in the art, between the level of proliferation and/or cytolytic activity and the predicted response to therapy. In particular, patients that display a higher antibody, proliferative and/or lytic response may be expected to show a greater response to therapy.

Within other methods, a biological sample obtained from a patient is tested for the level of antibody specific for one or more of the hematological malignancy-related peptides or polypeptide is disclosed herein. The biological sample is incubated with hematological malignancy-related peptide or polypeptide, or a polynucleotide encoding such a peptide or polypeptide, and/or an APC that expresses such a peptide or polypeptide under conditions and for a time sufficient to allow immunocomplexes to form. Immunocomplexes formed between the selected peptide or polypeptide and antibodies in the biological sample that specifically bind to the selected peptide or polypeptide are then detected. A biological sample for use within such methods may be any sample obtained from a patient that would be expected to contain antibodies. Suitable biological samples include blood, sera, ascites, bone marrow, pleural effusion, and cerebrospinal fluid.

The biological sample is incubated with the selected peptide or polypeptide in a reaction mixture under conditions and for a time sufficient to permit immunocomplexes to form between the selected peptide or polypeptide and antibodies that are immunospecific for such a peptide or polypeptide. For example, a biological sample and a selected peptide or polypeptide peptide may be incubated at 4° C. for 24-48 hrs.

Following the incubation, the reaction mixture is tested for the presence of immunocomplexes. Detection of immunocomplexes formed between the selected peptide or polypeptide and antibodies present in the biological sample may be accomplished by a variety of known techniques, such as radioimmunoassays (RIA) and enzyme linked immunosorbent assays (ELISA). Suitable assays are well known in the art and are amply described in the scientific and patent literature (Harlow and Lane, 1988). Assays that may be used include, but are not limited to, the double monoclonal antibody sandwich immunoassay technique (U.S. Pat. No. 4,376,110); monoclonal-polyclonal antibody sandwich assays (Wide et al., 1970); the "western blot" method (U.S. Pat. No. 4,452,901); immunoprecipitation of labeled ligand (Brown et al., 1980); enzyme-linked immunosorbent assays (Raines and Ross, 1982); immunocytochemical techniques, including the use of fluorochromes (Brooks et al., 1980); and neutralization of activity (Bowen-Pope et al., 1984). Other immunoassays include, but are not limited to, those described in U.S. Pat. Nos. 3,817,827; 3,850,752; 3,901,654; 3,935,074; 3,984,533; 3,996,345; 4,034,074; and 4,098,876.

For detection purposes, the selected peptide or polypeptide may either be labeled or unlabeled. Unlabeled polypeptide peptide may be used in agglutination assays or in combination with labeled detection reagents that bind to the immunocomplexes (e.g., anti-immunoglobulin, protein G, Protein A or a lectin and secondary antibodies, or antigen-binding fragments thereof, capable of binding to the antibodies that specifically bind to the selected hematological malignancy-related peptide or polypeptide). If the selected peptide or polypeptide is labeled, the reporter group may be any suitable reporter group known in the art, including radioisotopes, fluorescent groups, luminescent groups, enzymes, biotin and dye particles.

Within certain assays, unlabeled peptide or polypeptide is immobilized on a solid support. The solid support may be any material known to those of ordinary skill in the art to which the peptide may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The peptide may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the selected peptide or polypeptide, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of peptide ranging from about 10 ng to about 10 µg, and preferably about 100 ng to about 1 µg, is sufficient to immobilize an adequate amount of peptide.

Following immobilization, the remaining protein binding sites on the support are typically blocked. Any suitable blocking agent known to those of ordinary skill in the art, such as bovine serum albumin, Tween™ 20™ (Sigma Chemical Co., St. Louis, Mo.), heat-inactivated normal goat serum (NGS), or BLOTTO (buffered solution of nonfat dry milk which also contains a preservative, salts, and an antifoaming agent) may be used. The support is then incubated with a biological sample suspected of containing specific antibody. The sample can be applied neat, or, more often, it can be diluted, usually in a buffered solution which contains a small amount (0.1%-5.0% by weight) of protein, such as BSA, NGS, or BLOTTO. In general, an appropriate contact time (i.e., incubation time) is a period of time that is sufficient to detect the presence of antibody or an antigen binding fragment that is immunospecific for the selected peptide or polypeptide within a sample containing such an antibody or binding fragment thereof. Preferably, the contact time is sufficient to achieve a level of binding that is at least about 95% of that achieved at equilibrium between bound and unbound antibody or antibody fragment. Those of ordinary skill in the art will recognize that the time necessary to achieve equilibrium may be readily determined by assaying the level of binding that occurs over a period of time. At room temperature, an incubation time of about 30 min is generally sufficient.

Unbound sample may then be removed by washing the solid support with an appropriate buffer, such as PBS containing 0.1% Tween™ 20. A detection reagent that binds to the immunocomplexes and that comprises at least a first detectable label or "reporter" molecule may then be added. The detection reagent is incubated with the immunocomplex for an amount of time sufficient to detect the bound antibody or antigen binding fragment thereof. An appropriate amount of time may generally be determined by assaying the level of binding that occurs over a period of time. Unbound label or detection reagent is then removed and bound label or detection reagent is detected using a suitable assay or analytical instrument. The method employed for detecting the reporter group depends upon the nature of the reporter group. For radioactive labels, scintillation counting or autoradiographic methods are generally appropriate. Spectroscopic methods may be used to detect dyes, luminescent or chemiluminescent moieties and various chromogens, fluorescent labels and such like. Biotin may be detected using avidin, coupled to a different reporter group (commonly a radioactive or fluorescent group or an enzyme). Enzyme reporter groups (e.g., horseradish peroxidase, β-galactosidase, alkaline phosphatase and glucose oxidase) may generally be detected by the addition of substrate (generally for a specific period of time), followed by spectroscopic or other analysis of the reaction products. Regardless of the specific method employed, a level of bound detection reagent that is at least two fold greater than background (i.e., the level observed for a biological sample obtained from a disease-free individual) indicates the presence of a malignant disease associated with expression of the selected peptide or polypeptide.

In general, methods for monitoring the effectiveness of an immunization or therapy involve monitoring changes in the level of antibodies or T cells specific for the selected peptide or polypeptide in a sample, or in an animal such as a human patient. Methods in which antibody levels are monitored may comprise the steps of: (a) incubating a first biological sample, obtained from a patient prior to a therapy or immunization, with a selected peptide or polypeptide, wherein the incubation is performed under conditions and for a time sufficient to allow immunocomplexes to form; (b) detecting immunocomplexes formed between the selected peptide or polypeptide and antibodies or antigen binding fragments in the biological sample that specifically bind to the selected peptide or polypeptide; (c) repeating steps (a) and (b) using a second biological sample taken from the patient at later time, such as for example, following a given therapy or immunization; and (d) comparing the number of immunocomplexes detected in the first and second biological samples. Alternatively, a polynucleotide encoding the selected peptide or polypeptide, or an APC expressing the selected peptide or polypeptide may be employed in place of the selected peptide or polypeptide itself. Within such methods, immunocomplexes between the selected peptide or polypeptide encoded by a polynucleotide, or expressed by the APC, and antibodies and/or antigen binding fragments in the biological sample are detected.

Methods in which T cell activation and/or the number of hematological malignancy polypeptide-specific precursors are monitored may comprise the steps of: (a) incubating a first biological sample comprising $CD4^+$ and/or $CD8^+$ cells (e.g., bone marrow, peripheral blood or a fraction thereof), obtained from a patient prior to a therapy or immunization, with a hematological malignancy peptide or polypeptide, wherein the incubation is performed under conditions and for a time sufficient to allow specific activation, proliferation and/or lysis of T cells; (b) detecting an amount of activation, proliferation and/or lysis of the T cells; (c) repeating steps (a) and (b) using a second biological sample comprising $CD4^+$ and/or $CD8^+$ T cells, and taken from the same patient following therapy or immunization; and (d) comparing the amount of activation, proliferation and/or lysis of T cells in the first and second biological samples. Alternatively, a polynucleotide encoding a hematological malignancy related peptide, or an APC expressing such a peptide may be employed in place of the hematological malignancy peptide itself.

A biological sample for use within such methods may be any sample obtained from a patient that would be expected to contain antibodies, $CD4^+$ T cells and/or $CD8^+$ T cells. Suitable biological samples include blood, sera, ascites, bone marrow, pleural effusion and cerebrospinal fluid. A first biological sample may be obtained prior to initiation of therapy or immunization or part way through a therapy or vaccination regime. The second biological sample should be obtained in a similar manner, but at a time following additional therapy or immunization. The second biological sample may be obtained at the completion of, or part way through, therapy or immunization, provided that at least a portion of therapy or immunization takes place between the isolation of the first and second biological samples.

Incubation and detection steps for both samples may generally be performed as described above. A statistically significant increase in the number of immunocomplexes in the second sample relative to the first sample reflects successful therapy or immunization.

4.6 Administration of Pharmaceutical Compositions and Formulations

In certain embodiments, the present invention concerns formulation of one or more of the polynucleotide, polypeptide, peptide, antibody, or antigen binding fragment compositions disclosed herein in pharmaceutically acceptable solutions for administration to a cell or an animal, either alone, or in combination with one or more other modalities of anti-cancer therapy, or in combination with one or more diagnostic or therapeutic agents.

It will also be understood that, if desired, the nucleic acid segment, RNA, or DNA compositions disclosed herein may be administered in combination with other agents as well, such as, e.g., proteins or peptides or various pharmaceutically-active agents. As long as the composition comprises at least one of the genetic expression constructs disclosed herein, there is virtually no limit to other components that may also be included, given that the additional agents do not cause a significant adverse effect upon contact with the target cells or host tissues. The RNA- or DNA-derived compositions may thus be delivered along with various other agents as required in the particular instance. Such RNA or DNA compositions may be purified from host cells or other biological sources, or alternatively may be chemically synthesized as described herein. Likewise, such compositions may comprise substituted or derivatized RNA or DNA compositions. Such compositions may include one or more therapeutic gene constructs, either alone, or in combination with one or more modified peptide or nucleic acid substituent derivatives, and/or other anticancer therapeutics.

The formulation of pharmaceutically-acceptable excipients and carrier solutions are well-known to those of skill in the art, as is the development of suitable dosing and treatment regimens for using the particular compositions described herein in a variety of treatment regimens, including e.g., oral, intravenous, intranasal, transdermal, intraprostatic, intratumoral, and/or intramuscular administration and formulation.

4.6.1 Injectable Delivery

For example, the pharmaceutical compositions disclosed herein may be administered parenterally, intravenously, intramuscularly, or even intraperitoneally as described in U.S. Pat. No. 5,543,158, U.S. Pat. No. 5,641,515 and U.S. Pat. No. 5,399,363 (each specifically incorporated herein by reference in its entirety). Solutions of the active compounds as free-base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, Hoover, 1975). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions may be prepared by incorporating the gene therapy constructs in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

4.6.2 Intranasal Delivery

One may use nasal solutions or sprays, aerosols or even inhalants for the treatment of hematological malignancies with one of more of the disclosed peptides and polynucleotides. Nasal solutions are usually aqueous solutions designed for administration to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of from about 5.5 to about 6.5. In addition, antimicrobial preservatives, similar to those used in ophthalmic preparations, and appropriate drug stabilizers, if required, may be included in the formulation. Various commercial nasal preparations are known.

Inhalations and inhalants are pharmaceutical preparations designed for delivering a drug or compound into the respiratory tree of a patient. A vapor or mist is administered and reaches the affected area, often to give relief from symptoms of bronchial and nasal congestion. However, this route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, consists of finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient.

Particle size is of importance in the administration of this type of preparation. It has been reported that the optimum particle size for penetration into the pulmonary cavity is of the order of about 0.5 to about 7 µm. Fine mists are produced by pressurized aerosols and hence their use in considered advantageous.

4.6.3 Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the polynucleotide compositions of the present invention into suitable host cells. In particular, the polynucleotide compositions of the present invention may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-lives (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars, and drugs.

Alternatively, the invention provides for pharmaceutically acceptable nanocapsule formulations of the polynucleotide compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety). In particular, methods of polynucleotide delivery to a target cell using either nanoparticles or nanospheres (Schwab et al., 1994; Truong-Le et al., 1998) are also particularly contemplated to be useful in formulating the disclosed compositions for administration to an animal, and to a human in particular.

4.7 Therapeutic Agents and Kits

The invention also provides one or more of the hematological malignancy-related compositions formulated with one or more pharmaceutically acceptable excipients, carriers, diluents, adjuvants, and/or other components for use in the preparation of medicaments, or diagnostic reagents, as well as various kits comprising one or more of such compositions, medicaments, or formulations intended for administration to an animal in need thereof, or for use in one or more diagnostic assays for identifying polynucleotides, polypeptides, and/or antibodies that are specific for one or more hematological malignancy-related compounds as described herein. In addition to the disclosed epitopes, antibodies and antigen binding fragments, antibody- or antigen binding fragment-encoding polynucleotides or additional anticancer agents, polynucleotides, peptides, antigens, or other therapeutic compounds as may be employed in the formulation of particular compositions and formulations disclosed herein, and particularly in the preparation of anticancer agents or anti-hematological malignancies therapies for administration to the affected mammal.

As such, preferred animals for administration of the pharmaceutical compositions disclosed herein include mammals, and particularly humans. Other preferred animals include primates, sheep, goats, bovines, equines, porcines, lupines, canines, and felines, as well as any other mammalian species commonly considered pets, livestock, or commercially relevant animal species. The compositions and formulations may include partially or significantly purified polypeptide, polynucleotide, or antibody or antigen binding fragment compositions, either alone, or in combination with one or more additional active ingredients, anticancer agents, vaccines, adjuvants, or other therapeutics which may be obtained from natural or recombinant sources, or which may be obtainable naturally or either chemically synthesized, or alternatively produced in vitro from recombinant host cells expressing one or more nucleic acid segments that encode one or more such additional active ingredients, carriers, adjuvants, cofactors, or other therapeutic compound.

4.8 Diagnostic Reagents and Kits

The invention further provides diagnostic reagents and kits comprising one or more such reagents for use in a variety of diagnostic assays, including for example, immunoassays such as ELISA and "sandwich"-type immunoassays. Such kits may preferably include at least a first peptide, or a first antibody or antigen binding fragment of the invention, a functional fragment thereof, or a cocktail thereof, and means for signal generation. The kit's components may be pre-attached to a solid support, or may be applied to the surface of a solid support when the kit is used. The signal generating means may come pre-associated with an antibody of the invention or may require combination with one or more components, e.g., buffers, antibody-enzyme conjugates, enzyme substrates, or the like, prior to use. Kits may also include additional reagents, e.g., blocking reagents for reducing non-specific binding to the solid phase surface, washing reagents, enzyme substrates, and the like. The solid phase surface may be in the form of microtiter plates, microspheres, or other materials suitable for immobilizing proteins, peptides, or polypeptides. Preferably, an enzyme that catalyzes the formation of a chemiluminescent or chromogenic product or the reduction of a chemiluminescent or chromogenic substrate is a component of the signal generating means. Such enzymes are well known in the art.

Such kits are useful in the detection, monitoring and diagnosis of conditions characterized by over-expression or inappropriate expression of hematological malignancy-related peptides, polypeptides, antibodies, and/or polynucleotides, as well as hybridomas, host cells, and vectors comprising one or more such compositions as disclosed herein.

The therapeutic and diagnostic kits of the present invention may also be prepared that comprise at least one of the antibody, peptide, antigen binding fragment, hybridoma, vector, vaccine, polynucleotide, or cellular compositions disclosed herein and instructions for using the composition as a diagnostic reagent or therapeutic agent. Containers for use in such kits may typically comprise at least one vial, test tube, flask, bottle, syringe or other suitable container, into which one or more of the diagnostic and/or therapeutic composition(s) may be placed, and preferably suitably aliquoted. Where a second therapeutic agent is also provided, the kit may also contain a second distinct container into which this second diagnostic and/or therapeutic composition may be placed. Alternatively, a plurality of compounds may be prepared in a single pharmaceutical composition, and may be packaged in a single container means, such as a vial, flask, syringe, bottle, or other suitable single container. The kits of the present invention will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the diagnostic or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

4.9 Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a hematological malignancy-related tumor protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

4.10 Probes and Primers

In other embodiments of the present invention, the polynucleotide sequences provided herein can be advantageously used as probes or primers for nucleic acid hybridization. As such, it is contemplated that nucleic acid segments that comprise a sequence region of at least about 15, 20, 25, 30, 35, 40, 45, 50, 55, 60, 65, 70, 75, 80, 85, 90, or 95 nucleotide long contiguous sequence that has the same sequence as, or is complementary to, at least a 15, 20, 25, 30, 35, 40, 45, 50, 55, 60, 65, 70, 75, 80, 85, 90, or 95 nucleotide long contiguous sequence the disclosed polynucleotides will find particular utility in a variety of hybridization embodiments. Longer contiguous identical or complementary sequences, e.g., those of about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 525, 550, 575, 600, 650, 700, 750, 800, 850, 900, 950, or even 1000 or so nucleotides (including all intermediate lengths) and all full-length sequences as the disclosed polynucleotides will also be of use in certain embodiments as probes, primers, or amplification targets and such like.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers, for use in preparing other genetic constructions, and for identifying and characterizing full-length polynucleotides and full, or substantially full-length cDNAs, mRNAs, and such like.

Polynucleotide molecules having sequence regions consisting of contiguous nucleotide stretches identical or complementary to one or more polynucleotide sequences as disclosed herein, are particularly contemplated as hybridization probes for use in, e.g., Southern hybridization analyses and Northern blotting. This would allow a gene product, or fragment thereof, to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 15, 20, 25, 30, 35, 40, 45, 50, 55, 60 or so and up to and including larger contiguous complementary sequences, including those of about 70, 80, 90, 100, 120, 140, 160, 180, or 200 or so nucleotides in length may also be used, according to the given desired goal, and the particular length of the complementary sequences one wishes to detect by hybridization analysis.

The use of a hybridization probe of about between about 20 and about 500 nucleotides in length allows the formation of a duplex molecule that is both stable and selective. Molecules having contiguous complementary sequences over stretches greater than about 20 or so bases in length are generally preferred, though, in order to increase stability and selectivity of the hybrid, and thereby improve the quality and degree of specific hybrid molecules obtained. One will generally prefer to design nucleic acid molecules having gene-complementary stretches of between about 25 and 300 or so contiguous nucleotides, or even longer where desired.

Hybridization probes may be selected from any portion of any of the sequences disclosed herein. All that is required is to review the disclosed sequences, or to any contiguous portion of such a sequence, from about 15 to 30 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

4.11 Polynucleotide Identification and Characterization

Polynucleotides may be identified, prepared and/or manipulated using any of a variety of well established techniques. For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using a Synteni microarray (Palo Alto, Calif.) according to the manufacturer's instructions (and essentially as described by Schena et al., Proc. Natl. Acad. Sci. USA 93:10614-10619, 1996 and Heller et al., Proc. Natl. Acad. Sci. USA 94:2150-2155, 1997). Alternatively, polynucleotides may be amplified from cDNA prepared from cells expressing the proteins described herein, such as hematological malignancy-related tumor cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full length gene from a suitable library (e.g., a hematological malignancy-related tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software or algorithms or formulas well known in the art.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19, 1991) and walking PCR (Parker et al., *Nucl. Acids. Res.* 19:3055-60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

4.12 Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al (1980) Nucl. Acids Res. Symp. Ser. 215-223, Horn, T. et al (1980) Nucl. Acids Res. Symp. Ser. 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al (1995) Science 269:202-204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional E. coli cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) J. Biol. Chem. 264:5503-5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) EMBO J. 6:307-311. Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, Autographa californica nuclear polyhedrosis virus (AcNPV) is used as a vector to express foreign genes in Spodoptera frugiperda cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfluron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R C. Mulligan (1988) *Proc. Natl. Acad. Sci.* 85:8047-51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263-281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

4.13 Site-Specific Mutagenesis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the antigenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

4.14 Polynucleotide Amplification Techniques

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308 (specifically incorporated herein by reference in its entirety). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-target DNA and an internal or "Middle" sequence of the target protein specific RNA is hybridized to DNA which is present in a sample. Upon hybridization, the reaction is treated with RNaseH, and the products of the probe are identified as distinctive products by generating a signal that is released after digestion. The original template is annealed to another cycling probe and the reaction is repeated. Thus, CPR involves amplifying a signal generated by hybridization of a probe to a target gene specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR-like, template and enzyme dependent synthesis. The primers may be modified by labeling with a capture moiety (e.g., biotin) and/or a detector moiety (e.g. enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer that has sequences specific to the target sequence. Following polymerization, DNA/RNA hybrids are digested with RNase H while double stranded DNA molecules are heat-denatured again. In either case the single stranded DNA is made fully double stranded by addition of second target-specific primer, followed by polymerization. The double stranded DNA molecules are then multiply transcribed by a polymerase such as T7 or SP6. In an isothermal cyclic reaction, the RNAs are reverse transcribed into DNA, and transcribed once again with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

4.15 In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

4.15.1 Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

4.15.2 Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

4.15.3 Adeno-Associated Viruses

AAV (Ridgeway, 1988; Hermonat and Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

There are several factors that prompted researchers to study the possibility of using rAAV as an expression vector. One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4.15.4 Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polio viruses and herpes viruses may be employed. They offer several attractive features for various mammalian cells (Friedmann, 1989; Ridgeway, 1988; Coupar et al, 1988; Horwich et al, 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

4.15.5 Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

4.16 Antisense Oligonucleotides

The end result of the flow of genetic information is the synthesis of protein. DNA is transcribed by polymerases into messenger RNA and translated on the ribosome to yield a folded, functional protein. Thus there are several steps along the route where protein synthesis can be inhibited. The native DNA segment coding for a polypeptide described herein, as all such mammalian DNA strands, has two strands: a sense strand and an antisense strand held together by hydrogen bonding. The messenger RNA coding for polypeptide has the same nucleotide sequence as the sense DNA strand except that the DNA thymidine is replaced by uridine. Thus, synthetic antisense nucleotide sequences will bind to a mRNA and inhibit expression of the protein encoded by that mRNA.

The targeting of antisense oligonucleotides to mRNA is thus one mechanism to shut down protein synthesis, and, consequently, represents a powerful and targeted therapeutic approach. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829, each specifically incorporated herein by reference in its entirety). Further, examples of antisense inhibition have been demonstrated with the nuclear protein cyclin, the multiple drug resistance gene (MDG1), ICAM-1, E-selectin, STK-1, striatal GABAA receptor and human EGF (Jaskulski et al., 1988; Vasanthakumar and Ahmed, 1989; Peris et al., 1998; U.S. Pat. No. 5,801,154; U.S. Pat. No. 5,789,573; U.S. Pat. No. 5,718,709 and U.S. Pat. No. 5,610,288, each specifically incorporated herein by reference in its entirety). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683, each specifically incorporated herein by reference in its entirety).

Therefore, in exemplary embodiments, the invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein.

Selection of antisense compositions specific for a given gene sequence is based upon analysis of the chosen target sequence (i.e. in these illustrative examples the rat and human sequences) and determination of secondary structure, $T_m$, binding energy, relative stability, and antisense compositions were selected based upon their relative inability to form dimers, hairpins, or other secondary structures that would reduce or prohibit specific binding to the target mRNA in a host cell.

Highly preferred target regions of the mRNA, are those which are at or near the AUG translation initiation codon, and those sequences which were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It has been demonstrated that several molecules of the MPG-peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

4.17 Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically>98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al, 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes are well known in the art, and include detection of the presence of mRNA associated with an IL-5 related condition. Such RNA is detected by determining the presence of a cleavage product after treatment with a ribozyme using standard methodology.

4.18 Peptide Nucleic Acids

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (1997) and is incorporated herein by reference. As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass.). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or anti-parallel fashion, with the anti-parallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11-13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures.

Their solubility can be enhanced by attaching one or more positive charges to the PNA termini (Nielsen et al., 1991).

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

4.19 Polypeptide, Peptides and Peptide Variants

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

In the present invention, a polypeptide composition is also understood to comprise one or more polypeptides that are immunologically reactive with antibodies generated against a polypeptide of the invention, particularly a polypeptide having the amino acid sequence encoded by the disclosed polynucleotides, or to active fragments, or to variants or biological functional equivalents thereof.

Likewise, a polypeptide composition of the present invention is understood to comprise one or more polypeptides that are capable of eliciting antibodies that are immunologically reactive with one or more polypeptides encoded by one or more contiguous nucleic acid sequences disclosed in this application, or to active fragments, or to variants thereof, or to one or more nucleic acid sequences which hybridize to one or more of these sequences under conditions of moderate to high stringency.

As used herein, an active fragment of a polypeptide includes a whole or a portion of a polypeptide which is modified by conventional techniques, e.g., mutagenesis, or by addition, deletion, or substitution, but which active fragment exhibits substantially the same structure function, antigenicity, etc., as a polypeptide as described herein.

In certain illustrative embodiments, the polypeptides of the invention will comprise at least an immunogenic portion of a hematological malignancy-related tumor protein or a variant thereof, as described herein. As noted above, a "hematological malignancy-related tumor protein" is a protein that is expressed by hematological malignancy-related tumor cells. Proteins that are hematological malignancy-related tumor proteins also react detectably within an immunoassay (such as an ELISA) with antisera from a patient with hematological malignancy. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a hematological malignancy-related tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1-30 amino acids, preferably 5-15 amino acids), relative to the mature protein.

Immunogenic portions may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native hematological malignancy-related tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native hematological malignancy-related tumor protein. A polypeptide "variant," as used herein, is a polypeptide that differs from a native hematological malignancy-related tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, or 99% or more identity (determined as described above) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr, (2) cys, ser, tyr, thr, (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751, 180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86-91, 1997).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemagglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

4.20 Binding Agents

The present invention further employs agents, such as antibodies and antigen-binding fragments thereof, that specifically bind to a hematological malignancy-related antigen. As used herein, an antibody, or antigen-binding fragment thereof, is said to "specifically bind" to a hematological malignancy-related antigen if it reacts at a detectable level (within, for example, an ELISA) with, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant maybe determined using methods well known in the art.

Binding agents may be further capable of differentiating between patients with and without a hematological malignancy. Such binding agents generate a signal indicating the presence of a hematological malignancy in at least about 20% of patients with the disease, and will generate a negative signal indicating the absence of the disease in at least about 90% of individuals without the disease. To determine whether a binding agent satisfies this requirement, biological samples (e.g. blood, sera, urine and/or tumor biopsies) from patients with and without a hematological malignancy (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies, and fragments thereof, of the present invention may be coupled to one or more therapeutic agents, such as radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein. For certain in vivo and ex vivo therapies, an antibody or fragment thereof is preferably coupled to a cytotoxic agent, such as a radioactive or chemotherapeutic moiety.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid-halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234), peptides and polysaccharides such as aminodextran (e.g., U.S. Pat. No. 4,699,784). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562 discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

4.21 Vaccines

In certain preferred embodiments of the present invention, vaccines are provided. The vaccines will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235, 877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

Illustrative vaccines may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317-321, 1989; Flexner et al., *Ann. N.Y. Acad. Sci.* 569: 86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993. Techniques for incorporating DNA into such expression systems are well known to those of ordinary skill in the art. The DNA may also be "naked," as described, for example, in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the vaccine compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well-known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, California, United States), ISCOMS (CSL), MF-59 (Chiron), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

Any vaccine provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., Vaccine 14:1429-1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic antitumor immunity (see Timmerman and Levy, Ann. Rev. Med. 50:507-529, 1999). In general, dendritic cells may be identified based on their typical shape (stellate in situ, with marked, cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a hematological malignancy-related tumor protein (or portion or other variant thereof) such that the hematological malignancy-related tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456-460, 1997. Antigen loading of dendritic cells may be achieved by incubating dendritic cells or progenitor cells with the hematological malignancy-related tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

4.22 Cancer Therapy

In further aspects of the present invention, the compositions described herein may be used for immunotherapy of cancer, such as hematological malignancy. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs. Administration may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8$^+$ cytotoxic T lymphocytes and CD4$^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a hematological malignancy-related tumor protein generally correlate with an improved clinical outcome. Such immune responses may generally be evaluated using standard proliferation, cytotoxicity or cytokine assays, which may be performed using samples obtained from a patient before and after treatment.

4.23 Cancer Detection and Diagnosis

In general, a cancer may be detected in a patient based on the presence of one or more hematological malignancy-related tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as hematological malignancy. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a hematological malignancy-related tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length hematological malignancy-related tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support sing a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with hematological malignancy. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as hematological malignancy, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-107. Briefly, in this embodiment, the cut-off value may be determined from a plot of pairs of true positive rates (i.e., sensitivity) and false positive rates (100% specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use hematological malignancy-related tumor polypeptides to detect antibodies that bind to such polypeptides in a biological sample. The detection of such hematological malignancy-related tumor protein specific antibodies may correlate with the presence of a cancer.

A cancer may also, or alternatively, be detected based on the presence of T cells that specifically react with a hematological malignancy-related tumor protein in a biological sample. Within certain methods, a biological sample comprising $CD4^+$ and/or $CD8^+$ T cells isolated from a patient is incubated with a hematological malignancy-related tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37° C. with polypeptide (e.g., 5-25 µg/ml). It may be desirable to incubate another aliquot of a T cell sample in the absence of hematological malignancy-related tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a hematological malignancy-related tumor protein in a biological sample. For example, at least two oligonucleotide primers may be employed in a polymerase chain reaction (PCR) based assay to amplify a portion of a hematological malignancy-related tumor cDNA derived from a biological sample, wherein at least one of the oligonucleotide primers is specific for (i.e., hybridizes to) a polynucleotide encoding the hematological malignancy-related tumor protein. The amplified cDNA is then separated and detected using techniques well known in the art, such as gel electrophoresis. Similarly, oligonucleotide probes that specifically hybridize to a polynucleotide encoding a hematological malignancy-related tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a hematological malignancy-related tumor protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence disclosed in this application. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24-72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple hematological malignancy-related tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

4.24 Preparation of DNA Sequences

Certain nucleic acid sequences of cDNA molecules encoding portions of hematological malignancy-related antigens were isolated by PCR™-based subtraction. This technique serves to normalize differentially expressed cDNAs, facilitating the recovery of rare transcripts, and also has the advantage of permitting enrichment of cDNAs with small amounts of polyA RNA material and without multiple rounds of hybridization. To obtain antigens overexpressed in non-Hodgkin's lymphomas, two subtractions were performed with a tester library prepared from a pool of three T cell non-Hodgkin's lymphoma mRNAs. The two libraries were independently subtracted with different pools of driver cDNAs. Driver #1 contained cDNA prepared from specific normal tissues (lymph node, bone marrow, T cells, heart and brain), and this subtraction generated the library TCS-D1 (T cell non-Hodgkin's lymphoma subtracted library with driver #1). Driver #2 contained non-specific normal tissues (colon, large intestine, lung, pancreas, spinal cord, skeletal muscle, liver, kidney, skin and brain), and this subtraction generated the library TCS-D2 (T cell non-Hodgkin's lymphoma subtraction library with driver #2). Two other subtractions were performed with a tester library prepared from a pool of three B cell non-Hodgkin's lymphoma mRNAs. The two libraries were independently subtracted with different pools of driver cDNAs. Driver #1 contained cDNA prepared from specific normal tissues (lymph node, bone marrow, B cells, heart and brain), and this subtraction generated the library BCNHL/D1 (B cell non-Hodgkin's lymphoma subtracted library with driver #1). Driver #2 contained non-specific normal tissues (brain, lung, pancreas, spinal cord, skeletal muscle, colon, spleen, large intestine and PBMC), and this subtraction generated the library BCNHL/D2 (B cell non-Hodgkin's lymphoma subtraction library with driver #2). PCR™-amplified pools were generated from the subtracted libraries and clones were sequenced.

Hematological malignancy-related antigen sequences may be further characterized using any of a variety of well known techniques. For example, PCR™ amplified clones may be arrayed onto glass slides for microarray analysis. To determine tissue distribution, the arrayed clones may be used as targets to be hybridized with different first strand cDNA probes, including lymphoma probes, leukemia probes and probes from different normal tissues. Leukemia and lymphoma probes may be generated from cryopreserved samples obtained at the time of diagnosis from NHL, Hodgkin's disease, AML, CML, CLL, ALL, MDS and myeloma patients with poor outcome (patients who failed to achieve complete remission following conventional chemotherapy or relapsed) or good outcome (patients who achieved long term remission). To analyze gene expression during hematopoietic differentiation, probes may be generated from >95% pure fractions of CD34+, CD2+, CD14+, CD15+ and CD19+ cells derived from healthy individuals.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a hematological malignancy-related antigen, and administering the transfected cells to the patient).

A portion of a sequence complementary to a coding sequence (i.e., an antisense polynucleotide) may also be used as a probe or to modulate hematological malignancy-related antigen expression. cDNA constructs that can be transcribed into antisense RNA may also be introduced into cells or tissues to facilitate the production of antisense RNA. An antisense polynucleotide may be used, as described herein, to inhibit expression of a hematological malignancy-related antigen. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence or of a complementary sequence may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22-30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Hematological malignancy-related antigen polynucleotides may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

4.25 Therapeutic Methods

In further aspects of the present invention, the compositions described herein may be used for immunotherapy of hematological malignancies including adult and pediatric AML, CML, ALL, CLL, myelodysplastic syndromes (MDS), myeloproliferative syndromes (MPS), secondary leukemia, multiple myeloma, Hodgkin's lymphoma and Non-Hodgkin's lymphomas. In addition, compositions described herein may be used for therapy of diseases associated with an autoimmune response against hematopoetic precursor cells, such as severe aplastic anemia.

Immunotherapy may be performed using any of a variety of techniques, in which compounds or cells provided herein function to remove hematological malignancy-related antigen-expressing cells from a patient. Such removal may take place as a result of enhancing or inducing an immune response in a patient specific for hematological malignancy-related antigen or a cell expressing hematological malignancy-related antigen. Alternatively, hematological malignancy-related antigen-expressing cells may be removed ex vivo (e.g., by treatment of autologous bone marrow, peripheral blood or a fraction of bone marrow or peripheral blood). Fractions of bone marrow or peripheral blood may be obtained using any standard technique in the art.

Within such methods, pharmaceutical compositions and vaccines are typically administered to a patient. As used herein, a "patient" refers to any warm-blooded animal, preferably a human. A patient may or may not be afflicted with a hematological malignancy. Accordingly, the above pharmaceutical compositions and vaccines may be used to prevent the development of a malignancy or to treat a patient afflicted with a malignancy. A hematological malignancy may be diagnosed using criteria generally accepted in the art. Pharmaceutical compositions and vaccines may be administered either prior to or following surgical removal of primary tumors and/or treatment such as administration of radiotherapy or conventional chemotherapeutic drugs, or bone marrow transplantation (autologous, allogeneic or syngeneic).

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy.

The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

The compositions provided herein may be used alone or in combination with conventional therapeutic regimens such as surgery, irradiation, chemotherapy and/or bone marrow transplantation (autologous, syngeneic, allogeneic or unrelated). As discussed in greater detail below, binding agents and T cells as provided herein may be used for purging of autologous stem cells. Such purging may be beneficial prior to, for example, bone marrow transplantation or transfusion of blood or components thereof. Binding agents, T cells, antigen presenting cells (APC) and compositions provided herein may further be used for expanding and stimulating (or priming) autologous, allogeneic, syngeneic or unrelated hematological malignancy-related antigen-specific T-cells in vitro and/or in vivo. Such hematological malignancy-related antigen-specific T cells may be used, for example, within donor lymphocyte infusions.

Routes and frequency of administration of the therapeutic compositions described herein, as well as dosage, will vary from individual to individual, and may be readily established using standard techniques. In general, the pharmaceutical compositions and vaccines may be administered by injection (e.g. intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a hematological malignancy-related antigen generally correlate with an improved clinical outcome. Such immune responses may generally be evaluated using standard proliferation, cytotoxicity or cytokine assays, which may be performed using samples obtained from a patient before and after treatment.

Within further aspects, methods for inhibiting the development of a malignant disease associated with hematological malignancy-related antigen expression involve the administration of autologous T cells that have been activated in response to a hematological malignancy-related antigen polypeptide or hematological malignancy-related antigen-expressing APC, as described above. Such T cells may be $CD4^+$ and/or $CD8^+$, and may be proliferated as described above. The T cells may be administered to the individual in an amount effective to inhibit the development of a malignant disease. Typically, about $1\times10^9$ to $1\times10^{11}$ T cells/$M^2$ are administered intravenously, intracavitary or in the bed of a resected tumor. It will be evident to those skilled in the art that the number of cells and the frequency of administration will be dependent upon the response of the patient.

Within certain embodiments, T cells may be stimulated prior to an autologous bone marrow transplantation. Such stimulation may take place in vivo or in vitro. For in vitro stimulation, bone marrow and/or peripheral blood (or a fraction of bone marrow or peripheral blood) obtained from a patient may be contacted with a hematological malignancy-related antigen polypeptide, a polynucleotide encoding a hematological malignancy-related antigen polypeptide and/or an APC that expresses a hematological malignancy-related antigen polypeptide under conditions and for a time sufficient to permit the stimulation of T cells as described above. Bone marrow, peripheral blood stem cells and/or hematological malignancy-related antigen-specific T cells may then be administered to a patient using standard techniques.

Within related embodiments, T cells of a related or unrelated donor may be stimulated prior to a syngeneic or allogeneic (related or unrelated) bone marrow transplantation. Such stimulation may take place in vivo or in vitro. For in vitro stimulation, bone marrow and/or peripheral blood (or a fraction of bone marrow or peripheral blood) obtained from a related or unrelated donor may be contacted with a hematological malignancy-related antigen polypeptide, hematological malignancy-related antigen polynucleotide and/or APC that expresses a hematological malignancy-related antigen polypeptide under conditions and for a time sufficient to permit the stimulation of T cells as described above. Bone marrow, peripheral blood stem cells and/or hematological malignancy-related antigen-specific T cells may then be administered to a patient using standard techniques.

Within other embodiments, hematological malignancy-related antigen-specific T cells, antibodies or antigen-binding fragments thereof as described herein may be used to remove cells expressing hematological malignancy-related antigen from a biological sample, such as autologous bone marrow, peripheral blood or a fraction of bone marrow or peripheral blood (e.g., $CD34^+$ enriched peripheral blood (PB) prior to administration to a patient). Such methods may be performed by contacting the biological sample with such T cells, antibodies or antibody fragments under conditions and for a time sufficient to permit the reduction of hematological malignancy-related antigen expressing cells to less than 10%, preferably less than 5% and more preferably less than 1%, of the total number of myeloid or lymphatic cells in the bone marrow or peripheral blood. Such contact may be achieved, for example, using a column to which antibodies are attached using standard techniques. Antigen-expressing cells are retained on the column. The extent to which such cells have been removed may be readily determined by standard methods such as, for example, qualitative and quantitative PCR analysis, morphology, immunohistochemistry and FACS analysis. Bone marrow or PB (or a fraction thereof) may then be administered to a patient using standard techniques.

4.26 Diagnostic Methods

In general, a hematological malignancy may be detected in a patient based on the presence of hematological malignancy-related antigen and/or polynucleotide in a biological sample (such as blood, sera, urine and/or tumor biopsies) obtained from the patient. In other words, hematological malignancy-related antigens may be used as a marker to indicate the presence or absence of such a malignancy. The binding agents provided herein generally permit detection of the level of antigen that binds to the agent in the biological sample. Polynucleotide primers and probes may be used to detect the level of mRNA encoding hematological malignancy-related antigen, which is also indicative of the presence or absence of a hematological malignancy. In general, hematological malignancy-related antigen should be present at a level that is at least three fold higher in a sample obtained from a patient afflicted with a hematological malignancy than in the sample obtained from an individual not so afflicted.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a hematological malignancy in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length hematological malignancy-related antigens and portions thereof to which the binding agent binds, as described above.

The solid support may be any material known to those of ordinary skill in the art to which the hematological malignancy-related antigen polypeptide may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation.

In general, an appropriate contact time (i.e., incubation time) is a period of time that is sufficient to detect the presence of polypeptide within a sample obtained from an individual with a hematological malignancy. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a hematological malignancy, the signal detected from the reporter group that remains bound to the solid support is generally compared to a signal that corresponds to a predetermined cut-off value. In one preferred embodiment, the cut-off value for the detection of a hematological malignancy is the average mean signal obtained when the immobilized antibody is incubated with samples from patients without the malignancy. In general, a sample generating a signal that is three standard deviations above the predetermined cut-off value is considered positive for the malignancy. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a malignancy.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a hematological malignancy. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the hematological malignancy-related antigen sequences or binding agents of the present invention. The above descriptions are intended to be exemplary only. For example, it will be apparent to those of ordinary skill in the art that the above protocols may be readily modified to use hematological malignancy-related antigen polypeptides to detect antibodies that bind to such polypeptides in a biological sample. The detection of hematological malignancy-related antigen-specific antibodies may correlate with the presence of a hematological.

A malignancy may also, or alternatively, be detected based on the presence of T cells that specifically react with hematological malignancy-related antigen in a biological sample. Within certain methods, a biological sample comprising $CD4^+$ and/or $CD8^+$ T cells isolated from a patient is incubated with a hematological malignancy-related antigen polypeptide, a polynucleotide encoding such a polypeptide and/or an APC that expresses such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37° C. with Mtb-81 or Mtb-67.2 polypeptide (e.g., 5-25 µg/ml). It may be desirable to incubate another aliquot of a T cell sample in the absence of hematological malignancy-related antigen polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a hematological malignancy in the patient.

As noted above, a hematological malignancy may also, or alternatively, be detected based on the level of mRNA encoding hematological malignancy-related antigen in a biological sample. For example, at least two oligonucleotide primers may be employed in a polymerase chain reaction (PCR) based assay to amplify a portion of hematological malignancy-related antigen cDNA derived from a biological sample, wherein at least one of the oligonucleotide primers is specific for (i.e., hybridizes to) a polynucleotide encoding the hematological malignancy-related antigen protein. The amplified cDNA is then separated and detected using techniques well known in the art, such as gel electrophoresis. Similarly, oligonucleotide probes that specifically hybridize to a polynucleotide encoding hematological malignancy-related antigen may be used in a hybridization assay to detect the presence of polynucleotide encoding hematological malignancy-related antigen in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding hematological malignancy-related antigen that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample such as a biopsy tissue and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a hematological malignancy. The amplification reaction may be performed on several dilutions of cDNA spanning two orders of magnitude. A two-fold or greater increase in expression in several dilutions of the test patient sample as compared to the same dilutions of the sample from a normal individual is typically considered positive.

In preferred embodiments, such assays may be performed using samples enriched for cells expressing the hematological malignancy-related antigen(s) of interest. Such enrichment may be achieved, for example, using a binding agent as provided herein to remove the cells from the remainder of the biological sample. The removed cells may then be assayed as described above for biological samples.

In further embodiments, hematological malignancy-related-antigens may be used as markers for monitoring disease progression or the response to therapy of a hematological malignancy. In this embodiment, assays as described above for the diagnosis of a hematological malignancy may be performed over time, and the change in the level of reactive polypeptide(s) evaluated. For example, the assays may be performed every 24-72 hours for a period of 6 months to 1 year, and thereafter performed as needed. In general, a malignancy is progressing in those patients in whom the level of polypeptide detected by the binding agent increases over time. In contrast, the malignancy is not progressing when the level of reactive polypeptide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple markers may be assayed within a given sample. It will be apparent that binding agents specific for different proteins provided herein may be combined within a single assay. Further, multiple primers or probes may be used concurrently. The selection of markers may be based on routine experiments to determine combinations that results in optimal sensitivity.

Further diagnostic applications include the detection of extramedullary disease (e.g., cerebral infiltration of blasts in leukemias). Within such methods, a binding agent may be coupled to a tracer substance, and the diagnosis is performed in vivo using well known techniques. Coupled binding agent may be administered as described above, and extramedullary disease may be detected based on assaying the presence of tracer substance. Alternatively, a tracer substance may be associated with a T cell specific for hematological malignancy-related antigen, permitting detection of extramedullary disease based on assays to detect the location of the tracer substance.

4.27 Exemplary Definitions

In accordance with the present invention, nucleic acid sequences include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from native sources, chemically synthesized, modified, or otherwise prepared in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

A, an: In accordance with long standing patent law convention, the words "a" and "an" when used in this application, including the claims, denotes "one or more".

Expression: The combination of intracellular processes, including transcription and translation undergone by a polynucleotide such as a structural gene to synthesize the encoded peptide or polypeptide.

Promoter: a term used to generally describe the region or regions of a nucleic acid sequence that regulates transcription.

Regulatory Element: a term used to generally describe the region or regions of a nucleic acid sequence that regulates transcription.

Structural gene: A gene or sequence region that is expressed to produce an encoded peptide or polypeptide.

Transformation: A process of introducing an exogenous polynucleotide sequence (e.g., a vector, a recombinant DNA or RNA molecule) into a host cell or protoplast in which that exogenous nucleic acid segment is incorporated into at least a first chromosome or is capable of autonomous replication within the transformed host cell. Transfection, electroporation, and naked nucleic acid uptake all represent examples of techniques used to transform a host cell with one or more polynucleotides.

Transformed cell: A host cell whose nucleic acid complement has been altered by the introduction of one or more exogenous polynucleotides into that cell.

Transgenic cell: Any cell derived or regenerated from a transformed cell or derived from a transgenic cell, or from the progeny or offspring of any generation of such a transformed host cell.

Transgenic animal: An animal or a progeny or an offspring of any generation thereof that is derived from a transformed animal cell, wherein the animal's DNA contains an introduced exogenous nucleic acid molecule not originally present in a native, wild type, non-transgenic animal of the same species. The terms "transgenic animal" and "transformed animal" have sometimes been used in the art as synonymous terms to define an animal, the genetic contents of which has been modified to contain one or more exogenous nucleic acid segments.

Vector: A nucleic acid molecule, typically comprised of DNA, capable of replication in a host cell and/or to which another nucleic acid segment can be operatively linked so as to bring about replication of the attached segment. A plasmid, cosmid, or a virus is an exemplary vector.

The terms "substantially corresponds to", "substantially homologous", or "substantial identity" as used herein denotes a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared. The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides. Desirably, which highly homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

"Transcriptional regulatory element" refers to a polynucleotide sequence that activates transcription alone or in combination with one or more other nucleic acid sequences. A transcriptional regulatory element can, for example, comprise one or more promoters, one or more response elements, one or more negative regulatory elements, and/or one or more enhancers.

As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

As noted above, the present invention is generally directed to compositions and methods for using the compositions, for example in the therapy and diagnosis of cancer, such as hematological malignancy. Certain illustrative compositions described herein include hematological malignancy-related tumor polypeptides, polynucleotides encoding such polypeptides, binding agents such as antibodies, antigen presenting cells (APCs) and/or immune system cells (e.g., T cells). A "hematological malignancy-related tumor protein," as the term is used herein, refers generally to a protein that is expressed in hematological malignancy-related tumor cells at a level that is at least two fold, and preferably at least five fold, greater than the level of expression in a normal tissue, as determined using a representative assay provided herein. Certain hematological malignancy-related tumor proteins are tumor proteins that react detectably (within an immunoassay, such as an ELISA or Western blot) with antisera of a patient afflicted with hematological malignancy.

4.28 Biological Functional Equivalents

Modification and changes may be made in the structure of the polynucleotides and peptides of the present invention and still obtain a functional molecule that encodes a peptide with desirable characteristics, or still obtain a genetic construct with the desirable expression specificity and/or properties. As it is often desirable to introduce one or more mutations into a specific polynucleotide sequence, various means of introducing mutations into a polynucleotide or peptide sequence known to those of skill in the art may be employed for the preparation of heterologous sequences that may be introduced into the selected cell or animal species. In certain circumstances, the resulting encoded peptide sequence is altered by this mutation, or in other cases, the sequence of the peptide is unchanged by one or more mutations in the encoding polynucleotide. In other circumstances, one or more changes are introduced into the promoter and/or enhancer regions of the polynucleotide constructs to alter the activity, or specificity of the expression elements and thus alter the expression of the heterologous therapeutic nucleic acid segment operably positioned under the control of the elements.

When it is desirable to alter the amino acid sequence of one or more of the heterologous peptides encoded by the expression construct to create an equivalent, or even an improved, second-generation molecules, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |

TABLE 1-continued

| Amino Acids | | | Codons |
|---|---|---|---|
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those that are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine.

5. EXAMPLES

The following examples are included to demonstrate preferred embodiments of the invention. However, those of skill in the art should, in light of the present disclosure, appreciate that many changes can be made in the specific embodiments which are disclosed and still obtain a like or similar result without departing from the spirit and scope of the invention described in the appended claims.

5.1 Example 1
Identification of Hematological Malignancy-Related Antigen Polynucleotides This Example illustrates the identification of hematological malignancy-related antigen polynucleotides from non-Hodgkin's lymphomas.

Hematological malignancy-related antigen polynucleotides were isolated by PCR-based subtraction. PolyA mRNA was prepared from T cell non-Hodgkin's lymphomas, B cell non-Hodgkin's lymphomas and normal tissues. Six cDNA libraries were constructed, PCR-subtracted and analyzed. Two libraries were constructed using pools of three T cell non-Hodgkin's lymphoma mRNAs (referred to herein as TCS libraries). Two others were constructed using pools of three B cell non-Hodgkin's lymphoma mRNAs (referred to herein as BCNHL libraries). Two other libraries were constructed using a pool of 2 Hodgkin's lymphoma mRNAs (referred to herein as HLS libraries. cDNA synthesis, hybridization and PCR amplification were performed according to Clontech's user manual (PCR-Select cDNA Subtraction), with the following changes: 1) cDNA was restricted with a mixture of enzymes, including MscI, PvuII, StuI and DraI, instead of the single enzyme RsaI; and 2) the ratio of driver to tester cDNA was increased in the hybridization steps (to 76:1) to give a more stringent subtraction.

The two TCS libraries were independently subtracted with different pools of driver cDNAs. Driver #1 contained cDNA prepared from specific normal tissues (lymph node, bone marrow, T cells, heart and brain), and this subtraction generated the library TCS-D1 (T cell non-Hodgkin's lymphoma subtracted library with driver #1). Driver #2 contained non-specific normal tissues (colon, large intestine, lung, pancreas, spinal cord, skeletal muscle, liver, kidney, skin and brain), and this subtraction generated the library TCS-D2 (T cell non-Hodgkin's lymphoma subtraction library with driver #2).

Similarly, the two BCNHL libraries were independently subtracted with different pools of driver cDNAs. Driver #1 contained cDNA prepared from specific normal tissues (lymph node, bone marrow, B cells, heart and brain), and this subtraction generated the library BCNHL/D1 (B cell non-Hodgkin's lymphoma subtracted library with driver #1). Driver #2 contained non-specific normal tissues (brain, lung, pancreas, spinal cord, skeletal muscle, colon, spleen, large intestine and PBMC), and this subtraction generated the library BCNHL/D2 (B cell non-Hodgkin's lymphoma subtraction library with driver #2).

The two HLS libraries were independently subtracted with different pools of driver cDNAs. Driver #1 contained cDNA prepared from specific normal tissues (lymph node, bone marrow, B cells and lung) and this subtraction generated HLS-D1 (Hodgkin's lymphoma subtraction library with driver #1). Driver #2 contained non-specific normal tissues (colon, large intestine, lung, pancreas, spinal cord, skeletal muscle, liver, kidney, skin and brain) and this generated the library HLS-D2 (Hodgkin's lymphoma subtraction library with driver #2).

To analyze the efficiency of the subtraction, actin (a housekeeping gene) was PCR amplified from dilutions of subtracted as well as unsubtracted PCR samples. Furthermore, the complexity and redundancy of each library was characterized by sequencing 96 clones from each of the PCR subtraction libraries (TCS-D1, TCS-D2, BCNHL/D1, BCNHL/D2, HLS-D1 and HLS-D2). These analyses indicated that the libraries are enriched for genes overexpressed in leukemia tissues and specifically T cell and B cell non-Hodgkin's lymphoma and M. Hodgkin's lymphoma samples.

Following PCR amplification, the cDNAs were cloned into the pCR2.1-TOPO plasmid vector (Invitrogen).

Sequences obtained from these analyses were searched against known sequences in the publicly available databases using the BLAST 2.0 release. The default BLAST parameters used were as follows: GAP PARAMETERS: Open Gap=0, Extended Gap=0; OUTPUT PARAMETERS: Expect=10.0, Threshold=0, Number of Alignments=250; For BLASTN, the search parameters were as follows: Mismatch=−3, Reward=1, Word size=0. The alignments were presented pair-wise, with a window percent identity=22. All available protein and nucleotide databases were searched, including, PIR, SwissPROT, GenBank, Mouse EST, Human EST, Other EST, Human repeat and high throughput sequences, and published patents and patent application database.

From these, a number of unique sequences were identified that represented novel polynucleotide sequences that had not previously been described in the GenBank and other sequence databases. A number of other sequences were identified that appeared to contain significant homology with one or more sequences previously identified in the databases, although they were described only as genomic or cDNA clones, and had no known function. The remaining sequences corresponded to known genes. The clones obtained from this analysis are summarized in Tables 2-6 in co-pending application U.S. Ser. No. 09/796,692.

5.2 Example 2
Analysis of Subtracted cDNA Sequences by Microarray Analysis

Subtracted cDNA sequences were analyzed by microarray analysis to evaluate their expression in hematological malignancies and normal tissues. Using this approach, cDNA sequences were PCR amplified and their mRNA expression profiles in hematological malignancies and normal tissues are examined using cDNA microarray technology essentially as described (Shena et al., 1995).

In brief, the clones identified from the subtracted cDNA libraries analyses were immobilized and arrayed onto glass slides as multiple replicas on microarray slides and the slides were hybridized with two different sets of probes, with each location on the microarray slide corresponding to a unique cDNA clone (as many as 5500 clones can be arrayed on a single slide, or chip). Each chip is hybridized with a pair of cDNA probes that are fluorescence-labeled with Cy3 and Cy5, respectively. The set of probes derived from the hematological malignancies was labeled with cy3 while the other set of probes derived from a pool of normal tissues was labeled with cy5. Typically, 1 µg of polyA$^+$ RNA was used to generate each cDNA probe. After hybridization, the chips were scanned and the fluorescence intensity recorded for both Cy3 and Cy5 channels. The difference in intensities (i.e., cy3/cy5 ratios) following hybridization with both probe sets provided the information on the relative expression level of each cDNA sequences immobilized on the slide in tumor versus normal tissues. There are multiple built-in quality control steps. First, the probe quality is monitored using a panel of ubiquitously expressed genes. Secondly, the control plate also can include yeast DNA fragments of which complementary RNA may be spiked into the probe synthesis for measuring the quality of the probe and the sensitivity of the analysis. This methodology provides a sensitivity of 1 in 100,000 copies of mRNA, and the reproducibility of the technology may be ensured by including duplicated control cDNA elements at different locations.

Analysis of hematological malignancy subtracted clones by microarray analyses on a variety of microarray chips identified the sequences set forth in SEQ ID NO:1 through SEQ ID NO:668 of co-pending application U.S. Ser. No. 09/796,692 as being at least two-fold overexpressed in hematological malignancies versus normal tissues.

5.3 Example 3
Polynucleotide and Polypeptide Compositions: Brief Description of the cDNA Clones and Open Reading Frames Identified by Subtractive Hybridization and Microarray Analysis Table 7 in co-pending application U.S. Ser. No. 09/796,692 lists the sequences of the polynucleotides obtained during the analyses of the present invention. Shown are the 668 polynucleotide sequences, along with their clone name identifiers, as well as the serial number and filing date of the priority provisional patent application in which the clone was first identified.

Table 8 in co-pending application U.S. Ser. No. 09/796,692 identifies the putative open reading frames obtained from analyses of the cDNA sequences obtained in SEQ ID NO:1-SEQ ID NO:668 in the co-pending application. Shown are the sequence identifiers, the clone name and translation frame, and the start and stop nucleotides in the corresponding DNA sequence used to generate the polypeptide sequence of the open reading frame.

Table 9 in co-pending application U.S. Ser. No. 09/796,692 identifies an additional set of particular hematological malignancy-related cDNA sequences that were obtained using the subtractive library and microarray methods as described above. These sequences, designated SEQ ID NO:2533-SEQ ID NO:9597 in the co-pending application, are shown in the Table along with the original clone name, and the serial number and filing date of the priority provisional application in which the clone was first described.

5.4 Example 4
Additional Analysis of cDNA Clones and ORFS Identified by Subtractive Hybridization and Microarray Analysis This example describes microarray analysis of leukemia tumor- and tissue-specific cDNAs.

Microarray analysis identifies many potential genes that are overexpressed in specific tissues/tumors. However, these genes often represent known genes or genes that subsequently are found by RealTime PCR analysis to have a broader expression profile. This disclosure describes analyses which combine microarray analysis (CorixArray) and comparisons to public databases to identify and prioritize candidate sequences for RealTime analysis, thus allowing the identification of sequences with favorable expression profiles in a more efficient manner.

Clones are tested for overexpression in lymphoma tumor samples as compared to normal tissues using Corixa Leukemia/Lymphoma Chip#3 (LyC3). The analyzed clones are originally randomly picked from lymphoma PCR subtracted libraries: B-cell non-Hodgkin's lymphoma libraries (BC-NHL/D1 and BCNHL/D2; CID000153); T-cell non-Hodgkin's lymphoma libraries (ICS-D1 and TCS-D2; CID000166); Hodgkin's lymphoma libraries (HLS-D1 and HLS-D2; CID000204 and CID000275) and a Clontech-generated T8 leukemia PCR subtracted library. A total of 5184 clones were arrayed: 2304 from BCNHL libraries, 288 from TCS libraries, 1344 from HLS libraries, and 960 from a Clontech-T8 library. In addition, a selection of 288 clones from the above libraries that had been identified from prior leukemia/lymphoma chips were re-analyzed on LyC3.

cDNA inserts for arraying are amplified by PCR using vector-specific primers. The arrays are probed with 43 probe pairs. Analysis is performed using CorixArray computational analysis. Analysis consisted of determining the ratio of the mean or median hybridization signal for a particular element (cDNA) using two sets of probes. The ratio is a reflection of the over- or under-expression of the element (cDNA) within the probe population. Probe groups are set up to identify elements (cDNAs) with high differential expression in probe group #1. Probe group #1 typically consists of 20 tumor RNAs, each probe representing a subset of lymphoma (e.g., B-cell non-Hodgkins lymphoma, T-cell non-Hodgkins lymphoma and Hodgkin lymphoma). Probes in group #2 include 16 essential and non-essential normal tissues (see, FIG. 4). A threshold (fold-overexpression in probe group #1) is set at 3.0. This threshold is set to identify elements with overexpression that could be reproducibly detected based on the quality of the chip. The sequences are sorted initially based on their CorixArray analysis, specifically on the basis of their mean signal 2 values.

Sequences having a mean signal 2<0.1 can be considered as sequences with low/no expression in normal tissues. Sequences having a mean signal 2 between 0.1 and 0.2 can be considered as clones with a potential for some expression in normal tissues. Sequences having a mean signal 2>0.2 and can be considered as clones that have the potential to have expression in some normal tissues.

5.5 Example 5
Identification of Candidate Genes with the Same Tissue Expression Profile as CD20 and CD52

Figure 1:
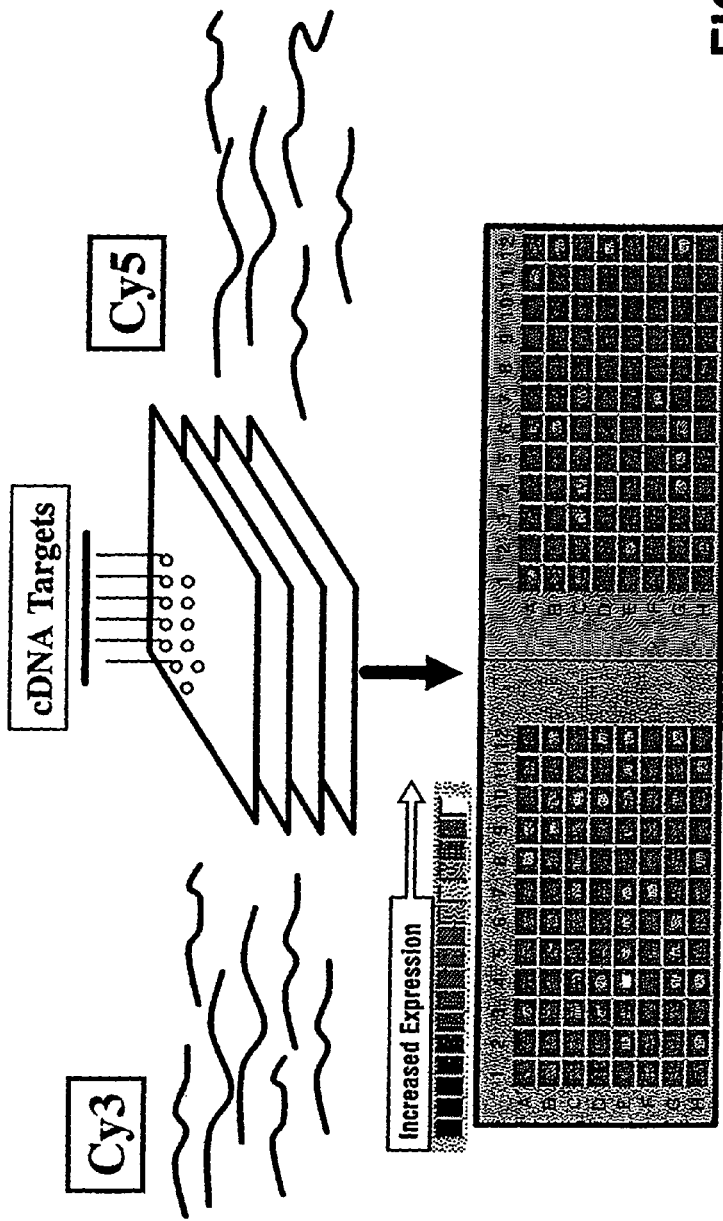
FIG. 1 illustrates a schematic outline of the microarray chip technology approach used to identify the cDNA targets of the present invention as described Section 5.1.
Figure 2:
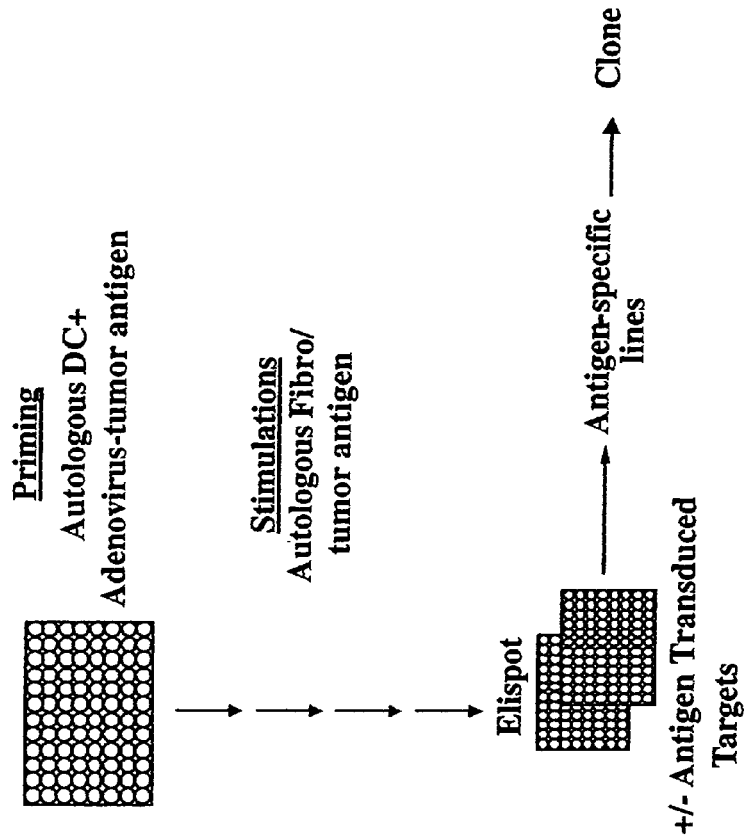
FIG. 2 illustrates a schematic outline of the general protocol for in vitro whole gene CD8+ T cell priming procedure used to generate antigen-specific lines and to identify clones of interest.
Figure 3:
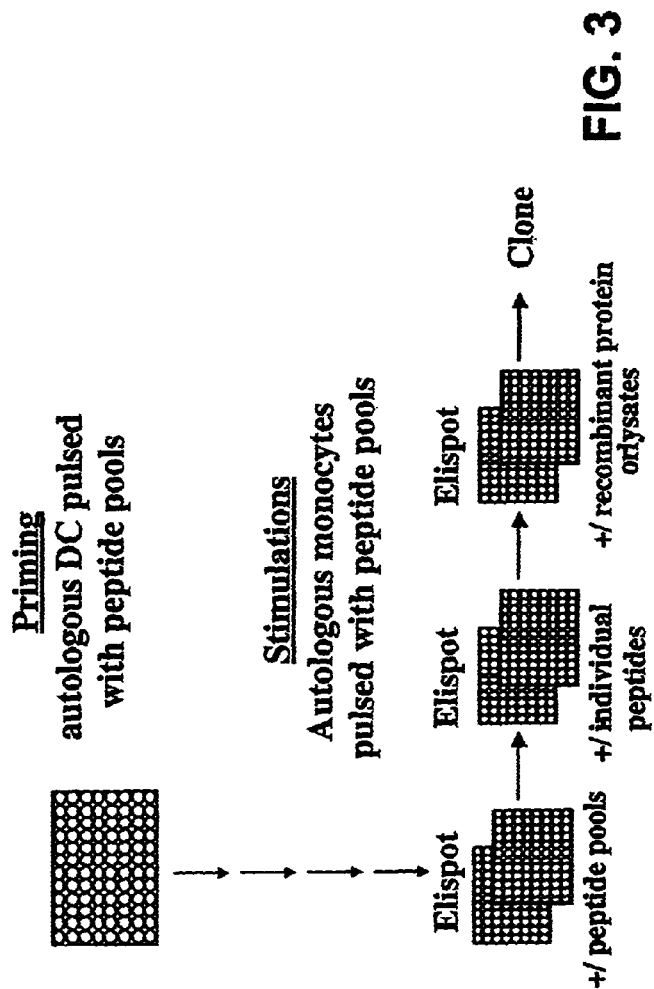
FIG. 3 illustrates a schematic outline of the general protocol for in vitro whole gene CD4+ T cell priming procedure used to generate antigen-specific lines and to identify clones of interest.

This example identifies leukemia tumor and tissue-specific genes that have similar tissue expression profiles as CD20 and CD52 (FIG. 3). Antibodies against these two markers have been used for the therapy of hematological malignancies and other diseases associated with expression of these markers, i.e., FDA-approved Rituximab (anti-CD20 Ab) and Campath (anti-CD52 Ab). The similarity in gene expression between our candidate genes and CD20 and CD52 suggests that the described genes will also be useful as compounds for the diagnosis and therapy of hematological malignancies and other cancerous and non-cancerous diseases associated with expression of one or more of the described antigens.

RealTime PCR was used to compare the expression profiles of the candidate genes with the expression profiles of CD20 and CD52. FIG. 8 illustrates the expression of the candidate genes in hematopoietic subsets and hematological malignancies. Data summarized in this sheets shows that using a combination of the PCR subtracted cDNA libraries, microarray analyses, and RealTime PCR, it is possible to identify genes differentially expressed in in normal B-cells, lymphomas, myeloma, chronic lymphocytic leukemia, and acute myeloid leukemia.

5.6 Example 6
Analysis of Ly1484 (SEQ ID NOS:16-18 and 120-121), One of the Genes with a Similar Expression Profile as CD20 and CD52

This example illustrates the typical procedure used to identify antigens for use as therapeutics, diagnostics, etc. and preferred methods for developing therapeutics and diagnostics for leukemia/lymphoma diseases. First, candidate genes highly enriched in leukemia/lymphoma cells are identified using PCR subtraction library cloning. Next, subtracted cDNA sequences are analyzed by microarray analysis to evaluate their expression in hematological malignancies and normal tissues. Since microarray analysis often identifies genes that represent known genes or genes that subsequently are found by RealTime analysis to have broader expression profiles, the microarray analysis is combined with comparisons to public databases to identify and prioritize candidate sequences for analysis. Next, RealTime PCR is used to analyze the expression profiles in various hematological subsets. In some cases, further analysis is focused on antigens with expression profiles similar to known therapeutics. For these genes, structural prediction programs are used to identify transmembrane domains, antigen-specific CTL are generated using human in vitro priming, and humanized monoclonal and polyclonal antibodies are generated as reagents for the diagnosis and therapy of malignancies and autoimmune disorders associated with antigen expression.

Ly1484P PCR subtraction library clone sequences matched the Genbank clone KIAA1607 (acc. no. XM033378, XM033379 and AB046827) and FJL00111 (acc. no. AK024502). Overexpression of Ly1484 was documented by microarray analyses and RealTime PCR. Ly1484P is overexpressed in B cell neoplasms, while expression in normal tissues is restricted to normal B-cells.

A full length sequence of candidate Ly1484P was obtained using the Genbank database. Ly1484P was mapped to human chromosome 10. There is both a long and short version of Ly1484P (long version—SEQ ID NO:120; short version—SEQ ID NO:121). TMpred analysis of Ly1484P indicates that this protein contains a transmembrane domain. Using the TSITES program, T-helper epitopes have also been identified (FIGS. 7 & 8). Polypeptides have been generated and are being used to generate antibodies that are specific for Ly1484P. These humanized monoclonal antibodies may be used (conjugated or unconjugated) for the diagnosis and therapy of malignancies and autoimmune disorders associated with Ly1484 expression.

5.7 Example 7
Identification of Transmembrane Domains

Structural prediction programs known to those of skill in the art were used to identify transmembrane domains in the candidate antigens described herein.

For Ly1728P, amino acid residues 6-22, 47-65, 227-243, and 228-245 of SEQ ID NO:2 were identified as putative transmembrane domains.

For Ly1732P, amino acid residues 60-76 and 55-76 of SEQ ID NO:4 were identified as putative transmembrane domains.

For Ly1888P, amino acids 1-22, 3-21, 52-68, 254-273, 252-273, and 256-272 of SEQ ID NO: 6 were identified as putative transmembrane domains.

For Ly1452P amino acids 354-375, 355-377 and 425-441 of SEQ ID NO: 10 (splice variant 1) were identified as putative transmembrane domains and amino acids 354-375, 355-377 and 425-441 of SEQ ID NO: 12 (splice variant 2) were identified as putative transmembrane domains.

Ly1462P, amino acids 2-23, 3-21, 369-385, 976-999, 977-993, and 979-1000 of SEQ ID NO: 15 were identified as putative transmembrane domains.

For Ly1484P, amino acids 51-67, 322-338, 666-682, 736-752, 1078-1094, 24-43, 53-69, 118-136, 319-335, 730-752, 1586-1602, 48-69, 88-109, 114-135, 196-217, 300-321, 323-344, 389-410, 502-523, 659-680, 714-735, 1076-1097, 1158-1179, and 1321-1342 of SEQ ID NO: 18 were identified as putative transmembrane domains, amino acids 10-86, 63-84, 118-139, 480-501, 562-583, 725-746, 70-86, 113-129, 134-156, 280-296, 481-497, 560-577, 653-674, 721-738, 734-752, 833-869, 879-895, 990-1006, 1023-1048, 1070-1087, 1112-1138, 1135-1170, and 1146-1170 of SEQ ID NO: 120 were identified as putative transmembrane domains, amino acids 94-129, 102-123, 367-383, 394-423, 447-464, and 493-513, of SEQ ID NO: 121 were identified as putative transmembrane domains.

For Ly1486P, amino acids 24-40 and 24-45 of SEQ ID NO: 21 were identified as putative transmembrane domains.

For Ly1693P, amino acids 47-63, 80-96, 114-130, 158-174, 207-223, 237-253, 289-305, 117-134, 144-160, 167-184, 516-535, 44-65, 85-106, 111-132, 150-171, 204-225, 242-263, and 290-311 of SEQ ID NO: 26 were identified as putative transmembrane domains.

For Ly1715P, amino acids 38-54, 38-56, and 34-55 of SEQ ID NO: 29 were identified as putative transmembrane domains.

For Ly1727P, amino acids 68-100, 214-234, 304-320, 84-105, 217-238, and 302-323 of SEQ ID NO: 32 were identified as putative transmembrane domains.

For Ly1905P, amino acids 68-100, 214-234, 84-105, and 217-238 of SEQ ID NO: 40 were identified as putative transmembrane domains.

For Ly1885P, amino acids 218-234, 219-235, 626-654, and 219-240 of SEQ ID NO: 35 were identified as putative transmembrane domains.

For Ly663S, amino acids 22-38, 41-57, 60-76, 92-108, 242-258, 20-38, 23-57, 60-77, 86-102, 241-257, 14-35, 89-110, and 248-269 of SEQ ID NO: 43 were identified as putative transmembrane domains.

For Ly664S, amino acids 11-27, 15-31, 74-93, 209-227, 8-29, and 67-88 of SEQ ID NO: 45 were identified as putative transmembrane domains.

For Ly667S, amino acids 13-31, 139-157, 184-202, 231-247, 329-351, 435-451, 473-490, 609-626, 685-705, 688-704, 7-28, 233-254, and 685-706 of SEQ ID NO: 48 were identified as putative transmembrane domains.

For Ly677S, amino acids 149-165, 10-30, 144-165, 7-28, and 144-165 of SEQ ID NO: 54 were identified as putative transmembrane domains.

For Ly1891P, amino acids 31-47, 66-82, 93-109, 128-144, 171-187, 205-221, 242-258, 3148, 64-82, 94-111, 120-145, 170-187, 205-221, 244-266, and 29-50, 63-84, 93-114, 124-145, 168-189, 206-227, and 241-262 of SEQ ID NO: 56 were identified as putative transmembrane domains.

For CD138, amino acids 255-271, 4-21, 258-276, 6-27, and 256-277 of SEQ ID NO: 58 were identified as putative transmembrane domains.

For CD22, amino acids 688-704, 3-19, 29-46, 157-174, 185-201, 349-366, 386-406, 479-505, 688-709, 1-22, 159-180, and 689-710 of SEQ ID NO: 61 were identified as putative transmembrane domains.

For CD79beta, amino acids 161-177, 4-29, 59-78, 160-181, 4-25, and 161-180 of SEQ ID NO: 66 were identified as putative transmembrane domains.

For Ly1454P, amino acids 5-22, 231-249, 7-28, and 425-446 of SEQ ID NO: 74 were identified as putative transmembrane domains.

For Ly1485P, amino acid residues 2-19 of SEQ ID NO:76 were identified as a putative transmembrane domain.

Ly1500P, amino acid residues 10-31 and 327-344 of SEQ ID NO: 80 (splice variant 1) were identified as putative transmembrane domains, amino acid residues 13-38, 71-92, and 388-405 of of SEQ ID NO: 82 (splice variant 2) were identified as putative transmembrane domains, and amino acids 25-46 and 341-359 of SEQ ID NO: 84 (splice variant 3) were identified as putative transmembrane domains.

For Ly1516P, amino acids 142-158, 177-193, 207-223, 238-254, 271-287, 142-158, 177-193, 207-223, 238-254, and 271-287 of SEQ ID NO:87 were identified as putative transmembrane domains.

For Ly1729P, amino acids 420-436 431-437, and 412-433 of SEQ ID NO:101 were identified as putative transmembrane domains.

For Ly1859P, amino acid residues 128-144, 293-311, 408-425, 435-454, 465-483, 516-533, 290-311, 435-456, and 507-528 of SEQ ID NO 107 were identified as putative transmembrane domains.

For Ly1866P, amino acids 47-65 and 50-71 of SEQ ID NO: 109 were identified as putative transmembrane domains.

For Ly669S, amino acids 489-505, 13-29, 38-57, 73-89, 94-114, 252-268, 307-324, 329-346, 489-509, 4-25, and 486-507 of SEQ ID NO:114 were identified as putative transmembrane domains.

For Ly672S, amino acids 11-27, 284-300, 325-341, 345-361, 407-423, 7-28, 102-118, 174-198, 283-299, 325-341, 347-383, 403-423, 431-454, 473-492, 11-32, 286-307, 322-343, 345-366, 404-425, 430-451, and 469-490 of SEQ ID NO:117 were identified as putative transmembrane domains.

For Ly675S, amino acids 154-170, 187-203, 428, 444, 518-534, 846-862, 81-97, 155-172, 235-251, 374-391, 428-444, 477-195, 520-542, 539-573, 694-714, 807-823, 843-862, 50-71, 77-98, 145-166, 518-539, 802-823, and 845-866 of SEQ ID NO:119 were identified as putative transmembrane domains.

5.8 Example 8
RealTime PCR Analysis to Identify Antigens Overexpressed in Chronic Lymphocytic Leukemia and Multiple Myeloma Overexpression of candidate antigens in chronic lymphocytic leukemia (CLL) and multiple myeloma (MM) was confirmed by RealTime PCR.

Real-time PCR evaluates the level of PCR product accumulation during amplification (see, e.g., Gibson et al., Genome Research 6:995-1001 (1996); Heid et al., Genome Research 6:986-994 (1996)). RealTime PCR permits quantitative evaluation of mRNA levels in multiple samples. Briefly, mRNA is extracted from tumor and normal tissue and cDNA is prepared using standard techniques. Real-time PCR is performed, for example, using a Perkin Elmer/Applied Biosystems (Foster City, Calif.) 9700 Prism instrument. Matching primers are designed for genes of interest using, for example, the primer express program provided by Perkin Elmer/Applied Biosystems (Foster City, Calif.). Optimal concentrations of primers and probes are initially determined by those of ordinary skill in the art, and control (e.g., β-actin) primers and probes are obtained commercially from, for example, Perkin Elmer/Applied Biosystems (Foster City, Calif.). To quantitate the amount of specific RNA in a sample, a standard curve is generated using a plasmid containing the gene of interest. Standard curves are generated using the Ct values determined in the real-time PCR, which are related to the initial cDNA concentration used in the assay. Standard dilutions ranging from 10-10$^6$ copies of the gene of interest are generally sufficient. In addition, a standard curve is generated for the control sequence. This permits standardization of initial RNA content of a tissue sample to the amount of control for comparison purposes.

| Summary of Results | | |
| --- | --- | --- |
| Antigen | CLL | MM |
| Ly1728P | no | yes |
| Ly1732P | yes | yes |
| Ly1888P | yes | no |
| Ly 1452P | yes | no |
| Ly1462P | yes | no |
| Ly1484P | not determined | not determined |
| Ly1486P | yes | no |
| Ly1677P | yes | no |
| Ly1682P | yes | no |
| Ly1693P | yes | yes |
| Ly1697P | yes | no |
| Ly1715P | yes | yes |
| Ly1727P | yes | yes |
| Ly1905P | yes | yes |
| Ly1885P | yes | yes |
| Ly663S | yes | yes |
| Ly664S | yes | yes |
| Ly667S | yes | yes |
| Ly677S | yes | yes |
| Ly1891P | not determined | not determined |
| CD138 | no | yes |
| CD22 | yes | no |
| CD79beta | yes | yes |
| Ly1450P | not determined | not determined |
| Ly1451P | yes | yes |
| Ly1454P | yes | not determined |
| Ly1485P | not determined | not determined |
| Ly1500P | yes | no |
| Ly1516P | not determined | not determined |
| Ly1678P | yes | yes |
| Ly1680P | yes | no |
| Ly1686P | yes | no |
| Ly1687P | yes | no |
| Ly1706P | yes | yes |
| Ly1712P | yes | yes |
| Ly1729P | yes | yes |
| Ly1848P | yes | yes |
| Ly1859P | yes | no |
| Ly1866P | yes | yes |
| Ly1867P | yes | no |
| Ly1868P | yes | no |
| Ly1886P | yes | no |
| Ly669S | yes | yes |
| Ly672S | yes | yes |
| Ly675S | yes | yes |

These sequences can conveniently be used to diagnose, treat, and prevent malignant diseases that overexpress these genes, including multiple myeloma, B-cell lymphomas, and B-CLL. For example, monoclonal antibodies, including humanized monoclonal antibodies can be used for diagnosis and therapy of disorders associated with expression of antigens overexpressed in hematological malignancies.

5.9 Example 9
Sequence Analyses, Expression Analyses, and Structure Analyses of Other Antigens with Similar Expression Profiles as CD20 & CD52

| Antigen | Sequence Analysis |
|---|---|
| | Summary of Results |
| Ly1728P | FOAP-2 ("novel gene over-expressed in macrophages") |
| Ly1732P | B-cell maturation factor (BCM), tumor necrosis factor receptor superfamily, member 17. BCM bins to TALL-1, a member of the TNF family. |
| Ly1888P | anti-Fas-induced apoptosis protein (TOSO); experimentally shown to be expressed on the cell surface. |
| Ly 1452P | anti-Fas-induced apoptosis protein (TOSO); experimentally shown to be expressed on the cell surface. |
| Ly1462P | Human Epstein-Barr virus complement receptor type II |
| Ly1484P | KIAA1607 (cDNA sequence present in GenBank). |
| Ly1486P | Fc fragment of IgE, low affinity II receptor. |
| Ly1677P | novel |
| Ly1682P | novel |
| Ly1693P | Chemokine receptor CXCR4 |
| Ly1697P | novel |
| Ly1715P | lectin-like NK cell receptor |
| Ly1727P | Splice variants of the hpim-2 gene (homologs of the mouse pim-2 oncogene). Predicted to be a serine threonine kinase with a role in cell proliferation. |
| Ly1905P | Splice variants of the hpim-2 gene (homologs of the mouse pim-2 oncogene). Predicted to be a serine threonine kinase with a role in cell proliferation. |
| Ly1885P | An apparent splice form of the cell cycle progression 8 protein: one of a family of proteins involved in restoration of cell cycle progression (by blocking arrest in G1 phase). |
| Ly663S | leukocyte surface antigen CD37 |
| Ly664S | protein with unknown function that shares 30–40% identity with various thioredoxins |
| Ly667S | Semaphorin B (semaphorins are a large family of secreted and transmembrane proteins; sema domains occur in the hepatocyte growth factor receptor) |
| Ly677S | leukocyte surface recptor CD79A |
| Ly1891P | orphan G-protein coupled receptor (GPRC5D) |
| CD138 | CD138 |
| CD22 | CD22 |
| CD79beta | CD79beta |
| Ly1450P | novel (matches GenBank seq FLJ23202; no ORF) |
| Ly1451P | novel (matches GenBank seq FLJ39358 no ORF) |
| Ly1454P | novel (matches GenBank seq FLJ40597; ORF) |
| Ly1485P | novel (matches genomic DNA only) |
| Ly1500P | BANK protein: B-cell scaffold protein with ankyrin repeats; a substrate for tyrosine phosphorylation upon B-cell antigen receptor stimulation. |
| Ly1516P | Rh-related antigen CD47, a signal transducer integrin-associated protein |
| Ly1678P | novel (matches genomic DNA only) |
| Ly1680P | novel (matches genomic DNA only) |
| Ly1686P | novel (matches genomic DNA only) |
| Ly1687P | novel (matches genomic DNA only) |
| Ly1706P | novel (matches genomic DNA only) |
| Ly1712P | novel |
| Ly1729P | Hematopoietic cell-specific Lyn substrate 1 (HCLS1) protein; N-terminal half hs repeats with significant identity to a helix-turn-helix DNA binding motif; the C-terminal half is similar to domains that act as substrates for protein tyrosine kinases suggesting that this protein may be involved in signal transduction and regulation of gene expression. |
| Ly1848P | novel (matches genomic DNA only) |
| Ly1859P | novel (matches GenBank seq FLJ00140; ORF) |
| Ly1866P | Matches a gene in GenBank referred to as "similar to hypothetical protein PRO1722." |
| Ly1867P | novel (matches genomic DNA only) |
| Ly1868P | novel (matches genomic DNA only) |
| Ly1886P | novel (matches genomic DNA only) |
| Ly669S | intercellular adhesion molecule 3 (ICAM3) |
| Ly672S | cisplatin resistance related protein CRR9p |
| Ly675S | KIAA0906 (partial cDNA/protein sequences present in GenBank). |

5.10 Example 10
Sequence Analysis of Ly1451

The Ly1451 (SEQ ID NOS:69-71 and 124) sequence derived from a lymphoma PCR subtraction library clone was used to query several public databases, including GenBank and GenSeq. No matches (>90 identity) were detected for the 5'-proximal 51 bp suggesting that this sequence may contain a repeat element. A BLASTN search of the LifeSeq database (Incyte) identified a 980 bp template (template #1076101.8; SEQ ID NO:124 that contained all 240 bp of Ly1451. This template consisted of sequences from 6 clones, of which 2 (33%) were derived from hematologic/immune tissue libraries. Template #1076101.8 was part of a bin containing 11 templates derived from a total of 104 clones, of which 12 (9%) were derived from hematologic/immune tissue libraries.

This sequence (SEQ ID NO:124) was used to search further public databases but no additional sequences were obtained. However, these searches indicate this sequence is a human endogenous retroviral sequence (HERV) encoding polypeptides corresponding to portions of the integrase and envelope genes. A single ORF with an ATG translational start site is contained in the forward read of LS1076101.8

The polypeptide encoded by this ORF (SEQ ID NO:124) is not predicted to have a transmembrane domain.

5.11 Example 11
Expression of Ly1452 Lymphoma Antigens Encoded by a Specific Gene, Ly1452, Associated with B Cell Leukemias, Lymphomas and Multiple Myelomas Recombinantly expressed Ly1452 antigens were constructed to allow for quick and easy purification of the protein.

The open reading frame for Ly1452 was PCR amplified and subcloned into a modified pET28 vector with a His tag in-frame and recombinantly expressed in *E. coli* (His-Ly1452: SEQ ID NO:10,482 (nt), SEQ ID NO:10,483 (protein).

Ly1452P Expression in *E. coli*

The open reading frame of the LS coding region was PCR amplified with the following primers:

```
PDM-797
                                    (SEQ ID NO:10,975)
5' gtgtcacaatctacagtcaggcaggattctcc 3'
Tin 64° C.

PDM-799
                                    (SEQ ID NO:10,976)
5' gttatgtagcggccgcttatcatgttgctgcagag 3'
Tm 67° C.
```

Using the following conditions:

| | |
|---|---|
| 10 μl | 10× Herculase buffer |
| 1 μl | 10 mM dNTPs |
| 2 μl | 10 μM each oligo |
| 83 μl | sterile water |
| 1.0 μl | Herculase DNA polymerase (Stratagene, La Jolla, CA) |
| 50 ng | DNA |

98° C. 3 minutes
98° C. 40 seconds  60° C. 30 seconds  72° C. 2 minute × 10 cycles
98° C. 40 seconds  60° C. 30 seconds  72° C. 2 minutes 30 seconds × 10 cycles
98° C. 40 seconds  60° C. 30 seconds  72° C. 3 minutes × 10 cycles
98° C. 40 seconds  60° C. 30 seconds  72° C. 3 minutes 30 seconds × 10 cycles
72° C. 4 minutes The PCR product was digested with Xho I and cloned into pPDM His (a modified pET28 vector with a His tag in frame on the 5' end) that had been digested with Eco72I and XhoI. Construct was confirmed through sequence analysis and transformed into BLR (DE3) pLysS and HMS 174 pLys S cells.

Recombinant proteins are also expressed without a histidine tag or with other lymphoma antigens. They are also expressed in other vectors, including other *E. coli* constructs, Baculovirus, yeast, and mammalian expression vectors. This recombinant antigen can be used to make polyclonal and monoclonal antibodies or used in immunological assays.

6. REFERENCES

The following references, to the extent that they provide exemplary procedural or other details supplementary to those set forth herein, are specifically incorporated herein by reference.

U.S. Pat. No. 3,817,827.
U.S. Pat. No. 3,850,752.
U.S. Pat. No. 3,901,654.
U.S. Pat. No. 3,935,074.
U.S. Pat. No. 3,984,533.
U.S. Pat. No. 3,996,345.
U.S. Pat. No. 4,034,074.
U.S. Pat. No. 4,098,876.
U.S. Pat. No. 4,235,877.
U.S. Pat. No. 4,376,110.
U.S. Pat. No. 4,429,008.
U.S. Pat. No. 4,436,727.
U.S. Pat. No. 4,452,901.
U.S. Pat. No. 4,489,710.
U.S. Pat. No. 4,507,234.
U.S. Pat. No. 4,554,101.
U.S. Pat. No. 4,569,789.
U.S. Pat. No. 4,603,112.
U.S. Pat. No. 4,625,014.
U.S. Pat. No. 4,638,045.
U.S. Pat. No. 4,671,958.
U.S. Pat. No. 4,673,562.
U.S. Pat. No. 4,683,195.
U.S. Pat. No. 4,699,784.
U.S. Pat. No. 4,735,792.
U.S. Pat. No. 4,751,180.
U.S. Pat. No. 4,769,330.
U.S. Pat. No. 4,777,127.
U.S. Pat. No. 4,866,034.
U.S. Pat. No. 4,873,088.
U.S. Pat. No. 4,877,611.
U.S. Pat. No. 4,897,268.
U.S. Pat. No. 4,912,094.
U.S. Pat. No. 4,935,233.
U.S. Pat. No. 5,017,487.
U.S. Pat. No. 5,075,109.
U.S. Pat. No. 5,145,684.
U.S. Pat. No. 5,151,254.
U.S. Pat. No. 5,215,926.
U.S. Pat. No. 5,240,856.
U.S. Pat. No. 5,350,840.
U.S. Pat. No. 5,359,681.
U.S. Pat. No. 5,399,346.
U.S. Pat. No. 5,399,363.
U.S. Pat. No. 5,466,468.
U.S. Pat. No. 5,472,869.
U.S. Pat. No. 5,543,158.
U.S. Pat. No. 5,552,157.

U.S. Pat. No. 5,565,213.
U.S. Pat. No. 5,567,434.
U.S. Pat. No. 5,633,234.
U.S. Pat. No. 5,641,515.
U.S. Pat. No. 5,738,868.
U.S. Pat. No. 5,741,516.
U.S. Pat. No. 5,795,587.
U.S. Pat. No. 5,811,128.
U.S. Pat. No. 5,814,344.
U.S. Pat. No. 5,820,883.
U.S. Pat. No. 5,853,763.
U.S. Pat. No. 5,874,265.
U.S. Pat. No. 5,928,647.
U.S. Pat. No. 5,942,252.
U.S. Pat. No. 6,110,702.
European Patent No. EP 0,345,242.
Great Britain Patent No. GB 2,200,651.
Intl. Pat. Appl. Publ. No. WO 89/01973.
Intl. Pat. Appl. Publ. No. WO 89/06280.
Intl. Pat. Appl. Publ. No. WO 91/02805.
Intl. Pat. Appl. Publ. No. WO 91/16116.
Intl. Pat. Appl. Publ. No. WO 92/07243.
Intl. Pat. Appl. Publ. No. WO 94/00153.
Intl. Pat. Appl. Publ. No. WO 94/20078.
Intl. Pat. Appl. Publ. No. WO/94/23701.
Intl. Pat. Appl. Publ. No. WO 95/17210.
Intl. Pat. Appl. Publ. No. WO 96/02555.
Intl. Pat. Appl. Publ. No. WO 96/06638.
Intl. Pat. Appl. Publ. No. WO 96/30516.
Intl. Pat. Appl. Publ. No. WO 96/33739.
Intl. Pat. Appl. Publ. No. WO 97/24447.
Intl. Pat. Appl. Publ. No. WO 99/33488.
Aaroston and Todaro, *J. Cell. Physiol.*, 72:141-48, 1968.
Adelman et al., *DNA*, 2:183, 1983.
Amin et al., *Am. J. Pathol.*, 146:344-56, 1995.
Akaza et al., "Expression of antitumor response. Role of attachment and viability of bacillus Calmette-Guerin to bladder cancer cells," *Cancer*, 72:558-63, 1993.
American Type Culture Collection, Catalogue of Cell Lines and Hybridomas, 7th ed., 1992.
Avrameas, "Natural autoantibodies: Self-recognition and physiological autoimmunity," In: *Natural autoantibodies: Their Physiological Role and Regulatory Significance*, Shoenfeld and Isenberg (eds.), CRC Press, Boca Raton, Fla., pp. 1-14, 1993.
Azuma et al., "Correlation Between Augmented Resistance to Influenza Virus Infection and Histological Changes in Lung of Mice Treated with Trehalose-6,6'-dimycolate," *Journal of Biological Response Modifiers*, 7:473-82, 1988.
Bajorin et al., *Proc. Annu. Meet. Am. Soc. Clin. Oncol.*, 7:A967, 1988.
Baker et al., "Ability of Monophosphoryl Lipid A To Augment the Antibody Response of Young Mice," *Infection and Immunity*, 56:3064-66, 1988a.
Baker et al., "Enrichment of Suppressor T Cells by Means of Binding to Monophosphoryl Lipid A," *Infection and Immunity*, 58:726-31, 1990.
Baker et al., "Inactivation of Suppressor T-Cell Activity by Nontoxic Monophosphoryl Lipid A," *Infection and Immunity*, 56:1076-83, 1988b.
Baker et al., "Molecular structures that influence the immunomodulatory properties of the lipid A and inner core region oligosaccharides of bacterial lipopolysaccharides," *Infection Immunity*, 62:2257-69, 1994.
Baker et al., "Structural Features That Influence the Ability of Lipid A and Its Analogs To Abolish Expression of Suppressor T Cell Activity," *Infection and Immunity*, 60:2694-701, 1992.
Bakker et al., "Melanocyte lineage-specific antigen gp100 is recognized by melanoma-derived tumor-infiltrating lymphocytes," *J. Exp. Med.*, 179:1005, 1994.
Banchereau and Steinman, *Nature*, 392:245-51, 1998.
Banerji et al., "Membrane lipid composition modulates the binding specificity of a monoclonal antibody against liposomes," *Biochim. Biophys. Acta.*, 689:319-26, 1982.
Barnd et al., "Specific tumor histocompatibility complex-unrestricted recognition of tumor-associated mucins by human cytotoxic T cells," *Proc. Natl. Acad. Sci. USA*, 86:7159, 1989.
Barnoud et al., *Am. J. Surg. Pathol.*, 24:830-36, 2000).
Bartlett and Zbar, *J. Natl. Cancer Inst.*, 48:1709, 1972.
Bast et al., "BCG and Cancer," *N. Engl. J. Med.*, 290:1413-20, 1974.
Bennett et al., "Endogenous Production of Cytotoxic Factors in Serum of BCG-Primed Mice by Monophosphoryl Lipid A, a Detoxified Form of Endotoxin," *Journal of Biological Response Modifiers*, 7:65-76, 1988
Berkner, *Biotechniques*, 6:616-27, 1988.
Berra et al., *Int. J. Cancer*, 36:363-66, 1985.
Berra et al., *J. Neurochem.*, 40:777-82, 1983.
Bogoch, "Demonstration of serum precipitin to brain gangliosides," *Nature*, 183:392-93, 1960.
Bouchon et al., *Biochem. Internatl.*, 10:531-38, 1985.
Bowen-Pope et al., *Proc. Nat'l Acad. Sci. USA*, 81:2396-400, 1984.
Bowness et al., "*Clostridium perfringens* enterotoxin is a superantigen reactive with human T cell receptors V beta 6.9 and V beta 22," *J. Exp. Med.*, 176:893-96, 1992.
Brade et al., "An Artificial Glycoconjugate Containing the Bisphosphorylated Glucosamine Disaccharide Backbone of Lipid A Binds Lipid A Monoclonal Antibodies," *Infection and Immunity*, 61:4514-17, 1993.
Brichard et al., "The tyrosinase gene codes for an antigen recognized by autologous cytolytic T lymphocytes on HLA-A2 melanomas," *J. Exp. Med.*, 178:489, 1993.
Brodin et al., "Mouse monoclonal antibodies with specificity for the melanoma-associated ganglioside disialyllactosyl ceramide (GD3) also react with the structural analogue disialylparagloboside," *Biochim. Biophys. Acta.*, 837:349-53, 1985.
Brooks et al., *Clin. Exp. Immunol.*, 39: 477, 1980.
Brown et al., *J. Biol. Chem.*, 255:4980-83, 1980.
Burchell et al., *J. Immunol.*, 131:508-13, 1983.
Bystryn et al., *Cancer*, 61:1065, 1988.
Cahan et al., "Identification of a human neuroectodermal tumor antigen (OFA-I-2) as ganglioside GD2," *Proc. Natl. Acad. Sci. USA*, 79:7629-33, 1982.
Campbell et al., "Intercellular adhesion molecule-1 expression by bladder cancer cells: functional effects," *J. Urol.*, 151:1385-90, 1994.
Campbell, in *Monoclonal Antibody Technology, Laboratory Techniques in Biochemistry and Molecular Biology, Vol. 13*, Burden and Von Knippenberg (eds.), Amsterdam, Elseview, pp. 75-83, 1984.
Campbell et al., *Int. J. Cancer*, 78:182-88, 1998.
Carr and Morrison, "A two-step mechanism for the interaction of Re lipopolysaccharide with erythrocyte membranes," *Rev. Infect. Dis.* 6:497-508, 1984.
Carubia et al., *Biochem. Biophys. Res. Commun.*, 120:500-04, 1984.
Chang et al., *Crit. Rev. Oncol. Hematol.*, 22:213, 1996.

Chase et al., "Effect of Monophosphoryl Lipid A on Host Resistance to Bacterial Infection," *Infection and Immunity*, 53(3):711-12, 1986.

Chen et al., "Activation of Macrophages From Aging Mice by Detoxified Lipid A," *Journal of Leukocyte Biology*, 49:416-22, 1991.

Chen et al., *Cancer Res.*, 54:1065-70, 1994.

Cheng et al., "Bacillus Calmette-Guerin interacts with the carboxyl-terminal heparin bindings domain of fibronectin: implications for BCG-mediated antitumor activity," *J. Urol.*, 152:1275-80, 1994.

Cheresh and Klier, "Disialoganglioside GD3 distributes preferentially into substrate associated microprocesses on human melanoma cells during their attachment to fibronectin," *J. Cell. Biol.*, 102:1887-97, 1986.

Cheresh et al., "A monoclonal antibody recognizes an O-acetyl sialic acid in a human melanoma-associated ganglioside," *J. Biol. Chem.*, 259:7453-59, 1984.

Cheresh et al., "Disialoganglioside GD3 on human melanoma serves as a relevant target antigen for monoclonal antibody-mediated tumor cytolysis," *Proc. Natl. Acad. Sci. USA*, 82:5155-59, 1985.

Cheresh et al., "Disialogangliosides GD2 and GD3 are involved in the attachment of human melanoma and neuroblastoma cells to extracellular matrix proteins," *J. Cell. Biol.*, 102:688-96, 1986.

Cheresh et al., "Localization of gangliosides GD2 and GD3 in adhesion plaques and on the surface of human melanoma cells," *Proc. Natl. Acad. Sci. USA*, 81:5767-71, 1984.

Cheung et al., "Detection of neuroblastoma cells in bone marrow using GD2 specific monoclonal antibodies," *J. Clin. Oncol.*, 4:363-69, 1986.

Chu and Sharom, "Gangliosides inhibit T-lymphocyte proliferation by preventing the interaction of interleukin-2 with its cell surface receptors," *Immunology*, 79:10-16, 1993.

Cohen, *Science*, 259:1691-92, 1993.

Colcher et al., *Proc. Natl. Acad. Sci. USA*, 78:3199, 1987.

Coligan et al., in *Current Protocols in Immunology*, Vol. 1, Wiley Interscience. Greene (ed.), 1998.

Coombes et al., *Vaccine*, 14:1429-38, 1996.

Coulie et al., "A new gene coding for a differentiation antigen recognized by autologous cytologic T lymphocytes on HLA-A2 melanomas," *J. Exp. Med.*, 180:35, 1994.

Deavin et al., *Mol. Immunol.*, 33:145-55, 1996.

DeBruijn et al., *Eur. J. Immunol.*, 21:2963-70, 1991.

Dippold et al., "Immunohistochemical localization of ganglioside GD3 in human malignant melanoma, epithelial tumors and normal tissues," *Cancer Res.*, 45:3699-705, 1985.

Dippold et al., "Inflammatory response at the tumor site after systemic application of monoclonal anti-GD3-ganglioside antibody to patients with malignant melanoma," *Am. Assoc. Cancer Res.*, 978:247, 1984.

Dippold et al., *Proc. Natl. Acad. Sci. USA*, 77:6115, 1980.

Dresser and Phillips, in *Immunopotentiation*, CIBA Foundation Symposium 18, Elsevier, Amsterdam, p. 3, 1973.

Dwivedi et al., "Plasma lipid-bound sialic acid alterations in neoplastic diseases," *Experientia*, 46:91-94, 1990.

Elder, "Skin Cancer," *Cancer*, 75:245-56, 1995.

Elliott et al., "The D-Galactosamine Loaded Mouse and Its Enhanced Sensitivity to Lipopolysaccharide and Monophosphoryl Lipid A: A Role for Superoxide," *J. Immunol.*, 10:69-74, 1991.

Euhus et al., *Cancer Immunol Immunother.*, 29:247-54, 1989.

Fawwaz et al., Statutory Invention Registration Patent No. H819, application no. 6-6-5,439, 1990.

Fischer, *Handb. Lipid Res.*, 6:123-234, 1990.

Fisher-Hoch et al., *Proc. Nat'l Acad. Sci. USA*, 86:317-21, 1989.

Fitzgerald, "Syphilis vaccine: up-regulation of immunogenicity by cyclophosphamide, Ribi adjuvant, and indomethacin confers significant protection against challenge infection in rabbits," *Vaccine*, 9:265-72, 1991.

Fleischmann, Park and Hassan, "Fibronectin expression on surgical specimens correlated with the response to intravesical bacillus Calmette-Guerin therapy," *J. Urol.*, 149:268-71, 1993.

Flexner et al., *Ann. N.Y. Acad. Sci.*, 569:86-103, 1989.

Flexner et al., *Vaccine*, 8:17-21, 1990.

Foster et al., *Cancer Res.*, 57:3325-30, 1997.

Fraizer et al., *Blood*, 86:4704-06, 1995.

Fredman et al., *Neurol. Res.*, 8:123-26, 1986.

Freimer et al., "Gangliosides elicit a T-cell independent antibody response," *J. Autoimmun.*, 6:281-89, 1993.

Freudenberg et al., "ELISA for antibodies to Lipid A, Lipopolyasscharides and other hydrophobic antigens," *Infection*, 17:322-24, 1989.

Gaiger et al., *Blood*, 96:1334, 2000

Garg and Subbarao, "Immune Responses of Systemic and Mucosal Lymphoid Organs to Pnu-Immune Vaccine as a Function of Age and the Efficacy of Monophosphoryl Lipid A as an Adjuvant," *Infection and Immunity*, 60:2329-36, 1992.

Gaugler et al., "Human gene MAGE-3 codes for an antigen recognized on a human melanoma by autologous cytolytic T lymphocytes," *J. Exp. Med.*, 179:921, 1994.

Gefter et al., *Somatic Cell Genet.*, 3:231-36, 1977.

Gennaro et al., *Am. J. Ind. Med.*, 37:275-82, 2000.

Gillard et al., "Antibodies against ganglioside $GT_3$ in the sera of patients with type I Diabetes mellitus," *J. Immunol.*, 142:3826-32, 1989.

Gillis, *Nature*, 268:154-56, 1977.

Glynn, McCoy and Fefer, *Cancer Res.*, 28:434-39, 1968.

Goding, in *Monoclonal Antibodies: Principles and Practice*, 2d ed., Orlando, Fla., Academic Press, pp. 60-61, 65-66, 71-74, 1986.

Goff et al., *Eur. J. Biochem.*, 130:553-57, 1983.

Grabarek et al., "Endotoxic Lipid A Interaction with Human Platelets," *The Journal of Biological Chemistry*, 265:8117-21, 1990.

Graus et al., "Distribution of the ganglioside GD3 in the human nervous system detected by R24 mouse monoclonal antibody," *Brain Res.*, 324:190-94, 1984.

Guzman et al., *Circulation*, 88:2838-48, 1993a

Guzman et al., *Cir. Res.*, 73:1202-07, 1993b.

Hachida et al., *Transplant Proc.*, 22:1663-70, 1990.

Hachida et al., *Transplantation*, 56:479-82, 1993.

Harada et al., *Mol. Urol.*, 3:357-364, 1999.

Hardings et al., "Effects of pH and polysaccharides on peptide binding to class II major histocompatibility complex molecules," *Proc. Natl. Acad. Sci. USA*, 88:2740-44, 1991.

Harel et al., *Cancer Res.*, 50:6311, 1990.

Harlow and Lane, *Antibodies: A Laboratory Manual*, Cold Spring Harbor Laboratory, 1988.

Helling et al., "Construction of Immunogenic $GD_3$-conjugate vaccines," *Ann. N.Y. Acad. Sci.*, 690:396-97, 1993.

Hellstrom et al., "Strong anti-tumor activities of IgG 3 antibodies to a human melanoma-associated ganglioside," *Proc. Natl. Acad. Sci. USA*, 82:1499-1502, 1985.

Hirabayashi et al., "Syngeneic monoclonal antibody against melanoma antigen with interspecies cross-reactivity recognize $GM_3$, a prominent ganglioside of B16 melanoma," *Biol. Chem.*, 260:13328-33, 1985.

Hirabayashi et al., "Reactivity of mouse monoclonal antibody M2590 against B16 melanoma cells with chemically synthesized GM3 ganglioside," *Biochim. Biophys. Acta*, 875:126-28, 1986.

Hirabayashi et al., *Jpn. J. Cancer Res.*, 78:614-20, 1987.

Hoon et al., "Gangliosides from melanoma immunomodulate response of T-cells to interleukin-2," *Cell Immunol.*, 4:1111-19, 1988.

Horibata and Harris, *Exp. Cell. Res.*, 60:61, 1970.

Horgan, "Total and lipid-bound sialic acid levels in sera from patients with Cancer," *Clin. Chim. Acta.*, 118:327-31, 1982.

Houghten et al., "Mouse monoclonal IgG3 antibody detecting GD3 ganglioside: A phase I trial in patients with malignant melanoma," *Proc. Natl. Acad. Sci. USA*, 82:1242-46, 1985.

Houghton, "Cancer Antigens: Immune Recognition of Self and Altered Self," *J. Exp. Med.*, 180:1-4, 1994.

Hraba et al., "The Influence of Monophosphoryl Lipid A (MPL™) on Erythrocyte Autoantibody Formation," *Immunobiol.*, 189:448-56, 1993.

Hunter et al., *Vaccine*, 9:250: 1991.

Inoue et al., *Blood*, 88:2267-78, 1996.

Irie and Morton, "Regression of cutaneous metastatic melanoma by intralesional injection with human monoclonal antibody to ganglioside GD2," *Proc. Natl. Acad. Sci. USA*, 83:8694-98, 1986.

Irie and Ravindranath, "Gangliosides as targets for monoclonal antibody therapy of cancer," in *Therapeutic monoclonal antibodies*, Borrebaeck and Larrick (eds.), Stockton Press, New York, p. 75-94, 1990.

Irie et al., "Human antibody to OFA-I, a tumor antigen, produced in vitro by Epstein-Barr virus transformed human B-lymphoid cell lines," *Proc. Natl. Acad. Sci. USA*, 79:5666-70, 1982.

Irie et al., "Melanoma gangliosides and human monoclonal antibody," in *Human Tumor Antigens and Specific Tumor Therapy*, Metzgar and Mitchell (eds.), Alan R. Liss, Inc., New York, pp. 115-126, 1989.

Ishioka et al., "MHC interaction and T cell recognition of carbohydrates and glycopeptides," *J. Immunol.*, 148:2446-51, 1992.

Jackson et al., "Induction of ICAM 1 expression on bladder tumours by BCG immunotherapy," *J. Clin. Pathol.*, 47:309-12, 1994.

Johnson and Tomai, "A Study of the Cellular and Molecular Mediators of the Adjuvant Action of a Nontoxic Monophosphoryl Lipid A," *Adv. Exp. Med. Biol.*, 133:567-79, 1988.

Johnson et al., "Characterization of a nontoxic monophosphoryl lipid A," *Rev. Infect. Dis.*, 9:512-16, 1987.

Johnson et al., "Structural Characterization of Monophosphoryl Lipid A Homologs Obtained from *Salmonella minnesota* Re595 Lipopolysaccharide," *J. Biol. Chem.*, 265: 8108-16, 1990.

Johnston and Bystryn, "Effect of Cell Wall Skeleton and Monophosphoryl Lipid A Adjuvant on the Immunogenicity of a Murine B16 Melanoma Vaccine," *Journal of the National Cancer Institute*, 83:1240-45, 1991.

Jones et al., *J Natl Cancer Inst*, 66:249-54, 1981.

Kabat et al., "Sequences of Proteins of Immunological Interest," 5th ed., Public Health Service, National Institutes of Health, Bethesda, Md., pp 647-669, 1991.

Kass-Eisler et al., *Proc. Nat'l Acad. Sci. USA*, 90:11498-502, 1993.

Katopodis et al., "Lipid-associated sialic acid test for the detection of human cancer," *Cancer Res.*, 42:5270-75, 1982.

Kawaguchi et al., "Characteristic mode of action of gangliosides in selective modulation of CD4 on human T lymphocytes," *Biochem. Biophys. Res. Commun.*, 158:1050-55, 1989.

Kawakami et al., "Cloning of the gene coding for a shared human melanoma antigen recognized by autologous T cells infiltrating into tumor," *Proc. Natl. Acad. Sci. USA*, 91:3515, 1994.

Kawakami, Eliyahu, Sakaguchi, Robbins, Rivoltini, Yannelli, Appella and Rosenberg, "Identification of the immunodominant peptides of the Mart-1 human melanoma antigen recognized by the majority of HLA-A2 restricted tumor infiltrating lymphocytes," *J. Exp. Med.*, 180:347-52, 1994.

Kensil et al., *J. Am. Vet. Med. Assoc.*, 199:1423, 1991.

Kloppel et al., "Glycolipid-bound sialic acid in serum: Increased levels in mice and humans bearing mammary carcinomas," *Proc. Natl. Acad. Sci. USA*, 74:3011-13, 1977.

Kohler and Milstein, *Nature*, 256:495-97, 1975.

Kohler and Milstein, *Eur. J. Immunol.*, 6:511-19, 1976.

Kolls et al., *Proc. Nat'l Acad. Sci. USA*, 91:215-19, 1994.

Koscielak et al., "Glycolipid antigen and its antibody," *Immunochemistry*, 5:441-55, 1968.

Kovach et al., "Lipid $IV_A$ Inhibits Synthesis and Release of Tumor Necrosis Factor Induced by Lipopolysaccharide in Human Whole Blood Ex Vivo," *J. Exp. Med.*, 172:77-84, 1990.

Kwok and Higuchi, *Nature*, 339:237-38, 1989.

Kyogashima et al., *Jpn. J. Cancer Res.*, 78:1229-32, 1987.

Ladisch et al., "Shedding of GD2 ganglioside by human neuroblastoma," *Int. J. Cancer*, 39:73-76, 1987.

Lamm et al., "A randomized trial of intravesical doxorubicin and immunotherapy with bacille Calmette-Guerin for transitional-cell carcinoma of the bladder," *N. Engl. J. Med.*, 325:1205, 1991.

Lengle et al., "Inhibition of the lectin-induced mitogenic response of thymocytes by glycolipids," *Cancer Res.*, 39:817-922, 1979.

Liepkalns et al., *J. Neurochem.* 36:1959-65, 1981.

Livingston et al., "The Serologic Response to Meth A Sarcoma Vaccines After Cyclophosphamide Treatment is Additionally Increased by Various Adjuvants," *The Journal of Immunology*, 135(2):1505-09, 1985.

Livingston et al., "Approaches to augmenting immunogenicity of the ganglioside $GM_2$ in mice: purified $GM_2$ is superior to whole cells," *J. Immunol.*, 138:1524-29, 1987a.

Livingston et al., "Vaccines containing purified $GM_2$ gangliosides elicit $GM_2$ antibodies in melanoma patients," *Proc. Natl. Acad. Sci. USA*, 84:2911-15, 1987b.

Ljunggren et al., *Nature*, 346:476-80, 1990.

Lozzio and Lozzio, *Blood*, 45:321-34, 1975.

Madonna and Vogel, "Induction of Early-Phase Endotoxin Tolerance in Athymic (Nude) Mice, B-Cell-Deficient (xid) Mice, and Splenectomized Mice," *Infection and Immunity*, 53:707-10, 1986.

Mahvi et al., *Immunology and cell Biology*, 75:456-60, 1997.

Maratea et al., *Gene*, 40:39-46, 1985.

Masihi et al., "Effects of Nontoxic Lipid A and Endotoxin on Resistance of Mice to *Toxoplasma gondii*," *Journal of Biological Response Modifiers*, 7:535-39, 1988

Melling et al., *J. Immunol.*, 117:1267-74, 1976.

Menssen et al., *J. Cancer Res. Clin. Oncol.*, 126:226-32, 2000.

Merrifield, *J. Am. Chem. Soc.*, 85:2149-46, 1963.

Miller and Esselman, "Modulation of immune response by antigen reactive lymphocytes after cultivation with gangliosides," *J. Immunol.*, 115:839-43, 1975.

Minden, "Shared Antigens Between Animal and Human Tumors and Microorganisms," in *BCG in Cancer Immunotherapy*, Lamoureux, Turcotte and Portelance (eds.); pp. 73-81, 1976.

Miotti et al., *Cancer Res.*, 65:826, 1985.

Mitchell et al., "Active specific Immunotherapy of melanoma with allogeneic cell lysates: Rationale, results and possible mechanisms of action," *Ann. N.Y. Acad. Sci.*, 690:153-66, 1993.

Mitchell et al., "Active specific immunotherapy of melanoma: Phase I trial of allogeneic lysates and a novel adjuvant," *Cancer Res.*, 48:5883-93, 1988.

Mitchell et al., "Active-Specific Immunotherapy for Melanoma," *Journal of Clinical Oncology*, 8:856-59, 1990.

Miyake et al., *Cancer Res.*, 48:6154-60, 1988.

Mooney et al., "Bacterial superantigen signaling via HLA class II on human B lymphocytes," *Mol. Immunol.*, 31:675-81, 1994.

Morrison et al., "Specific ganglioside binding to receptor sites on T lymphocytes that couple to ganglioside-induced decrease of CD4 expression," *Life Sci.*, 45:1219-24, 1989.

Morton and Ravindranath, in *Cancer Medicine*, 3rd ed., Holland et al. (eds.), Lea and Febiger, Philadelphia, p. 967, 1993.

Morton et al., "Polyvalent Melanoma Vaccine Improves Survival of Patients with Metastatic Melanoma," John Wayne Cancer Institute at Saint John's Hospital and Health Center, Santa Monica, Calif., reprinted from *Specific Immunotherapy of Cancer with Vaccines, Volume* 690 of the *Annals of the New York Academy of Sciences*, 1993.

Morton et al., *Ann. Surg.*, 216:463, 1992.

Morton et al., in *Biological Function of Gangliosides, Progress in Brain Research*, Vol. 101, pp 251-275, 1994.

Mosmann and Coffman, *Ann. Rev. Immunol.*, 7:145-73, 1989.

Munjal et al., "Combined measurement and significance of lipid-bound sialic acid and carcinoembryonic antigen in detection of human cancer," *Diagn. Immunol.*, 2:36-43, 1984.

Murphy et al., *Proc. Natl. Acad. Sci. USA*, 83:8258-62, 1986.

Myers et al., "Monophosphoryl Lipid A Behaves as a T-Cell-Independent Type 1 Carrier for Hapten-Specific Antibody Responses in Mice," *Infection and Immunity*, 63:168-74, 1995.

Naiki et al., "Properties of antisera to ganglioside $GM_1$ and Asialo $GM_1$", *J. Immunol.*, 113:84-93, 1974.

Nair et al., *Nature Biotechnol.*, 16:364-69, 1998.

Natoli et al., "A murine monoclonal antibody detecting the ganglioside GM2: Characterization of cell surface reactivity," *Cancer Res.*, 46:4116-20, 1986.

Nonomura et al., *Hinyokika Kiyo*, 45:593-97, 1999.

Nudelman et al., "Characterization of a human melanoma-associated ganglioside antigen defined by a monoclonal antibody 4.2," *J. Biol. Chem.*, 257:12752-56, 1982.

Odean et al., "Involvement of Gamma Interferon in Antibody Enhancement by Adjuvants," *Infection and Immunity*, 58:427-32, 1990.

Oji et al., *Jpn. J. Cancer Res.*, 90:194-204, 1999.

Old et al., *Ann. N.Y. Acad. Sci.*, 101:80-106, 1962.

Pan et al., *Leukemia*, 14:1634, 2000.

Parker et al., *J. Immunol.*, 152:163, 1994.

Pascal et al., "Immunochemical studies on normal and Tay-Sachs' brain gangliosides," *Proc. Soc. Exp. Biol. Med.*, 121:739-43, 1966.

Patek, Collins and Cohn, "Transformed cell lines susceptible or resistant to in vivo surveillance against tumorigenesis," *Nature*, 276:510-11, 1978.

Patmasiriwat et al., *Leukemia*, 13:891-900, 1999.

Paul, *Fundamental Immunology*, 3rd ed., Raven Press, pp. 24347, 1993.

Portoukalian et al., "Humoral immune response in disease-free advanced melanoma patients after vaccination with melanoma-associated gangliosides," *Int. J. Cancer*, 49:893-99, 1991.

Portoukalian, "Alteration of gangliosides in plasma and red cells of human bearing melanoma tumors," *Biochem. Biophys. Res. Commun.*, 85:916-20, 1978.

Portoukalian, "Immunoregulatory activity of gangliosides shed by melanoma tumors," in *Gangliosides and Cancer*, Oettgen (ed.), New York, VCH Publishers, pp. 207-16, 1989.

Powell and Newman (eds.), "Vaccine Design (the subunit and adjuvant approach)," Plenum Press, NY, 1995.

Prokazova et al., "Sialylated lactosylceramides. Possible inducers of non-specific immunosuppression and atherosclerotic lesions," *Eur. J. Biochem.*, 171:1-10, 1988.

Pukel et al., "GD3, a prominent ganglioside of human melanoma: Detection and characterization of mouse monoclonal antibody," *J. Exp. Med.*, 155:1133-47, 1982.

Qureshi et al., "Purification and structural determination of nontoxic lipid A obtained from the Lipopolysaccharide of *Salmonella typhimurium*," *J. Biol. Chem.*, 257:11808-15, 1985.

Rabinovich et al., "Vaccine Technologies: View to the Future," *Science*, 265:1401-02, 1994.

Raines and Ross, *J. Biol. Chem.*, 257:5154-60, 1982.

Rapport and Graf, "Immunochemical Reactions of Lipids," *Prog. Allergy*, 13:273-331, 1969.

Ravindranath and Irie, in *Malignant Melanoma: Biology, Diagnosis, and Therapy*, Nathanson (ed.), Kluwer Acad., Boston, p. 17, 1988.

Ravindranath and Morton, "Role of gangliosides in active immunotherapy with melanoma vaccine," *Int. Rev. Immunol.*, 7:303, 1991.

Ravindranath et al., "Human melanoma antigen O-acetylated Ganglioside $GD_3$ is recognized by *Cancer antennarius* lectin," *J. Biol. Chem.*, 263:2079-86, 1988.

Ravindranath et al., "An epitope common to gangliosides O-acetyl GD3 and GD3 recognized by antibodies in melanoma patients after active specific immunotherapy," *Cancer Res.*, 49:3891-97, 1989.

Ravindranath et al., "Ganglioside $GM_3$:$GD_3$ Ratio as an Index for the Management of Melanoma," *Cancer*, 67:3029-35, 1991.

Ravindranath et al., "Efficacy of tumor cell vaccine after incorporating monophosphoryl lipid A (MPL) in tumor cell membranes containing tumor-associated ganglioside," *Experientia*, 50:648-653, 1994a.

Ravindranath et al., "Attachment of Monophosphoryl Lipid A (MPL) to Cells and Liposomes Augments Antibody Response to membrane-bound Gangliosides," *Journal of Autoimmunity*, 7:803-16, 1994b.

Ravindranath et al., "Factors affecting the fine specificity and sensitivity of serum antiganglioside antibodies in ELISA," *J. Immunol. Methods*, 169:257-72, 1994c.

Real et al., "Class I (unique) tumor antigens of human melanoma Identification of a 90,000 dalton cell surface glycoprotein by autologous antibody," *J. Exp. Med.*, 160:1219, 1984.

Reeves et al., *Cancer Res.*, 56:5672-77, 1996.

Reisfeld et al., *Melanoma Antigens and Antibodies*, p. 317, 1982.

Ribi, "Beneficial modification of the endotoxin molecule," *J. Biol. Resp. Mod.*, 3:1-9, 1984.

Ribi et al., "Lipid A and immunotherapy," *Rev. Infect. Dis.*, 6:567-72, 1984.

Ribi et al., "Modulation of humoral and cell mediated immune responses by a structurally established nontoxic lipid A," in *Immunobiology and Immunopharmacology of Bacterial Endotoxins*, Szentivanji and Friedman (eds.), Plenum Press, New York, pp. 407-420, 1986.

Rickman et al., *Lancet* 337:998, 1991.

Rolland, *Crit. Rev. Therap. Drug Carrier Systems*, 15:143-98, 1998.

Rosenberg et al., *Ann. Surg.*, 210:474, 1989.

Rosenberg et al., *N. Engl. J. Med.*, 319:1676, 1988.

Rosenfeld et al., *Science*, 252:431-34, 1991.

Rothbard and Taylor, *EMBO J.*, 7:93-100, 1988.

Rott et al., "Protection from experimental allergic encephalomyelitis by application of a bacterial superantigen," *Int. Immunol.*, 4:347-53, 1992.

Sato et al., "Cytoplasmic membrane-associated protein (CAP) isolated from *Streptococcus* pyrogenes: as a new bacterial superantigen," *Microbiol. Immunol.*, 38:139-47, 1994.

Sato et al., *Science*, 273:352, 1996.

Satoh et al., *Pathol. Int.*, 50:458-71, 2000.

Schuster et al., "Production of antibodies against phosphocholine, phosphatidylcholine, sphingomyelin, and lipid A by injection of liposomes containing lipid A," *J. Immunol.*, 122:900-05, 1979.

Schwab et al., "Superantigen can reactivate bacterial cell wall-induced arthritis," *J. Immunol.*, 150:4151-59, 1993.

Shafer and Spitznagel, "Sensitivity of *Salmonella typhimurium* to polymorphonuclear granulocyte extracts: Role of lipid A," *Rev. Infect. Dis.*, 6:577-81, 1984.

Shepard et al., *J. Clin. Immunol.*, 11:117-27, 1991.

Sherwin et al., "The production of antisera to gangliosides from human nervous tissue," *Canad. J. Biochem.*, 42:1640-48, 1964.

Shimizu et al., *Int. J. Gynecol. Pathol.*, 19:158-63, 2000.

Shy et al., "Antibodies to $GM_1$ and $GD_{1b}$ in patients with motor neuron disease with plasma cell dyscrasia," *Ann. Neurol.*, 25:511-18, 1989.

Siddiqui et al., *Cancer Res.*, 44:5262-65, 1984.

Sidell et al., *Cancer Immunol Immunother*, 7:151-55, 1979.

Sigma Cell Culture, Volume 9, Number 2, 1993.

Skeiky et al., *Infection and Immun.*, 67:3998-4007, 1999.

Slavin and Strober, *Nature*, 272:624-26, 1977.

Spinsanti et al., *Leuk Lymphoma*, 38:611-19, 2000.

Stiess and Krüger, "Mammalian Cell Culture Media—Overview and Applications," *The Source* (Sigma Cell Culture Technical and Product News), 9:1-8, 1993.

Stoute et al. *New Engl. J. Med.*, 336:86-91, 1997.

Svennerholm et al., "Tumor gangliosides as targets for active specific immunotherapy of melanoma in man," in *Biological Function of Gangliosides, Progress in Brain Research*, Vol. 101, 1994.

Tai et al., "Ganglioside GM2 as a human tumor antigen (OFA-I-1)," *Proc. Natl. Acad. Sci.*, 80:5392-96, 1983.

Takada et al., "Molecular and Structural Requirements of a Lipoteichoic Acid from *Enterococcus hirae* ATCC 9790 for Cytokine-Inducing, Antitumor, and Antigenic Activities," *Infection and Immunity*, 63:57-65, 1995.

Takahashi et al., *J. Immunol.*, 140:3244, 1988.

Tamaki et al., *Leukemia*, 13:393-99, 1999.

Tamauchi et al., *Immunology*, 50:605, 1983.

Tanamoto, "Dissociation of Endotoxic Activities in a Chemically Synthesized Lipid A Precursor after Acetylation," *Infection and Immunity*, 63:690-92, 1995.

Tanamoto, "Free Hydroxyl Groups Are Not Required for Endotoxic Activity of Lipid A," *Infection and Immunity*, 62:1705-09, 1994a.

Tanamoto, *FEBS Lett.*, 351:325-29, 1994b.

Tautu et al., "Improved procedure for determination of serum lipid-associated sialic acid: Application for early diagnosis of colorectal cancer," *J. Natl. Cancer Inst.*, 80:1333-37, 1988.

Thor et al., *Cancer Res.*, 46:3118, 1986.

Thurin et al., "Proton NMR and fast-atom bombardment mass spectrometry analysis of the melanoma-associated ganglioside 9-O-acetyl GD3," *J. Biol. Chem.*, 260:14556-563, 1985.

Timmerman and Levy, *Ann. Rev. Med.*, 50:507-29, 1999.

Tomai and Johnson, "T Cell and Interferon-γ Involvement in the Adjuvant Action of a Detoxified Endotoxin," *Journal of Biological Response Modifiers*, 8:625-43, 1989.

Tomai et al., "The Adjuvant Properties of a Nontoxic Monophosphoryl Lipid A in Hyporesponsive and Aging Mice," *Journal of Biological Response Modifiers*, 6:99-107, 1987.

Tsuchida et al., *J. Dermatol.*, 11:129-38, 1984.

Tsuchida et al., "Gangliosides of Human Melanoma: Altered Expression in Vivo and in Vitro," *Cancer Research*, 47:1278-81, 1987.

Tsuchida et al., "Gangliosides as tumor markers of human melanoma: bio-chemical and immunologic assays," in *New Horizons of Tumor Immunotherapy*, Torisu and Yoshida (eds.), pp. 315-325, 1989.

Tuting et al., *J. Immunol.*, 160:1139-47, 1998.

Ulmer et al., *Science*, 259:1745-49, 1993.

Vadhan-Raj et al., *J. Clin. Oncol.*, 6:1636, 1988.

van der Bruggen et al., "A gene encoding an antigen recognized by cytolytic T lymphocytes on a human melanoma," *Science*, 264:716, 1991.

Verma et al., "Adjuvant Effects of Liposomes Containing Lipid A: Enhancement of Liposomal Antigen Presentation and Recruitment of Macrophages," *Infection and Immunity*, 60:2438-44, 1992.

Vijayasaradhi et al., "The melanoma antigen gp75 is the human homologue of the mouse b (brown) locus gene product," *J. Exp. Med.*, 171:1375, 1990.

Von Bultzingslowen, *Pneumologie*, 53:266-75, 1999.

Vosika et al., *Cancer Immunol. Immunother.*, 18:107, 1984.

Watson, Ralph, Sarkar and Cohn, "Leukemia viruses associated with mouse myeloma cells," *Proc. Natl. Acad. Sci. USA*, 66:344, 1970.

Westrick et al., *Biochim. Biophys. Acta*, 750:141-48, 1983a

Westrick et al., *Cancer Res.*, 43:5890-94, 1983b

Whisler and Yates, "Regulation of lymphocyte responses by human gangliosides. I. Characteristics of inhibitory effects and the induction of impaired activation," *J. Immunol.*, 125:2106-12, 1980.

Wide et al., in *Radioimmunoassay Methods*, Kirkham and Hunter (eds.), E. and S. Livingstone, Edinburgh, 1970.

Wilschut, "Preparation and properties of phospholipid vesicles," in *Methodologie des liposomes appliquee a la pharmacologie et a la biologies cellulaire*, Leserman and Barbet (eds.), INSERM, Paris, pp. 1-10, 1982.

Yamaguchi et al., "Cell-surface antigens of melanoma recognized by human monoclonal antibodies," *Proc. Natl. Acad. Sci. USA*, 84:2416-20, 1987.

Yamamoto et al., "In vitro Augmentation of Natural Killer Cell Activity and Production of Interferon-α/β and -γ with Deoxyribonucleic Acid Fraction from *Mycobacterium bovis* BCG," *Jpn. J. Cancer Res.,* 79:866-73, 1988.

Yeh et al., "A cell-surface antigen which is present in the ganglioside fraction and shared by human melanomas," *Int. J. Cancer,* 29:269-75, 1982.

Yin et al., "Effect of Various Adjuvants on the Antibody Response of Mice to Pneumococcal Polysaccharides," *J. Biol. Resp. Modifiers,* 8:190-205, 1989.

Yokoyama et al., "Immunochemical studies with gangliosides," *J. Immunol.,* 90:372-80, 1963.

Zapata et al., *Protein Eng.,* 8:1057-62, 1995.

Zitvogel et al., *Nat. Med.,* 4:594-600, 1998.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All publications, patents, and patent applications cited herein are hereby incorporated by reference in their entirety for all purposes. Accordingly, the exclusive rights sought to be patented are as described in the claims below:

What is claimed is:

1. A method for treating chronic lymphocytic leukemia (CLL) in a mammalian subject wherein a B-cell from said subject overexpresses SEQ ID NO:4 comprising administering to said subject an effective amount of an isolated monoclonal antibody that specifically binds to a polypeptide comprising the sequence set forth in SEQ ID NO: 4 wherein said monoclonal antibody has a binding constant for SEQ ID NO:4 that exceeds $10^3$ L/mol.

2. The method of claim 1, wherein said antibody is a humanized antibody.

3. The method of claim 1, wherein said antibody is a chimeric antibody.

4. The method of claim 1, wherein said antibody is a Fab fragment.

5. The method of claim 1, wherein said antibody is a Fv fragment.

6. The method of claim 1, wherein said antibody is a scFv.

7. The method of claim 1, wherein said antibody further comprises a therapeutic moiety.

8. The method of claim 7, wherein the therapeutic moiety is a radionuclide.

9. The method of claim 8, wherein the radionuclide is a member selected from the group consisting of; $^{90}$Y, $^{123}$I, $^{125}$I, $^{131}$I, $^{186}$Re, $^{211}$At, and $^{212}$Bi.

10. The method of claim 8, wherein the mammalian subject is a human.

11. The method of claim 1, wherein administration is intravenous.

12. The method of claim 1, wherein the monoclonal antibody is not a bi-specific antibody.

* * * * *

SEQUENCE LISTING

```
<160> NUMBER OF SEQ ID NOS: 124

<210> SEQ ID NO 1
<211> LENGTH: 2672
<212> TYPE: DNA
<213> ORGANISM: Homo sapiens

<400> SEQUENCE: 1
cttccagaga gcaatatggc tggttcccca acatgcctca ccctcatcta tatcctttgg      60
cagctcacag ggtcagcagc ctctggaccc gtgaaagagc tggtcggttc cgttggtggg     120
gccgtgactt tccccctgaa gtccaaagta aagcaagttg actctattgt ctggaccttc     180
aacacaaccc ctcttgtcac catacagcca gaaggggggca ctatcatagt gacccaaaat     240
cgtaataggg agagagtaga cttcccagat ggaggctact ccctgaagct cagcaaactg     300
aagaagaatg actcagggat ctactatgtg gggatataca gctcatcact ccagcagccc     360
tccacccagg agtacgtgct gcatgtctac gagcacctgt caaagcctaa agtcaccatg     420
ggtctgcaga gcaataagaa tggcacctgt gtgaccaatc tgacatgctg catggaacat     480
ggggaagagg atgtgattta tacctggaag gccctggggc aagcagccaa tgagtcccat     540
aatgggtcca tcctccccat ctcctggaga tggggagaaa gtgatatgac cttcatctgc     600
gttgccagga accctgtcag cagaaacttc tcaagcccca tccttgccag gaagctctgt     660
gaaggtgctg ctgatgaccc agattcctcc atggtcctcc tgtgtctcct gttggtgccc     720
ctcctgctca gtctctttgt actggggcta tttctttggt ttctgaagag agagagacaa     780
gaagagtaca ttgaagagaa gaagagagtg gacatttgtc gggaaactcc taacatatgc     840
ccccattctg gagagaacac agagtacgac acaatccctc acactaatag aacaatccta     900
aaggaagatc cagcaaatac ggtttactcc actgtggaaa taccgaaaaa gatggaaaat    960
ccccactcac tgctcacgat gccagacaca ccaaggctat ttgcctatga gaatgttatc    1020
tagacagcag tgcactcccc taagtctctg ctcaaaaaaa aaacaattct cggcccaaag    1080
aaaacaatca gaagaattca ctgatttgac tagaaacatc aaggaagaat gaagaacgtt    1140 gactttttc caggataaat tatctctgat gcttctttag atttaagagt tcataattcc     1200
atccactgct gagaaatctc ctcaaaccca gaaggtttaa tcacttcatc ccaaaaatgg    1260
gattgtgaat gtcagcaaac cataaaaaaa gtgcttagaa gtattcctat agaaatgtaa    1320
atgcaaggtc acacatatta atgacagcct gttgtattaa tgatggctcc aggtcagtgt    1380
ctggagtttc attccatccc agggcttgga tgtaaggatt ataccaagag tcttgctacc    1440
```

-continued

```
aggagggcaa gaagaccaaa acagacagac aagtccagca gaagcagatg cacctgacaa    1500
aaatggatgt attaattggc tctataaact atgtgcccag cactatgctg agcttacact    1560
aattggtcag acgtgctgtc tgccctcatg aaattggctc caaatgaatg aactactttc    1620
atgagcagtt gtagcaggcc tgaccacaga ttcccagagg gccaggtgtg gatccacagg    1680
acttgaaggt caaagttcac aaagatgaag aatcagggta gctgaccatg tttggcagat    1740
actataatgg agacacagaa gtgtgcatgg cccaaggaca aggacctcca gccaggcttc    1800
atttatgcac ttgtgctgca aagaaaagt ctaggtttta aggctgtgcc agaacccatc    1860
ccaataaaga gaccgagtct gaagtcacat tgtaaatcta gtgtaggaga cttggagtca    1920
ggcagtgaga ctggtggggc acggggggca gtgggtactt gtaaacctttt aaagatggtt   1980 aattcattca atagatattt attaagaacc tatgcggccc ggcatggtgg ctcacacctg    2040
taatcccagc actttgggag gccaaggtgg gtgggtcatc tgaggtcagg agttcaagac    2100
cagcctggcc aacatggtga aaccccatct ctactaaaga tacaaaaatt tgctgagcgt    2160
ggtggtgtgc acctgtaatc ccagctactc gagaggccaa ggcatgagaa tcgcttgaac    2220
ctgggaggtg gaggttgcag tgagctgaga tggcaccact gcactccggc ctaggcaacg    2280
agagcaaaac tccaatacaa acaaacaaac aaacacctgt gctaggtcag tctggcacgt    2340
aagatgaaca tccctaccaa cacagagctc accatctctt atacttaagt gaaaaacatg    2400
gggaagggga aaggggaatg gctgcttttg atatgttccc tgcacacatat cttgaatgga    2460 gacctcccta ccaagtgatg aaagtgttga aaaacttaat aacaaatgct tgttgggcaa    2520
gaatgggatt gaggattatc ttctctcaga aaggcattgt gaaggaattg agccagatct    2580
ctctccctac tgcaaaaccc tattgtagta aaaaagtctt ctttactatc ttaataaaac    2640
agatattgtg agattcaaaa aaaaaaaaaa aa                                    2672
```

<210> SEQ ID NO 2
<211> LENGTH: 335
<212> TYPE: PRT
<213> ORGANISM: Homo sapiens

<400> SEQUENCE: 2

```
Met Ala Gly Ser Pro Thr Cys Leu Thr Leu Ile Tyr Ile Leu Trp Gln
  1               5                  10                  15

Leu Thr Gly Ser Ala Ala Ser Gly Pro Val Lys Glu Leu Val Gly Ser
                 20                  25                  30

Val Gly Gly Ala Val Thr Phe Pro Leu Lys Ser Lys Val Lys Gln Val
             35                  40                  45

Asp Ser Ile Val Trp Thr Phe Asn Thr Thr Pro Leu Val Thr Ile Gln
         50                  55                  60

Pro Glu Gly Gly Thr Ile Ile Val Thr Gln Asn Arg Asn Arg Glu Arg
     65                  70                  75                  80

Val Asp Phe Pro Asp Gly Gly Tyr Ser Leu Lys Leu Ser Lys Leu Lys
                 85                  90                  95

Lys Asn Asp Ser Gly Ile Tyr Tyr Val Gly Ile Tyr Ser Ser Ser Leu
                100                 105                 110

Gln Gln Pro Ser Thr Gln Glu Tyr Val Leu His Val Tyr Glu His Leu
            115                 120                 125

Ser Lys Pro Lys Val Thr Met Gly Leu Gln Ser Asn Lys Asn Gly Thr
        130                 135                 140

Cys Val Thr Asn Leu Thr Cys Cys Met Glu His Gly Glu Glu Asp Val
145                 150                 155                 160
```

```
Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val Leu Leu Cys Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
        275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 3
<211> LENGTH: 834
<212> TYPE: DNA
<213> ORGANISM: Homo sapiens

<400> SEQUENCE: 3
ttgtaagata ttacttgtcc ttccaggctg ttctttctgt agctcccttg ttttcttttt      60
gtgatcatgt tgcagatggc tgggcagtgc tcccaaaatg aatattttga cagtttgttg     120
catgcttgca taccttgtca acttcgatgt tcttctaata ctcctcctct aacatgtcag     180
cgttattgta atgcaagtgt gaccaattca gtgaaggaa cgaatgcgat tctctggacc      240
tgtttgggac tgagcttaat aatttctttg gcagttttcg tgctaatgtt tttgctaagg     300
aagataagct ctgaaccatt aaaggacgag tttaaaaaca caggatcagg tctcctgggc     360
atggctaaca ttgacctgga aaagagcagg actggtgatg aaattattct tccgagaggc     420
ctcgagtaca cggtggaaga atgcacctgt gaagactgca tcaagagcaa accgaaggtc     480
gactctgacc attgctttcc actcccagct atggaggaag cgcaaccat tcttgtcacc      540 acgaaaacga atgactattg caagagcctg ccagctgctt tgagtgctac ggagatagag     600
aaatcaattt ctgctaggta attaaccatt tcgactcgag cagtgccact ttaaaaatct     660
tttgtcagaa tagatgatgt gtcagatctc tttaggatga ctgtattttt cagttgccga     720
tacagctttt tgtcctctaa ctgtggaaac tctttatgtt agatatattt ctctaggtta     780
ctgttgggag cttaatggta gaaacttcct tggtttctat gattaaagtc tttt           834

<210> SEQ ID NO 4
<211> LENGTH: 184
<212> TYPE: PRT
<213> ORGANISM: Homo sapiens

<400> SEQUENCE: 4

Met Leu Gln Met Ala Gly Gln Cys Ser Gln Asn Glu Tyr Phe Asp Ser
```

```
              1               5              10              15
Leu Leu His Ala Cys Ile Pro Cys Gln Leu Arg Cys Ser Ser Asn Thr
              20                  25                  30
Pro Pro Leu Thr Cys Gln Arg Tyr Cys Asn Ala Ser Val Thr Asn Ser
              35                  40                  45
Val Lys Gly Thr Asn Ala Ile Leu Trp Thr Cys Leu Gly Leu Ser Leu
      50                  55                  60
Ile Ile Ser Leu Ala Val Phe Val Leu Met Phe Leu Leu Arg Lys Ile
65                  70                  75                  80
Ser Ser Glu Pro Leu Lys Asp Glu Phe Lys Asn Thr Gly Ser Gly Leu
              85                  90                  95
Leu Gly Met Ala Asn Ile Asp Leu Glu Lys Ser Arg Thr Gly Asp Glu
              100                 105                 110
Ile Ile Leu Pro Arg Gly Leu Glu Tyr Thr Val Glu Glu Cys Thr Cys
              115                 120                 125
Glu Asp Cys Ile Lys Ser Lys Pro Lys Val Asp Ser Asp His Cys Phe
          130                 135                 140
Pro Leu Pro Ala Met Glu Glu Gly Ala Thr Ile Leu Val Thr Thr Lys
145                 150                 155                 160
Thr Asn Asp Tyr Cys Lys Ser Leu Pro Ala Ala Leu Ser Ala Thr Glu
              165                 170                 175
Ile Glu Lys Ser Ile Ser Ala Arg
              180

<210> SEQ ID NO 5
<211> LENGTH: 1339
<212> TYPE: DNA
<213> ORGANISM: Homo sapiens

<400> SEQUENCE: 5
ttgcactcta gaagggacaa tggacttctg gctttggcca ctttacttcc tgccagtatc      60
gggggccctg aggatcctcc cagaagtaaa ggtagagggg gagctgggcg atcagttac     120
catcaagtgc ccacttcctg aaatgcatgt gaggatatat ctgtgccggg agatggctgg     180
atctggaaca tgtggtaccg tggtatccac caccaacttc atcaaggcag aatacaaggg     240
ccgagttact ctgaagcaat acccacgcaa gaatctgttc ctagtggagg taacacagct     300
gacagaaagt gacagcggag tctatgcctg cggagcgggc atgaacacag accggggaaa     360
gacccagaaa gtcaccctga atgtccacag tgaatacgag ccatcatggg aagagcagcc     420
aatgcctgag actccaaaat ggtttcatct gccctatttg ttccagatgc ctgcatatgc     480
cagttcttcc aaaattcgta accagagtta cacaccagct caaggggca aggtccctcc     540
agttcaccac tcctccccca ccacccaaat caccaccgc cctcgagtgt ccagagcatc     600
ttcagtagca ggtgacaagc ccgaaccttc ctgccatcc actacagcct caaaaatctc     660
agctctggag gggctgctca gccccagac gcccagctac aaccaccaca ccaggctgca     720
caggcagaga gcactggact atggctcaca gtctgggagg aaggccaag gatttcacat     780
cctgatcccg accatcctgg cctttttcct gctggcactt ctggggctgg tggtgaaaag     840
ggccgttgaa aggaggaaag ccctctccag gcgggcccgc cgactggccg tgaggatgcg     900
cgccctggag agctcccaga ggccccgcgg gtcgccgcga ccgcgctccc aaaacaacat     960
ctacagcgcc tgcccgcggc gcgctcgtgg agcggacgct gcaggcacag ggaagcccc    1020
cgttcccggc cccggagcgc cgttgccccc cgccccgctg caggtgtctg aatctccctg    1080
```

```
gctccatgcc ccatctctga agaccagctg tgaatacgtg agcctctacc accagcctgc    1140
cgccatgatg gaggacagtg attcagatga ctacatcaat gttcctgcct gacaactccc    1200
cagctatccc ccaaccccag gctcggactg tggtgccaag gagtctcatc tatctgctga    1260
tgtccaatac ctgcttcatg tgttctcaga gccctcatca ttcccatgcc ccatctcgat    1320
cccatcccca tctatctgt                                                 1339

<210> SEQ ID NO 6
<211> LENGTH: 390
<212> TYPE: PRT
<213> ORGANISM: Homo sapiens

<400> SEQUENCE: 6

Met Asp Phe Trp Leu Trp Pro Leu Tyr Phe Leu Pro Val Ser Gly Ala
1               5                   10                  15

Leu Arg Ile Leu Pro Glu Val Lys Val Glu Gly Glu Leu Gly Gly Ser
            20                  25                  30

Val Thr Ile Lys Cys Pro Leu Pro Glu Met His Val Arg Ile Tyr Leu
        35                  40                  45

Cys Arg Glu Met Ala Gly Ser Gly Thr Cys Gly Thr Val Val Ser Thr
    50                  55                  60

Thr Asn Phe Ile Lys Ala Glu Tyr Lys Gly Arg Val Thr Leu Lys Gln
65                  70                  75                  80

Tyr Pro Arg Lys Asn Leu Phe Leu Val Glu Val Thr Gln Leu Thr Glu
                85                  90                  95

Ser Asp Ser Gly Val Tyr Ala Cys Gly Ala Gly Met Asn Thr Asp Arg
            100                 105                 110

Gly Lys Thr Gln Lys Val Thr Leu Asn Val His Ser Glu Tyr Glu Pro
        115                 120                 125

Ser Trp Glu Glu Gln Pro Met Pro Glu Thr Pro Lys Trp Phe His Leu
    130                 135                 140

Pro Tyr Leu Phe Gln Met Pro Ala Tyr Ala Ser Ser Lys Phe Val
145                 150                 155                 160

Thr Arg Val Thr Thr Pro Ala Gln Arg Gly Lys Val Pro Pro Val His
                165                 170                 175

His Ser Ser Pro Thr Thr Gln Ile Thr His Arg Pro Arg Val Ser Arg
            180                 185                 190

Ala Ser Ser Val Ala Gly Asp Lys Pro Arg Thr Phe Leu Pro Ser Thr
        195                 200                 205

Thr Ala Ser Lys Ile Ser Ala Leu Glu Gly Leu Leu Lys Pro Gln Thr
    210                 215                 220

Pro Ser Tyr Asn His His Thr Arg Leu His Arg Gln Arg Ala Leu Asp
225                 230                 235                 240

Tyr Gly Ser Gln Ser Gly Arg Glu Gly Gln Gly Phe His Ile Leu Ile
                245                 250                 255

Pro Thr Ile Leu Gly Leu Phe Leu Leu Ala Leu Leu Gly Leu Val Val
            260                 265                 270

Lys Arg Ala Val Glu Arg Arg Lys Ala Leu Ser Arg Arg Ala Arg
        275                 280                 285

Leu Ala Val Arg Met Arg Ala Leu Glu Ser Ser Gln Arg Pro Arg Gly
    290                 295                 300

Ser Pro Arg Pro Arg Ser Gln Asn Asn Ile Tyr Ser Ala Cys Pro Arg
305                 310                 315                 320

Arg Ala Arg Gly Ala Asp Ala Ala Gly Thr Gly Glu Ala Pro Val Pro
```

```
                    325                 330                 335
Gly Pro Gly Ala Pro Leu Pro Pro Ala Pro Leu Gln Val Ser Glu Ser
                340                 345                 350

Pro Trp Leu His Ala Pro Ser Leu Lys Thr Ser Cys Glu Tyr Val Ser
            355                 360                 365

Leu Tyr His Gln Pro Ala Ala Met Met Glu Asp Ser Asp Ser Asp Asp
        370                 375                 380

Tyr Ile Asn Val Pro Ala
385                 390

<210> SEQ ID NO 7
<211> LENGTH: 2007
<212> TYPE: DNA
<213> ORGANISM: Artificial Sequence
<220> FEATURE:
<223> OTHER INFORMATION: Description of Artificial Sequence:Ly1452 open
      reading frame His tag fusion

<400> SEQUENCE: 7
atgcagcatc accaccatca ccacgtgtca caatctacag tcaggcagga ttctcctgtg      60
gagccctggg aagggatcag cgatcactct ggcattattg atggttcgcc cagactcctg     120
aacactgacc atcctccttg ccaattagac atcaggctca tgaggcacaa agctgtctgg     180
attaaccccc aggatgtgca gcaacagccg caggacttgc aatctcaggt gccagcagca     240
gggaacagtg ggacccattt tgtgacagat gctgcctctc cctcaggccc ttcaccttcg     300
tgcctcgggg actccctggc agagacaacg ttgtctgagg ataccacaga ctccgttggc     360
agcgcttctc cccatggctc gagtgaaaag agtagcagct tctctctgtc ctcaacagag     420
gtacacatgg tccgcccagg atactctcat cgggtgtctc tgcccacaag ccctgggatt     480
ttggccacct ccccatatcc tgagactgac agtgcttttt tgagccttc ccatctgaca      540 tctgctgctg atgaaggtgc tgttcaagtc agtagaagaa ccatttcttc gaattccttc     600
tcaccagagg tatttgtgct gcctgttgat gtagaaaagg aaaatgccca cttttatgtt     660
gcagatatga ttatatcagc aatggagaaa atgaagtgta acattctgag tcaacagcag     720
acagagagct ggagtaaaga agtcagtggg ttacttggga gtgatcagcc tgactctgaa     780
atgacttttg ataccaacat aaagcaagag tctgggtctt ctacttcttc atacagtggc     840
tatgaaggtt gtgctgtgtt acaggtcagc ccagtgactg aaacacgtac ttaccatgat     900
gtgaaagaga tttgcaaatg cgatgttgat gaatttgtta ttttagagct tggagatttt     960
aatgatatca cagaaacctg tagctgttcc tgcagctcct ctaagagtgt cacttatgag    1020
ccagacttca attctgcaga actattagcc aaagagctgt accgcgtgtt ccagaagtgc    1080
tggatactgt cagtagttaa ttctcagctg gcaggttccc tgagtgcagc tggctcgata    1140
gtcgtaaatg aagagtgtgt ccgaaaagac tttgaatcca gtatgaatgt agtacaggaa    1200
attaaattta gtctaggat cagagggact gaagactggg ctcctcctag atttcaaatc     1260
atatttaata ttcatccacc actcaagagg gaccttgtgg tggcagccca gaattttttc    1320
tgtgccggct gtggaactcc agtagagcct aagtttgtga gcggctccg gtactgcgaa     1380 tacctaggga agtatttctg tgactgctgc cactcatatg cagagtcgtg catccctgcc    1440
cgaatcctga tgatgtggga cttcaagaag tactacgtca gcaatttctc caaacagctg    1500
ctcgacagca tatggcacca gcccattttc aatttgctga gcatcggcca aagcctgtat    1560
gcgaaagcca aggagctgga cagagtgaag gaaattcagg agcagctctt ccatatcaag    1620
```

-continued

```
aagctgttga agacctgtag gtttgctaac agtgcattaa aggagttcga gcaggtgccg    1680
ggacacttga ctgatgagct ccacctgttc tcccttgagg acctggtcag gatcaagaaa    1740
gggctgctgg caccttact caaggacatt ctgaaagctt cccttgcaca tgtggctggc     1800
tgtgagctgt gtcaaggaaa gggctttatt tgtgaattt gccagaatac gactgtcatc    1860
ttcccatttc agacagcaac atgtagaaga tgttcagcgt gcagggcttg ctttcacaaa    1920
cagtgcttcc agtcctccga gtgccccggg tgtgcgagga tcacagcgag gagaaaactt    1980
ctggaaagtg tggcctctgc agcaaca                                        2007
```

<210> SEQ ID NO 8
<211> LENGTH: 669
<212> TYPE: PRT
<213> ORGANISM: Artificial Sequence
<220> FEATURE:
<223> OTHER INFORMATION: Description of Artificial Sequence:Ly1452 open reading frame His tag fusion

<400> SEQUENCE: 8

```
Met Gln His His His His His Val Ser Gln Ser Thr Val Arg Gln
 1               5                   10                  15

Asp Ser Pro Val Glu Pro Trp Glu Gly Ile Ser Asp His Ser Gly Ile
            20                  25                  30

Ile Asp Gly Ser Pro Arg Leu Leu Asn Thr Asp His Pro Cys Gln
        35                  40                  45

Leu Asp Ile Arg Leu Met Arg His Lys Ala Val Trp Ile Asn Pro Gln
 50                  55                  60

Asp Val Gln Gln Gln Pro Gln Asp Leu Gln Ser Gln Val Pro Ala Ala
 65                  70                  75                  80

Gly Asn Ser Gly Thr His Phe Val Thr Asp Ala Ala Ser Pro Ser Gly
                85                  90                  95

Pro Ser Pro Ser Cys Leu Gly Asp Ser Leu Ala Glu Thr Thr Leu Ser
            100                 105                 110

Glu Asp Thr Thr Asp Ser Val Gly Ser Ala Ser Pro His Gly Ser Ser
        115                 120                 125

Glu Lys Ser Ser Ser Phe Ser Leu Ser Ser Thr Glu Val His Met Val
    130                 135                 140

Arg Pro Gly Tyr Ser His Arg Val Ser Leu Pro Thr Ser Pro Gly Ile
145                 150                 155                 160

Leu Ala Thr Ser Pro Tyr Pro Glu Thr Asp Ser Ala Phe Phe Glu Pro
                165                 170                 175

Ser His Leu Thr Ser Ala Ala Asp Glu Gly Ala Val Gln Val Ser Arg
            180                 185                 190

Arg Thr Ile Ser Ser Asn Ser Phe Ser Pro Glu Val Phe Val Leu Pro
        195                 200                 205

Val Asp Val Glu Lys Glu Asn Ala His Phe Tyr Val Ala Asp Met Ile
    210                 215                 220

Ile Ser Ala Met Glu Lys Met Lys Cys Asn Ile Leu Ser Gln Gln Gln
225                 230                 235                 240

Thr Glu Ser Trp Ser Lys Glu Val Ser Gly Leu Leu Gly Ser Asp Gln
                245                 250                 255

Pro Asp Ser Glu Met Thr Phe Asp Thr Asn Ile Lys Gln Glu Ser Gly
            260                 265                 270

Ser Ser Thr Ser Ser Tyr Ser Gly Tyr Glu Gly Cys Ala Val Leu Gln
        275                 280                 285
```

```
Val Ser Pro Val Thr Glu Thr Arg Thr Tyr His Asp Val Lys Glu Ile
    290                 295                 300
Cys Lys Cys Asp Val Asp Glu Phe Val Ile Leu Glu Leu Gly Asp Phe
305                 310                 315                 320
Asn Asp Ile Thr Glu Thr Cys Ser Cys Ser Cys Ser Ser Ser Lys Ser
                325                 330                 335
Val Thr Tyr Glu Pro Asp Phe Asn Ser Ala Glu Leu Leu Ala Lys Glu
            340                 345                 350
Leu Tyr Arg Val Phe Gln Lys Cys Trp Ile Leu Ser Val Val Asn Ser
        355                 360                 365
Gln Leu Ala Gly Ser Leu Ser Ala Ala Gly Ser Ile Val Val Asn Glu
    370                 375                 380
Glu Cys Val Arg Lys Asp Phe Glu Ser Ser Met Asn Val Val Gln Glu
385                 390                 395                 400
Ile Lys Phe Lys Ser Arg Ile Arg Gly Thr Glu Asp Trp Ala Pro Pro
                405                 410                 415
Arg Phe Gln Ile Ile Phe Asn Ile His Pro Pro Leu Lys Arg Asp Leu
            420                 425                 430
Val Val Ala Ala Gln Asn Phe Phe Cys Ala Gly Cys Gly Thr Pro Val
        435                 440                 445
Glu Pro Lys Phe Val Lys Arg Leu Arg Tyr Cys Glu Tyr Leu Gly Lys
    450                 455                 460
Tyr Phe Cys Asp Cys His Ser Tyr Ala Glu Ser Cys Ile Pro Ala
465                 470                 475                 480
Arg Ile Leu Met Met Trp Asp Phe Lys Lys Tyr Tyr Val Ser Asn Phe
                485                 490                 495
Ser Lys Gln Leu Leu Asp Ser Ile Trp His Gln Pro Ile Phe Asn Leu
            500                 505                 510
Leu Ser Ile Gly Gln Ser Leu Tyr Ala Lys Ala Lys Glu Leu Asp Arg
        515                 520                 525
Val Lys Glu Ile Gln Glu Gln Leu Phe His Ile Lys Lys Leu Leu Lys
    530                 535                 540
Thr Cys Arg Phe Ala Asn Ser Ala Leu Lys Glu Phe Glu Gln Val Pro
545                 550                 555                 560
Gly His Leu Thr Asp Glu Leu His Leu Phe Ser Leu Glu Asp Leu Val
                565                 570                 575
Arg Ile Lys Lys Gly Leu Leu Ala Pro Leu Leu Lys Asp Ile Leu Lys
            580                 585                 590
Ala Ser Leu Ala His Val Ala Gly Cys Glu Leu Cys Gln Gly Lys Gly
        595                 600                 605
Phe Ile Cys Glu Phe Cys Gln Asn Thr Thr Val Ile Phe Pro Phe Gln
    610                 615                 620
Thr Ala Thr Cys Arg Arg Cys Ser Ala Cys Arg Ala Cys Phe His Lys
625                 630                 635                 640
Gln Cys Phe Gln Ser Ser Glu Cys Pro Arg Cys Ala Arg Ile Thr Ala
                645                 650                 655
Arg Arg Lys Leu Leu Glu Ser Val Ala Ser Ala Ala Thr
            660                 665

<210> SEQ ID NO 9
<211> LENGTH: 3604
<212> TYPE: DNA
<213> ORGANISM: Homo sapiens

<400> SEQUENCE: 9
```

-continued

```
gggagcctat agggttcaat aacttgcagt gtggttgggg cttatggatg ctggatgaag      60
ataagtgagg gaggtttaca gggacagcat catgtcaggc cttgagggca agaatagctc     120
tccagacccc cagctggcca tgtggtgagt tcagggccca aatcaagtag taccagcaat     180
cagggaactc ctatctgttt tgaatggatt cacaccagcc acaagcctgg aaagatggtg     240
tcacaatcta cagtcaggca ggattctcct gtggagccct gggaagggat cagcgatcac     300
tctggcatta ttgatggttc gcccagactc ctgaacactg accatcctcc ttgccaatta     360
gacatcaggc tcatgaggca caaagctgtc tggattaacc cccaggatgt gcagcaacag     420
ccgcaggact tgcaatctca ggtgccagca gcagggaaca gtgggaccca ttttgtgaca     480
gatgctgcct ctccctcagg cccttcacct tcgtgcctcg ggactccct ggcagagaca      540
acgttgtctg aggataccac agactccgtt ggcagcgctt ctccccatgg ctcgagtgaa     600
aagagtagca gcttctctct gtcctcaaca gaggtacaca tggtccgccc aggatactct     660
catcgggtgt ctctgcccac aagccctggg attttggcca cctccccata tcctgagact     720
gacagtgctt tttttgagcc ttcccatctg acatctgctg ctgatgaagg tgctgttcaa     780
gtcagtagaa gaaccatttc ttcgaattcc ttctcaccag aggtatttgt gctgcctgtt     840
gatgtagaaa aggaaaatgc ccactttat gttgcagata tgattatatc agcaatggag      900
aaaatgaagt gtaacattct gagtcaacag cagacagaga gctggagtaa agaagtcagt     960
gggttacttg ggagtgatca gcctgactct gaaatgactt ttgataccaa cataaagcaa    1020
gagtctgggt cttctacttc ttcatacagt ggctatgaag gttgtgctgt gttacaggtc    1080
agcccagtga ctgaaacacg tacttaccat gatgtgaaag agatttgcaa atgcgatgtt    1140
gatgaatttg ttatttaga gcttggagat tttaatgata tcacagaaac ctgtagctgt     1200
tcctgcagct cctctaagag tgtcacttat gagccagact tcaattctgc agaactatta    1260
gccaaagagc tgtaccgcgt gttccagaag tgctggatac tgtcagtagt taattctcag    1320
ctggcaggtt ccctgagtgc agctggctcg atagtcgtaa atgaagagtg tgtccgaaaa    1380
gactttgaat ccagtatgaa tgtagtacag gaaattaaat ttaagtctag gatcagaggg    1440
actgaagact gggctcctcc tagatttcaa atcatattta atattcatcc accactcaag    1500
agggaccttg tggtggcagc ccagaatttt ttctgtgccg gctgtggaac tccagtagag    1560
cctaagtttg tgaagcggct ccggtactgc gaatacctag ggaagtattt ctgtgactgc    1620
tgccactcat atgcagagtc gtgcatccct gcccgaatcc tgatgatgtg ggacttcaag    1680
aagtactacg tcagcaattt ctccaaacag ctgctcgaca gcatatggca ccagcccatt    1740
ttcaatttgc tgagcatcgg ccaaagcctg tatgcgaaag ccaaggagct ggacagagtg    1800
aaggaaattc aggagcagct cttccatatc aagaagctgt tgaagacctg taggtttgct    1860
aacagtgcat taaggagtt cgagcaggtg ccgggacact tgactgatga gctccacctg    1920
ttctcccttg aggacctggt caggatcaag aaagggctgc tggcacccttt actcaaggac    1980
attctgaaag cttcccttgc acatgtggct ggctgtgagc tgtgtcaagg aaagggcttt    2040
atttgtgaat tttgccagaa tacgactgtc atcttcccat tcagacagc aacatgtaga     2100
agatgttcag cgtgcagggc ttgctttcac aaacagtgct tccagtcctc cgagtgcccc    2160
cggtgtgcga ggatcacagc gaggagaaaa cttctggaaa gtgtggcctc tgcagcaaca    2220
tgatgccct gagtactgtg aaaaagactg ttcaacatgc cttatgataa caccgatttg      2280
tgtctattat tggtgacatt gttttagata ttgggtattg tatattaagg aaaaagatgg    2340
```

-continued

```
tctatattct ctttattgca tatacttaat gtttcaaaag aatgcagatt ctgtgtttaa    2400
gcacagggct gatagttgtg gttttgttta caaatgttct gttttggctg ctattggttt    2460
tttaaagagg ttttttatac ttttgtattt gaatagttat gtttcactga tgctgagcca    2520
gtttgtatgt gtgtgcatat atgtgaactg taactgacaa gatgaattac tcagtttctc    2580
tttctctaaa gcttgtttga tgaaactggt tggtcctttc agtgaacaaa aatatgaccc    2640
caaatctgtt tgctctggct tttatttctt caggaagcag acttccactt aaatgccatt    2700
ttgtgattgt gtcaatcata cacattttat ttacttcaga gtttgaatag agagtacaca    2760
tttcttctgc agatttattt catgatgagt ttgagttgct tagcagggcg tgtgggtccc    2820
gttgaagtgc agtttgaagc aactgcttct agatggcact ctttcaggtg gcacaaattg    2880
aacctgtatt tgtcatctct gttccacaca ctgcaatgtc aagggatgca gaagtgagta    2940
gaattccatc cctgcccttg aggatcttgc tttaacagat gtaaaactga acataaggta    3000
tttgcagatt taaacgaact gggggaaata atgaacagtg tgattctagt aataacatta    3060
aaatcataga cattgactaa taaggttaaa tgaatcacaa aacctttatg aatttctttt    3120
ttctaatagt tcttatatgt tttcctgaaa catgtgagcc tattctttt tcttctactt     3180
tctatatact ttctcccact tgagaaaggg gccttgaggc tgggtccctt catggtatac    3240
ctttagactg aacggtttgc aacctagggc ttgggcatta cattccctgg gattcacatg    3300
ccctaactaa acctaccttg attttctcag acagcacagg caggcaataa agcgtcacag    3360
attgtcccct aaccccatcc agccatgtgt atgagtgtgt tttattcaat gggatagtac    3420
tgagcacatg aaagaaatga atgacttctg tcaatctctt ttcattcagt cttctcattc    3480
tgtcaattgt tttctcatcc gcagtgcctc tgccagaact gtgctcacat ccattattta    3540
agccagatct tttctaagta ttatagaagt gtagaggcac atagaataaa taaaaccaga    3600
cttc                                                                 3604
```

<210> SEQ ID NO 10
<211> LENGTH: 662
<212> TYPE: PRT
<213> ORGANISM: Homo sapiens

<400> SEQUENCE: 10

```
Met Val Ser Gln Ser Thr Val Arg Gln Asp Ser Pro Val Glu Pro Trp
  1               5                  10                  15

Glu Gly Ile Ser Asp His Ser Gly Ile Ile Asp Gly Ser Pro Arg Leu
             20                  25                  30

Leu Asn Thr Asp His Pro Pro Cys Gln Leu Asp Ile Arg Leu Met Arg
         35                  40                  45

His Lys Ala Val Trp Ile Asn Pro Gln Asp Val Gln Gln Pro Gln
     50                  55                  60

Asp Leu Gln Ser Gln Val Pro Ala Ala Gly Asn Ser Gly Thr His Phe
 65                  70                  75                  80

Val Thr Asp Ala Ala Ser Pro Ser Gly Pro Ser Pro Ser Cys Leu Gly
                 85                  90                  95

Asp Ser Leu Ala Glu Thr Thr Leu Ser Glu Asp Thr Thr Asp Ser Val
            100                 105                 110

Gly Ser Ala Ser Pro His Gly Ser Ser Glu Lys Ser Ser Ser Phe Ser
        115                 120                 125

Leu Ser Ser Thr Glu Val His Met Val Arg Pro Gly Tyr Ser His Arg
    130                 135                 140
```

```
Val Ser Leu Pro Thr Ser Pro Gly Ile Leu Ala Thr Ser Pro Tyr Pro
145                 150                 155                 160

Glu Thr Asp Ser Ala Phe Phe Glu Pro Ser His Leu Thr Ser Ala Ala
            165                 170                 175

Asp Glu Gly Ala Val Gln Val Ser Arg Arg Thr Ile Ser Ser Asn Ser
        180                 185                 190

Phe Ser Pro Glu Val Phe Val Leu Pro Val Asp Val Glu Lys Glu Asn
    195                 200                 205

Ala His Phe Tyr Val Ala Asp Met Ile Ile Ser Ala Met Glu Lys Met
210                 215                 220

Lys Cys Asn Ile Leu Ser Gln Gln Gln Thr Glu Ser Trp Ser Lys Glu
225                 230                 235                 240

Val Ser Gly Leu Leu Gly Ser Asp Gln Pro Asp Ser Glu Met Thr Phe
            245                 250                 255

Asp Thr Asn Ile Lys Gln Glu Ser Gly Ser Thr Ser Ser Tyr Ser
            260                 265                 270

Gly Tyr Glu Gly Cys Ala Val Leu Gln Val Ser Pro Val Thr Glu Thr
        275                 280                 285

Arg Thr Tyr His Asp Val Lys Glu Ile Cys Lys Cys Asp Val Asp Glu
    290                 295                 300

Phe Val Ile Leu Glu Leu Gly Asp Phe Asn Asp Ile Thr Glu Thr Cys
305                 310                 315                 320

Ser Cys Ser Cys Ser Ser Lys Ser Val Thr Tyr Glu Pro Asp Phe
            325                 330                 335

Asn Ser Ala Glu Leu Leu Ala Lys Glu Leu Tyr Arg Val Phe Gln Lys
        340                 345                 350

Cys Trp Ile Leu Ser Val Val Asn Ser Gln Leu Ala Gly Ser Leu Ser
            355                 360                 365

Ala Ala Gly Ser Ile Val Val Asn Glu Glu Cys Val Arg Lys Asp Phe
        370                 375                 380

Glu Ser Ser Met Asn Val Val Gln Glu Ile Lys Phe Lys Ser Arg Ile
385                 390                 395                 400

Arg Gly Thr Glu Asp Trp Ala Pro Pro Arg Phe Gln Ile Ile Phe Asn
            405                 410                 415

Ile His Pro Pro Leu Lys Arg Asp Leu Val Val Ala Ala Gln Asn Phe
        420                 425                 430

Phe Cys Ala Gly Cys Gly Thr Pro Val Glu Pro Lys Phe Val Lys Arg
            435                 440                 445

Leu Arg Tyr Cys Glu Tyr Leu Gly Lys Tyr Phe Cys Asp Cys His
    450                 455                 460

Ser Tyr Ala Glu Ser Cys Ile Pro Ala Arg Ile Leu Met Met Trp Asp
465                 470                 475                 480

Phe Lys Lys Tyr Tyr Val Ser Asn Phe Ser Lys Gln Leu Leu Asp Ser
            485                 490                 495

Ile Trp His Gln Pro Ile Phe Asn Leu Leu Ser Ile Gly Gln Ser Leu
        500                 505                 510

Tyr Ala Lys Ala Lys Glu Leu Asp Arg Val Lys Glu Ile Gln Glu Gln
            515                 520                 525

Leu Phe His Ile Lys Lys Leu Lys Thr Cys Arg Phe Ala Asn Ser
        530                 535                 540

Ala Leu Lys Glu Phe Glu Gln Val Pro Gly His Leu Thr Asp Glu Leu
545                 550                 555                 560

His Leu Phe Ser Leu Glu Asp Leu Val Arg Ile Lys Lys Gly Leu Leu
```

```
                565                 570                 575
Ala Pro Leu Leu Lys Asp Ile Leu Lys Ala Ser Leu Ala His Val Ala
                580                 585                 590

Gly Cys Glu Leu Cys Gln Gly Lys Gly Phe Ile Cys Glu Phe Cys Gln
            595                 600                 605

Asn Thr Thr Val Ile Phe Pro Phe Gln Thr Ala Thr Cys Arg Arg Cys
        610                 615                 620

Ser Ala Cys Arg Ala Cys Phe His Lys Gln Cys Phe Gln Ser Ser Glu
625                 630                 635                 640

Cys Pro Arg Cys Ala Arg Ile Thr Ala Arg Arg Lys Leu Leu Glu Ser
                645                 650                 655

Val Ala Ser Ala Ala Thr
                660

<210> SEQ ID NO 11
<211> LENGTH: 2494
<212> TYPE: DNA
<213> ORGANISM: Homo sapiens

<400> SEQUENCE: 11
ctttctgctg ttaccgggag cgcggtggcc acggaacgct gcccggagcc gcgcgaggga      60
ggacccgacg cgcggcgttt acccagcgca gcgttccacc gctcgggttt ggctggaata     120
gctctccaga cccccagctg gccatgtggt gagttcaggg cccaaatcaa gtagtaccag     180
caatcaggga actcctatct gttttgaatg gattcacacc agccacaagc ctggaaagat     240
ggtgtcacaa tctacagtca ggcaggattc tcctgtggag ccctgggaag ggatcagcga     300
tcactctggc attattgatg gttcgcccag actcctgaac actgaccatc ctccttgcca     360
attagacatc aggctcatga ggcacaaagc tgtctggatt aaccccccagg atgtgcagca     420 acagccgcag gacttgcaat ctcaggtgcc agcagcaggg aacagtggga cccatttttgt     480 gacagatgct gcctctccct caggcccttc accttcgtgc ctcggggact ccctggcaga     540
dacaacgttg tctgaggata ccacagactc cgttggcagc gcttctcccc atggctcgag     600
tgaaaagagt agcagcttct ctctgtcctc aacagaggta cacatggtcc gcccaggata     660
ctctcatcgg gtgtctctgc ccacaagccc tgggattttg gccacctccc catatcctga     720
gactgacagt gctttttttg agccttccca tctgacatct gctgctgatg aaggtgctgt     780
tcaagtcagt agaagaacca tttcttcgaa ttccttctca ccagaggtat tgtgctgcc      840 tgttgatgta gaaaaggaaa atgcccactt ttatgttgca gatatgatta tatcagcaat     900
ggagaaaatg aagtgtaaca ttctgagtca acagcagaca gagagctgga gtaaagaagt     960
cagtgggtta cttgggagtg atcagcctga ctctgaaatg acttttgata ccaacataaa    1020
gcaagagtct gggtcttcta cttcttcata cagtggctat gaaggttgtg ctgtgttaca    1080
ggtcagccca gtgactgaaa cacgtactta ccatgatgtg aaagagattt gcaaatgcga    1140
tgttgatgaa tttgttattt tagagcttgg agatttaat gatatcacag aaacctgtag     1200
ctgttcctgc agctcctcta agagtgtcac ttatgagcca gacttcaatt ctgcagaact    1260
attagccaaa gagctgtacc gcgtgttcca gaagtgctgg atactgtcag tagttaattc    1320
tcagctggca ggttccctga gtgcagctgg ctcgatagtc gtaaatgaag agtgtgtccg    1380
aaaagacttt gaatccagta tgaatgtagt acaggaaatt aaatttaagt ctaggatcag    1440
agggactgaa gactgggctc ctcctagatt tcaaatcata tttaatattc atccaccact    1500
caagagggac cttgtggtgg cagcccagaa ttttttctgt gccggctgtg gaactccagt    1560
```

```
agagcctaag tttgtgaagc ggctccggta ctgcgaatac ctagggaagt atttctgtga   1620
ctgctgccac tcatatgcag agtcgtgcat ccctgcccga atcctgatga tgtgggactt   1680
caagaagtac tacgtcagca atttctccaa acagctgctc gacagcatat ggcaccagcc   1740
cattttcaat ttgctgagca tcggccaaag cctgtatgcg aaagccaagg agctggacag   1800
agtgaaggaa attcaggagc agctcttcca tatcaagaag ctgttgaaga cctgtaggtt   1860
tgctaacagc tgtgtcaagg aaagggcttt atttgtgaat tttgccagaa tacgactgtc   1920
atcttcccat ttcagacagc aacatgtaga agatgttcag cgtgcagggc ttgctttcac   1980
aaacagtgct tccagtcctc cgagtgcccc cggtgtgcga ggatcacagc gaggagaaaa   2040
cttctggaaa gtgtggcctc tgcagcaaca tgatgcccct gagtactgtg aaaaagactg   2100
ttcaacatgc cttatgataa caccgatttg tgtctattat tggtgacatt gttttagata   2160
ttgggtattg tatattaagg aaaaagatgg tctatattct ctttattgca tatacttaat   2220
gtttcaaaag aatgcagatt ctgtgtttaa gcacagggct gatagttgtg gttttgttta   2280
caaatgttct gttttggctg ctattggttt tttaaagagg ttttttatac ttttgtattt   2340
gaatagttat gtttcactga tgctgagcca gtttgtatgt gtgtgcatat atgtgaactg   2400
taactgacaa gatgaattac tcagtttctc tttctctaaa gcttgtttga tgaaactggt   2460
tggtcctttc agtgaacaaa aatatgaccc caaa                               2494

<210> SEQ ID NO 12
<211> LENGTH: 635
<212> TYPE: PRT
<213> ORGANISM: Homo sapiens

<400> SEQUENCE: 12

Met Val Ser Gln Ser Thr Val Arg Gln Asp Ser Pro Val Glu Pro Trp
  1               5                  10                  15

Glu Gly Ile Ser Asp His Ser Gly Ile Ile Asp Gly Ser Pro Arg Leu
             20                  25                  30

Leu Asn Thr Asp His Pro Pro Cys Gln Leu Asp Ile Arg Leu Met Arg
         35                  40                  45

His Lys Ala Val Trp Ile Asn Pro Gln Asp Val Gln Gln Pro Gln
     50                  55                  60

Asp Leu Gln Ser Gln Val Pro Ala Ala Gly Asn Ser Gly Thr His Phe
 65                  70                  75                  80

Val Thr Asp Ala Ala Ser Pro Ser Gly Pro Ser Pro Ser Cys Leu Gly
                 85                  90                  95

Asp Ser Leu Ala Glu Thr Thr Leu Ser Glu Asp Thr Thr Asp Ser Val
            100                 105                 110

Gly Ser Ala Ser Pro His Gly Ser Ser Glu Lys Ser Ser Phe Ser
        115                 120                 125

Leu Ser Ser Thr Glu Val His Met Val Arg Pro Gly Tyr Ser His Arg
    130                 135                 140

Val Ser Leu Pro Thr Ser Pro Gly Ile Leu Ala Thr Ser Pro Tyr Pro
145                 150                 155                 160

Glu Thr Asp Ser Ala Phe Phe Glu Pro Ser His Leu Thr Ser Ala Ala
                165                 170                 175

Asp Glu Gly Ala Val Gln Val Ser Arg Arg Thr Ile Ser Ser Asn Ser
            180                 185                 190

Phe Ser Pro Glu Val Phe Val Leu Pro Val Asp Val Glu Lys Glu Asn
        195                 200                 205
```

-continued

```
Ala His Phe Tyr Val Ala Asp Met Ile Ile Ser Ala Met Glu Lys Met
    210                 215                 220

Lys Cys Asn Ile Leu Ser Gln Gln Gln Thr Glu Ser Trp Ser Lys Glu
225                 230                 235                 240

Val Ser Gly Leu Leu Gly Ser Asp Gln Pro Asp Ser Glu Met Thr Phe
                245                 250                 255

Asp Thr Asn Ile Lys Gln Glu Ser Gly Ser Ser Thr Ser Ser Tyr Ser
                260                 265                 270

Gly Tyr Glu Gly Cys Ala Val Leu Gln Val Ser Pro Val Thr Glu Thr
            275                 280                 285

Arg Thr Tyr His Asp Val Lys Glu Ile Cys Lys Cys Asp Val Asp Glu
    290                 295                 300

Phe Val Ile Leu Glu Leu Gly Asp Phe Asn Asp Ile Thr Glu Thr Cys
305                 310                 315                 320

Ser Cys Ser Cys Ser Ser Lys Ser Val Thr Tyr Glu Pro Asp Phe
                325                 330                 335

Asn Ser Ala Glu Leu Leu Ala Lys Glu Leu Tyr Arg Val Phe Gln Lys
                340                 345                 350

Cys Trp Ile Leu Ser Val Val Asn Ser Gln Leu Ala Gly Ser Leu Ser
            355                 360                 365

Ala Ala Gly Ser Ile Val Asn Glu Glu Cys Val Arg Lys Asp Phe
    370                 375                 380

Glu Ser Ser Met Asn Val Val Gln Glu Ile Lys Phe Lys Ser Arg Ile
385                 390                 395                 400

Arg Gly Thr Glu Asp Trp Ala Pro Pro Arg Phe Gln Ile Ile Phe Asn
                405                 410                 415

Ile His Pro Pro Leu Lys Arg Asp Leu Val Val Ala Ala Gln Asn Phe
                420                 425                 430

Phe Cys Ala Gly Cys Gly Thr Pro Val Glu Pro Lys Phe Val Lys Arg
        435                 440                 445

Leu Arg Tyr Cys Glu Tyr Leu Gly Lys Tyr Phe Cys Asp Cys Cys His
    450                 455                 460

Ser Tyr Ala Glu Ser Cys Ile Pro Ala Arg Ile Leu Met Met Trp Asp
465                 470                 475                 480

Phe Lys Lys Tyr Tyr Val Ser Asn Phe Ser Lys Gln Leu Leu Asp Ser
                485                 490                 495

Ile Trp His Gln Pro Ile Phe Asn Leu Leu Ser Ile Gly Gln Ser Leu
                500                 505                 510

Tyr Ala Lys Ala Lys Glu Leu Asp Arg Val Lys Glu Ile Gln Glu Gln
        515                 520                 525

Leu Phe His Ile Lys Lys Leu Leu Lys Thr Cys Arg Phe Ala Asn Ser
    530                 535                 540

Cys Val Lys Glu Arg Ala Leu Phe Val Asn Phe Ala Arg Ile Arg Leu
545                 550                 555                 560

Ser Ser Ser His Phe Arg Gln Gln His Val Glu Asp Val Gln Arg Ala
                565                 570                 575

Gly Leu Ala Phe Thr Asn Ser Ala Ser Ser Pro Pro Ser Ala Pro Gly
                580                 585                 590

Val Arg Gly Ser Gln Arg Gly Glu Asn Phe Trp Lys Val Trp Pro Leu
            595                 600                 605

Gln Gln His Asp Ala Pro Glu Tyr Cys Glu Lys Asp Cys Ser Thr Cys
    610                 615                 620
```

Leu Met Ile Thr Pro Ile Cys Val Tyr Tyr Trp
625                 630                 635

<210> SEQ ID NO 13
<211> LENGTH: 148
<212> TYPE: DNA
<213> ORGANISM: Homo sapiens

<400> SEQUENCE: 13
ctggttcacg tgtggagcta gttaatacgt cctgccaaga tgggtaccag ttgactggac    60
atgcttatca gatgtgtcaa gatgctgaaa atggaatttg gttcaaaaag attccacttt   120
gtaaagttat ccactgcacc ctccacca                                      148

<210> SEQ ID NO 14
<211> LENGTH: 4094
<212> TYPE: DNA
<213> ORGANISM: Homo sapiens

<400> SEQUENCE: 14
ccagagctgc cggacgctcg cgggtctcgg aacgcatccc gccgcggggg cttcggccgt    60
ggcatgggcg ccgcgggcct gctcggggtt ttcttggctc tcgtcgcacc ggggggtcctc  120 gggatttctt gtggctctcc tccgcctatc ctaaatggcc ggattagtta ttattctacc   180
cccattgctg ttggtaccgt gataaggtac agttgttcag gtaccttccg cctcattgga   240
gaaaaaagtc tattatgcat aactaaagac aaagtggatg gaacctggga taaacctgct   300
cctaaatgtg aatatttcaa taatatttct tcttgccctg agcccatagt accaggagga   360
tacaaaatta gaggctctac accctacaga catggtgatt ctgtgacatt tgcctgtaaa   420
accaacttct ccatgaacgg aaacaagtct gtttggtgtc aagcaaataa tatgtggggg   480
ccgacacgac taccaacctg tgtaagtgtt ttccctctcg agtgtccagc acttcctatg   540
atccacaatg gacatcacac aagtgagaat gttggctcca ttgctccagg attgtctgtg   600
acttacagct gtgaatctgg ttacttgctt gttggagaaa agatcattaa ctgtttgtct   660
tcgggaaaat ggagtgctgt ccccccaca tgtgaagagg cacgctgtaa atctctagga   720
cgatttccca tgggaaggt aaaggagcct ccaattctcc gggttggtgt aactgcaaac   780
tttttctgtg atgaagggta tcgactgcaa ggcccacctt ctagtcggtg tgtaattgct   840
ggacagggag ttgcttggac caaaatgcca gtatgtgaag aaattttttg cccatcacct   900 cccctattc tcaatggaag acatataggc aactcactag caaatgtctc atatggaagc   960
atagtcactt acacttgtga cccggaccca gaggaaggga tgaacttcat ccttattgga  1020
gagagcactc tccgttgtac agttgatagt cagaagactg ggacctggag tggccctgcc  1080
ccacgctgtg aactttctac ttctgcggtt cagtgtccac atcccagat cctaagaggc  1140 cgaatggtat ctgggcagaa agatcgatat acctataacg acactgtgat atttgcttgc  1200
atgtttggct tcaccttgaa gggcagcaag caaatccgat gcaatgccca aggcacatgg  1260
gagccatctg caccagtctg tgaaaaggaa tgccaggccc ctcctaacat cctcaatggg  1320
caaaaggaag atagacacat ggtccgcttt gaccctggaa catctataaa atatagctgt  1380
aaccctggct atgtgctggt gggagaagaa tccatacagt gtacctctga gggggtgtgg  1440 acacccctg taccccaatg caaagtggca gcgtgtgaag ctacaggaag gcaactcttg  1500
acaaaacccc agcaccaatt tgttagacca gatgtcaact cttcttgtgg tgaagggtac  1560
aagttaagtg ggagtgttta tcaggagtgt caaggcacaa ttccttggtt tatggagatt  1620

-continued

```
cgtctttgta aagaaatcac ctgcccacca ccccctgtta tctacaatgg ggcacacacc      1680
gggagttcct tagaagattt tccatatgga accacggtca cttacacatg taaccctggg      1740
ccagaaagag gagtggaatt cagcctcatt ggagagagca ccatccgttg tacaagcaat      1800
gatcaagaaa gaggcacctg gagtggccct gctcccctat gtaaactttc cctccttgct      1860
gtccagtgct cacatgtcca tattgcaaat ggatacaaga tatctggcaa ggaagcccca      1920
tatttctaca atgacactgt gacattcaag tgttatagtg gatttacttt gaagggcagt      1980
agtcagattc gttgcaaacg tgataacacc tgggatcctg aaataccagt ttgtgaaaaa      2040
ggctgccagc cacctcctgg gctccaccat ggtcgtcata caggtggaaa tacggtcttc      2100
tttgtctctg ggatgactgt agactacact tgtgaccctg ctatttgct tgtgggaaac       2160 aaatccattc actgtatgcc ttcaggaaat tggagtcctt ctgccccacg tgtgaagaa       2220 acatgccagc atgtgagaca gagtcttcaa gaacttccag ctggttcacg tgtggagcta      2280
gttaatacgt cctgccaaga tgggtaccag ttgactggac atgcttatca gatgtgtcaa      2340
gatgctgaaa atggaatttg gttcaaaaag attccacttt gtaaagttat tcactgtcac      2400
cctccaccag tgattgtcaa tgggaagcac acaggcatga tggcagaaaa ctttctatat      2460
ggaaatgaag tctcttatga atgtgaccaa ggattctatc ccctgggaga gaaaaattgc      2520
agtgcagaag tgattctaaa ggcatggatc ttggagcgag ccttcccaca gtgcttacga      2580
tctctgtgcc ctaatccaga agtcaaacat gggtacaagc tcaataaaac acattctgca      2640
tattcccaca atgacatagt gtatgttgac tgcaatcctg gcttcatcat gaatggtagt      2700
cgcgtgatta ggtgtcatac tgataacaca tgggtgccag gtgtgccaac ttgtatcaaa      2760
aaagccttca tagggtgtcc acctccgcct aagacccctg acgggaacca tactggtgga      2820
aacatagctc gattttctcc tggaatgtca atcctgtaca gctgtgacca aggctacctg      2880
gtggtgggag agccactcct tctttgcaca catgagggaa cctggagcca acctgccct       2940 cattgtaaag aggtaaactg tagctcacca gcagatatgg atggaatcca gaaagggctg      3000
gaaccaagga aaatgtatca gtatggagct gttgtaactc tggagtgtga agatgggtat      3060
atgctggaag gcagtcccca gagccagtgc caatcggatc accaatggaa ccctcccctg      3120
gcggtttgca gatcccgttc acttgctcct gtcctttgtg gtattgctgc aggtttgata      3180
cttcttacct tcttgattgt cattaccttc tacgtgatat caaaacacag agaacgcaat      3240
tattatacag atacaagcca gaaagaagct tttcatttag aagcacgaga agtatattct      3300
gttgatccat acaacccagc cagctgatca gaagacaaaa ctggtgtgtg cctcattgct      3360
tggaattcag cggaatattg attagaaaga aactgctcta tatcagcaa gtctctttat       3420 atggcctcaa gatcaatgaa atgatgtcat aagcgatcac ttcctatatg cacttattct      3480
caagaagaac atctttatgg taaagatggg agcccagttt cactgccata tactcttcaa      3540 ggacttctg aagcctcact tatgagatgc ctgaagccag gccatggcta taaacattac        3600
atggctctaa aagttttgcc cttttttaagg aggcactaaa aagagctgtc ctggtatcta     3660
gacccatctt cttttgaaa tcacatactc atgttactat ctgcttttgg ttataatgtg      3720 ttttaatta tctaaagtat gaagcatttt ctggggttat gatggcctta cttttattag       3780
gaagtatggt tttattttga tagtagcttc cttcctcggt ggtgttaatc atttcgtttt      3840
taccctttac cttcggattt gagtttctct cacattactg tatatacttt gccttccata      3900
atcactcagt gattgcaatt tgcacaagtt tttttaaatt atgggaatca agatttaatc      3960
ctagagattt ggtgtacaat tcaggctttg gatgtttctt tagcagtttt gtgataagtt      4020
```

```
ctagttgctt gtaaaatttc acttaataat gtgtacatta gtcattcaat aaattgtaat    4080
tgtaaagaaa acat                                                     4094
```

<210> SEQ ID NO 15
<211> LENGTH: 1033
<212> TYPE: PRT
<213> ORGANISM: Homo sapiens

<400> SEQUENCE: 15

```
Met Gly Ala Ala Gly Leu Leu Gly Val Phe Leu Ala Leu Val Ala Pro
 1               5                  10                  15

Gly Val Leu Gly Ile Ser Cys Gly Ser Pro Pro Ile Leu Asn Gly
             20                  25                  30

Arg Ile Ser Tyr Tyr Ser Thr Pro Ile Ala Val Gly Thr Val Ile Arg
                 35                  40                  45

Tyr Ser Cys Ser Gly Thr Phe Arg Leu Ile Gly Glu Lys Ser Leu Leu
         50                  55                  60

Cys Ile Thr Lys Asp Lys Val Asp Gly Thr Trp Asp Lys Pro Ala Pro
 65                  70                  75                  80

Lys Cys Glu Tyr Phe Asn Lys Tyr Ser Ser Cys Pro Glu Pro Ile Val
                 85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
            180                 185                 190

Lys Ile Ile Asn Cys Leu Ser Ser Gly Lys Trp Ser Ala Val Pro Pro
        195                 200                 205

Thr Cys Glu Glu Ala Arg Cys Lys Ser Leu Gly Arg Phe Pro Asn Gly
    210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
            260                 265                 270

Glu Ile Phe Cys Pro Ser Pro Pro Ile Leu Asn Gly Arg His Ile
        275                 280                 285

Gly Asn Ser Leu Ala Asn Val Ser Tyr Gly Ser Ile Val Thr Tyr Thr
    290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
                325                 330                 335

Gly Pro Ala Pro Arg Cys Glu Leu Ser Thr Ser Ala Val Gln Cys Pro
            340                 345                 350
```

```
His Pro Gln Ile Leu Arg Gly Arg Met Val Ser Gly Lys Asp Arg
        355                 360                 365

Tyr Thr Tyr Asn Asp Thr Val Ile Phe Ala Cys Met Phe Gly Phe Thr
370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
                405                 410                 415

Leu Asn Gly Gln Lys Glu Asp Arg His Met Val Arg Phe Asp Pro Gly
                420                 425                 430

Thr Ser Ile Lys Tyr Ser Cys Asn Pro Gly Tyr Val Leu Val Gly Glu
                435                 440                 445

Glu Ser Ile Gln Cys Thr Ser Glu Gly Val Trp Thr Pro Pro Val Pro
            450                 455                 460

Gln Cys Lys Val Ala Ala Cys Glu Ala Thr Gly Arg Gln Leu Leu Thr
465                 470                 475                 480

Lys Pro Gln His Gln Phe Val Arg Pro Asp Val Asn Ser Ser Cys Gly
                    485                 490                 495

Glu Gly Tyr Lys Leu Ser Gly Ser Val Tyr Gln Glu Cys Gln Gly Thr
                500                 505                 510

Ile Pro Trp Phe Met Glu Ile Arg Leu Cys Lys Glu Ile Thr Cys Pro
            515                 520                 525

Pro Pro Pro Val Ile Tyr Asn Gly Ala His Thr Gly Ser Ser Leu Glu
        530                 535                 540

Asp Phe Pro Tyr Gly Thr Thr Val Thr Tyr Thr Cys Asn Pro Gly Pro
545                 550                 555                 560

Glu Arg Gly Val Glu Phe Ser Leu Ile Gly Glu Ser Thr Ile Arg Cys
                565                 570                 575

Thr Ser Asn Asp Gln Glu Arg Gly Thr Trp Ser Gly Pro Ala Pro Leu
                580                 585                 590

Cys Lys Leu Ser Leu Leu Ala Val Gln Cys Ser His Val His Ile Ala
                595                 600                 605

Asn Gly Tyr Lys Ile Ser Gly Lys Glu Ala Pro Tyr Phe Tyr Asn Asp
                610                 615                 620

Thr Val Thr Phe Lys Cys Tyr Ser Gly Phe Thr Leu Lys Gly Ser Ser
625                 630                 635                 640

Gln Ile Arg Cys Lys Ala Asp Asn Thr Trp Asp Pro Glu Ile Pro Val
                    645                 650                 655

Cys Glu Lys Glu Thr Cys Gln His Val Arg Gln Ser Leu Gln Glu Leu
                660                 665                 670

Pro Ala Gly Ser Arg Val Glu Leu Val Asn Thr Ser Cys Gln Asp Gly
                675                 680                 685

Tyr Gln Leu Thr Gly His Ala Tyr Gln Met Cys Gln Asp Ala Glu Asn
                690                 695                 700

Gly Ile Trp Phe Lys Lys Ile Pro Leu Cys Lys Val Ile His Cys His
705                 710                 715                 720

Pro Pro Pro Val Ile Val Asn Gly Lys His Thr Gly Met Met Ala Glu
                725                 730                 735

Asn Phe Leu Tyr Gly Asn Glu Val Ser Tyr Glu Cys Asp Gln Gly Phe
                740                 745                 750

Tyr Leu Leu Gly Glu Lys Lys Leu Gln Cys Arg Ser Asp Ser Lys Gly
                755                 760                 765

His Gly Ser Trp Ser Gly Pro Ser Pro Gln Cys Leu Arg Ser Pro Pro
```

```
                770             775             780
Val Thr Arg Cys Pro Asn Pro Glu Val Lys His Gly Tyr Lys Leu Asn
785             790             795             800

Lys Thr His Ser Ala Tyr Ser His Asn Asp Ile Val Tyr Val Asp Cys
                805             810             815

Asn Pro Gly Phe Ile Met Asn Gly Ser Arg Val Ile Arg Cys His Thr
                820             825             830

Asp Asn Thr Trp Val Pro Gly Val Pro Thr Cys Met Lys Lys Ala Phe
            835             840             845

Ile Gly Cys Pro Pro Pro Lys Thr Pro Asn Gly Asn His Thr Gly
850             855             860

Gly Asn Ile Ala Arg Phe Ser Pro Gly Met Ser Ile Leu Tyr Ser Cys
865             870             875             880

Asp Gln Gly Tyr Leu Leu Val Gly Glu Ala Leu Leu Leu Cys Thr His
                885             890             895

Glu Gly Thr Trp Ser Gln Pro Ala Pro His Cys Lys Glu Val Asn Cys
            900             905             910

Ser Ser Pro Ala Asp Met Asp Gly Ile Gln Lys Gly Leu Glu Pro Arg
            915             920             925

Lys Met Tyr Gln Tyr Gly Ala Val Val Thr Leu Glu Cys Glu Asp Gly
930             935             940

Tyr Met Leu Glu Gly Ser Pro Gln Ser Gln Cys Gln Ser Asp His Gln
945             950             955             960

Trp Asn Pro Pro Leu Ala Val Cys Arg Ser Arg Ser Leu Ala Pro Val
            965             970             975

Leu Cys Gly Ile Ala Ala Gly Leu Ile Leu Leu Thr Phe Leu Ile Val
            980             985             990

Ile Thr Leu Tyr Val Ile Ser Lys His Arg Glu Arg Asn Tyr Tyr Thr
            995             1000            1005

Asp Thr Ser Gln Lys Glu Ala Phe His Leu Glu Ala Arg Glu Val Tyr
    1010            1015            1020

Ser Val Asp Pro Tyr Asn Pro Ala Ser
1025            1030

<210> SEQ ID NO 16
<211> LENGTH: 637
<212> TYPE: DNA
<213> ORGANISM: Homo sapiens
<220> FEATURE:
<221> NAME/KEY: modified_base
<222> LOCATION: (9)
<223> OTHER INFORMATION: n = g, a, c or t

<400> SEQUENCE: 16
ctgggcaana ccaagtcaca gtttccagcg tgctgctcag ccctccgagt gtgtgtgctc      60
atccttttca tagaagtccc atmkgscatg gagagggttg ggctgcaaag ctwgattgc      120 cagaggccct tccttgagaa ctgtggggaa ggaggccctg ggggtttctt ctgtaggcag     180
agctcaggcc ccagtcacct ctgccaccct cagcctggca ctgttgtgcc agagcctctg     240
ctgcctctct cttcctaccc atctgcagac cagcagaata ttctcccct ctcatcacca     300 accaggagtt tggtgtggtt tctggacacg gccagagcag tcactgcggg gctggttttg     360
ctgggcttcc ctgtcaaagc aatgctaacg tccagctctc gactcaaggc caggttcttc     420
tcccacttgt ggcctcttgg gcttggaggc tgagccaggg gctcctctcc tgctggccgt     480
ccaggaacag acatcttcac atcctcagtc ttccaaaccc ggaccatgcc gtcttgactc     540
```

-continued

| | |
|---|---|
| ccggtgatga tgatctggct tgtgtcccat gctgggccct ccatcaggca gcaacaggtt | 600 |
| atggctcctt ctgggcccca ggctgtggtg atgctgg | 637 |

<210> SEQ ID NO 17
<211> LENGTH: 4191
<212> TYPE: DNA
<213> ORGANISM: Homo sapiens

<400> SEQUENCE: 17

| | |
|---|---|
| agcgagactt ccagtccgag gtcctgcttt ctgctatgga actattccac atgacaagtg | 60 |
| gaggtgatgc agcgatgttc agagacggca aagagcctca gccaagtgca gaagctgctg | 120 |
| ctgccccttc tcttgccaac atctcctgct tcacccagaa gctggtggag aagctgtaca | 180 |
| gtgggatgtt ctcggcagac cccaggcata tcctcctctt catcctggag cacatcatgg | 240 |
| tggtcattga gactgcctct tctcaaaggg acactgtcct cagcacttta tacagcagtt | 300 |
| taaataaagt cattctttat tgcctatcca agccccagca gtccctctcc gaatgcctcg | 360 |
| gccttctcag catcctgggc tttctgcagg agcactggga tgttgtcttt gccacctaca | 420 |
| attccaacat cagcttcctc ctgtgtctca tgcattgcct tttgctactc aatgagagaa | 480 |
| gttacccaga aggatttgga ttggagccca gcctagaat gtctacttat catcaagtct | 540 |
| tcctttcccc aaatgaagac gtgaaagaaa aagagaaga cttaccaagt ttgagtgatg | 600 |
| tccaacacaa catccagaag acagtgcaga ctctctggca gcagctggtg gcacaaaggc | 660 |
| agcagaccct ggaggatgcc ttcaagatcg atctctctgt gaaacctgga gagagggaag | 720 |
| tgaagattga agaggtcaca ccgctctggg aggagacgat gctcaaggcc tggcagcatt | 780 |
| acttagcatc tgagaagaag tcactggcaa gtcgttcaaa tgttgcacac cacagcaaag | 840 |
| tcactttgtg gagtggaagc ctgtcctcag ccatgaagct gatgcccggg cggcaggcca | 900 |
| aggaccctga gtgcaagaca gaggattttg tgtcatgtat agagaactac agaagaagag | 960 |
| gacaagagct atatgcatct ttatacaaag accatgtgca aaggcgaaaa tgtggcaaca | 1020 |
| tcaaggcagc caacgcctgg gccaggatcc aggagcagct ttttgggag ctgggcttgt | 1080 |
| ggagccaggg ggaagaaacc aagccctgtt ccccatggga actcgactgg agagaaggac | 1140 |
| cagctcgaat gaggaaacgc atcaaacgct gtctcctttt ggaggccctg agctcaggaa | 1200 |
| ggcacaagga aagccaagac aaaaatgatc atatttctca aacaaatgct gaaaaccaag | 1260 |
| atgaactgac actgagggag gctgagggcg agccggacga ggtgggggtg gactgcaccc | 1320 |
| agctgacctt cttcccagcc ttacacgaaa gtctgcactc agaagacttc ttggaactgt | 1380 |
| gtcgggaaag acaagttatt ttacaagagc ttcttgataa agaaaaggtg acgcagaagt | 1440 |
| tctcccctggt gattgtgcag ggccacctgg tgtcagaagg ggtcctgctt tttggccacc | 1500 |
| aacacttcta catctgcgag aacttcacac tgtctcccac gggtgatgtc tactgtaccc | 1560 |
| gtcactgctt atccaacatc agcgatccgt tcattttcaa cctgtgcagc aaagacaggt | 1620 |
| ccactgacca ttactcgtgc cagtgccaca gctacgctga catgcgggag ctacggcagg | 1680 |
| ctcgcttcct cctgcaggac atcgccctgg agatcttctt ccacaatgga tattccaagt | 1740 |
| ttcttgtctt ctacaacaat gatcggagta aggcctttaa aagcttctgc tctttccaac | 1800 |
| ccagcctgaa ggggaaagcc acctcggagg acaccctcaa tctaaggaga taccccggct | 1860 |
| ctgacaggat catgctgcag aagtggcaga aaagggacat cagcaatttt gagtatctca | 1920 |
| tgtacctcaa caccgcggct gggagaacct gcaatgacta catgcagtac ccagtgttcc | 1980 |

```
cctgggtcct cgcagactac acctcagaga cattgaactt ggcaaatccg aagatttcc    2040 gggatctttc aaagcccatg ggggctcaga ccaaggaaag gaagctgaaa tttatccaga    2100
ggtttaaaga agttgagaaa actgaaggag acatgactgt ccagtgccac tactacaccc    2160
actactcctc ggccatcatc gtggcctcct acctggtccg gatgccaccc ttcacccagg    2220
ccttctgcgc tctgcagggc ggaagcttcg acgtggcaga cagaatgttc cacagtgtga    2280
agagcacgtg ggagtcggcc tccagagaga acatgagtga cgtcagggag ctgaccccag    2340
agttcttcta cctgcctgag ttcttaacca actgcaacgg ggtagagttc ggctgcatgc    2400
aggacgggac tgtgctagga gacgtgcagc tccctccctg ggctgatggg accctcgga    2460 aattcatcag cctgcacaga aaggccctgg aaagtgactt tgtcagtgcc aacctccacc    2520
attggataga ccttattttt gggtacaagc agcaggggcc agccgcagtg gatgctgtta    2580
atatcttcca ccccctactcc tacggtgaca gaatggacct cagcagcatc actgaccccc    2640
tcatcaaaag caccatcctg ggttttgtca gcaactttgg acaggtgccc aaacagctct    2700
ttaccaaacc tcacccagcc aggactgcag cagggaagcc tctgcctgga aaggatgtct    2760 ccaccccgt gagcctgcct ggccaccac agccttttt ctacagcctg cagtcgctga    2820
ggccctccca ggtcacggtc aaagatatgt acctcttttc tctaggctca gagtccccca    2880
aaggggccat tggccacatt gtctctactg agaagaccat tctggctgta gagaggaaca    2940
aagtgctgct gcctcctctc tggaacagga ccttcagctg gggctttgat gacttcagct    3000
gctgcttggg gagctacggc tccgacaagg tcctgatgac attcgagaac ctggctgcct    3060
ggggccgctg tctgtgcgcc gtgtgcccat ccccaacaac gattgtcacc tctgggacca    3120
gcactgtggt gtgtgtgtgg gagctcagca tgaccaaagg ccgcccgagg ggcttgcgcc    3180
tccggcaggc cttgtatgga cacacacagg ctgtcacgtg cctggcagcg tcagtcacct    3240
tcagcctcct ggtgagcggc tcccaggact gcacctgtat cctgtgggat ctggaccacc    3300
tcacccacgt gacccgcctg cccgcccatc gggaaggcat ctcagccatc accatcagtg    3360
acgtctcagg caccattgtc tcctgtgcgg gagcacactt gtccctgtgg aatgtcaatg    3420
gacagcccct ggccagcatc accacagcct ggggcccaga aggagccata acctgttgct    3480
gcctgatgga gggccagca tgggacacaa gccagatcat catcaccggg agtcaagacg    3540
gcatggtccg ggtttggaag actgaggatg tgaagatgtc tgttcctgga cggccagcag    3600
gagaggagcc cctggctcag cctccaagcc caagaggcca caagtgggag aagaacctgg    3660
ccttgagtcg agagctggac gttagcattg cttttgacagg gaagcccagc aaaaccagcc    3720
ccgcagtgac tgctctggcc gtgtccagaa accacaccaa actcctggtt ggtgatgaga    3780 ggggagaat attctgctgg tctgcagatg ggtaggaaga gagaggcagc agaggctctg    3840
gcacaacagt gccaggctga gggtggcaga ggtgactggg gcctgagctc tgcctacaga    3900
agaaaccccc agggcctcct tccccacagt tctcaaggaa gggcctctgg caatcacagc    3960
tctgcagccc aaccctctcc atggccgatg ggacttctat gaaaaggatg agcacacaca    4020
ctcggagggc tgagcagcac gctggaaact gtgacttggt gatgcccagc tgcacacgaa    4080
attacacatg actcacctta ttaagggcta ttgcactgaa aaaaaaaaaa agatgggtcg    4140
cttactggaa attattgtat tgtctttatt ttattaaagc aactatgttt t                4191

<210> SEQ ID NO 18
<211> LENGTH: 1606
<212> TYPE: PRT
<213> ORGANISM: Homo sapiens
```

<400> SEQUENCE: 18

```
Met Asn Ile Ser Ser Arg Asp Asn Ala Met Pro Val Phe Leu Leu Arg
  1               5                  10                  15

Asn Cys Ala Gly His Leu Ser Gly Ser Leu Arg Thr Ile Gly Ala Val
             20                  25                  30

Ala Val Gly Gln Leu Gly Val Arg Val Phe His Ser Ser Pro Ala Ala
         35                  40                  45

Ser Ser Leu Asp Phe Ile Gly Gly Pro Ala Ile Leu Gly Leu Ile
     50                  55                  60

Ser Leu Ala Thr Asp Asp His Thr Met Tyr Ala Ala Val Lys Val Leu
 65                  70                  75                  80

His Ser Val Leu Thr Ser Asn Ala Met Cys Asp Phe Leu Met Gln His
                 85                  90                  95

Ile Cys Gly Tyr Gln Ile Met Ala Phe Leu Leu Arg Lys Lys Ala Ser
            100                 105                 110

Leu Leu Asn His Arg Ile Phe Gln Leu Ile Leu Ser Val Ala Gly Thr
            115                 120                 125

Val Glu Leu Gly Phe Arg Ser Ser Ala Ile Thr Asn Thr Gly Val Phe
        130                 135                 140

Gln His Ile Leu Cys Asn Phe Glu Leu Trp Met Asn Thr Ala Asp Asn
145                 150                 155                 160

Leu Glu Leu Ser Leu Phe Ser His Leu Leu Glu Ile Leu Gln Ser Pro
                165                 170                 175

Arg Glu Gly Pro Arg Asn Ala Glu Ala Ala His Gln Ala Gln Leu Ile
            180                 185                 190

Pro Lys Leu Ile Phe Leu Phe Asn Glu Pro Ser Leu Ile Pro Ser Lys
        195                 200                 205

Ile Pro Thr Ile Ile Gly Ile Leu Ala Cys Gln Leu Arg Gly His Phe
    210                 215                 220

Ser Thr Gln Asp Leu Leu Arg Ile Gly Leu Phe Val Val Tyr Thr Leu
225                 230                 235                 240

Lys Pro Ser Ser Val Asn Glu Arg Gln Ile Cys Met Asp Gly Ala Leu
                245                 250                 255

Asp Pro Ser Leu Pro Ala Gly Ser Gln Thr Ser Gly Lys Thr Ile Trp
            260                 265                 270

Leu Arg Asn Gln Leu Leu Glu Met Leu Leu Ser Val Ile Ser Ser Pro
        275                 280                 285

Gln Leu His Leu Ser Ser Glu Ser Lys Glu Glu Met Phe Leu Lys Leu
    290                 295                 300

Gly Pro Asp Trp Phe Leu Leu Leu Gln Gly His Leu His Ala Ser
305                 310                 315                 320

Thr Thr Val Leu Ala Leu Lys Leu Leu Leu Tyr Phe Leu Ala Ser Pro
                325                 330                 335

Ser Leu Arg Thr Arg Phe Arg Asp Gly Leu Cys Ala Gly Ser Trp Val
            340                 345                 350

Glu Arg Ser Thr Glu Gly Val Asp Ile Val Met Asp Asn Leu Lys Ser
        355                 360                 365

Gln Ser Pro Leu Pro Glu Gln Ser Pro Cys Leu Leu Pro Gly Phe Arg
    370                 375                 380

Val Leu Asn Asp Phe Leu Ala His His Val His Ile Pro Glu Val Tyr
385                 390                 395                 400

Leu Ile Val Ser Thr Phe Phe Leu Gln Thr Pro Leu Thr Glu Leu Met
```

```
                        405                 410                 415
Asp Gly Pro Lys Asp Ser Leu Asp Ala Met Leu Gln Trp Leu Leu Gln
                420                 425                 430

Arg His His Gln Glu Glu Val Leu Gln Ala Gly Leu Cys Thr Glu Gly
            435                 440                 445

Ala Leu Leu Leu Leu Glu Met Leu Lys Ala Thr Met Ser Gln Pro Leu
        450                 455                 460

Ala Gly Ser Glu Asp Gly Ala Trp Ala Gln Thr Phe Pro Ala Ser Val
465                 470                 475                 480

Leu Gln Phe Leu Ser Leu Val His Arg Thr Tyr Pro Gln Asp Pro Ala
                485                 490                 495

Trp Arg Ala Pro Glu Phe Leu Gln Thr Leu Ala Ile Ala Ala Phe Pro
            500                 505                 510

Leu Gly Ala Gln Lys Gly Val Gly Ala Glu Ser Thr Arg Asn Thr Ser
        515                 520                 525

Ser Pro Glu Ala Ala Glu Gly Asp Ser Thr Val Glu Gly Leu Gln
530                 535                 540

Ala Pro Thr Lys Ala His Pro Ala Arg Arg Lys Leu Arg Glu Phe Thr
545                 550                 555                 560

Gln Leu Leu Leu Arg Glu Leu Leu Leu Gly Ala Ser Ser Pro Lys Gln
                565                 570                 575

Trp Leu Pro Leu Glu Val Leu Leu Glu Ala Ser Pro Asp His Ala Thr
            580                 585                 590

Ser Gln Gln Lys Arg Asp Phe Gln Ser Glu Val Leu Leu Ser Ala Met
        595                 600                 605

Glu Leu Phe His Met Thr Ser Gly Gly Asp Ala Ala Met Phe Arg Asp
610                 615                 620

Gly Lys Glu Pro Gln Pro Ser Ala Glu Ala Ala Ala Pro Ser Leu
625                 630                 635                 640

Ala Asn Ile Ser Cys Phe Thr Gln Lys Leu Val Glu Lys Leu Tyr Ser
                645                 650                 655

Gly Met Phe Ser Ala Asp Pro Arg His Ile Leu Leu Phe Ile Leu Glu
            660                 665                 670

His Ile Met Val Val Ile Glu Thr Ala Ser Ser Gln Arg Asp Thr Val
        675                 680                 685

Leu Ser Thr Leu Tyr Ser Ser Leu Asn Lys Val Ile Leu Tyr Cys Leu
690                 695                 700

Ser Lys Pro Gln Gln Ser Leu Ser Glu Cys Leu Gly Leu Leu Ser Ile
705                 710                 715                 720

Leu Gly Phe Leu Gln Glu His Trp Asp Val Val Phe Ala Thr Tyr Asn
                725                 730                 735

Ser Asn Ile Ser Phe Leu Leu Cys Leu Met His Cys Leu Leu Leu Leu
            740                 745                 750

Asn Glu Arg Ser Tyr Pro Glu Gly Phe Gly Leu Glu Pro Lys Pro Arg
        755                 760                 765

Met Ser Thr Tyr His Gln Val Phe Leu Ser Pro Asn Glu Asp Val Lys
770                 775                 780

Glu Lys Arg Glu Asp Leu Pro Ser Leu Ser Asp Val Gln His Asn Ile
785                 790                 795                 800

Gln Lys Thr Val Gln Thr Leu Trp Gln Gln Leu Val Ala Gln Arg Gln
                805                 810                 815

Gln Thr Leu Glu Asp Ala Phe Lys Ile Asp Leu Ser Val Lys Pro Gly
            820                 825                 830
```

```
Glu Arg Glu Val Lys Ile Glu Val Thr Pro Leu Trp Glu Glu Thr
        835                 840                 845

Met Leu Lys Ala Trp Gln His Tyr Leu Ala Ser Glu Lys Lys Ser Leu
        850                 855                 860

Ala Ser Arg Ser Asn Val Ala His His Ser Lys Val Thr Leu Trp Ser
865                 870                 875                 880

Gly Ser Leu Ser Ser Ala Met Lys Leu Met Pro Gly Arg Gln Ala Lys
                885                 890                 895

Asp Pro Glu Cys Lys Thr Glu Asp Phe Val Ser Cys Ile Glu Asn Tyr
            900                 905                 910

Arg Arg Arg Gly Gln Glu Leu Tyr Ala Ser Leu Tyr Lys Asp His Val
        915                 920                 925

Gln Arg Arg Lys Cys Gly Asn Ile Lys Ala Ala Asn Ala Trp Ala Arg
    930                 935                 940

Ile Gln Glu Gln Leu Phe Gly Glu Leu Gly Leu Trp Ser Gln Gly Glu
945                 950                 955                 960

Glu Thr Lys Pro Cys Ser Pro Trp Glu Leu Asp Trp Arg Glu Gly Pro
                965                 970                 975

Ala Arg Met Arg Lys Arg Ile Lys Arg Leu Ser Pro Leu Glu Ala Leu
            980                 985                 990

Ser Ser Gly Arg His Lys Glu Ser Gln Asp Lys Asn Asp His Ile Ser
        995                 1000                1005

Gln Thr Asn Ala Glu Asn Gln Asp Glu Leu Thr Leu Arg Glu Ala Glu
    1010                1015                1020

Gly Glu Pro Asp Glu Val Gly Val Asp Cys Thr Gln Leu Thr Phe Phe
1025                1030                1035                1040

Pro Ala Leu His Glu Ser Leu His Ser Glu Asp Phe Leu Glu Leu Cys
                1045                1050                1055

Arg Glu Arg Gln Val Ile Leu Gln Glu Leu Leu Asp Lys Glu Lys Val
            1060                1065                1070

Thr Gln Lys Phe Ser Leu Val Ile Val Gln Gly His Leu Val Ser Glu
        1075                1080                1085

Gly Val Leu Leu Phe Gly His Gln His Phe Tyr Ile Cys Glu Asn Phe
    1090                1095                1100

Thr Leu Ser Pro Thr Gly Asp Val Tyr Cys Thr Arg His Cys Leu Ser
1105                1110                1115                1120

Asn Ile Ser Asp Pro Phe Ile Phe Asn Leu Cys Ser Lys Asp Arg Ser
                1125                1130                1135

Thr Asp His Tyr Ser Cys Gln Cys His Ser Tyr Ala Asp Met Arg Glu
            1140                1145                1150

Leu Arg Gln Ala Arg Phe Leu Leu Gln Asp Ile Ala Leu Glu Ile Phe
        1155                1160                1165

Phe His Asn Gly Tyr Ser Lys Phe Leu Val Phe Tyr Asn Asn Asp Arg
    1170                1175                1180

Ser Lys Ala Phe Lys Ser Phe Cys Ser Phe Gln Pro Ser Leu Lys Gly
1185                1190                1195                1200

Lys Ala Thr Ser Glu Asp Thr Leu Asn Leu Arg Arg Tyr Pro Gly Ser
                1205                1210                1215

Asp Arg Ile Met Leu Gln Lys Trp Gln Lys Arg Asp Ile Ser Asn Phe
            1220                1225                1230

Glu Tyr Leu Met Tyr Leu Asn Thr Ala Ala Gly Arg Thr Cys Asn Asp
        1235                1240                1245
```

```
Tyr Met Gln Tyr Pro Val Phe Pro Trp Val Leu Ala Asp Tyr Thr Ser
1250                1255                1260

Glu Thr Leu Asn Leu Ala Asn Pro Lys Ile Phe Arg Asp Leu Ser Lys
1265                1270                1275                1280

Pro Met Gly Ala Gln Thr Lys Glu Arg Lys Leu Lys Phe Ile Gln Arg
            1285                1290                1295

Phe Lys Glu Val Glu Lys Thr Glu Gly Asp Met Thr Val Gln Cys His
            1300                1305                1310

Tyr Tyr Thr His Tyr Ser Ser Ala Ile Ile Val Ala Ser Tyr Leu Val
            1315                1320                1325

Arg Met Pro Pro Phe Thr Gln Ala Phe Cys Ala Leu Gln Gly Gly Ser
1330                1335                1340

Phe Asp Val Ala Asp Arg Met Phe His Ser Val Lys Ser Thr Trp Glu
1345                1350                1355                1360

Ser Ala Ser Arg Glu Asn Met Ser Asp Val Arg Glu Leu Thr Pro Glu
            1365                1370                1375

Phe Phe Tyr Leu Pro Glu Phe Leu Thr Asn Cys Asn Gly Val Glu Phe
            1380                1385                1390

Gly Cys Met Gln Asp Gly Thr Val Leu Gly Asp Val Gln Leu Pro Pro
            1395                1400                1405

Trp Ala Asp Gly Asp Pro Arg Lys Phe Ile Ser Leu His Arg Lys Ala
1410                1415                1420

Leu Glu Ser Asp Phe Val Ser Ala Asn Leu His His Trp Ile Asp Leu
1425                1430                1435                1440

Ile Phe Gly Tyr Lys Gln Gln Gly Pro Ala Ala Val Asp Ala Val Asn
            1445                1450                1455

Ile Phe His Pro Tyr Phe Tyr Gly Asp Arg Met Asp Leu Ser Ser Ile
            1460                1465                1470

Thr Asp Pro Leu Ile Lys Ser Thr Ile Leu Gly Phe Val Ser Asn Phe
1475                1480                1485

Gly Gln Val Pro Lys Gln Leu Phe Thr Lys Pro His Pro Ala Arg Thr
1490                1495                1500

Ala Ala Gly Lys Pro Leu Pro Gly Lys Asp Val Ser Thr Pro Val Ser
1505                1510                1515                1520

Leu Pro Gly His Pro Gln Pro Phe Phe Tyr Ser Leu Gln Ser Leu Arg
            1525                1530                1535

Pro Ser Gln Val Thr Val Lys Asp Met Tyr Leu Phe Ser Leu Gly Ser
            1540                1545                1550

Glu Ser Pro Lys Gly Ala Ile Gly His Ile Val Ser Thr Glu Lys Thr
            1555                1560                1565

Ile Leu Ala Val Glu Arg Asn Lys Val Leu Leu Pro Pro Leu Trp Asn
1570                1575                1580

Arg Thr Phe Ser Trp Gly Phe Asp Asp Phe Ser Cys Cys Leu Gly Ser
1585                1590                1595                1600

Tyr Gly Ser Asp Lys Ser
            1605
```

<210> SEQ ID NO 19
<211> LENGTH: 426
<212> TYPE: DNA
<213> ORGANISM: Homo sapiens

<400> SEQUENCE: 19
ctgcccttcc atgtcgtcac aggcataccg ggcgtggacc cactgcttgg tgcccttgcc    60

```
gaagtagtag cacttccgtt ggaaattgat ccactttca gggcacgtgt tgcacacaaa    120
gccgctggac acctgcaact ccatccttag ctttgtcacc tcctcccgga gtctttccag    180
caaatctgaa gcttcgttcc tctcgttcaa ttcctgggac ttgaagctgc tcagatctgc    240
ttgaagcccg ttcaggttcc aggacagctc caagtcctga gatttcaatc tctgctgttc    300
agctcgaagt tcctccagtt cctgtgaaat ctgcgtggac tgggatttct gcgccatctg    360
gtcaccgtgg tggctttcca agttcttgga aacttgagag acgttccggg cagccctctc    420
ttccag                                                                 426
```

<210> SEQ ID NO 20
<211> LENGTH: 1569
<212> TYPE: DNA
<213> ORGANISM: Homo sapiens

<400> SEQUENCE: 20

```
ggcacgaggc tgcttaaacc tctgtctctg acggtccctg ccaatcgctc tggtcgaccc     60
caacacacta ggaggacaga cacaggctcc aaactccact aaccagagct gtgattgtgc    120
ccgctgagtg gactgcgttg tcagggagtg agtgctccat catcgggaga atccaagcag    180
gaccgccatg gaggaaggtc aatattcaga gatcgaggag cttcccagga ggcggtgttg    240
caggcgtggg actcagatcg tgctgctggg gctggtgacc gccgctctgt gggctgggct    300
gctgactctg cttctcctgt ggcactggga caccacacag agtctaaaac agctggaaga    360
gagggctgcc cggaacgtct ctcaagtttc caagaacttg gaaagccacc acggtgacca    420
gatggcgcag aaatcccagt ccacgcagat ttcacaggaa ctggaggaac ttcgagctga    480
acagcagaga ttgaaatctc aggacttgga gctgtcctgg aacctgaacg ggcttcaagc    540
agatctgagc agcttcaagt cccaggaatt gaacgagagg aacgaagctt cagatttgct    600
ggaaagactc cgggaggagg tgacaaagct aaggatggag ttgcaggtgt ccagcggctt    660
tgtgtgcaac acgtgccctg aaaagtggat caatttccaa cggaagtgct actacttcgg    720
caagggcacc aagcagtggg tccacgcccg gtatgcctgt gacgacatgg aagggcagct    780
ggtcagcatc cacagcccgg aggagcagga cttcctgacc aagcatgcca gccacaccgg    840
ctcctggatt ggccttcgga acttggacct gaaggggag tttatctggg tggatgggag    900
ccacgtggac tacagcaact gggctccagg ggagcccacc agccggagcc agggcgagga    960
ctgcgtgatg atgcggggct ccggtcgctg gaacgacgcc ttctgcgacc gtaagctggg   1020
cgcctgggtg tgcgaccggc tggccacatg cacgccgcca gccagcgaag ttccgcggga   1080
gtccatggga cctgattcaa gaccagaccc tgacggccgc ctgcccaccc cctctgcccc   1140
tctccactct tgagcatgga tacagccagg cccagagcaa gacctgaag accccaacc     1200
acggcctaaa agcctctttg tggctgaaag gtccctgtga cattttctgc cacccaaacg   1260
gaggcagctg acacatctcc cgctcctcta tggcccctgc cttccagga gtacacccca    1320
acagcaccct ctccagatgg gagtgccccc aacagcaccc tctccagatg agagtacacc   1380
ccaacagcac cctctccaga tgagagtaca ccccaacagc accctctcca gatgagagta   1440
cacccccaaca gcaccctctc cagatgcagc cccatctcct cagcaccca ggacctgagt    1500
atccccagct caggtggtga gtcctcctgt ccagcctgca tcaataaaat ggggcagtga   1560
tggcctccc                                                           1569
```

<210> SEQ ID NO 21
<211> LENGTH: 321

<212> TYPE: PRT
<213> ORGANISM: Homo sapiens

<400> SEQUENCE: 21

```
Met Glu Glu Gly Gln Tyr Ser Glu Ile Glu Leu Pro Arg Arg Arg
 1               5                  10                  15

Cys Cys Arg Arg Gly Thr Gln Ile Val Leu Gly Leu Val Thr Ala
                20                  25                  30

Ala Leu Trp Ala Gly Leu Leu Thr Leu Leu Leu Trp His Trp Asp
                35                  40                  45

Thr Thr Gln Ser Leu Lys Gln Leu Glu Glu Arg Ala Ala Arg Asn Val
 50                  55                  60

Ser Gln Val Ser Lys Asn Leu Glu Ser His His Gly Asp Gln Met Ala
 65                  70                  75                  80

Gln Lys Ser Gln Ser Thr Gln Ile Ser Gln Glu Leu Glu Glu Leu Arg
                85                  90                  95

Ala Glu Gln Gln Arg Leu Lys Ser Gln Asp Leu Glu Leu Ser Trp Asn
                100                 105                 110

Leu Asn Gly Leu Gln Ala Asp Leu Ser Ser Phe Lys Ser Gln Glu Leu
                115                 120                 125

Asn Glu Arg Asn Glu Ala Ser Asp Leu Leu Glu Arg Leu Arg Glu Glu
 130                 135                 140

Val Thr Lys Leu Arg Met Glu Leu Gln Val Ser Ser Gly Phe Val Cys
 145                 150                 155                 160

Asn Thr Cys Pro Glu Lys Trp Ile Asn Phe Gln Arg Lys Cys Tyr Tyr
                165                 170                 175

Phe Gly Lys Gly Thr Lys Gln Trp Val His Ala Arg Tyr Ala Cys Asp
                180                 185                 190

Asp Met Glu Gly Gln Leu Val Ser Ile His Ser Pro Glu Glu Gln Asp
                195                 200                 205

Phe Leu Thr Lys His Ala Ser His Thr Gly Ser Trp Ile Gly Leu Arg
 210                 215                 220

Asn Leu Asp Leu Lys Gly Glu Phe Ile Trp Val Asp Gly Ser His Val
225                  230                 235                 240

Asp Tyr Ser Asn Trp Ala Pro Gly Glu Pro Thr Ser Arg Ser Gln Gly
                245                 250                 255

Glu Asp Cys Val Met Met Arg Gly Ser Gly Arg Trp Asn Asp Ala Phe
                260                 265                 270

Cys Asp Arg Lys Leu Gly Ala Trp Val Cys Asp Arg Leu Ala Thr Cys
                275                 280                 285

Thr Pro Pro Ala Ser Glu Gly Ser Ala Glu Ser Met Gly Pro Asp Ser
                290                 295                 300

Arg Pro Asp Pro Asp Gly Arg Leu Pro Thr Pro Ser Ala Pro Leu His
305                  310                 315                 320

Ser
```

<210> SEQ ID NO 22
<211> LENGTH: 1076
<212> TYPE: DNA
<213> ORGANISM: Homo sapiens
<220> FEATURE:
<221> NAME/KEY: modified_base
<222> LOCATION: (1)..(1076)
<223> OTHER INFORMATION: n = g, a, c or t

<400> SEQUENCE: 22

| | |
|---|---:|
| atcagcacga atacattcac gtccaacaac acatcaacta ccaacaccat caccacgagc | 60 |
| acattcatgc ccaacaacac atcaaccacc aacacctttg ccacaaacac attcatgtct | 120 |
| aacaacacat caattaccaa caccagcgcc acgaacacat tcacgtccat caacacatca | 180 |
| accaccaaca ccatcagcac gagcacattc acatccaata acatcaac taccaacacc | 240 |
| agcaccatga acacattcat gcccaacaac acgtaaaccc ctaacactgt cacccacaaac | 300 |
| accttacagc cagcagaacg ccagtcacta acaccatcgc catcagcact tcgtggttag | 360 |
| caacacctca gctgacgcca atgtcaccac aaacacctca tggccagaag cagctcaacc | 420 |
| accaacaccg ttattataaa tacattcttg accatcaatg cttcaactgc tgacaccatt | 480 |
| accataaata catccatggc cagcaatact tcaatcacca acaccatgac cagcagcacg | 540 |
| tcagcggcca tcactgtcac cacaaacacc ttcatatcca ataacacttc aaccaccatc | 600 |
| atcaccacaa cacctcata gccaacagtg cctcagccac caaccccatc atgacaaaca | 660 |
| cctcatggcc agcagcactt caaccaccaa caaaccccctc caaggtcagc aacaccttca | 720 |
| tcaccgacat cattaacaga ggtacccacc accagcagca gcttatctcc accacccaca | 780 |
| ccacagccaa caccatcttt accaaccaca ccagccgtgt cttcatcact ggcaccgaca | 840 |
| gcaaaaccag tgctgtggcc aggtccacca gcgattactt tccccaagca ccatccctac | 900 |
| caacagccct ggtcatcatc actggcagaa cccgccaaac cagcactcct agccaatgtc | 960 |
| tgggaaattg ngatnatttt cttccagtgg gaggctntgg tcaggagagc caatgggatt | 1020 |
| gcaagactag gtcccacaat ccctcaatat ggtctcttn tccccttccc cccacc | 1076 |

<210> SEQ ID NO 23
<211> LENGTH: 476
<212> TYPE: DNA
<213> ORGANISM: Homo sapiens

<400> SEQUENCE: 23

| | |
|---|---:|
| aggtacgcgg ggacgttcaa cgacttactg gggagagaaa gaaaaggaac gggagctgag | 60 |
| agctgggagt ggagtatgaa gaccaaggaa ttctcttaaa gacctgagca gttatctgga | 120 |
| actcctcaca aaatcacagt aatggatatt atttcccagt tcctactcta cactgggcat | 180 |
| agatgttatg gacatcttct gagtcccaca acacccctgc aaggcagata tgatacactc | 240 |
| ctttcaccta tggagaacgg aggctcaaag aggctaggtg accctcagga acacagatg | 300 |
| agaggtcccc gcccagtctg cccagctctg aaatcttcca tgccaactcc cttagggcga | 360 |
| tcctgagtct agcctgtaca ggcagttcat gtggttgtat ttgaataaaa tccctttcct | 420 |
| ccagaataaa aaaaaaaaaa taaaaaaaaa aatgaaaaat tgaagggaa aaaaaa | 476 |

<210> SEQ ID NO 24
<211> LENGTH: 421
<212> TYPE: DNA
<213> ORGANISM: Homo sapiens

<400> SEQUENCE: 24

| | |
|---|---:|
| ccaccaacag tcagaggcca aggaagctgt tggctgaaaa ggtggtctat gttggcgtct | 60 |
| ggatccctgc cctcctgctg actattcccg acttcatctt tgccaacgtc agtgaggcag | 120 |
| atgacagata tatctgtgac cgcttctacc ccaatgactt gtgggtggtt gtgttccagt | 180 |
| ttcagcacat catggttggc cttatcctgc ctggtattgt catcctgtcc tgctattgca | 240 |
| ttatcatctc caagctgtca cactccaagg gccaccagaa gcgcaaggcc ctcaagacca | 300 |
| cagtcatcct catcctggct tcttcgcct gttggctgcc ttactacatt gggatcagca | 360 |

```
tcgactcctt catcctcctg gaaatcatca agcaagggtg tgagtttgag aacactgtgc    420
a                                                                    421

<210> SEQ ID NO 25
<211> LENGTH: 8747
<212> TYPE: DNA
<213> ORGANISM: Homo sapiens

<400> SEQUENCE: 25
caattctgaa tcctgccttt tgcacttaat gtttcataag tatttcccca tgtcactaaa     60
aattcttcca ataacattc acgatgtcca tatggaattt cagatgtgga tgaaccaaaa    120
tcttgtcaac tattccacta acagtggtta tttagggatg ttcagacatt tcactattta    180
aaaaaaaatg tttccacaaa tacctttgtg gcataagttt ttatgagtgg agttactgtt    240
ctgaagttcc tgctgaatag aaaatgcttt ccagtgaggc tgtcccaagc cacattccca    300
tcagtgacaa gcgagagaca gctggtcttt tcaaatccgg agaccaaata ttatctttga    360
aaaaaaatgg attttgcct aatttggtag tcaccaaata gcatctcatt gttcttttaa    420
ttatctgctt ccttttagta gagatcccta aaaagatctg aaaggagtct tcagataaag    480
gaaggagctt tcttttgtct gtctacaatc aacaaatatt tattatgcaa accattttgc    540
tccgagtttt ctcctctttc ccttttggga cagatttggg agatctcacc tttcaggttt    600
tagacatcgt gcagggagga gttttgaggt agggtgcagc ttacggtcca ggataaaaca    660
tactgattct gccactacca ggctttgtga aaagcaagtc atgaaaacgc tctgaaattc    720
tagaccttca gtagatagga tctaccgtgt ctataaaaat atgaagatcc ttaagtttta    780
ttaaagattc gaaaaagta aaagtgtttt tacggtttta ttttcatttt tatttcttac    840
cgttatcgtt tattataaag gatattataa aggatacaga tgaagagata cgtaatgcaa    900
ggcctgtgag aagggcgtg gagcttccga aacctcttcc agccaccacc ctccaagaac    960
ctggagtttc ttttttttt tttaattcta caaatgtaat attagaattg attttatctg   1020
gccattagtg tgtgtcctaa ctcgttcgtt tctgagagtc ccatctcccg gcccgggata   1080
tcatctttcc tgtgtcagtg aaagtgcaga gtagatgaga acctttaacc accaacatta   1140
gggaggggtc ccagacaaag ggggtaagtc atgctctgta gagaaaaggt tccctgcctc   1200
cgaactacct ctggaacact ccagtaaatg tttcctcttt tgatatagaa agagggatc   1260
gtgtgtagag tgcagtctgg gcaatccctc tcctcgggac catttcgggg tagggcctc   1320
tggggtccgt gtcgcgacgc acgcgcctcg gtcccagcta tctccgcagc gggccacccc   1380
gcctgcggac gcagtttctc ggccccgccc cacactcgct ccccgcccc acccagtctc   1440
cgcgccggag ggaagtggcg cgagggggaa agcactgtct gcgcgccac tgcaaacctc   1500
agccagtctg agatcgcttt aaacgtctga ccccaccc cactccgccc cgcccagttc   1560
ttcaacctaa tttctgattc gtgccaaagc ttgtcctctg ctcaaaatcg tggaagacgc   1620
cgagtatggg gaccgaagac ctgggttcaa gcccggcttg gaatccctgc ccatccctgg   1680
catttcatct ctccgggctt atttgctggt ttctccgaat gcgggccttg tctggttcac   1740
gctggatccc caacgcctag aacagtgcgt ggcacgcagt tcgtccttct ataaatatcg   1800
gactaaatgc atctctgtga tggtaatacc cacacggtgt tgtgagaatg aatgagtgat   1860
tctgtgcaag ttcctagtga tctgttacaa aaagtactgg tcgctaaatt actcttataa   1920
taaagcatac ttttaggata ataaagcact attcgcgaat tggttaccgc tattatgaaa   1980
```

| | |
|---|---|
| ttactgagca atacatatct acatctgatc agtctccaga attatgccaa atcctacctt | 2040 |
| cttctgaaag tatctcctaa ttatctgcac ctgaccctag tgatgctgtg aatgtgcaag | 2100 |
| tatagctaca tcctccgaag gaaaggatct ttactccttt tacctcctga atgggctgcg | 2160 |
| tctgctgaaa gcgcggggga atgggcggtt ggaagcttgg ccctacttcc agcattgccg | 2220 |
| cctactggtt gggttactcc agcaagtcac tccccttccc tgggcctcag tgtctctact | 2280 |
| gtagcattcc caggtctgga attccatcca ctttagcaag gatggacgcg ccacagagag | 2340 |
| acgcgttcct agcccgcgct tcccacctgt cttcaggcgc atcccgcttc cctcaaactt | 2400 |
| aggaaatgcc tctgggaggt cctgtccggc tccggactca ctaccgacca cccgcaaaca | 2460 |
| gcagggtccc ctgggcttcc caagccgcgc acctctccgc cccgcccctg cgcctccttt | 2520 |
| cctcgcgtct gccctctcc cccacccgc cttctccctc cccgcccag cggcgcatgc | 2580 |
| gccgcgctcg gagcgtgttt ttataaaagt ccggccgcgg ccagaaactt cagtttgttg | 2640 |
| gctgcggcag caggtagcaa agtgacgccg agggcctgag tgctccagta gccaccgcat | 2700 |
| ctggagaacc agcggttacc atggagggga tcagtgtaag tccagtttca acctgctttg | 2760 |
| tcataaatgt acaaacgttt gaacttagag cgcagcccct ctccgagcgg gcagaagcgg | 2820 |
| ccaggacatt ggaggtaccc gtactccaaa aagggtcac cgaaaggagt tttcttgacc | 2880 |
| atgcctatat agtgcgggtg ggtggggggg gagcaggatt ggaatctttt tctctgtgag | 2940 |
| tcgaggagaa acgactggaa agagcgttcc agtggctgca tgtgtctccc ccttgagtcc | 3000 |
| cgccgcgcgc ggcggcttgc acgctgtttg caaacgtaag aacattctgt gcacaagtgc | 3060 |
| agagaaggcg tgcgcgctgc ctcgggactc agaccaccgg tctcttcctt ggggaagcgg | 3120 |
| ggatgtcttg gagcgagtta cattgtctga atttagaggc ggagggcggc gtgcctgggc | 3180 |
| tgagttccca ggaggagatt gcgcccgctt taacttcggg gttaagcgcc tggtgactgt | 3240 |
| tcttgacact gggtgcgtgt ttgttaaact ctgtgcggcc gacggagctg tgccagtctc | 3300 |
| ccagcacagt aggcagaggg cgggagaggc gggtggaccc accgcgccga tcctctgagg | 3360 |
| ggatcgagtg gtggcagcag ctaggagttg atccgcccgc gcgctttggg tttgaggggg | 3420 |
| aaaccttccc gccgtccgaa gcgcgcctct tccccacggc cgcgagtggg tcctgcagtt | 3480 |
| cgagagtttg gggtcgtgca gaggtcagcg gagtggtttg acctcccctt tgacaccgcg | 3540 |
| cagctgccag ccctgagatt tgcgctccgg ggataggagc gggtacgggg tgaggggcgg | 3600 |
| gggcggttaa gaccgcacct gggctgccag gtcgccgccg cgaagactgg caggtgcaag | 3660 |
| tggggaaacc gtttggctct ctccgagtcc agttgtgatg tttaaccgtc ggtggtttcc | 3720 |
| agaaaccttt tgaaaccctc ttgctaggga gttttttggtt tcctgcagcg gcgcgcaatt | 3780 |
| caaagacgct cgcggcggag ccgcccagtc gctccccagc accctgtggg acagagcctg | 3840 |
| gcgtgtcgcc cagcggagcc cctgcagcgc tgcttgcggg cggttggcgt gggtgtagtg | 3900 |
| ggcagccgcg gcggcccggg gctggacgac ccggcccccc gcgtgcccac cgcctggagg | 3960 |
| cttccagctg cccacctccg gccgggttaa ctggatcagt ggcggggtaa tgggaaacca | 4020 |
| cccgggagag tgaggaaatg aaacttgggg cgaggaccac gggtgcagac cccgttacct | 4080 |
| tctccaccca ggaaaatgcc ccgctcccta acgtcccaaa cgcgccaagt gataaacacg | 4140 |
| aggatggcaa gagacccaca caccggagga gcgcccgctt gggggaggag gtgccgtttg | 4200 |
| ttcattttct gacactcccg cccaatatac cccaagcacc gaaggccttc cgttttaaga | 4260 |
| ccgcattctc tttacccact acaagttgct tgaagcccaa aatggtttgt atttaggcag | 4320 |
| gcgtgggaaa attaagtttt tgcgccttag gagaatgagt cttttgcaacg ccccgccct | 4380 |

```
cccccccgtga tcctcccttc tccctcttc  cctccctggg cgaaaaactt cttacaaaaa  4440
gttaatcact gccctccta  gcagcaccca ccccacccc  cacgccgcct gggagtggcc  4500
tctttgtgtg tatttttttt ttcctcctaa ggaaggtttt ttttcttccc tctagtgggc  4560
ggggcagagg agttagccaa gatgtgactt tgaaaccctc agcgtctcag tgcccttttg  4620
ttctaaacaa agaattttgt aattggttct accaagaag  gatataatga agtcactatg  4680
ggaaaagatg gggaggagag ttgtaggatt ctacattaat tctcttgtgc ccttagccca  4740
ctacttcaga atttcctgaa gaaagcaagc ctgaattggt ttttaaatt  gctttaaaaa  4800
attttttaa  ctgggttaat gcttgctgaa ttggaagtga atgtccattc ctttgcctct  4860
tttgcagata tacacttcag ataactacac cgaggaaatg ggctcagggg actatgactc  4920
catgaaggaa ccctgtttcc gtgaagaaaa tgctaatttc aataaaatct tcctgcccac  4980
catctactcc atcatcttct taactggcat tgtgggcaat ggattggtca tcctggtcat  5040
gggttaccag aagaaactga gaagcatgac ggacaagtac aggctgcacc tgtcagtggc  5100
cgacctcctc tttgtcatca cgcttccctt ctgggcagtt gatgccgtgg caaactggta  5160
ctttgggaac ttcctatgca aggcagtcca tgtcatttac acagtcaacc tctacagcag  5220
tgtcctcatc ctggccttca tcagtctgga ccgctacctg gccatcgtcc acgccaccaa  5280
cagtcagagg ccaaggaagc tgttggctga aaaggtggtc tatgttggcg tctggatccc  5340
tgccctcctg ctgactattc ccgacttcat ctttgccaac gtcagtgagg cagatgacag  5400
atatatctgt gaccgcttct accccaatga cttgtgggtg gttgtgttcc agtttcagca  5460
catcatggtt ggccttatcc tgcctggtat tgtcatcctg tcctgctatt gcattatcat  5520
ctccaagctg tcacactcca agggccacca gaagcgcaag gccctcaaga ccacagtcat  5580
cctcatcctg gctttcttcg cctgttggct gccttactac attgggatca gcatcgactc  5640
cttcatcctc ctggaaatca tcaagcaagg gtgtgagttt gagaacactg tgcacaagtg  5700
gatttccatc accgaggccc tagctttctt ccactgttgt ctgaacccca tcctctatgc  5760
tttccttgga gccaaattta aaacctctgc ccagcacgca ctcacctctg tgagcagagg  5820
gtccagcctc aagatcctct ccaaaggaaa gcgaggtgga cattcatctg tttccactga  5880
gtctgagtct tcaagttttc actccagcta acacagatgt aaaagacttt tttttatacg  5940
ataaataact ttttttaag  ttacacattt ttcagatata aaagactgac caatattgta  6000
cagtttttat tgcttgttgg attttttgtct tgtgtttctt tagttttgt  gaagtttaat  6060
tgacttattt atataaattt tttttgtttc atattgatgt gtgtctaggc aggacctgtg  6120
gccaagttct tagttgctgt atgtctcgtg gtaggactgt agaaaaggga actgaacatt  6180
ccagagcgtg tagtgaatca cgtaaagcta gaaatgatcc ccagctgttt atgcatagat  6240
aatctctcca ttccgtgga  acgttttttcc tgttcttaag acgtgatttt gctgtagaag  6300
atggcactta taaccaaagc ccaaagtggt atagaaatgc tggttttca  gttttcagga  6360
gtgggttgat ttcagcacct acagtgtaca gtcttgtatt aagttgttaa taaaagtaca  6420
tgttaaactt acttagtgtt atgttctgat ttctgttgac attcttttgg ctagtagaag  6480
acaaaagtaa tacattatg  gtatgcaaag cactatccta ggtatttcat tgtaatattt  6540
tacttaccccc ttatcacaac tctgatagat tctgcttctg ttactaatta cattttatag  6600
aagaggaaac ggaggcacag aaagcctaag taacttggtt aaaggcatgt agtaagtatc  6660
aaatcctgta tttaaaacca ggtaacatga cttaacgaat ctgaagcctt caccactta   6720
```

-continued

| | |
|---|---|
| aattcaaatg gaagtttaga aatggccagc cagcacctat ttgtatgaaa ggtcatcttt | 6780 |
| cagaggataa gcatgtataa agaagaaaag gtatgcagtc gtgtttggat tttactccac | 6840 |
| catccacttg tgaaacccag gtctgtgcaa tgccagacgg tgtgtgcttt cctcatccag | 6900 |
| tatcctcagt gtagataacc atcactccct tttcacagac aagagaactg agattcagag | 6960 |
| actttccata cattgcactt tcaaggggc aaagccaaga actaattctg tttattgttc | 7020 |
| cagctcttgc tcttaactct tacctactat tgcccttcag aacacctggg cataagtcaa | 7080 |
| ctgaactgct aataaagaaa gccaaaagtg aatgttttct tcataaaatt aaccatgacc | 7140 |
| aaaatactcc tcttgtaata tcttctatgc aaatctcaac acttttattc ttaaactatc | 7200 |
| gcaacaccta gcacctcctc aaggactcag ccaagcagct acaagttaat actgatattt | 7260 |
| gttagagtca gaaggaaggt ccactgaagc aagctccctg ttgctcacat tttgcacaag | 7320 |
| attttggaga cttatgtaac cacccgttgc tattaacacg accattgtgc aagcccagg | 7380 |
| ctcttgagta aatttcagct ttggtttcta tttaaagata atttctaaac tctagccata | 7440 |
| cctacctcac attggaacac aaacagggta cactccaggc atgcactcag ataataagta | 7500 |
| ggatataatt acgacaatat ttggtctact tttagtaatt gtttctggca cagaaaatcc | 7560 |
| attttggagg aaaaattgca atgccttatc tttctgaggc aaatcacatt tgttcaaggc | 7620 |
| aaattataga tcctgtgaag ggaaataact taattactta aaatagaatc caatttggct | 7680 |
| gtacattttt gctgccgtct atggatctgg ggtaattcaa agtggtattc atattctact | 7740 |
| tgaggacaca attagatttc agataggaaa ttatcttgag gtttcttggt tttccctgag | 7800 |
| aagcctaatt ggatcaccct tcatttaagc atagttttac atgcactctc tcaaaggctt | 7860 |
| agtcttaaag ccacaaccat tgagacagac ttcacttgaa ccctctctat aaatatttat | 7920 |
| tctccgggag acaatagaag aaatccttgg aaggcatgct ttttcttttct catcttggct | 7980 |
| tgaaacctcc ttaccccaga ttcctctcct ttaccgtgga gtcacaacaa aaggaactga | 8040 |
| gccaaaacaa aattcccagt gtcaccagtc ttaatggata tttcattctc ccttggaaca | 8100 |
| aagatggaat agctttttt ccaaaagaaa aacaagcctt ggctctctcc ctgccccaaa | 8160 |
| agggtgcccc ccaccccat cattctctgt cccaaccctg ccatgttaga gcgtctccaa | 8220 |
| agccttccct gtgtcgtggt ttgtctgaca atgtggggaa acccagtctg ctggccagcc | 8280 |
| cttgcatgaa gtagctgatt gttccctctc ctcatccctt atgaatgggg cccttgaagt | 8340 |
| tcagtcatgt agattcagtt gtataatgaa agctaaaata tttaaattgt atgcatgctg | 8400 |
| ccaataacag catacatctg acatctaact tattaataac attaagcctg caactagggg | 8460 |
| ggaaagtgga tgttttttct tgcaaagcct ttgttttcct aaaatgacac ttgaaaattt | 8520 |
| atctccccct actgcaggct tcccagcccc cttttataat tatgcttaaa ttaaaataat | 8580 |
| gattctggga tactcttttg gggagatacc ctacaggctt tattttaata attgaactaa | 8640 |
| gtgtttgtga ctttctccta gatattgtca aatattaaat aaaggctcca taaacaattg | 8700 |
| agctgtctta ttcccagata atacccattt aggagggga aggatcc | 8747 |

<210> SEQ ID NO 26
<211> LENGTH: 568
<212> TYPE: PRT
<213> ORGANISM: Homo sapiens

<400> SEQUENCE: 26

Met Asp Val Asp Glu Gly Gln Asp Met Ser Gln Val Ser Gly Lys Glu
1               5                   10                  15

-continued

```
Ser Pro Pro Val Ser Asp Thr Pro Asp Glu Gly Asp Glu Pro Met Pro
             20                  25                  30

Val Pro Glu Asp Leu Ser Thr Thr Ser Gly Ala Gln Gln Asn Ser Lys
         35                  40                  45

Ser Asp Arg Gly Met Ala Ser Asn Val Lys Val Glu Thr Gln Ser Asp
     50                  55                  60

Glu Glu Asn Gly Arg Ala Cys Glu Met Asn Gly Glu Glu Cys Ala Glu
 65                  70                  75                  80

Asp Leu Arg Met Leu Asp Ala Ser Gly Glu Lys Met Asn Gly Ser His
                 85                  90                  95

Arg Asp Gln Gly Ser Ser Ala Leu Ser Gly Val Gly Gly Ile Arg Leu
                100                 105                 110

Pro Asn Gly Lys Leu Lys Cys Asp Ile Cys Gly Ile Val Cys Ile Gly
            115                 120                 125

Pro Asn Val Leu Met Val His Lys Arg Ser His Thr Gly Glu Arg Pro
        130                 135                 140

Phe Gln Cys Asn Gln Cys Ser Ala Leu Ser Gly Val Gly Gly Ile
145                 150                 155                 160

Arg Leu Pro Asn Gly Lys Leu Lys Cys Asp Ile Cys Gly Ile Val Cys
                165                 170                 175

Ile Gly Pro Asn Val Leu Met Val His Lys Arg Ser His Thr Gly Glu
            180                 185                 190

Arg Pro Phe Gln Cys Asn Gln Cys Gly Ala Ser Phe Thr Gln Lys Gly
        195                 200                 205

Asn Leu Leu Arg His Ile Lys Leu His Ser Gly Glu Lys Pro Phe Lys
    210                 215                 220

Cys His Leu Cys Asn Tyr Ala Cys Arg Arg Arg Asp Ala Leu Thr Gly
225                 230                 235                 240

His Leu Arg Thr His Ser Val Gly Lys Pro His Lys Cys Gly Tyr Cys
                245                 250                 255

Gly Arg Ser Tyr Lys Gln Arg Ser Ser Leu Glu Glu His Lys Glu Arg
            260                 265                 270

Cys His Asn Tyr Leu Glu Ser Met Gly Leu Pro Gly Met Tyr Pro Val
        275                 280                 285

Ile Lys Glu Glu Thr Asn His Asn Glu Met Ala Glu Asp Leu Cys Lys
290                 295                 300

Ile Gly Ala Glu Arg Ser Leu Val Leu Asp Arg Leu Ala Ser Asn Val
305                 310                 315                 320

Ala Lys Arg Lys Ser Ser Met Pro Gln Lys Phe Leu Gly Asp Lys Cys
                325                 330                 335

Leu Ser Asp Met Pro Tyr Asp Ser Ala Asn Tyr Glu Lys Glu Asp Met
            340                 345                 350

Met Thr Ser His Val Met Asp Gln Ala Ile Asn Asn Ala Ile Asn Tyr
        355                 360                 365

Leu Gly Ala Glu Ser Leu Arg Pro Leu Val Gln Thr Pro Pro Gly Ser
    370                 375                 380

Ser Glu Val Val Pro Val Ile Ser Ser Met Tyr Gln Leu His Lys Pro
385                 390                 395                 400

Pro Ser Asp Gly Pro Pro Arg Ser Asn His Ser Ala Gln Asp Ala Val
                405                 410                 415

Asp Asn Leu Leu Leu Leu Ser Lys Ala Lys Ser Val Ser Ser Glu Arg
            420                 425                 430

Glu Ala Ser Pro Ser Asn Ser Cys Gln Asp Ser Thr Asp Thr Glu Ser
```

```
            435                 440                 445
Asn Ala Glu Glu Gln Arg Ser Gly Leu Ile Tyr Leu Thr Asn His Ile
    450                 455                 460

Asn Pro His Ala Arg Asn Gly Leu Ala Leu Lys Glu Glu Gln Arg Ala
465                 470                 475                 480

Tyr Glu Val Leu Arg Ala Ala Ser Glu Asn Ser Gln Asp Ala Phe Arg
                485                 490                 495

Val Val Ser Thr Ser Gly Glu Gln Leu Lys Val Tyr Lys Cys Glu His
            500                 505                 510

Cys Arg Val Leu Phe Leu Asp His Val Met Tyr Thr Ile His Met Gly
                515                 520                 525

Cys His Gly Cys His Gly Phe Arg Asp Pro Phe Glu Cys Asn Met Cys
            530                 535                 540

Gly Tyr His Ser Gln Asp Arg Tyr Glu Phe Ser Ser His Ile Thr Arg
545                 550                 555                 560

Gly Glu His Arg Tyr His Leu Ser
                565

<210> SEQ ID NO 27
<211> LENGTH: 350
<212> TYPE: DNA
<213> ORGANISM: Homo sapiens

<400> SEQUENCE: 27
ccagagagta agaataggag gagaaaacat gctgcagatg taggcggggc ccagattgta      60
gacagcatag aaataatttt gggcttttcc tgttaaattc ctctagcttc taggatacat     120
tttttttaac ttttgtcttt gagataattt tagatttaca gaagagttgc aaaaagagta     180
gagagagttc ctgtacaccc ttcacccagc ttcctctact gctaacatct tacataatca     240
tagtttcaac ctgagaaatt agcatggggt acagtcctat taatgaaacc ccaggcttta     300
ttcagatttc accaggtttt cagtaacatc ctttatctgt ttcagaattt              350

<210> SEQ ID NO 28
<211> LENGTH: 850
<212> TYPE: DNA
<213> ORGANISM: Homo sapiens

<400> SEQUENCE: 28
gaattccggc aaaatgcatg acagtaacaa tgtggagaaa gacattacac catctgaatt      60
gcctgcaaac ccaggttgtc tgcattcaaa agagcattct attaaagcta ccttaatttg     120
gcgcttattt ttcttaatca tgtttctgac aatcatagtg tgtggaatgg ttgctgcttt     180
aagcgcaata agagctaact gccatcaaga gccatcagta tgtcttcaag ctgcatgccc     240
agaaagctgg attggttttc aaagaaagtg tttctatttt tctgatgaca ccaagaactg     300
gacatcaagt cagaggtttt gtgactcaca agatgctgat cttgctcagg ttgaaagctt     360
ccaggaactg aatttcctgt tgagatataa aggcccatct gatcactgga ttgggctgag     420
cagagaacaa ggccaaccat ggaaatggat aaatggtact gaatggacaa gacagtttcc     480
tatcctggga gcaggagagt gtgcctattt gaatgacaaa ggtgccagta gtgccaggca     540
ctacacagag aggaagtgga tttgttccaa atcagatata catgtctaga tgttacagca     600
aagccccaac taatctttag aagcatattg gaactgataa ctccatttta aaatgagcaa     660
agaatttatt tcttatacca acaggtatat gaaaatatgc tcaatatcac taataactgg     720
gaaaatacaa atcaaaatca tagtaaaata ttacctgttt tcatggtgct aatattacct     780
```

```
gttctcccac tgctaatgac atacccgaga atgagtaatt tataaataaa agagatttaa    840
ttgaaaaaaa                                                           850
```

<210> SEQ ID NO 29
<211> LENGTH: 191
<212> TYPE: PRT
<213> ORGANISM: Homo sapiens

<400> SEQUENCE: 29

```
Met His Asp Ser Asn Asn Val Glu Lys Asp Ile Thr Pro Ser Glu Leu
 1               5                  10                  15

Pro Ala Asn Pro Gly Cys Leu His Ser Lys Glu His Ser Ile Lys Ala
            20                  25                  30

Thr Leu Ile Trp Arg Leu Phe Phe Leu Ile Met Phe Leu Thr Ile Ile
        35                  40                  45

Val Cys Gly Met Val Ala Ala Leu Ser Ala Ile Arg Ala Asn Cys His
    50                  55                  60

Gln Glu Pro Ser Val Cys Leu Gln Ala Ala Cys Pro Glu Ser Trp Ile
65                  70                  75                  80

Gly Phe Gln Arg Lys Cys Phe Tyr Phe Ser Asp Asp Thr Lys Asn Trp
                85                  90                  95

Thr Ser Ser Gln Arg Phe Cys Asp Ser Gln Asp Ala Asp Leu Ala Gln
            100                 105                 110

Val Glu Ser Phe Gln Glu Leu Asn Phe Leu Leu Arg Tyr Lys Gly Pro
        115                 120                 125

Ser Asp His Trp Ile Gly Leu Ser Arg Glu Gln Gly Gln Pro Trp Lys
    130                 135                 140

Trp Ile Asn Gly Thr Glu Trp Thr Arg Gln Phe Pro Ile Leu Gly Ala
145                 150                 155                 160

Gly Glu Cys Ala Tyr Leu Asn Asp Lys Gly Ala Ser Ser Ala Arg His
                165                 170                 175

Tyr Thr Glu Arg Lys Trp Ile Cys Ser Lys Ser Asp Ile His Val
            180                 185                 190
```

<210> SEQ ID NO 30
<211> LENGTH: 558
<212> TYPE: DNA
<213> ORGANISM: Homo sapiens
<220> FEATURE:
<221> NAME/KEY: modified_base
<222> LOCATION: (1)..(558)
<223> OTHER INFORMATION: n = g, a, c or t

<400> SEQUENCE: 30

```
ccatgggatg gctcttctga ccattggggg ccaggccagg ccaggccagg cttagggcag    60
caaggaccag gccaaagggg cagggcctcc tttggagggg ttgagggta catcctcggc    120 tggtgtttgc atccaggggt ccagcaggat ctcttccagt gagggtcggg aagaaggttt    180
gggggccagg caccggcgga ttagggcaca gcaatcttgg ggaaaacatg gcttgggaa    240 gtggagctca gcttccagaa tctcctggtc cctctcaaag gaatgtccc cacacaccat    300 gtcatagagg aggatgccca gtgaccagac agtggccggg agtgcatggt actggtgtcg    360
agagatccac tctggggggc tgtacaccct tgtcccatca agtcagtgt agggttcatc    420 atgaagcagg gcaccagaac caaaatcaat gagtttggca cagccacggc gtaggtctat    480
caggatgntc tcatccttga tgtcacgatg gacaactnca cgggaaatgg cagtgctgga    540
```

```
tggctgccac tactttgg                                              558
```

<210> SEQ ID NO 31
<211> LENGTH: 2088
<212> TYPE: DNA
<213> ORGANISM: Homo sapiens

<400> SEQUENCE: 31

```
gaattcggca cgagcgcgcg gcgaatctca acgctgcgcc gtctgcgggc gcttccgggc    60
caccagtttc tctgctttcc accctggcgc ccccagccc tggctcccca gctgcgctgc    120
cccgggcgtc cacgccctgc gggcttagcg ggttcagtgg gctcaatctg cgcagcgcca    180
cctccatgtt gaccaagcct ctacaggggc ctcccgcgcc ccccgggacc cccacgccgc    240
cgccaggagg caaggatcgg gaagcgttcg aggccgagta tcgactcggc ccctcctgg    300
gtaaggggg ctttggcacc gtcttcgcag gacaccgcct cacagatcga ctccaggtgg    360
ccatcaaagt gattccccgg aatcgtgtgc tgggctggtc ccccttgtca gactcagtca    420
catgcccact cgaagtcgca ctgctatgga aagtgggtgc aggtggtggg caccctggcg    480
tgatccgcct gcttgactgg tttgagacac aggaaggctt catgctggtc ctcgagcggc    540
cttttgcccgc ccaggatctc tttgactata tcacagagaa gggcccactg ggtgaaggcc    600
caagccgctg cttctttggc caagtagtgg cagccatcca gcactgccat tcccgtggag    660
ttgtccatcg tgacatcaag gatgagaaca tcctgataga cctacgccgt ggctgtgcca    720
aactcattga ttttggttct ggtgccctgc ttcatgatga cccctacact gactttgatg    780
ggacaagggt gtacagcccc ccagagtgga tctctcgaca ccagtaccat gcactcccgg    840
ccactgtctg gtcactgggc atcctcctct atgacatggt gtgtgggac attcccttg    900
agagggacca ggagattctg gaagctgagc tccacttccc agcccatgtc tccccagact    960
gctgtgccct aatccgccgg tgcctggccc ccaaaccttc ttcccgaccc tcactggaag    1020
agatcctgct ggaccctgg atgcaaacac cagccgagga tgttaccccct caaccccctcc    1080
aaaggaggcc ctgccccttt ggcctggtcc ttgctaccct aagcctggcc tggcctggcc    1140
tggcccccaa tggtcagaag agccatccca tggccatgtc acaggataag atggacattt    1200
gttgacttgg ttttacaggt cattaccagt cattaaagtc cagtattact aaggtaaggg    1260
attgaggatc aggggttaga agacataaac caagtttgcc cagttccctt cccaatccta    1320
caaaggagcc ttcctcccag aacctgtggt ccctgatttt ggagggggaa cttcttgctt    1380
ctcattttgc taaggaagtt tattttggtg aagttgttcc catttgagc cccgggactc    1440
ttatttgat gatgtgtcac cccacattgg cacctcctac taccaccaca caaacttagt    1500
tcatatgctt ttacttgggc aagggtgctt tccttccaat accccagtag ctttatttt    1560
agtaaaggga cccttttcccc tagcctaggg tcccatattg ggtcaagctg cttacctgcc    1620
tcagcccagg attttttatt ttgggggagg taatgccctg ttgttacccc aaggcttctt    1680
tttttttttt ttttttttg ggtgagggga ccctactttg ttatcccaag tgctcttatt    1740
ctggtgagaa gaaccttaat tccataaattt gggaaggaat ggaagatgga caccaccgga    1800
caccaccaga caataggatg ggatggatgg tttttgggg gatgggctag gggaaataag    1860
gcttgctgtt tgttttcctg gggcgctccc tccaattttg cagattttg caacctcctc    1920
ctgagccggg attgtccaat tactaaaatg taaataatca cgtattgtgg ggaggggagt    1980
tccaagtgtg ccctccttttt ttttcctgcc tggattattt aaaaagccat gtgtggaaac    2040
ccactattta ataaaagtaa tagaatcaga aaaaaaaaa aaaaaaa         2088
```

```
<210> SEQ ID NO 32
<211> LENGTH: 334
<212> TYPE: PRT
<213> ORGANISM: Homo sapiens

<400> SEQUENCE: 32

Met Leu Thr Lys Pro Leu Gln Gly Pro Pro Ala Pro Gly Thr Pro
  1               5                  10                  15

Thr Pro Pro Gly Gly Lys Asp Arg Glu Ala Phe Glu Ala Glu Tyr
                 20                  25                  30

Arg Leu Gly Pro Leu Leu Gly Lys Gly Gly Phe Gly Thr Val Phe Ala
             35                  40                  45

Gly His Arg Leu Thr Asp Arg Leu Gln Val Ala Ile Lys Val Ile Pro
         50                  55                  60

Arg Asn Arg Val Leu Gly Trp Ser Pro Leu Ser Asp Ser Val Thr Cys
 65                  70                  75                  80

Pro Leu Glu Val Ala Leu Leu Trp Lys Val Gly Ala Gly Gly His
                 85                  90                  95

Pro Gly Val Ile Arg Leu Leu Asp Trp Phe Glu Thr Gln Glu Gly Phe
                100                 105                 110

Met Leu Val Leu Glu Arg Pro Leu Pro Ala Gln Asp Leu Phe Asp Tyr
            115                 120                 125

Ile Thr Glu Lys Gly Pro Leu Gly Glu Gly Pro Ser Arg Cys Phe Phe
            130                 135                 140

Gly Gln Val Val Ala Ala Ile Gln His Cys His Ser Arg Gly Val Val
145                 150                 155                 160

His Arg Asp Ile Lys Asp Glu Asn Ile Leu Ile Asp Leu Arg Arg Gly
                165                 170                 175

Cys Ala Lys Leu Ile Asp Phe Gly Ser Gly Ala Leu Leu His Asp Glu
                180                 185                 190

Pro Tyr Thr Asp Phe Asp Gly Thr Arg Val Tyr Ser Pro Pro Glu Trp
                195                 200                 205

Ile Ser Arg His Gln Tyr His Ala Leu Pro Ala Thr Val Trp Ser Leu
            210                 215                 220

Gly Ile Leu Leu Tyr Asp Met Val Cys Gly Asp Ile Pro Phe Glu Arg
225                 230                 235                 240

Asp Gln Glu Ile Leu Glu Ala Glu Leu His Phe Pro Ala His Val Ser
                245                 250                 255

Pro Asp Cys Cys Ala Leu Ile Arg Arg Cys Leu Ala Pro Lys Pro Ser
                260                 265                 270

Ser Arg Pro Ser Leu Glu Glu Ile Leu Leu Asp Pro Trp Met Gln Thr
            275                 280                 285

Pro Ala Glu Asp Val Thr Pro Gln Pro Leu Gln Arg Arg Pro Cys Pro
            290                 295                 300

Phe Gly Leu Val Leu Ala Thr Leu Ser Leu Ala Trp Pro Gly Leu Ala
305                 310                 315                 320

Pro Asn Gly Gln Lys Ser His Pro Met Ala Met Ser Gln Gly
                325                 330

<210> SEQ ID NO 33
<211> LENGTH: 1215
<212> TYPE: DNA
<213> ORGANISM: Homo sapiens

<400> SEQUENCE: 33
```

```
gggggacatt gagtatcctt tgttaccctc aggagatcct gaaaccagtc ccccatggat      60
actgagggct gactgtatag tcctatcctc acgaacttt cattctaatg ggggaagact      120
gactataaac aaaatatatg taataggtgg tggtaagtac cgtggagaag taacaaatgg     180
ggcaaagtga gttatacagc tccattctta gaaaccttgg agtacttttc ttagtttata    240
ctcgtggtgg tttccttttg tctcctttat tacatgggac tctgacatgt gcccatagct    300
agggtgacag taggatctac ccgatagtag ggtggcagta ggatctaccc aaaaagcgtc    360
ctgctgatac aggaccaaag catcctgttg ttctcgagcc tataaaaaga gctaatggtg    420
ttgcttctct taactgtggc ctcctacact gtgttttgga tgattggtga tgtcttggat    480
attctgtttc tttggaactt tgaatataca acactttact agggaattag caatggaagc    540
agagcaaaga tgtacagagg aaacaatgcg taactctgat ggaattgaag tcatgaggca    600
gcagagagct taaattacag ctttaaaaat ttttattttt tagagggaat ttacttggga    660
gtaacagcag taatagttaa cggagccaga atgcttgagt catataattg caaagcagag    720
ttgggagcaa cagatgctaa agagtagttg ctgtagttcc tctttgggtc gtaggagcag    780
ttgtcatatt actatatagc tactgcatga agaagagttc ttagtgaggc ctgggtgatc    840
agctcttctt agtattctgt gtgaccccat ttgacctttt aacaaatccc taagtaaata    900
aatagcccct caggaaaaact aagttttttct ctgctgtttt tttgcttgag agagctataa   960
ctgtaataga cttatatttc tgaacatttt agtgcttgcc aatatttggt aatatttatg   1020
tttcctatat ttgtaatgaa cattcttctt ccggtacatt ttttgttaaa ttattgtttg   1080
atggataaaa gttcacctt tattgtataa aattgactga gattaattta tacacattga    1140
caatgggtaa atagaatttt tcagattatt aaaagctgaa ggatgcccac gtaagcaaaa   1200
aaaaaaaaaa aaaaa                                                     1215

<210> SEQ ID NO 34
<211> LENGTH: 3144
<212> TYPE: DNA
<213> ORGANISM: Homo sapiens

<400> SEQUENCE: 34
tcctctttcc gtgcgcgagt gcacagctcc ggaggcccga gccgaccctg gggcgtccgg      60
tccggtggtc ttgcagcctc caaaccccga gtgctatacc gaactgcgcg ccaagggtgg    120
gagagctgac ggcctgggcc acccttcttc cttcactggg caggctttga ggtgcttgtc    180
ggtctggact gatgaaaatc catatgacct gaaagatgtc tgaaaattcc agtgacagtg    240
attcatcttg tggttggact gtcatcagtc atgagggtc agatatagaa atgttgaatt     300
ctgtgacccc cactgacagc tgtgagcccg cccagaatg ttcatcttta gagcaagagg     360
agcttcaagc attgcagata gagcaaggag aaagcagcca aaatggcaca gtgcttatgg    420
aagaaactgc ttatccagct ttggaggaaa ccagctcaac aattgaggca gaggaacaaa    480
agatacccga agacagtatc tatattggaa ctgccagtga tgattctgat attgttaccc    540
ttgagccacc taagttagaa gaaattggaa atcaagaagt tgtcattgtt gaagaagcac    600
agagttcaga agactttaac atgggctctt cctctagcag ccagtatact ttctgtcagc    660
cagaaactgt atttcatctc cagcctagtg acgatgaatc aagtagtgat gaaaccagta    720
atcagcccag tcctgccttt agacgacgcc gtgctaggaa gagaccgtt tctgcttcag     780 aatctgaaga ccggctagtt gctgaacaag aaactgaacc ttctaaggag ttgagtaaac    840
```

```
gtcagttcag tagtggtctc aataagtgtg ttatacttgc tttggtgatt gcaatcagca      900
tgggatttgg ccatttctat ggcacaattc agattcagaa gcgtcaacag ttagtcagaa      960
agatacatga agatgaattg aatgatatga aggattatct ttcccagtgt caacaggaac     1020
aagaatcttt tatagattat aagtcattga aagaaaatct tgcaaggtgt tggacactta     1080
ctgaagcaga gaagatgtcc tttgaaactc agaaaacgaa ccttgctaca gaaaatcagt     1140
atttaagagt atccctggag aaggaagaaa aagccttatc ctcattacag gaagagttaa     1200
acaaactaag agaacagatt agaatattgg aagataaagg acaagtact gaattagtta      1260
aagaaaatca gaaacttaag cagcatttgg aagaggaaaa gcagaaaaaa cacagctttc     1320
ttagtcaaag ggagactctg ttgacagaag caaagatgct aaagagagaa ctggagagag     1380
aacgactagt aactacggct ttaagggggg aactccagca gttaagtggt agtcagttac     1440
atggcaagtc agattctccc aatgtatata ctgaaaaaaa ggaaatagca atcttacggg     1500
aaagactcac tgagctggaa cggaagctaa ccttcgaaca gcagcgttct gatttgtggg     1560
aaagattgta tgttgaggca aaagatcaaa atggaaaaca aggaacagat ggaaaaaaga     1620
aaggggcag aggaagccac agggctaaaa ataagtcaaa ggaacatttt tggggttcag      1680
ttaaggaaac atttgatgcc atgaagaatt ctaccaagga gtttgtaagg catcataaag     1740
agaaaattaa gcaggctaaa gaagctgtga aggaaaatct gaaaaaattc tcagattcag     1800
ttaaatccac tttcagacac tttaaagata ccaccaagaa tatctttgat gaaagggta     1860
ataaagatt tggtgctaca aaagaagcag ctgaaaaacc aagaacagtt tttagtgact     1920
atttacatcc acagtataag gcacctacag aaaaccattc aaggccctac tatgcaaaaa     1980
gatggaagga agaaaagcca gttcacttta agaattcag aaaaaataca aattcaaaga     2040
aatgcagtcc tgggcatgat tgtagagaaa attctcattc tttcagaaag gcttgttctg     2100
gtgtatttga ttgtgctcaa caagagtcca tgagccttt taacacagtg gtgatcccta     2160
taaggatgga tgaatttaga cagataattc aaaggtacat gttaaagaa ctggatactt      2220
tttgtcgctg gaacgaactt gatcagttca tcaataagtt tttcctaaac ggtgtcttta     2280
tacatgatca gaagctcttc actgactttg ttaatgatgt taagattatc ttaggaaaca     2340
tgaaggaata tgaagtagat aatgatggag tatttgagaa gttggatgaa tatatatata     2400
gacacttctt tggtcacact ttttcccctc catatggacc caggtcggtt tacataaaac     2460
cgtgtcatta cagtagtttg taacatttgt agattggata cgatttttat gatttgatga     2520
gtttcttgta aggttaccgt ttctaagagt tgtgctttat ggccactgag agaattcaga     2580
ataaattgaa agatggagtc taaaaattat tagctgttac aaatggaaca atttcattat     2640
aacgtgatca ctttgacttg agcaaatggt ttaattttta tcttaaaatc agttaagaat     2700
atataaaatc ctacctttgg ccaagtttgt ttcttttcat tatagtttat atgaaaagat     2760
caccttaagt gaaattattt tccttatttt cctttaatct tttatgtatt tattcacttc     2820
tggaagctag gaatgagcaa cacaaatttt actctgaagt cagaagagct catatatata     2880
attctaatgt cccacctatg tccattccat gtaccagctt agttatatac tagtcacata     2940
attatctttg ataaaggtag aggcacaaag aggcaaacta acaagtcaaa ttctaatgtg     3000
tgtacttcat aataatttt tatccatttt catcttcttt atctttatat tctgtaacat      3060
gaaacttacc taatcttcaa atgttagctt catttttac ctttgaaata cttaatcttt      3120
ctgaataaat ataatggtct ataa                                            3144
```

```
<210> SEQ ID NO 35
<211> LENGTH: 755
<212> TYPE: PRT
<213> ORGANISM: Homo sapiens

<400> SEQUENCE: 35

Met Ser Glu Asn Ser Ser Asp Ser Asp Ser Ser Cys Gly Trp Thr Val
1               5                   10                  15

Ile Ser His Glu Gly Ser Asp Ile Glu Met Leu Asn Ser Val Thr Pro
            20                  25                  30

Thr Asp Ser Cys Glu Pro Ala Pro Glu Cys Ser Ser Leu Glu Gln Glu
        35                  40                  45

Glu Leu Gln Ala Leu Gln Ile Glu Gln Gly Ser Ser Gln Asn Gly
    50                  55                  60

Thr Val Leu Met Glu Glu Thr Ala Tyr Pro Ala Leu Glu Glu Thr Ser
65              70                  75                  80

Ser Thr Ile Glu Ala Glu Glu Gln Lys Ile Pro Glu Asp Ser Ile Tyr
                85                  90                  95

Ile Gly Thr Ala Ser Asp Asp Ser Asp Ile Val Thr Leu Glu Pro Pro
            100                 105                 110

Lys Leu Glu Glu Ile Gly Asn Gln Glu Val Val Ile Val Glu Glu Ala
        115                 120                 125

Gln Ser Ser Glu Asp Phe Asn Met Gly Ser Ser Ser Ser Gln Tyr
    130                 135                 140

Thr Phe Cys Gln Pro Glu Thr Val Phe Ser Ser Gln Pro Ser Asp Asp
145                 150                 155                 160

Glu Ser Ser Ser Asp Glu Thr Ser Asn Gln Pro Ser Pro Ala Phe Arg
                165                 170                 175

Arg Arg Arg Ala Arg Lys Lys Thr Val Ser Ala Ser Glu Ser Glu Asp
            180                 185                 190

Arg Leu Val Ala Glu Gln Glu Thr Glu Pro Ser Lys Glu Leu Ser Lys
        195                 200                 205

Arg Gln Phe Ser Ser Gly Leu Asn Lys Cys Val Ile Leu Ala Leu Val
    210                 215                 220

Ile Ala Ile Ser Met Gly Phe Gly His Phe Tyr Gly Thr Ile Gln Ile
225                 230                 235                 240

Gln Lys Arg Gln Gln Leu Val Arg Lys Ile His Glu Asp Glu Leu Asn
                245                 250                 255

Asp Met Lys Asp Tyr Leu Ser Gln Cys Gln Gln Glu Gln Glu Ser Phe
            260                 265                 270

Ile Asp Tyr Lys Ser Leu Lys Glu Asn Leu Ala Arg Cys Trp Thr Leu
        275                 280                 285

Thr Glu Ala Glu Lys Met Ser Phe Glu Thr Lys Thr Asn Leu Ala
    290                 295                 300

Thr Glu Asn Gln Tyr Leu Arg Val Ser Leu Glu Lys Glu Lys Ala
305                 310                 315                 320

Leu Ser Ser Leu Gln Glu Glu Leu Asn Lys Leu Arg Glu Gln Ile Arg
                325                 330                 335

Ile Leu Glu Asp Lys Gly Thr Ser Thr Glu Leu Val Lys Glu Asn Gln
            340                 345                 350

Lys Leu Lys Gln His Leu Glu Glu Lys Gln Lys His Ser Phe
        355                 360                 365

Leu Ser Gln Arg Glu Thr Leu Leu Thr Glu Ala Lys Met Leu Lys Arg
    370                 375                 380
```

```
Glu Leu Glu Arg Glu Arg Leu Val Thr Thr Ala Leu Arg Gly Glu Leu
385                 390                 395                 400

Gln Gln Leu Ser Gly Ser Gln Leu His Gly Lys Ser Asp Ser Pro Asn
            405                 410                 415

Val Tyr Thr Glu Lys Lys Glu Ile Ala Ile Leu Arg Glu Arg Leu Thr
        420                 425                 430

Glu Leu Glu Arg Lys Leu Thr Phe Glu Gln Gln Arg Ser Asp Leu Trp
        435                 440                 445

Glu Arg Leu Tyr Val Glu Ala Lys Asp Gln Asn Gly Lys Gln Gly Thr
450                 455                 460

Asp Gly Lys Lys Lys Gly Gly Arg Gly Ser His Arg Ala Lys Asn Lys
465                 470                 475                 480

Ser Lys Glu Thr Phe Leu Gly Ser Val Lys Glu Thr Phe Asp Ala Met
            485                 490                 495

Lys Asn Ser Thr Lys Glu Phe Val Arg His His Lys Glu Lys Ile Lys
            500                 505                 510

Gln Ala Lys Glu Ala Val Lys Glu Asn Leu Lys Phe Ser Asp Ser
        515                 520                 525

Val Lys Ser Thr Phe Arg His Phe Lys Asp Thr Thr Lys Asn Ile Phe
530                 535                 540

Asp Glu Lys Gly Asn Lys Arg Phe Gly Ala Thr Lys Glu Ala Ala Glu
545                 550                 555                 560

Lys Pro Arg Thr Val Phe Ser Asp Tyr Leu His Pro Gln Tyr Lys Ala
            565                 570                 575

Pro Thr Glu Asn His Ser Arg Pro Tyr Tyr Ala Lys Arg Trp Lys Glu
        580                 585                 590

Glu Lys Pro Val His Phe Lys Glu Phe Arg Lys Asn Thr Asn Ser Lys
        595                 600                 605

Lys Cys Ser Pro Gly His Asp Cys Arg Glu Asn Ser His Ser Phe Arg
610                 615                 620

Lys Ala Cys Ser Gly Val Phe Asp Cys Ala Gln Gln Glu Ser Met Ser
625                 630                 635                 640

Leu Phe Asn Thr Val Val Ile Pro Ile Arg Met Asp Glu Phe Arg Gln
            645                 650                 655

Ile Ile Gln Arg Tyr Met Leu Lys Glu Leu Asp Thr Phe Cys Arg Trp
        660                 665                 670

Asn Glu Leu Asp Gln Phe Ile Asn Lys Phe Phe Leu Asn Gly Val Phe
            675                 680                 685

Ile His Asp Gln Lys Leu Phe Thr Asp Phe Val Asn Asp Val Lys Ile
        690                 695                 700

Ile Leu Gly Asn Met Lys Glu Tyr Glu Val Asp Asn Asp Gly Val Phe
705                 710                 715                 720

Glu Lys Leu Asp Glu Tyr Ile Tyr Arg His Phe Gly His Thr Phe
            725                 730                 735

Ser Pro Pro Tyr Gly Pro Arg Ser Val Tyr Ile Lys Pro Cys His Tyr
            740                 745                 750

Ser Ser Leu
        755

<210> SEQ ID NO 36
<211> LENGTH: 558
<212> TYPE: DNA
<213> ORGANISM: Homo sapiens
<220> FEATURE:
<221> NAME/KEY: modified_base
```

```
<222> LOCATION: (1)..(558)
<223> OTHER INFORMATION: n = g, a, c or t

<400> SEQUENCE: 36
ccatgggatg gctcttctga ccattggggg ccaggccagg ccaggccagg cttagggcag    60
caaggaccag gccaaagggg cagggcctcc tttggagggg ttgagggggta catcctcggc   120 tggtgtttgc atccagggggt ccagcaggat ctcttccagt gagggtcggg aagaaggttt   180 ggggggccagg caccggcgga ttagggcaca gcaatcttgg ggaaaacatg ggcttgggaa   240
gtggagctca gcttccagaa tctcctggtc cctctcaaag ggaatgtccc cacacaccat   300
gtcatagagg aggatgccca gtgaccagac agtggccggg agtgcatggt actggtgtcg   360
agagatccac tctgggggggc tgtacaccct tgtcccatca aagtcagtgt agggttcatc   420
atgaagcagg gcaccagaac caaaatcaat gagtttggca cagccacggc gtaggtctat   480
caggatgntc tcatccttga tgtcacgatg acaactnca cgggaaatgg cagtgctgga   540
tggctgccac tactttgg                                                 558

<210> SEQ ID NO 37
<211> LENGTH: 86
<212> TYPE: PRT
<213> ORGANISM: Homo sapiens
<220> FEATURE:
<221> NAME/KEY: MOD_RES
<222> LOCATION: (1)..(86)
<223> OTHER INFORMATION: Xaa = any amino acid

<400> SEQUENCE: 37

Gln Val Val Ala Xaa Ile Gln His Cys His Ser Arg Gly Val Val His
 1               5                   10                  15

Arg Asp Ile Lys Asp Glu Asn Ile Leu Ile Asp Leu Arg Arg Gly Cys
                20                  25                  30

Ala Lys Leu Ile Asp Phe Gly Ser Gly Ala Leu Leu His Asp Glu Pro
            35                  40                  45

Tyr Thr Asp Phe Asp Gly Thr Arg Val Tyr Ser Pro Pro Glu Trp Ile
        50                  55                  60

Ser Arg His Gln Tyr His Ala Leu Pro Ala Thr Val Trp Ser Leu Gly
65                  70                  75                  80

Ile Xaa Leu Tyr Asp Met
                85

<210> SEQ ID NO 38
<211> LENGTH: 584
<212> TYPE: DNA
<213> ORGANISM: Homo sapiens
<220> FEATURE:
<221> NAME/KEY: modified_base
<222> LOCATION: (1)..(584)
<223> OTHER INFORMATION: n = g, a, c or t

<400> SEQUENCE: 38
aaataatcca ggcaggagaa gagaggaggg cacacttgga actcccctcc ccacaatacg    60
tgattattta catttttagta attggacaat cccggctcag gaggaggttg caagaatctg   120
caaaagttgg agggagcgcc ccaggagaac aaacagcaag ccttatttcc cctagcccat   180 ccccaaaaa accatccatc ccatcctagt gtctggtggt gtcggtggt gtccatcttc     240 cattccttcc caaattatgg aagtaaggtt cttctcacca gaataagagc acttgggata   300
acagagtagg gtcccctcac ccaaaaaaaa aaaaaaaan gaagccttgg ggtaacaaca   360
```

| | |
|---|---|
| gggcattacc tcccccagaa taaagaatcc tgggctgagg caggtaagca gcttgaccca | 420 |
| atatgggacc ctaggctagg ggaaagggtc cctttactaa aataaaagct actgggtat | 480 |
| tggaaggaaa gcacccttgc ccaagtaaga gcatatgaac taagtttgng tggnggtagt | 540 |
| aggaggngcc aatgtggggt gacacatcat cagaataaga gtcc | 584 |

<210> SEQ ID NO 39
<211> LENGTH: 2052
<212> TYPE: DNA
<213> ORGANISM: Homo sapiens

<400> SEQUENCE: 39

| | |
|---|---|
| cgcgcgcggc gaatctcaac gctgcgccgt ctgcgggcgc ttccgggcca ccagtttctc | 60 |
| tgctttccac cctggcgccc ccagccctg gctcccagc tgcgctgccc cgggcgtcca | 120 |
| cgccctgcgg gcttagcggg ttcagtgggc tcaatctgcg cagcgccacc tccatgttga | 180 |
| ccaagcctct acaggggcct cccgcgcccc ccgggacccc cacgccgccg ccaggaggca | 240 |
| aggatcggga agcgttcgag gccgagtatc gactcggccc cctcctgggt aagggggct | 300 |
| ttggcaccgt cttcgcagga caccgcctca cagatcgact ccaggtggcc atcaaagtga | 360 |
| ttccccgaa tcgtgtgctg ggctggtccc ccttgtcaga ctcagtcaca tgcccactcg | 420 |
| aagtcgcact gctatggaaa gtgggtgcag gtggtgggca ccctggcgtg atccgcctgc | 480 |
| ttgactggtt tgagacacag gagggcttca tgctggtcct cgagcggcct ttgcccgccc | 540 |
| aggatctctt tgactatatc acagagaagg gcccactggg tgaaggccca agccgctgct | 600 |
| tctttggcca agtagtggca gccatccagc actgccattc ccgtggagtt gtccatcgtg | 660 |
| acatcaagga tgagaacatc ctgatagacc tacgccgtgg ctgtgccaaa ctcattgatt | 720 |
| ttggttctgg tgccctgctt catgatgaac cctacactga cttgatggg acaagggtgt | 780 |
| acagccccc agagtggatc tctcgacacc agtaccatgc actcccggcc actgtctggt | 840 |
| cactgggcat cctcctctat gacatggtgt gtggggacat tccctttgag agggaccagg | 900 |
| agattctgga agctgagctc cacttcccag cccatgtctc cccagactgc tgtgccctaa | 960 |
| tccgccggtg cctggccccc aaaccttctt cccgaccctc actggaagag atcctgctgg | 1020 |
| acccctggat gcaaacacca gccgaggatg taccctcaa cccctccaaa ggaggccctg | 1080 |
| ccctttggc ctggtccttg ctaccctaag cctggcctgg cctggcctgg ccccaatgg | 1140 |
| tcagaagagc catcccatgg ccatgtcaca gggatagatg gacatttgtt gacttggttt | 1200 |
| tacaggtcat taccagtcat taaagtccag tattactaag gtaagggatt gaggatcagg | 1260 |
| ggttagaaga cataaaccaa gtctgcccag ttcccttccc aatcctacaa aggagccttc | 1320 |
| ctcccagaac ctgtggtccc tgattctgga gggggaactt cttgcttctc attttgctaa | 1380 |
| ggaagtttat tttggtgaag ttgttcccat tctgagcccc gggactctta ttctgatgat | 1440 |
| gtgtcacccc acattggcac ctcctactac caccacacaa acttagttca tatgctctta | 1500 |
| cttgggcaag ggtgctttcc ttccaatacc ccagtagctt ttattttagt aaagggaccc | 1560 |
| tttcccctag cctagggtcc catattgggt caagctgctt acctgcctca gcccaggatt | 1620 |
| ctttattctg ggggaggtaa tgccctgttg ttacccaag gcttcttttt ttttttttt | 1680 |
| tgggtgaggg gaccctactc tgttatccca agtgctctta ttctggtgag aagaacctta | 1740 |
| cttccataat ttgggaagga atggaagatg acaccaccg gacaccacca gacactagga | 1800 |
| tgggatggat ggttttttgg gggatgggct aggggaaata aggcttgctg tttgttctcc | 1860 |
| tggggcgctc cctccaactt ttgcagattc ttgcaacctc ctcctgagcc gggattgtcc | 1920 |

-continued

```
aattactaaa atgtaaataa tcacgtattg tggggagggg agttccaagt gtgccctcct    1980
ctcttctcct gcctggatta tttaaaaagc catgtgtgga aacccactat ttaataaaag    2040
taatagaatc ag                                                       2052
```

<210> SEQ ID NO 40
<211> LENGTH: 311
<212> TYPE: PRT
<213> ORGANISM: Homo sapiens

<400> SEQUENCE: 40

```
Met Leu Thr Lys Pro Leu Gln Gly Pro Pro Ala Pro Pro Gly Thr Pro
 1               5                  10                  15

Thr Pro Pro Gly Gly Lys Asp Arg Glu Ala Phe Glu Ala Glu Tyr
                20                  25                  30

Arg Leu Gly Pro Leu Leu Gly Lys Gly Gly Phe Gly Thr Val Phe Ala
                35                  40                  45

Gly His Arg Leu Thr Asp Arg Leu Gln Val Ala Ile Lys Val Ile Pro
            50                  55                  60

Arg Asn Arg Val Leu Gly Trp Ser Pro Leu Ser Asp Ser Val Thr Cys
 65                 70                  75                  80

Pro Leu Glu Val Ala Leu Leu Trp Lys Val Gly Ala Gly Gly His
                85                  90                  95

Pro Gly Val Ile Arg Leu Leu Asp Trp Phe Glu Thr Gln Glu Gly Phe
                100                 105                 110

Met Leu Val Leu Glu Arg Pro Leu Pro Ala Gln Asp Leu Phe Asp Tyr
                115                 120                 125

Ile Thr Glu Lys Gly Pro Leu Gly Glu Gly Pro Ser Arg Cys Phe Phe
            130                 135                 140

Gly Gln Val Val Ala Ala Ile Gln His Cys His Ser Arg Gly Val Val
145                 150                 155                 160

His Arg Asp Ile Lys Asp Glu Asn Ile Leu Ile Asp Leu Arg Arg Gly
                165                 170                 175

Cys Ala Lys Leu Ile Asp Phe Gly Ser Gly Ala Leu Leu His Asp Glu
                180                 185                 190

Pro Tyr Thr Asp Phe Asp Gly Thr Arg Val Tyr Ser Pro Pro Glu Trp
                195                 200                 205

Ile Ser Arg His Gln Tyr His Ala Leu Pro Ala Thr Val Trp Ser Leu
            210                 215                 220

Gly Ile Leu Leu Tyr Asp Met Val Cys Gly Asp Ile Pro Phe Glu Arg
225                 230                 235                 240

Asp Gln Glu Ile Leu Glu Ala Glu Leu His Phe Pro Ala His Val Ser
                245                 250                 255

Pro Asp Cys Cys Ala Leu Ile Arg Arg Cys Leu Ala Pro Lys Pro Ser
                260                 265                 270

Ser Arg Pro Ser Leu Glu Glu Ile Leu Leu Asp Pro Trp Met Gln Thr
                275                 280                 285

Pro Ala Glu Asp Val Pro Leu Asn Pro Ser Lys Gly Gly Pro Ala Pro
                290                 295                 300

Leu Ala Trp Ser Leu Leu Pro
305                 310
```

<210> SEQ ID NO 41
<211> LENGTH: 105
<212> TYPE: DNA

<213> ORGANISM: Homo sapiens
<220> FEATURE:
<221> NAME/KEY: modified_base
<222> LOCATION: (1)..(105)
<223> OTHER INFORMATION: n = g, a, c or t

<400> SEQUENCE: 41

```
ctggaactgc acntagtccc agctctcctc ggccgcggtc tcctcggggn tggtgccgta    60
cttttggatg gttttctcta cnacntcccg caagcttccn tccag                  105
```

<210> SEQ ID NO 42
<211> LENGTH: 1125
<212> TYPE: DNA
<213> ORGANISM: Homo sapiens

<400> SEQUENCE: 42

```
gtctccccca ctgtcagcac ctcttctgtg tggtgagtgg accgcttacc ccactaggtg    60
aagatgtcag cccaggagag ctgcctcagc ctcatcaagt acttcctctt cgttttcaac   120
ctcttcttct tcgtcctcgg cagcctgatc ttctgcttcg gcatctggat cctcatcgac   180
aagaccagct tcgtgtcctt tgtgggcttg gccttcgtgc ctctgcagat ctggtccaaa   240
gtcctggcca tctcaggaat cttcaccatg ggcatcgccc tcctgggttg tgtgggggcc   300
ctcaaggagc tccgctgcct cctgggcctg tatttggga tgctgctgct cctgtttgcc    360
acacagatca ccctgggaat cctcatctcc actcagcggg cccagctgga gcgaagcttg   420
cgggacgtcg tagagaaaac catccaaaag tacggcacca accccgagga ccgcgggcc    480
gaggagagct gggactatgt gcagttccag ctgcgctgct gcggctggca ctacccgcag   540
gactggttcc aagtcctcat cctgagaggt aacgggtcgg aggcgcaccg cgtgccctgc   600
tcctgctaca cttgtcggc gaccaacgac tccacaatcc tagataaggt gatcttgccc    660
cagctcagca ggcttggaca cctggcgcgg tccagacaca gtgcagacat ctgcgctgtc   720
cctgcagaga gccacatcta ccgcgagggc tgcgcgcagg gcctccagaa gtggctgcac   780
aacaaccta tttccatagt gggcatttgc ctgggcgtcg gcctactcga gctcgggttc   840
atgacgctct cgatattcct gtgcagaaac ctggaccacg tctacaaccg gctcgctcga   900
taccgttagg ccccgccctc cccaaagtcc cgccccgccc ccgtcacgtg cgctgggcac   960
ttccctgctg cctgtaaata tttgtttaat ccccagttcg cctggagccc tccgccttca  1020
cattcccctg gggacccacg tggctgcgtg ccctgctgc tgtcacctct cccacgggac   1080
ctggggcttt cgtccacagc ttcctgtccc catctgtcgg cctac                 1125
```

<210> SEQ ID NO 43
<211> LENGTH: 281
<212> TYPE: PRT
<213> ORGANISM: Homo sapiens

<400> SEQUENCE: 43

```
Met Ser Ala Gln Glu Ser Cys Leu Ser Leu Ile Lys Tyr Phe Leu Phe
 1               5                  10                  15

Val Phe Asn Leu Phe Phe Phe Val Leu Gly Ser Leu Ile Phe Cys Phe
                20                  25                  30

Gly Ile Trp Ile Leu Ile Asp Lys Thr Ser Phe Val Ser Phe Val Gly
            35                  40                  45

Leu Ala Phe Val Pro Leu Gln Ile Trp Ser Lys Val Leu Ala Ile Ser
        50                  55                  60

Gly Ile Phe Thr Met Gly Ile Ala Leu Leu Gly Cys Val Gly Ala Leu
```

```
                65                  70                  75                  80
Lys Glu Leu Arg Cys Leu Leu Gly Leu Tyr Phe Gly Met Leu Leu Leu
                        85                  90                  95
Leu Phe Ala Thr Gln Ile Thr Leu Gly Ile Leu Ile Ser Thr Gln Arg
                100                 105                 110
Ala Gln Leu Glu Arg Ser Leu Arg Asp Val Val Glu Lys Thr Ile Gln
            115                 120                 125
Lys Tyr Gly Thr Asn Pro Glu Glu Thr Ala Ala Glu Glu Ser Trp Asp
        130                 135                 140
Tyr Val Gln Phe Gln Leu Arg Cys Cys Gly Trp His Tyr Pro Gln Asp
145                 150                 155                 160
Trp Phe Gln Val Leu Ile Leu Arg Gly Asn Gly Ser Glu Ala His Arg
                    165                 170                 175
Val Pro Cys Ser Cys Tyr Asn Leu Ser Ala Thr Asn Asp Ser Thr Ile
                180                 185                 190
Leu Asp Lys Val Ile Leu Pro Gln Leu Ser Arg Leu Gly His Leu Ala
            195                 200                 205
Arg Ser Arg His Ser Ala Asp Ile Cys Ala Val Pro Ala Glu Ser His
        210                 215                 220
Ile Tyr Arg Glu Gly Cys Ala Gln Gly Leu Gln Lys Trp Leu His Asn
225                 230                 235                 240
Asn Leu Ile Ser Ile Val Gly Ile Cys Leu Gly Val Gly Leu Leu Glu
                    245                 250                 255
Leu Gly Phe Met Thr Leu Ser Ile Phe Leu Cys Arg Asn Leu Asp His
                260                 265                 270
Val Tyr Asn Arg Leu Ala Arg Tyr Arg
            275                 280

<210> SEQ ID NO 44
<211> LENGTH: 2915
<212> TYPE: DNA
<213> ORGANISM: Homo sapiens

<400> SEQUENCE: 44
agccccgccg cgatgcccgc gcgcccagga cgcctcctcc cgctgctggc ccggccggcg    60
gccctgactg cgctgctgct gctgctgctg ggccatggcg gcggcgggcg ctggggcgcc   120
cgggcccagg aggcggcggc ggcggcggcg gacgggcccc ccgcggcaga cggcgaggac   180
ggacaggacc cgcacagcaa gcacctgtac acggccgaca tgttcacgca cgggatccag   240
agcgccgcgc acttcgtcat gttcttcgcg ccctggtgtg acactgcca gcggctgcag    300 ccgacttgga tgacctggga gacaaatac aacagcatgg aagatgccaa agtctatgtg   360
gctaaagtgg actgcacggc ccactccgac gtgtgctccg cccagggggt gcaggatac    420 cccaccttaa agcttttcaa gccaggccaa gaagctgtga agtaccaggg tcctcgggac   480
ttccagacac tggaaaactg gatgctgcag acactgaacg aggagccagt gacaccagag   540
ccggaagtgg aaccgcccag tgccccgag ctcaagcaag gctgtatga gctctcagca   600 agcaactttg agctgcacgt tgcacaaggc gaccacttta tcaagttctt cgctccgtgg   660
tgtggtcact gcaaagccct ggctccaacc tgggagcagc tggctctggg ccttgaacat   720
tccgaaactg tcaagattgg caaggttgat tgtacacagc actatgaact ctgctccgga   780
aaccaggttc gtggctatcc cactcttctc tggttccgag atgggaaaaa ggtggatcag   840
tacaagggaa agcgggattt ggagtcactg aggggagtacg tggagtcgca gctgcagcgc   900
```

```
acagagactg gagcgacgga gaccgtcacg ccctcagagg ccccggtgct ggcagctgag      960
cccgaggctg acaagggcac tgtgttggca ctcactgaaa ataacttcga tgacaccatt     1020
gcagaaggaa taaccttcat caagttttat gctccatggt gtggtcattg taggactctg     1080
gctcctactt gggaggaact ctctaaaaag gaattccctg gtctggcggg ggtcaagatc     1140
gccgaagtag actgcactgc tgaacggaat atctgcagca agtattcggt acgaggctac     1200
cccacgttat tgcttttccg aggagggaag aaagtcagtg agcacagtgg aggcagagac     1260
cttgactcgt tacaccgctt tgtcctgagc caagcgaaag acgaacttta ggaacacagt     1320
tggaggtcac ctctcctgcc cagctcccgc accctgcgtt taggagttca gtcccacaga     1380
ggccactggg ttcccagtgg tggctgttca gaaagcagaa catactaagc gtgaggtatc     1440
ttctttgtgt gtgtgttttc caagccaaca cactctacag attctttatt aaatgtgtaa     1500
ctcatggtca ctgtgtaaac attttcagtg gcgatatatc ccctttgacc ttctcttgat     1560
gaaatttaca tggtttcctt tgagactaaa atagcgttga gggaaatgaa attgctggac     1620
tatttgtggc tcctgagttg agtgattttg gtgaaagaaa gcacatccaa agcatagttt     1680
acctgcccac gagttctgga aaggttgcct tgtggcagta ttgacgttcc tctgatctta     1740
aggtcacagt tgactcaata ctgtgttggt ccgtagcatg gagcagattg aaatgcaaaa     1800
acccacacct ctggaggata ccttcacggc cgctgctgga gcttctgttg ctgtgaatac     1860
ttctctcagt gtgagaggtt agccgtgatg aaagcagcgt tacttctgac cgtgcctgag     1920
taagagaatg ctgatgccat aactttatgt gtcgatactt gtcaaatcag ttactgttca     1980
ggggatcctt ctgtttctca cggggtgaaa catgtcttta gttcctcatg ttaacacgaa     2040
gccagagccc acatgaactg ttggatgtct tccttagaaa gggtaggcat ggaaaattcc     2100
acgaggctca ttctcagtat ctcattaact cattgaaaga ttccagttgt atttgtcacc     2160
tggggtgaca agaccagaca ggctttccca ggcctgggta tccagggagg ctctgcagcc     2220
ctgctgaagg gccctaacta gagttctaga gtttctgatt ctgtttctca gtagtccttt     2280
tagaggcttg ctatacttgg tctgcttcaa ggaggtcgac cttctaatgt atgaagaatg     2340
ggatgcattt gatctcaaga ccaaagacag atgtcagtgg gctgctctgg ccctggtgtg     2400
cacggctgtg gcagctgttg atgccagtgt cctctaactc atgctgtcct tgtgattaaa     2460
cacctctatc tcccttggga ataagcacat acaggcttaa gctctaagat agataggtgt     2520
ttgtcctttt accatcgagc tacttcccat aataaccact ttgcatccaa cactcttcac     2580
ccacctccca tacgcaaggg gatgtggata cttggcccaa agtaactggt ggtaggaatc     2640
ttagaaacaa gaccacttat actgtctgtc tgaggcagaa gataacagca gcatctcgac     2700
cagcctctgc cttaaaggaa atctttatta atcacgtatg gttcacagat aattcttttt     2760
ttaaaaaaac ccaacctcct agagaagcac aactgtcaag agtcttgtac acacaacttc     2820
agctttgcat cacgagtctt gtattccaag aaaatcaaag tggtacaatt tgtttgttta     2880
cactatgata ctttctaaat aaactccttt ttttt                                2915
```

<210> SEQ ID NO 45
<211> LENGTH: 432
<212> TYPE: PRT
<213> ORGANISM: Homo sapiens

<400> SEQUENCE: 45

```
Met Pro Ala Arg Pro Gly Arg Leu Leu Pro Leu Leu Ala Arg Pro Ala
 1               5                  10                  15
```

```
Ala Leu Thr Ala Leu Leu Leu Leu Leu Gly His Gly Gly Gly
             20                  25                  30

Arg Trp Gly Ala Arg Ala Gln Glu Ala Ala Ala Ala Asp Gly
         35                  40                  45

Pro Pro Ala Ala Asp Gly Glu Asp Gly Gln Asp Pro His Ser Lys His
     50                  55                  60

Leu Tyr Thr Ala Asp Met Phe Thr His Gly Ile Gln Ser Ala Ala His
 65                  70                  75                  80

Phe Val Met Phe Phe Ala Pro Trp Cys Gly His Cys Gln Arg Leu Gln
                 85                  90                  95

Pro Thr Trp Asn Asp Leu Gly Asp Lys Tyr Asn Ser Met Glu Asp Ala
             100                 105                 110

Lys Val Tyr Val Ala Lys Val Asp Cys Thr Ala His Ser Asp Val Cys
             115                 120                 125

Ser Ala Gln Gly Val Arg Gly Tyr Pro Thr Leu Lys Leu Phe Lys Pro
     130                 135                 140

Gly Gln Glu Ala Val Lys Tyr Gln Gly Pro Arg Asp Phe Gln Thr Leu
145                 150                 155                 160

Glu Asn Trp Met Leu Gln Thr Leu Asn Glu Glu Pro Val Thr Pro Glu
                 165                 170                 175

Pro Glu Val Glu Pro Pro Ser Ala Pro Glu Leu Lys Gln Gly Leu Tyr
             180                 185                 190

Glu Leu Ser Ala Ser Asn Phe Glu Leu His Val Ala Gln Gly Asp His
     195                 200                 205

Phe Ile Lys Phe Phe Ala Pro Trp Cys Gly His Cys Lys Ala Leu Ala
210                 215                 220

Pro Thr Trp Glu Gln Leu Ala Leu Gly Leu Glu His Ser Glu Thr Val
225                 230                 235                 240

Lys Ile Gly Lys Val Asp Cys Thr Gln His Tyr Glu Leu Cys Ser Gly
                 245                 250                 255

Asn Gln Val Arg Gly Tyr Pro Thr Leu Leu Trp Phe Arg Asp Gly Lys
             260                 265                 270

Lys Val Asp Gln Tyr Lys Gly Lys Arg Asp Leu Glu Ser Leu Arg Glu
     275                 280                 285

Tyr Val Glu Ser Gln Leu Gln Arg Thr Glu Thr Gly Ala Thr Glu Thr
     290                 295                 300

Val Thr Pro Ser Glu Ala Pro Val Leu Ala Ala Glu Pro Glu Ala Asp
305                 310                 315                 320

Lys Gly Thr Val Leu Ala Leu Thr Glu Asn Asn Phe Asp Asp Thr Ile
                 325                 330                 335

Ala Glu Gly Ile Thr Phe Ile Lys Phe Tyr Ala Pro Trp Cys Gly His
             340                 345                 350

Cys Arg Thr Leu Ala Pro Thr Trp Glu Glu Leu Ser Lys Lys Glu Phe
     355                 360                 365

Pro Gly Leu Ala Gly Val Lys Ile Ala Glu Val Asp Cys Thr Ala Glu
     370                 375                 380

Arg Asn Ile Cys Ser Lys Tyr Ser Val Arg Gly Tyr Pro Thr Leu Leu
385                 390                 395                 400

Leu Phe Arg Gly Gly Lys Lys Val Ser Glu His Ser Gly Gly Arg Asp
                 405                 410                 415

Leu Asp Ser Leu His Arg Phe Val Leu Ser Gln Ala Lys Asp Glu Leu
             420                 425                 430
```

```
<210> SEQ ID NO 46
<211> LENGTH: 551
<212> TYPE: DNA
<213> ORGANISM: Homo sapiens

<400> SEQUENCE: 46
ccagccagtg acagaaaaaa gagtgaatgt gcctttaaga agaagagcaa tgagacacag      60
tgtttcaact tcatccgtgt cctggttttct tacaatgtca cccatctcta cacctgcggc     120
accttcgcct tcagccctgc ttgtaccttc attgaacttc aagattccta cctgttgccc     180
atctcggagg acaaggtcat ggagggaaaa ggccaaagcc cctttgaccc cgctcacaag     240
catacggctg tcttggtgga tgggatgctc tattctggta ctatgaacaa cttcctgggc     300
agtgagccca tcctgatgcg cacactggga tcccagcctg tcctcaagac cgacaacttc     360
ctccgctggc tgcatcatga cgcctccttt gtggcagcca tccctttcgac ccaggtcgtc     420 tacttcttct tcgaggagac agccagcgag tttgacttct ttgagaggct ccacacatcg     480
cgggtggcta agtctgcaa gaatgacgtg ggcggcgaaa agctgctgca gaagaagtgg     540
accaccttcc t                                                           551

<210> SEQ ID NO 47
<211> LENGTH: 3252
<212> TYPE: DNA
<213> ORGANISM: Homo sapiens

<400> SEQUENCE: 47
aggatgatga aagtgagacc gtcttagggc ccttccagat agtgaacctt ctctgcccca      60
atgccccacc cctgccacca atacacacgc ttctgctgcc tggggctctc ctattggtcc     120 tcgggggggat gtggtaagaa ctgctcaccc agaaagtgcc cggtgcctg tttcccaga     180 cctccctggt gacagtctgt ggctgagcat ggccctccca gccctgggcc tggacccctg     240
gagcctcctg ggccttttcc tcttccaact gcttcagctg ctgctgccga cgacgaccgc     300
ggggggaggc gggcaggggc ccatgcccag ggtcagatac tatgcagggg atgaacgtag     360
ggcacttagc ttcttccacc agaagggcct ccaggatttt gacactctgc tcctgagtgg     420
tgatggaaat actctctacg tgggggctcg agaagccatt ctggccttgg atatccagga     480
tccaggggtc cccaggctaa agaacatgat accgtggcca gccagtgaca gaaaaaagag     540
tgaatgtgcc tttaagaaga agagcaatga gacacagtgt ttcaacttca tccgtgtcct     600
ggtttcttac aatgtcaccc atctctacac ctgcggcacc ttcgccttca gccctgcttg     660
taccttcatt gaacttcaag attcctacct gttgcccatc tcggaggaca aggtcatgga     720 gggaaaggc caaagcccct ttgaccccgc tcacaagcat acggctgtct tggtggatgg     780
gatgctctat tctggtacta tgaacaactt cctgggcagt gagcccatcc tgatgcgcac     840
actgggatcc cagcctgtcc tcaagaccga caacttcctc cgctggctgc atcatgacgc     900 ctccttgtg gcagccatcc cttcgaccca ggtcgtctac ttcttcttcg aggagacagc     960
cagcgagttt gacttctttg agaggctcca cacatcgcgg gtggctagag tctgcaagaa    1020
tgacgtgggc ggcgaaaagc tgctgcagaa gaagtggacc accttcctga aggcccagct    1080
gctctctgca cccagccggg gcagctgccc ttcaacgtca tccgccacgc ggtcctgctc    1140
cccgccgatt ctcccacagc tccccacatc tacgcagtct tcacctccca gtgggcaggt    1200
tggcgggacc aggagctctg cggtttgtgc cttctctctc ttggacattg aacgtgtctt    1260 taagggggaaa ttcaaagagt tgaacaaaga aacttcacgc tggactactt atagggggccc    1320
```

```
tgagaccaac ccccggccag gcagttgctc agtgggcccc tcctctgata aggccctgac    1380
cttcatgaag gaccatttcc tgatggatga gcaagtggtg gggacgcccc tgctggtgaa    1440
atctggcgtg gagtatacac ggcttgcagt ggagacagcc cagggccttg atgggcacag    1500
ccatcttgtc atgtacctgg gaaccaccac agggtcgctc acaaggctg tggtaagtgg     1560
ggacagcagt gctcatctgg tggaagagat tcagctgttc cctgaccctg aacctgttcg    1620
caacctgcag ctggcccca cccagggtgc agtgtttgta ggcttctcag gaggtgtctg     1680
gagggtgccc cgagccaact gtagtgtcta tgagagctgt gtggactgtg tccttgcccg    1740
ggaccccac tgtgcctggg accctgagtc ccgaacctgt tgcctcctgt ctgccccccaa    1800
cctgaactcc tggaagcagg acatggagcg ggggaaccca gagtgggcat gtgccagtgg    1860
ccccatgagc aggagccttc ggcctcagag ccgcccgcaa atcattaaag aagtcctggc    1920
tgtccccaac tccatcctgg agctcccctg ccccacctg tcagccttgg cctcttatta     1980
ttggagtcat ggcccagcag cagtcccaga agcctcttcc actgtctaca atggctccct    2040
cttgctgata gtgcaggatg gagttggggg tctctaccag tgctgggcaa ctgagaatgg    2100
cttttcatac cctgtgatct cctactgggt ggacagccag gaccagaccc tggccctgga    2160
tcctgaactg gcaggcatcc cccggggagca tgtgaaggtc ccgttgacca gggtcagtgg    2220
tggggccgcc ctggctgccc agcagtccta ctggccccac tttgtcactg tcactgtcct    2280
cttttgcctta gtgcttttcag gagccctcat catcctcgtg gcctccccat tgagagcact    2340
ccgggctcgg ggcaaggttc agggctgtga ccctgcgc cctggggaga aggccccgtt      2400
aagcagagag caaacacctcc agtctcccaa ggaatgcagg acctctgcca gtgatgtgga    2460
cgctgacaac aactgcctag gcactgaggt agcttaaaact ctaggcacag gccggggctg    2520
cggtgcaggc acctggccat gctggctggg cggcccaagc acagccctga ctaggatgac    2580
agcagcacaa aagaccacct ttctcccctg agaggagctt ctgctactct gcatcactga    2640
tgacactcag cagggtgatg cacagcagtc tgcctccct atgggactcc cttctaccaa     2700
gcacatgagc tctctaacag ggtgggggct accccagac ctgctcctac actgatattg     2760
aagaacctgg agaggatcct tcagttctgg ccattccagg gaccctccag aaacacagtg    2820
tttcaagaga ccctaaaaaa cctgcctgtc ccaggaccct atggtaatga acaccaaaca    2880
tctaaacaat catatgctaa catgccactc ctggaaactc cactctgaag ctgccgcttt    2940
ggacaccaac actcccttct cccagggtca tgcagggatc tgctccctcc tgcttccctt    3000
accagtcgtg caccgctgac tcccaggaag tctttcctga agtctgacca cctttcttct    3060
tgcttcagtt ggggcagact ctgatcccctt ctgccctggc agaatggcag gggtaatctg    3120
agccttcttc actcctttac cctagctgac cccttcacct ctcccctcc cttttccttt     3180
gttttgggat tcagaaaact gcttgtcaga gactgtttat tttttattaa aaatataagg    3240
cttatgtatg at                                                         3252
```

<210> SEQ ID NO 48
<211> LENGTH: 762
<212> TYPE: PRT
<213> ORGANISM: Homo sapiens

<400> SEQUENCE: 48

Met Ala Leu Pro Ala Leu Gly Leu Asp Pro Trp Ser Leu Leu Gly Leu
1               5                   10                  15

Phe Leu Phe Gln Leu Leu Gln Leu Leu Leu Pro Thr Thr Thr Ala Gly
            20                  25                  30

```
Gly Gly Gly Gln Gly Pro Met Pro Arg Val Arg Tyr Tyr Ala Gly Asp
        35                  40                  45
Glu Arg Arg Ala Leu Ser Phe Phe His Gln Lys Gly Leu Gln Asp Phe
 50                  55                  60
Asp Thr Leu Leu Leu Ser Gly Asp Gly Asn Thr Leu Tyr Val Gly Ala
 65                  70                  75                  80
Arg Glu Ala Ile Leu Ala Leu Asp Ile Gln Asp Pro Gly Val Pro Arg
                 85                  90                  95
Leu Lys Asn Met Ile Pro Trp Pro Ala Ser Asp Arg Lys Lys Ser Glu
                100                 105                 110
Cys Ala Phe Lys Lys Ser Asn Glu Thr Gln Cys Phe Asn Phe Ile
            115                 120                 125
Arg Val Leu Val Ser Tyr Asn Val Thr His Leu Tyr Thr Cys Gly Thr
        130                 135                 140
Phe Ala Phe Ser Pro Ala Cys Thr Phe Ile Glu Leu Gln Asp Ser Tyr
145                 150                 155                 160
Leu Leu Pro Ile Ser Glu Asp Lys Val Met Glu Gly Lys Gly Gln Ser
                165                 170                 175
Pro Phe Asp Pro Ala His Lys His Thr Ala Val Leu Val Asp Gly Met
                180                 185                 190
Leu Tyr Ser Gly Thr Met Asn Asn Phe Leu Gly Ser Glu Pro Ile Leu
        195                 200                 205
Met Arg Thr Leu Gly Ser Gln Pro Val Leu Lys Thr Asp Asn Phe Leu
        210                 215                 220
Arg Trp Leu His His Asp Ala Ser Phe Val Ala Ile Pro Ser Thr
225                 230                 235                 240
Gln Val Val Tyr Phe Phe Phe Glu Glu Thr Ala Ser Glu Phe Asp Phe
                245                 250                 255
Phe Glu Arg Leu His Thr Ser Arg Val Ala Arg Val Cys Lys Asn Asp
                260                 265                 270
Val Gly Gly Glu Lys Leu Leu Gln Lys Lys Trp Thr Thr Phe Leu Lys
        275                 280                 285
Ala Gln Leu Leu Ser Ala Pro Ser Arg Gly Ser Cys Pro Ser Thr Ser
        290                 295                 300
Ser Ala Thr Arg Ser Cys Ser Pro Pro Ile Leu Pro Gln Leu Pro Thr
305                 310                 315                 320
Ser Thr Gln Ser Ser Pro Pro Ser Gly Gln Val Gly Thr Arg Ser
                325                 330                 335
Ser Ala Val Cys Ala Phe Ser Leu Leu Asp Ile Glu Arg Val Phe Lys
                340                 345                 350
Gly Lys Phe Lys Glu Leu Asn Lys Glu Thr Ser Arg Trp Thr Thr Tyr
        355                 360                 365
Arg Gly Pro Glu Thr Asn Pro Arg Pro Gly Ser Cys Ser Val Gly Pro
370                 375                 380
Ser Ser Asp Lys Ala Leu Thr Phe Met Lys Asp His Phe Leu Met Asp
385                 390                 395                 400
Glu Gln Val Val Gly Thr Pro Leu Leu Val Lys Ser Gly Val Glu Tyr
                405                 410                 415
Thr Arg Leu Ala Val Glu Thr Ala Gln Gly Leu Asp Gly His Ser His
                420                 425                 430
Leu Val Met Tyr Leu Gly Thr Thr Thr Gly Ser Leu His Lys Ala Val
        435                 440                 445
```

Val Ser Gly Asp Ser Ser Ala His Leu Val Glu Glu Ile Gln Leu Phe
450                 455                 460

Pro Asp Pro Glu Pro Val Arg Asn Leu Gln Leu Ala Pro Thr Gln Gly
465                 470                 475                 480

Ala Val Phe Val Gly Phe Ser Gly Gly Val Trp Arg Val Pro Arg Ala
                485                 490                 495

Asn Cys Ser Val Tyr Glu Ser Cys Val Asp Cys Val Leu Ala Arg Asp
                500                 505                 510

Pro His Cys Ala Trp Asp Pro Glu Ser Arg Thr Cys Cys Leu Leu Ser
            515                 520                 525

Ala Pro Asn Leu Asn Ser Trp Lys Gln Asp Met Glu Arg Gly Asn Pro
530                 535                 540

Glu Trp Ala Cys Ala Ser Gly Pro Met Ser Arg Ser Leu Arg Pro Gln
545                 550                 555                 560

Ser Arg Pro Gln Ile Ile Lys Glu Val Leu Ala Val Pro Asn Ser Ile
                565                 570                 575

Leu Glu Leu Pro Cys Pro His Leu Ser Ala Leu Ala Ser Tyr Tyr Trp
                580                 585                 590

Ser His Gly Pro Ala Ala Val Pro Glu Ala Ser Ser Thr Val Tyr Asn
            595                 600                 605

Gly Ser Leu Leu Leu Ile Val Gln Asp Gly Val Gly Gly Leu Tyr Gln
610                 615                 620

Cys Trp Ala Thr Glu Asn Gly Phe Ser Tyr Pro Val Ile Ser Tyr Trp
625                 630                 635                 640

Val Asp Ser Gln Asp Gln Thr Leu Ala Leu Asp Pro Glu Leu Ala Gly
                645                 650                 655

Ile Pro Arg Glu His Val Lys Val Pro Leu Thr Arg Val Ser Gly Gly
                660                 665                 670

Ala Ala Leu Ala Ala Gln Gln Ser Tyr Trp Pro His Phe Val Thr Val
            675                 680                 685

Thr Val Leu Phe Ala Leu Val Leu Ser Gly Ala Leu Ile Ile Leu Val
690                 695                 700

Ala Ser Pro Leu Arg Ala Leu Arg Ala Arg Gly Lys Val Gln Gly Cys
705                 710                 715                 720

Glu Thr Leu Arg Pro Gly Glu Lys Ala Pro Leu Ser Arg Glu Gln His
                725                 730                 735

Leu Gln Ser Pro Lys Glu Cys Arg Thr Ser Ala Ser Asp Val Asp Ala
                740                 745                 750

Asp Asn Asn Cys Leu Gly Thr Glu Val Ala
            755                 760

<210> SEQ ID NO 49
<211> LENGTH: 182
<212> TYPE: DNA
<213> ORGANISM: Homo sapiens
<220> FEATURE:
<221> NAME/KEY: modified_base
<222> LOCATION: (1)..(182)
<223> OTHER INFORMATION: n = g, a, c or t

<400> SEQUENCE: 49
accagcagtc ctgcggcacc tacctccgcg tgcgccagcc gcccccagg cccttcctgg      60 acatggggga gggcaccaag aaccgaatca tcacagccga ggggatcatc ctcctgttct     120
gcgcggtggt gcctgggacg ctgctgctgt tnaggaaacg atggcaagaa cganaactcn    180
gg                                                                    182

```
<210> SEQ ID NO 50
<211> LENGTH: 60
<212> TYPE: PRT
<213> ORGANISM: Homo sapiens
<220> FEATURE:
<221> NAME/KEY: MOD_RES
<222> LOCATION: (1)..(60)
<223> OTHER INFORMATION: Xaa = any amino acid

<400> SEQUENCE: 50

Gln Gln Ser Cys Gly Thr Tyr Leu Arg Val Arg Gln Pro Pro Arg
 1               5                  10                  15

Pro Phe Leu Asp Met Gly Glu Gly Thr Lys Asn Arg Ile Ile Thr Ala
            20                  25                  30

Glu Gly Ile Ile Leu Leu Phe Cys Ala Val Val Pro Gly Thr Leu Leu
        35                  40                  45

Leu Xaa Arg Lys Arg Trp Gln Glu Arg Xaa Leu Xaa
    50                  55                  60

<210> SEQ ID NO 51
<211> LENGTH: 182
<212> TYPE: DNA
<213> ORGANISM: Homo sapiens
<220> FEATURE:
<221> NAME/KEY: modified_base
<222> LOCATION: (1)..(182)
<223> OTHER INFORMATION: n = g, a, c or t

<400> SEQUENCE: 51
accagcagtc ctgcggcacc tacctccgcg tgcgccagcc gcccccagg cccttcctgg     60 acatgggga gggcaccaag aaccgaatca tcacagccga ggggatcatc ctcctgttct    120
gcgcggtggt gcctgggacg ctgctgctgt tnaggaaacg atggcaagaa cganaactcn    180
gg                                                                  182

<210> SEQ ID NO 52
<211> LENGTH: 60
<212> TYPE: PRT
<213> ORGANISM: Homo sapiens
<220> FEATURE:
<221> NAME/KEY: MOD_RES
<222> LOCATION: (1)..(60)
<223> OTHER INFORMATION: Xaa = any amino acid

<400> SEQUENCE: 52

Gln Gln Ser Cys Gly Thr Tyr Leu Arg Val Arg Gln Pro Pro Arg
 1               5                  10                  15

Pro Phe Leu Asp Met Gly Glu Gly Thr Lys Asn Arg Ile Ile Thr Ala
            20                  25                  30

Glu Gly Ile Ile Leu Leu Phe Cys Ala Val Val Pro Gly Thr Leu Leu
        35                  40                  45

Leu Xaa Arg Lys Arg Trp Gln Glu Arg Xaa Leu Xaa
    50                  55                  60

<210> SEQ ID NO 53
<211> LENGTH: 1107
<212> TYPE: DNA
<213> ORGANISM: Homo sapiens

<400> SEQUENCE: 53
tgctgcaact caaactaacc aacccactgg gagaagatgc ctgggggtcc aggagtcctc     60
```

-continued

```
caagctctgc ctgccaccat cttcctcctc ttcctgctgt ctgctgtcta cctgggccct      120
gggtgccagg ccctgtggat gcacaaggtc ccagcatcat tgatggtgag cctgggggaa      180
gacgcccact tccaatgccc gcacaatagc agcaacaacg ccaacgtcac ctggtggcgc      240
gtcctccatg gcaactacac gtggccccct gagttcttgg gcccgggcga ggacccccaat    300
ggtacgctga tcatccagaa tgtgaacaag agccatgggg gcatatacgt gtgccgggtc     360
caggagggca acgagtcata ccagcagtcc tgcggcacct acctccgcgt gcgccagccg     420
cccccccaggc ccttcctgga catgggggag ggcaccaaga accgaatcat cacagccgag    480
gggatcatcc tcctgttctg cgcggtggtg cctgggacgc tgctgctgtt caggaaacga     540
tggcagaacg agaagctcgg gttggatgcc ggggatgaat atgaagatga aaacctttat     600
gaaggcctga acctgacga ctgctccatg tatgaggaca tctcccgggg cctccagggc      660
acctaccagg atgtgggcag cctcaacata ggagatgtcc agctggagaa gccgtgacac     720
ccctactcct gccaggctgc ccccgcctgc tgtgcaccca gctccagtgt ctcagctcac     780
ttccctggga cattctcctt tcagcccttc tgggggcttc cttagtcata ttcccccagt      840
gggggggtggg agggtaacct cactcttctc caggccaggc ctccttggac tcccctgggg    900
gtgtcccact cttcttccct ctaaactgcc ccacctccta acctaatccc cacgcccgc      960
tgcctttccc aggctcccct cacccagcgg gtaatgagcc cttaatcgct gcctctaggg    1020
gagctgattg tagcagcctc gttagtgtca ccccctcctc cctgatctgt cagggccact    1080
tagtgataat aaattcttcc caactgc                                        1107
```

```
<210> SEQ ID NO 54
<211> LENGTH: 226
<212> TYPE: PRT
<213> ORGANISM: Homo sapiens

<400> SEQUENCE: 54
```

```
Met Pro Gly Gly Pro Gly Val Leu Gln Ala Leu Pro Ala Thr Ile Phe
  1               5                  10                  15
Leu Leu Phe Leu Leu Ser Ala Val Tyr Leu Gly Pro Gly Cys Gln Ala
                 20                  25                  30
Leu Trp Met His Lys Val Pro Ala Ser Leu Met Val Ser Leu Gly Glu
             35                  40                  45
Asp Ala His Phe Gln Cys Pro His Asn Ser Ser Asn Ala Asn Val
         50                  55                  60
Thr Trp Trp Arg Val Leu His Gly Asn Tyr Thr Trp Pro Pro Glu Phe
 65                  70                  75                  80
Leu Gly Pro Gly Glu Asp Pro Asn Gly Thr Leu Ile Ile Gln Asn Val
                 85                  90                  95
Asn Lys Ser His Gly Gly Ile Tyr Val Cys Arg Val Gln Glu Gly Asn
            100                 105                 110
Glu Ser Tyr Gln Gln Ser Cys Gly Thr Tyr Leu Arg Val Arg Gln Pro
        115                 120                 125
Pro Pro Arg Pro Phe Leu Asp Met Gly Glu Gly Thr Lys Asn Arg Ile
    130                 135                 140
Ile Thr Ala Glu Gly Ile Ile Leu Leu Phe Cys Ala Val Val Pro Gly
145                 150                 155                 160
Thr Leu Leu Leu Phe Arg Lys Arg Trp Gln Asn Glu Lys Leu Gly Leu
                165                 170                 175
Asp Ala Gly Asp Glu Tyr Glu Asp Glu Asn Leu Tyr Glu Gly Leu Asn
            180                 185                 190
```

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
        210                 215                 220

Lys Pro
225

<210> SEQ ID NO 55
<211> LENGTH: 1038
<212> TYPE: DNA
<213> ORGANISM: Homo sapiens

<400> SEQUENCE: 55

| | | | | | |
|---|---|---|---|---|---|
| atgtacaagg | actgcatcga | gtccactgga | gactattttc | ttctctgtga | cgccgagggg | 60 |
| ccatggggca | tcattctgga | gtccctggcc | atacttggca | tcgtggtcac | aattctgcta | 120 |
| ctcttagcat | ttctcttcct | catgcgaaag | atccaagact | gcagccagtg | gaatgtcctc | 180 |
| cccacccagc | tcctcttcct | cctgagtgtc | ctggggctct | tcggactcgc | ttttgccttc | 240 |
| atcatcgagc | tcaatcaaca | aactgccccc | gtacgctact | ttctctttgg | ggttctcttt | 300 |
| gctctctgtt | tctcatgcct | cttagctcat | gcctccaatc | tagtgaagct | ggttcggggt | 360 |
| tgtgtctcct | tctcctggac | gacaattctg | tgcattgcta | ttggttgcag | tctgttgcaa | 420 |
| atcattattg | ccactgagta | tgtgactctc | atcatgacca | gaggtatgat | gtttgtgaat | 480 |
| atgacaccct | gccagctcaa | tgtggacttt | gttgtactcc | tggtctatgt | cctcttcctg | 540 |
| atggccctca | cattcttcgt | ctccaaagcc | accttctgtg | cccgtgtgga | aactggaag | 600 |
| cagcatggaa | ggctcatctt | tatcactgtg | ctcttctcca | tcatcatctg | ggtggtgtgg | 660 |
| atctccatgc | tcctgagagg | caacccgcag | ttccagcgac | agcccagtg | ggacgacccg | 720 |
| gtcgtctgca | ttgctctggt | caccaacgca | tgggttttcc | tgctgctgta | catcgtccct | 780 |
| gagctctgca | ttctctacag | atcgtgtaga | caggagtgcc | ctttacaagg | caatgcctgc | 840 |
| cccgtcacag | cctaccaaca | cagcttccaa | gtggagaacc | aggagctctc | cagagcccga | 900 |
| gacagtgatg | gagctgagga | ggatgtagca | ttaacttcat | atggtactcc | cattcagccg | 960 |
| cagactgttg | atcccacaca | agagtgtttc | atcccacagg | ctaaactaag | cccccagcaa | 1020 |
| gatgcaggag | gagtataa | | | | | 1038 |

<210> SEQ ID NO 56
<211> LENGTH: 345
<212> TYPE: PRT
<213> ORGANISM: Homo sapiens

<400> SEQUENCE: 56

Met Tyr Lys Asp Cys Ile Glu Ser Thr Gly Asp Tyr Phe Leu Leu Cys
1               5                   10                  15

Asp Ala Glu Gly Pro Trp Gly Ile Ile Leu Glu Ser Leu Ala Ile Leu
            20                  25                  30

Gly Ile Val Val Thr Ile Leu Leu Leu Ala Phe Leu Phe Leu Met
        35                  40                  45

Arg Lys Ile Gln Asp Cys Ser Gln Trp Asn Val Leu Pro Thr Gln Leu
    50                  55                  60

Leu Phe Leu Leu Ser Val Leu Gly Leu Phe Gly Leu Ala Phe Ala Phe
65                  70                  75                  80

Ile Ile Glu Leu Asn Gln Gln Thr Ala Pro Val Arg Tyr Phe Leu Phe
                85                  90                  95

```
Gly Val Leu Phe Ala Leu Cys Phe Ser Cys Leu Leu Ala His Ala Ser
            100                 105                 110
Asn Leu Val Lys Leu Val Arg Gly Cys Val Ser Phe Ser Trp Thr Thr
        115                 120                 125
Ile Leu Cys Ile Ala Ile Gly Cys Ser Leu Leu Gln Ile Ile Ala
    130                 135                 140
Thr Glu Tyr Val Thr Leu Ile Met Thr Arg Gly Met Met Phe Val Asn
145                 150                 155                 160
Met Thr Pro Cys Gln Leu Asn Val Asp Phe Val Leu Leu Val Tyr
                165                 170                 175
Val Leu Phe Leu Met Ala Leu Thr Phe Phe Val Ser Lys Ala Thr Phe
                180                 185                 190
Cys Gly Pro Cys Glu Asn Trp Lys Gln His Gly Arg Leu Ile Phe Ile
            195                 200                 205
Thr Val Leu Phe Ser Ile Ile Ile Trp Val Val Trp Ile Ser Met Leu
        210                 215                 220
Leu Arg Gly Asn Pro Gln Phe Gln Arg Gln Pro Gln Trp Asp Asp Pro
225                 230                 235                 240
Val Val Cys Ile Ala Leu Val Thr Asn Ala Trp Val Phe Leu Leu Leu
                245                 250                 255
Tyr Ile Val Pro Glu Leu Cys Ile Leu Tyr Arg Ser Cys Arg Gln Glu
                260                 265                 270
Cys Pro Leu Gln Gly Asn Ala Cys Pro Val Thr Ala Tyr Gln His Ser
            275                 280                 285
Phe Gln Val Glu Asn Gln Glu Leu Ser Arg Ala Arg Asp Ser Asp Gly
        290                 295                 300
Ala Glu Glu Asp Val Ala Leu Thr Ser Tyr Gly Thr Pro Ile Gln Pro
305                 310                 315                 320
Gln Thr Val Asp Pro Thr Gln Glu Cys Phe Ile Pro Gln Ala Lys Leu
                325                 330                 335
Ser Pro Gln Gln Asp Ala Gly Gly Val
            340                 345

<210> SEQ ID NO 57
<211> LENGTH: 2457
<212> TYPE: DNA
<213> ORGANISM: Homo sapiens

<400> SEQUENCE: 57
ggcacgagga agggcctgtg ggtttattat aaggcggagc tcggcgggag aggtgcgggc      60
cgaatccgag ccgagcggag aggaatccgg cagtagagag cggactccag ccggcggacc     120
ctgcagccct cgcctgggac agcggcgcgc tgggcaggcg cccaagagag catcgagcag     180
cggaacccgc gaagccggcc cgcagccgcg acccgcgcag cctgccgctc tcccgccgcc     240
ggtccgggca gcatgaggcg cgcggcgctc tggctctggc tgtgcgcgct ggcgctgagc     300
ctgcagccgg ccctgccgca aattgtggct actaatttgc cccctgaaga tcaagatggc     360
tctggggatg actctgacaa cttctccggc tcaggtgcag gtgctttgca agatatcacc     420
ttgtcacagc agacccctc cacttggaag gacacgcagc tcctgacggc tattccacg      480
tctccagaac ccaccggcct ggaggctaca gctgcctcca cctccaccct gccggctgga     540
gaggggccca aggagggaga ggctgtagtc ctgccagaag tggagcctgg cctcaccgcc     600
cgggagcagg aggccacccc ccgacccagg gagaccacac agctcccgac cactcatcag     660
```

```
gcctcaacga ccacagccac cacggcccag gagcccgcca cctcccaccc ccacagggac    720
atgcagcctg ccaccatgga gacctcaacc cctgcaggac ccagccaagc tgaccttcac    780
actccccaca cagaggatgg aggtccttct gccaccgaga gggctgctga ggatggagcc    840
tccagtcagc tcccagcagc agagggctct ggggagcagg acttcacctt tgaaacctcg    900
ggggagaata cggctgtagt ggccgtggag cctgaccgcc ggaaccagtc cccagtggat    960 caggggggcca cggggggcctc acagggcctc ctggacagga agaggtgct gggaggggtc   1020 attgccgtag gcctcgtggg gctcatcttt gctgtgtgcc tggtgggttt catgctgtac   1080
cgcatgaaga agaaggacga aggcagctac tccttggagg agccgaaaca agccaacggc   1140
ggggcctacc agaagcccac caaacaggag gaattctatg cctgacgcgg gagccatgcg   1200 cccccctccgc cctgccactc actaggcccc cacttgcctc ttccttgaag aactgcaggc   1260
cctggcctcc cctgccacca ggccacctcc ccagcattcc agcccctctg gtcgctcctg   1320
cccacggagt cgtgggggtgt gctgggagct ccactctgct tctctgactt ctgcctggag   1380
acttagggca ccaggggttt ctcgcatagg acctttccac cacagccagc acctggcatc   1440
gcaccattct gactcggttt ctccaaactg aagcagcctc tccccaggtc cagctctgga   1500 ggggagggg atccgactgc tttggaccta aatggcctca tgtggctgga agatcctgcg    1560
ggtgggcttt ggggctcaca cacctgtagc acttactggt aggaccaagc atcttggggg   1620
ggtggccgct gagtggcagg ggacaggagt ccactttgtt tcgtggggag gtctaatcta   1680
gatatcgact tgttttttgca catgtttcct ctagttcttt gttcatagcc cagtagacct   1740
tgttacttct gaggtaagtt aagtaagttg attcggtatc cccccatctt gcttccctaa   1800
tctatggtcg ggagacagca tcagggttaa gaagactttt tttttttttt ttttttaaact  1860 aggagaacca aatctggaag ccaaaatgta ggcttagttt gtgtgttgtc tcttgagttt   1920
gtcgctcatg tgtgcaacag ggtatggact atctgtctgg tggccccgtt tctggtggtc   1980
tgttggcagg ctggccagtc caggctgccg tggggccgcc gcctctttca agcagtcgtg   2040
cctgtgtcca tgcgctcagg gccatgctga ggcctgggcc gctgccacgt tggagaagcc   2100
cgtgtgagaa gtgaatgctg ggactcagcc ttcagacaga gaggactgta gggagggcgg   2160 cagggggcctg gagatcctcc tgcagaccac gcccgtcctg cctgtggcgc cgtctccagg   2220
ggctgcttcc tcctgaaaat tgacgagggg tgtcttgggc agagctggct ctgagcgcct   2280
ccatccaagg ccaggttctc cgttagctcc tgtggcccca cctgggccc tgggctggaa    2340 tcaggaatat tttccaaaga gtgatagtct tttgctttg gcaaaactct acttaatcca   2400 atggggttttt ccctgtacag tagatttcc aaatgtaata aactttaata taaagta     2457
```

<210> SEQ ID NO 58
<211> LENGTH: 310
<212> TYPE: PRT
<213> ORGANISM: Homo sapiens

<400> SEQUENCE: 58

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

```
Trp Lys Asp Thr Gln Leu Leu Thr Ala Ile Pro Thr Ser Pro Glu Pro
 65                  70                  75                  80

Thr Gly Leu Glu Ala Thr Ala Ala Ser Thr Ser Leu Pro Ala Gly
                 85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
            115                 120                 125

Thr Gln Leu Pro Thr Thr His Gln Ala Ser Thr Thr Ala Thr Thr
            130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
                180                 185                 190

Glu Asp Gly Ala Ser Ser Gln Leu Pro Ala Ala Glu Gly Ser Gly Glu
            195                 200                 205

Gln Asp Phe Thr Phe Glu Thr Ser Gly Glu Asn Thr Ala Val Val Ala
210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Val Gly Leu Val Gly Leu Ile Phe Ala Val Cys Leu Val Gly
                260                 265                 270

Phe Met Leu Tyr Arg Met Lys Lys Lys Asp Glu Gly Ser Tyr Ser Leu
                275                 280                 285

Glu Glu Pro Lys Gln Ala Asn Gly Gly Ala Tyr Gln Lys Pro Thr Lys
            290                 295                 300

Gln Glu Glu Phe Tyr Ala
305                 310

<210> SEQ ID NO 59
<211> LENGTH: 357
<212> TYPE: DNA
<213> ORGANISM: Homo sapiens

<400> SEQUENCE: 59
ctggggctga ggatggagtc caagactgag aaatggatgg aacgaataca cctcaatgtc      60
tctgaagggc cttttccacc tcatatccag ctccctccag aaattcaaga gtcccaggaa     120
gtcactctga cctgcttgct gaatttctcc tgctatgggt atccgatcca attgcagtgg     180
ctcctagagg gggttccaat gaggcaggct gctgtcacct cgacctcctt gaccatcaag     240
tctgtcttca cccggagcga gctcaagttc tccccacagt ggagtcacca tgggaagatt     300
gtgacctgcc agcttcagga tgcagatggg aagttcctct ccaatgacac ggtgcag         357

<210> SEQ ID NO 60
<211> LENGTH: 3260
<212> TYPE: DNA
<213> ORGANISM: Homo sapiens

<400> SEQUENCE: 60
ccatcccata gtgagggaag acacgcggaa acaggcttgc acccagacac gacaccatgc      60
```

-continued

| | | |
|---|---|---|
| atctcctcgg cccctggctc ctgctcctgg ttctagaata cttggctttc tctgactcaa | 120 |
| gtaaatgggt ttttgagcac cctgaaaccc tctacgcctg gaggggggcc tgcgtctgga | 180 |
| tcccctgcac ctacagagcc ctagatggtg acctggaaag cttcatcctg ttccacaatc | 240 |
| ctgagtataa caagaacacc tcgaagtttg atgggacaag actctatgaa agcacaaagg | 300 |
| atgggaaggt tccttctgag cagaaagggg tgcaattcct gggagacaag aataagaact | 360 |
| gcacactgag tatccacccg gtgcacctca atgacagtgg tcagctgggg ctgaggatgg | 420 |
| agtccaagac tgagaaatgg atggaacgaa tacacctcaa tgtctctgaa aggccttttc | 480 |
| cacctcatat ccagctccct ccagaaattc aagagtccca ggaagtcact ctgacctgct | 540 |
| tgctgaattt ctcctgctat gggtatccga tccaattgca gtggctccta gaggggttc | 600 |
| caatgaggca ggctgctgtc acctcgacct ccttgaccat caagtctgtc ttcacccgga | 660 |
| gcgagctcaa gttctcccca cagtggagtc accatgggaa gattgtgacc tgccagcttc | 720 |
| aggatgcaga tgggaagttc ctctccaatg acacggtgca gctgaacgtg aagcacaccc | 780 |
| cgaagttgga gatcaaggtc actcccagtg atgccatagt gagggagggg gactctgtga | 840 |
| ccatgacctg cgaggtcagc agcagcaacc cggagtacac gacggtatcc tggctcaagg | 900 |
| atgggaccct gctgaagaag cagaatacat tcacgctaaa cctgcgcgaa gtgaccaagg | 960 |
| accagagtgg gaagtactgc tgtcaggtct ccaatgacgt gggcccggga aggtcggaag | 1020 |
| aagtgttcct gcaagtgcag tatgccccgg aaccttccac ggttcagatc ctccactcac | 1080 |
| cggctgtgga gggaagtcaa gtcgagtttc tttgcatgtc actggccaat cctcttccaa | 1140 |
| caaattacac gtggtaccac aatgggaaag aaatgcaggg aaggacagag gagaaagtcc | 1200 |
| acatcccaaa gatcctcccc tggcacgctg ggacttattc ctgtgtggca gaaaacattc | 1260 |
| ttggtactgg acagaggggc ccgggagctg agctggatgt ccagtatcct cccaagaagg | 1320 |
| tgaccacagt gattcaaaac cccatgccga ttcgagaagg agacacagtg accctttcct | 1380 |
| gtaactacaa ttccagtaac cccagtgtta cccggtatga atggaaaccc catgcgcct | 1440 |
| gggaggagcc atcgcttggg gtgctgaaga tccaaaacgt tggctgggac aacacaacca | 1500 |
| tcgcctgcgc acgttgtaat agttggtgct cgtgggcctc ccctgtcgcc ctgaatgtcc | 1560 |
| agtatgcccc ccgagacgtg agggtccgga aaatcaagcc cctttccgag attcactctg | 1620 |
| gaaactcggt cagcctccaa tgtgacttct caagcagcca ccccaaagaa gtccagttct | 1680 |
| tctgggagaa aaatggcagg cttctgggga agaaagcca gctgaatttt gactccatct | 1740 |
| ccccagaaga tgctgggagt tacagctgct gggtgaacaa ctccatagga cagacagcgt | 1800 |
| ccaaggcctg gacacttgaa gtgctgtatg cacccaggag gctgcgtgtg tccatgagcc | 1860 |
| cgggggacca agtgatggag gggaagagtg caacccctgac ctgtgagagt gacgccaacc | 1920 |
| ctcccgtctc ccactacacc tggtttgact ggaataacca aagcctcccc caccacagcc | 1980 |
| agaagctgag attggagccg gtgaaggtcc agcactcggg tgcctactgg tgccaggggc | 2040 |
| ccaacagtgt gggcaagggc cgttcgcctc tcagcaccct tactgtctac tatagcccgg | 2100 |
| agaccatcgg caggcgagtg gctgtgggac tcgggtcctg cctcgccatc ctcatcctgg | 2160 |
| caatctgtgg gctcaagctc cagcgacgtt ggaagaggac acagagccag caggggcttc | 2220 |
| aggagaattc cagcggccag agcttctttg tgaggaataa aaaggttaga agggccccccс | 2280 |
| tctctgaagg cccccactcc ctgggatgct acaatccaat gatggaagat ggcattagct | 2340 |
| acaccaccct gcgctttccc gagatgaaca taccacgaac tggagatgca gagtcctcag | 2400 |
| agatgcagag acctccccgg acctgcgatg acacggtcac ttattcagca ttgcacaagc | 2460 |

-continued

```
gccaagtggg cgactatgag aacgtcattc cagattttcc agaagatgag gggattcatt    2520
actcagagct gatccagttt ggggtcgggg agcggcctca ggcacaagaa aatgtggact    2580
atgtgatcct caaacattga cactggatgg gctgcagcag aggcactggg ggcagcgggg    2640
gccagggaag tccccgagtt tccccagaca ccgccacatg gcttcctcct gcgtgcatgt    2700
gcgcacacac acacacacac gcacacacac acacacacac tcactgcgga gaaccttgtg    2760
cctggctcag agccagtctt tttggtgagg gtaaccccaa acctccaaaa ctcctgcccc    2820
tgttctcttc cactctcctt gctacccaga aatcatctaa atacctgccc tgacatgcac    2880
acctcccctg ccccaccagc ccactggcca tctccacccg gagctgctgt gtcctctgga    2940
tctgctcgtc attttccttc ccttctccat ctctctggcc ctctacccct gatctgacat    3000
ccccactcac gaatattatg cccagtttct gcctctgagg aaagcccag aaaaggacag     3060 aaacgaagta gaaaggggcc cagtcctggc ctggcttctc ctttggaagt gaggcattgc    3120
acggggagac gtacgtatca gcggcccctt gactctgggg actccgggtt tgagatggac    3180
acactggtgt ggattaacct gccagggaga cagagctcac aataaaaatg gctcagatgc    3240
cacttcaaag aaaaaaaaaa                                                 3260
```

<210> SEQ ID NO 61
<211> LENGTH: 847
<212> TYPE: PRT
<213> ORGANISM: Homo sapiens

<400> SEQUENCE: 61

```
Met His Leu Leu Gly Pro Trp Leu Leu Leu Val Leu Glu Tyr Leu
  1               5                  10                  15

Ala Phe Ser Asp Ser Ser Lys Trp Val Phe Glu His Pro Glu Thr Leu
                 20                  25                  30

Tyr Ala Trp Glu Gly Ala Cys Val Trp Ile Pro Cys Thr Tyr Arg Ala
             35                  40                  45

Leu Asp Gly Asp Leu Glu Ser Phe Ile Leu Phe His Asn Pro Glu Tyr
         50                  55                  60

Asn Lys Asn Thr Ser Lys Phe Asp Gly Thr Arg Leu Tyr Glu Ser Thr
 65                  70                  75                  80

Lys Asp Gly Lys Val Pro Ser Glu Gln Lys Arg Val Gln Phe Leu Gly
                 85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220
```

-continued

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
            245                 250                 255

Glu Gly Asp Ser Val Thr Met Thr Cys Glu Val Ser Ser Asn Pro
        260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
                340                 345                 350

Cys Met Ser Leu Ala Asn Pro Leu Pro Thr Asn Tyr Thr Trp Tyr His
            355                 360                 365

Asn Gly Lys Glu Met Gln Gly Arg Thr Glu Glu Lys Val His Ile Pro
370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
            435                 440                 445

Pro Ser Val Thr Arg Tyr Glu Trp Lys Pro His Gly Ala Trp Glu Glu
450                 455                 460

Pro Ser Leu Gly Val Leu Lys Ile Gln Asn Val Gly Trp Asp Asn Thr
465                 470                 475                 480

Thr Ile Ala Cys Ala Arg Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
            515                 520                 525

Cys Asp Phe Ser Ser Ser His Pro Lys Glu Val Gln Phe Phe Trp Glu
530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
            565                 570                 575

Ile Gly Gln Thr Ala Ser Lys Ala Trp Thr Leu Glu Val Leu Tyr Ala
            580                 585                 590

Pro Arg Arg Leu Arg Val Ser Met Ser Pro Gly Asp Gln Val Met Glu
            595                 600                 605

Gly Lys Ser Ala Thr Leu Thr Cys Glu Ser Asp Ala Asn Pro Pro Val
            610                 615                 620

Ser His Tyr Thr Trp Phe Asp Trp Asn Asn Gln Ser Leu Pro His His
625                 630                 635                 640

Ser Gln Lys Leu Arg Leu Glu Pro Val Lys Val Gln His Ser Gly Ala

```
                    645                 650                 655
Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
        675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
        755                 760                 765

Glu Met Asn Ile Pro Arg Thr Gly Asp Ala Glu Ser Ser Glu Met Gln
    770                 775                 780

Arg Pro Pro Arg Thr Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845
```

<210> SEQ ID NO 62
<211> LENGTH: 340
<212> TYPE: DNA
<213> ORGANISM: Homo sapiens

<400> SEQUENCE: 62

```
ctgggggtc cgggaaaggg gttgggccat gagccaggca gctccgaagc agtcactgag      60
gccagggagc ctgcacccag gtcatggggc gacctggctc tcactcctgg cctgggtgct     120
cacctacaga ccacttcact tcccctgtcc gcagcgtcac tatgtcctca taggtggctg    180
tctggtcaat gtccaggccc tcgtaggtgt gatcttcctc catgccagcc ttgctgtcat    240
ccttgtccag cagcaggaag ataggcacga tgatgaagag gatgatcagc agcgtctgga    300
tcatgatgat accatccttc agcgtgttcc tctgcttcag                          340
```

<210> SEQ ID NO 63
<211> LENGTH: 79
<212> TYPE: PRT
<213> ORGANISM: Homo sapiens

<400> SEQUENCE: 63

```
Leu Lys Gln Arg Asn Thr Leu Lys Asp Gly Ile Ile Met Ile Gln Thr
1               5                   10                  15

Leu Leu Ile Ile Leu Phe Ile Ile Val Pro Ile Phe Leu Leu Leu Asp
            20                  25                  30

Lys Asp Asp Ser Lys Ala Gly Met Glu Glu Asp His Thr Tyr Glu Gly
        35                  40                  45

Leu Asp Ile Asp Gln Thr Ala Thr Tyr Glu Asp Ile Val Thr Leu Arg
    50                  55                  60

Thr Gly Glu Val Lys Trp Ser Val Gly Glu His Pro Gly Gln Glu
```

<210> SEQ ID NO 64
<211> LENGTH: 340
<212> TYPE: DNA
<213> ORGANISM: Homo sapiens

<400> SEQUENCE: 64

```
ctgggggtc cgggaaaggg gttgggccat gagccaggca gctccgaagc agtcactgag      60
gccagggagc ctgcacccag gtcatggggc gacctggctc tcactcctgg cctgggtgct     120
cacctacaga ccacttcact tccctgtcc gcagcgtcac tatgtcctca taggtggctg      180
tctggtcaat gtccaggccc tcgtaggtgt gatcttcctc catgccagcc ttgctgtcat     240
ccttgtccag cagcaggaag ataggcacga tgatgaagag gatgatcagc agcgtctgga     300
tcatgatgat accatccttc agcgtgttcc tctgcttcag                           340
```

<210> SEQ ID NO 65
<211> LENGTH: 1226
<212> TYPE: DNA
<213> ORGANISM: Homo sapiens

<400> SEQUENCE: 65

```
ccacgcgtcc gcccacgcgt ccgcagagcg gtgaccatgg ccaggctggc gttgtctcct      60
gtgcccagcc actggatggt ggcgttgctg ctgctgctct cagctgagcc agtaccagca     120
gccagatcgg aggaccggta ccggaatccc aaaggtagtg cttgttcgcg gatctggcag     180
agcccacgtt tcatagccag gaaacggggc ttcacggtga aaatgcactg ctacatgaac     240
agcgcctccg gcaatgtgag ctggctctgg aagcaggaga tggacgagaa tccccagcag     300
ctgaagctgg aaaagggccg catggaagag tcccagaacg aatctctcgc caccctcacc     360
atccaaggca tccggtttga ggacaatggc atctacttct gccagcagaa gtgcaacaac     420
acctcggagg tctaccaggg ctgcggcaca gagctgcgag tcatgggatt cagcaccttg     480
gcacagctga agcagaggaa cacgctgaag gatggtatca tcatgatcca gacgctgctg     540
atcatcctct tcatcatcgt gcctatcttc ctgctgctgg acaaggatga cagcaaggct     600
ggcatggagg aagatcacac ctacgagggc ctggacattg accagacagc cacctatgag     660
gacatagtga cgctgcggac aggggaagtg aagtggtctg taggtgagca cccaggccag     720
gagtgagagc caggtcgccc catgacctgg gtgcaggctc cctggcctca gtgactgctt     780
cggagctgcc tggctcatgg cccaacccct ttccggacc ccccagctgg cctctgaagc      840
tggcccacca gagctgccat ttgtctccag ccctggtcc ccagctcttg ccaaagggcc      900
tggagtagaa ggacaacagg gcagcaactt ggagggagtt ctctggggat ggacgggacc     960
cagccttctg ggggtgctat gaggtgatcc gtccccacac atgggatggg ggaggcagag    1020
actggtccag agcccgcaaa tggactcgga gccgagggcc tcccagcaga gcttgggaag    1080
ggccatggac ccaactgggc cccagaagag ccacaggaac atcattcctc tcccgcaacc    1140
actcccaccc cagggaggcc ctggcctcca gtgccttccc ccgtggaata acggtgtgt     1200
cctgagaaac caaaaaaaaa aaaaaa                                         1226
```

<210> SEQ ID NO 66
<211> LENGTH: 229
<212> TYPE: PRT
<213> ORGANISM: Homo sapiens

<400> SEQUENCE: 66

```
Met Ala Arg Leu Ala Leu Ser Pro Val Pro Ser His Trp Met Val Ala
  1               5                  10                  15

Leu Leu Leu Leu Leu Ser Ala Glu Pro Val Pro Ala Ala Arg Ser Glu
                 20                  25                  30

Asp Arg Tyr Arg Asn Pro Lys Gly Ser Ala Cys Ser Arg Ile Trp Gln
             35                  40                  45

Ser Pro Arg Phe Ile Ala Arg Lys Arg Gly Phe Thr Val Lys Met His
 50                  55                  60

Cys Tyr Met Asn Ser Ala Ser Gly Asn Val Ser Trp Leu Trp Lys Gln
 65                  70                  75                  80

Glu Met Asp Glu Asn Pro Gln Gln Leu Lys Leu Glu Lys Gly Arg Met
                 85                  90                  95

Glu Glu Ser Gln Asn Glu Ser Leu Ala Thr Leu Thr Ile Gln Gly Ile
                100                 105                 110

Arg Phe Glu Asp Asn Gly Ile Tyr Phe Cys Gln Gln Lys Cys Asn Asn
            115                 120                 125

Thr Ser Glu Val Tyr Gln Gly Cys Gly Thr Glu Leu Arg Val Met Gly
130                 135                 140

Phe Ser Thr Leu Ala Gln Leu Lys Gln Arg Asn Thr Leu Lys Asp Gly
145                 150                 155                 160

Ile Ile Met Ile Gln Thr Leu Leu Ile Ile Leu Phe Ile Ile Val Pro
                165                 170                 175

Ile Phe Leu Leu Leu Asp Lys Asp Asp Ser Lys Ala Gly Met Glu Glu
                180                 185                 190

Asp His Thr Tyr Glu Gly Leu Asp Ile Asp Gln Thr Ala Thr Tyr Glu
                195                 200                 205

Asp Ile Val Thr Leu Arg Thr Gly Glu Val Lys Trp Ser Val Gly Glu
210                 215                 220

His Pro Gly Gln Glu
225

<210> SEQ ID NO 67
<211> LENGTH: 449
<212> TYPE: DNA
<213> ORGANISM: Homo sapiens
<220> FEATURE:
<221> NAME/KEY: modified_base
<222> LOCATION: (16)
<223> OTHER INFORMATION: n = g, a, c or t

<400> SEQUENCE: 67
aaaattgatc acaacnaggg aaaacaaaat aaaattaggg ggcaaagggt aggagtatgg      60
ggggagggga gagcaaacct atcgaatata tcttagaatt ttgctcagaa atcactgctg    120
cctctcaagt gttgcattgt ccctgcctaa accaagaagg ctaaacaaag cccctcctgt    180
ttgaattctt aaggtaagaa atttctaagc taagaaaaca ctattgccta aaaccaatga    240
tagtggagct catttacaaa taggcatgcc tcacacacac agtccaaagg caagacactg    300
gctttgaaat taggctcatg atgtgattcc tattatatgt acctgatttt tttaggcccc    360
aggtatgtgg accagagtta atgtcatgac tcttcaaaga tatgatgaaa agttgcccta    420
gaaatctaga gatgcatgtt tatttaatt                                      449

<210> SEQ ID NO 68
<211> LENGTH: 2359
<212> TYPE: DNA
<213> ORGANISM: Homo sapiens
```

<400> SEQUENCE: 68

```
ctttcaagaa aatacatctg tgctgtattt tccccttccc tcaggccatg atctctgctg    60
ttttccttac taactggcat gtcagtacaa gagtgattgt gaagctgctc cggaagggct   120
ttatgctaac ctctgttgct tgatgacatg tcctcaggac tctgatatta aaactcaatc   180
cttagataac aggtagcttt atcatggaag taggtagcaa tttggaatta gaccattctt   240
agttattttt ttcttaatga attgatacat gcactttaaa aaatattttt gttattttgg   300
gaagaaaaac tcagactttt aaaaaagtgt atattgtccc attataatat gtatatggaa   360
gagtgaaatc tgaacgctgt cttatattaa gcagtagaat taggtattat cataaaaagt   420
cttaatctgt agggaatatg agtttatgtt tatgagtcct gctcagtccc tctttgagag   480
aattagttga aacccagact ctaaagtctg cttttatatt tgtttgttaa gaccacttat   540
ctgcagaagg ttgcctttta accccagtgg ttctaaggtg tggaattgag tgaccctaat   600
atttacataa gagacttgtt ttagtggagc ataagggagg ggcataagtt acaccgtttt   660
gtgctgcttg agaactgtct tttaaaattg atcacaacga gggaaaacaa aataaaatta   720
ggggcaaag gtaggagta tggggggagg ggagagcaaa cctatcgaat atatcttaga   780
attttgctca gaaatcactg ctgcctctca agtgttgcat tgtccctgcc taaaccaaga   840
aggctaaaca aagcccctcc tgtttgaatt cttaaggtaa gaaatttcta agctaagaaa   900
acactattgc ctaaaaccaa tgatagtgga gctcatttac aaataggcat gcctcacaca   960
cacagtccaa aggcaagaca ctggctttga aattaggctc atgatgtgat tcctattata  1020
tgtacctgat ttttttaggc cccaggtatg tggaccagag ttaatgtcat gactcttcaa  1080
agatatgatg aaaagttgcc ctagaaatct agagatgcat gtttatttaa ttccatagtt  1140
taaaaaaaaa tttaagcagg tagttgtggc ttatctgggg gcaaataat atatgtgaaa  1200
ttgcttccag aggacaaagt atattttcta aagtcctgaa ataggatcat gaacccttct  1260
gaagttttgg tttgaaatat tatagtatat gatattacca aagagccctt aattcagagt  1320
ttaaggggct ctcttcctga actctcttca tcactcaggg ttgaatgtgt aatgttcctt  1380
gctattgatt gttattgttg attcttagga tcaggccaag aatcatctgg aaaacattat  1440
cttaattccg tctctcatat cctaaacagt acattttact aagaaattcc atatgaaaaa  1500
ctccactcat gtctcctgag attatcctgt aagtgaagta gctttcattt aaccaagcta  1560
aattatttcc atttagccat gttaaagaga agccaagtct agagaaagca atcctgtaac  1620
ccatgaatct ggtgtaccca ttttcccta acgtaacggg aagtgttttg aaattcccag  1680
aagagagctg ttttgtaatc aaagtgatgg attataagaa agccagactt tggaaaagga  1740
taattggaat aaagggaggt gcttgaagat tttccaaact actttatgtc atttagcttc  1800
tattttctga agggctttct ttggtgccat gtactcagat cagtcagttg actgaaagat  1860
gatcatgttt tcttcgtaaa gatttaagca attggcaact acaaagacat tatttctta  1920
ctgttctata tcatgtactg ttgctgacat tacaaaaagg gtctggaagg gaaaccgtgt  1980
cactgttta tcttttttct ttaaaataca aaagtatccc aactaatcat ttattatggt  2040
cagcttgttt tacatgtccc ctatgatgag aaatgctatc aacatctgtg atttctaaga  2100
gtcttaccaa attgttactt taattcttgt gtcctgctga gtggtttttc ttttaaaata  2160
ccatttttat caccctgtgg cactgggtgt gttactgcga ttacactgat gattctgagc  2220
tgtgcttctt caagtagctc agttcttgcg tttatatta ggtaacagtt ttgtgatgct  2280
```

```
tttgtgcatt ctttgtcatc tcttctgagt tttcgaatct gtcataaata aacttttca      2340 ctatgcacct ggtaaaaaa                                                   2359

<210> SEQ ID NO 69
<211> LENGTH: 240
<212> TYPE: DNA
<213> ORGANISM: Homo sapiens

<400> SEQUENCE: 69
cctaagccgc ctaaggggct gcctcggctg tccatcagtt acctcgtttc ctgagcagag       60
taattgggtg agattgttca tggaggcatt gctggctctc tagtcctgga acctacagtt      120
ggtccaattc attatgccaa agggtccgtc taggaggttc ttgttccaag tattgagatt      180
cccgagagaa gtaggtcccc ttagatagaa gcagagtttc tcagaggtat ttagcagcag      240

<210> SEQ ID NO 70
<211> LENGTH: 980
<212> TYPE: DNA
<213> ORGANISM: Homo sapiens

<400> SEQUENCE: 70
gccgctgccg ctccaggaga caggttccca tgcaggaatg aaagacatgg aagggaagag       60
gggggccagc tccctgagtc ctgtgtccac cagctgctgc taaataccct gagaaactc       120 tgcttctatc taaggggacc tacttctctc gggaatctca atacttggaa caagaacctc      180
ctagacggac cctttggcat aatgaattgg accaactgta ggttccagga ctagagagcc      240
agcaatgcct ccatgaacaa tctcacccaa ttactctgct caggaaacga ggtaactgat      300
ggacagccga ggcagcccct taggcggctt aggcctcccc tgtggagcat ccctgaggcg      360
gactccggcc agcccgagtg atgcgatcca agagcactc ccgggtagga aattgccccg       420
gtggaatgcc tcaccagagc agcgtgtagc agttccctgt ggaggattaa cacagtggct      480
gaacaccgga aaggaactgg cacttggagt ccggacatct gaaacttgta gactgggagc      540
tgtacatgga tgggagcagc ttcaccaacc cctgcaaagt gactctgaag aagacgacaa      600
gccctgctcc agtcacaccc ggaagctgac tggtccacgc acagctgaag catgaggaaa      660
ctcatcgcgg gactaatttt ccttaaaatt tagacttgca cagtaaggac ttcaactgac      720
cttcctcaga ctgagaactg tttccagtat atacatcaag tcactgaggt aggacaaaag      780
attgctacat tcctattatt ttaaggttac attttttgggg acccctcttt cttctgttct      840
agctattacc tttcttgtgt cacctagaaa aggaccagtc cttaattgta ttttaaaaac      900
tgtgatcatg ggaagcttta aattggttca ataacacgca tcaagttggt tatttcctgg      960
gctacatacc ttggatagat                                                  980

<210> SEQ ID NO 71
<211> LENGTH: 118
<212> TYPE: PRT
<213> ORGANISM: Homo sapiens

<400> SEQUENCE: 71

Met Asp Ser Arg Gly Ser Pro Leu Gly Gly Leu Gly Leu Pro Cys Gly
 1               5                  10                  15

Ala Ser Leu Arg Arg Thr Pro Ala Ser Pro Ser Asp Ala Ile Gln Arg
            20                  25                  30

Ala Leu Pro Gly Arg Lys Leu Pro Arg Trp Asn Ala Ser Pro Glu Gln
        35                  40                  45
```

```
Arg Val Ala Val Pro Cys Gly Gly Leu Thr Gln Trp Leu Asn Thr Gly
 50                  55                  60

Lys Glu Leu Ala Leu Gly Val Arg Thr Ser Glu Thr Cys Arg Leu Gly
 65                  70                  75                  80

Ala Val His Gly Trp Glu Gln Leu His Gln Pro Leu Gln Ser Asp Ser
                 85                  90                  95

Glu Glu Asp Asp Lys Pro Cys Ser Ser His Thr Arg Lys Leu Thr Gly
             100                 105                 110

Pro Arg Thr Ala Glu Ala
        115
```

```
<210> SEQ ID NO 72
<211> LENGTH: 531
<212> TYPE: DNA
<213> ORGANISM: Homo sapiens
<220> FEATURE:
<221> NAME/KEY: modified_base
<222> LOCATION: (519)
<223> OTHER INFORMATION: n = g, a, c or t

<400> SEQUENCE: 72
aaaaaggtaa ttttcagcat tttggcacct aaaagggaaa ctttcatctg cttacacagg    60
ccagaagcaa agacaaagat tgcatgttgt tcttacagat gacttaaatc atctctttga   120
tgataaaaat attttttaagc cgtgaaagtt atgagatatt ctgggtaagc ctgattatca   180
aagaatacca caaatagctt tggagatcgt gtattgtttg tcactgagtc aaagagatct   240
gtgggattgt gaggattctt gggtggaggg gtgactaatc ctgcacgtcc ctttgtgaag   300
actccagtaa gtactcgcac aacgtacatg tgctttctcc cattgctgtc tggcttggag   360
taggtgtcct tggcagaata actggcatcc acagcaaaat aggttccttt tccataggat   420
acagcatttt tcccacacaa cttctattaa agccgtgctg attgacatat ggcactgagt   480
ctgcatctgt cccatggaag aggagtctct cattattcnt atggtcattc t             531

<210> SEQ ID NO 73
<211> LENGTH: 1956
<212> TYPE: DNA
<213> ORGANISM: Homo sapiens

<400> SEQUENCE: 73
attgttatca actctttgat atctgatgat caatgctcca agaaattgga ttaatatttt    60
tacacaatat tgttgtagtc agtaactgtt tctatttcca ggcatttttta gatgaattca   120
ctaactggtc aagaataaat cccaacaagg ccaggattcc catggcagga gatacccaag   180
gtgtggtcgg gactgtctct aagccttgtt tcacagcata tgaaatgaaa atcggtgcaa   240
ttacttttca ggttgctact ggagatatag ccactgaaca ggtagatgtt attgtaaact   300
caacagcaag gacatttaat cggaaatcag gtgtgtcaag agctatttta gaaggtgctg   360
gacaagctgt ggaaagtgaa tgtgctgtac tagctgcaca gcctcacaga gattttataa   420
ttacaccagg tggatgctta aagtgcaaaa taataattca tgttcctggg ggaaaagatg   480
tcaggaaaac ggtcaccagt gttctagaag agtgtgaaca gaggaagtac acatcggttt   540
cccttccagc cattggaaca ggaaatgccg gaaaaaaccc tatcacagtt gctgataaca   600
taatcgatgc tattgtagac ttctcatcac aacattccac cccatcatta aaaacagtta   660
aagttgtcat ttttcaacct gagctgctaa atatattcta cgacagcatg aaaaaaagag   720
acctctctgc atcactgaac tttcagtcca cattctccat gactacatgt aatcttcctg   780
```

-continued

```
aacactggac tgacatgaat catcagctgt tttgcatggt ccagctagag ccaggacaat    840
cagaatataa taccataaag gacaagttca cccgaacttg ttcttcctac gcaatagaga    900
agattgagag gatacagaat gcatttctct ggcagagcta ccaggtaaag aaaaggcaaa    960
tggatatcaa gaatgaccat aagaataatg agagactcct cttccatggg acagatgcag   1020
actcagtgcc atatgtcaat cagcacggct ttaatagaag ttgtgctggg aaaaatgctg   1080
tatcctatgg aaaaggaacc tattttgctg tggatgccag ttattctgcc aaggacacct   1140
actccaagcc agacagcaat gggagaaagc acatgtacgt tgtgcgagta cttactggag   1200
tcttcacaaa gggacgtgca ggattagtca ccccctccacc caagaatcct cacaatccca   1260
cagatctctt tgactcagtg acaaacaata cacgatctcc aaagctattt gtggtattct   1320
ttgataatca ggcttaccca gaatatctca aactttcac ggcttaaaaa tattttatc    1380 atcaaagaga tgatttaagt catctgtaag aacaacatgc aatctttgtc tttgcttctg   1440
gcctgtgtaa gcagatgaaa gtttccctt taggtgccaa aatgctgaaa attaccttt    1500 taaagtgctc tattgctgcg atttgtagca tacctttttt tctcagcaaa ttgatgggtg   1560
gaagctgaga aatgtatggt aaatgtcaca gagctacaac cattcacaga caccaaatct   1620
ctaggagaat aaaaagcaca ttattctttt tctatcagaa aaaacaaga tgcatcacct    1680 taaaaccaag atgacattgt tcttcttgga acatgttaag acatcgaatg gtggcgggtt   1740
aaactgtact gcttaagtgg agcggctacc gttatgcatc tatcacagtt ggggattttg   1800
ccttattaag gaaaacttgt caatagttca gctgaaatga ctgaatcaca gaatattaac   1860
tctgttatgg aacaaatcat aacagatttt acctgtttac atttcaggta aaatgtatc    1920 gcattgttat ctaatattaa aaaattaccc ccaatt                             1956
```

<210> SEQ ID NO 74
<211> LENGTH: 444
<212> TYPE: PRT
<213> ORGANISM: Homo sapiens

<400> SEQUENCE: 74

```
Met Leu Gln Arg Ile Gly Leu Ile Phe Leu His Asn Ile Val Val
  1               5                  10                 15

Ser Asn Cys Phe Tyr Phe Gln Ala Phe Leu Asp Glu Phe Thr Asn Trp
                 20                  25                  30

Ser Arg Ile Asn Pro Asn Lys Ala Arg Ile Pro Met Ala Gly Asp Thr
             35                  40                  45

Gln Gly Val Val Gly Thr Val Ser Lys Pro Cys Phe Thr Ala Tyr Glu
         50                  55                  60

Met Lys Ile Gly Ala Ile Thr Phe Gln Val Ala Thr Gly Asp Ile Ala
     65                  70                  75                  80

Thr Glu Gln Val Asp Val Ile Val Asn Ser Thr Ala Arg Thr Phe Asn
                 85                  90                  95

Arg Lys Ser Gly Val Ser Arg Ala Ile Leu Glu Gly Ala Gly Gln Ala
            100                 105                 110

Val Glu Ser Glu Cys Ala Val Leu Ala Ala Gln Pro His Arg Asp Phe
        115                 120                 125

Ile Ile Thr Pro Gly Gly Cys Leu Lys Cys Lys Ile Ile His Val
    130                 135                 140

Pro Gly Gly Lys Asp Val Arg Lys Thr Val Thr Ser Val Leu Glu Glu
145                 150                 155                 160

Cys Glu Gln Arg Lys Tyr Thr Ser Val Ser Leu Pro Ala Ile Gly Thr
```

```
                165                 170                 175
Gly Asn Ala Gly Lys Asn Pro Ile Thr Val Ala Asp Asn Ile Ile Asp
            180                 185                 190

Ala Ile Val Asp Phe Ser Ser Gln His Ser Thr Pro Ser Leu Lys Thr
        195                 200                 205

Val Lys Val Val Ile Phe Gln Pro Glu Leu Leu Asn Ile Phe Tyr Asp
    210                 215                 220

Ser Met Lys Lys Arg Asp Leu Ser Ala Ser Leu Asn Phe Gln Ser Thr
225                 230                 235                 240

Phe Ser Met Thr Thr Cys Asn Leu Pro Glu His Trp Thr Asp Met Asn
                245                 250                 255

His Gln Leu Phe Cys Met Val Gln Leu Glu Pro Gly Gln Ser Glu Tyr
            260                 265                 270

Asn Thr Ile Lys Asp Lys Phe Thr Arg Thr Cys Ser Ser Tyr Ala Ile
        275                 280                 285

Glu Lys Ile Glu Arg Ile Gln Asn Ala Phe Leu Trp Gln Ser Tyr Gln
    290                 295                 300

Val Lys Lys Arg Gln Met Asp Ile Lys Asn Asp His Lys Asn Asn Glu
305                 310                 315                 320

Arg Leu Leu Phe His Gly Thr Asp Ala Asp Ser Val Pro Tyr Val Asn
                325                 330                 335

Gln His Gly Phe Asn Arg Ser Cys Ala Gly Lys Asn Ala Val Ser Tyr
            340                 345                 350

Gly Lys Gly Thr Tyr Phe Ala Val Asp Ala Ser Tyr Ser Ala Lys Asp
        355                 360                 365

Thr Tyr Ser Lys Pro Asp Ser Asn Gly Arg Lys His Met Tyr Val Val
    370                 375                 380

Arg Val Leu Thr Gly Val Phe Thr Lys Gly Arg Ala Gly Leu Val Thr
385                 390                 395                 400

Pro Pro Pro Lys Asn Pro His Asn Pro Thr Asp Leu Phe Asp Ser Val
                405                 410                 415

Thr Asn Asn Thr Arg Ser Pro Lys Leu Phe Val Val Phe Phe Asp Asn
            420                 425                 430

Gln Ala Tyr Pro Glu Tyr Leu Ile Thr Phe Thr Ala
        435                 440

<210> SEQ ID NO 75
<211> LENGTH: 449
<212> TYPE: DNA
<213> ORGANISM: Homo sapiens

<400> SEQUENCE: 75
cgaggtctga gctcctctgg ttcttctcta gacctgctcc ctctctgaaa tgcaaggccg      60
tgcctttaat gggcttttgg cattctgtct ccagacctcc cttctcatct gaaggctct     120 caggagaaca gagaaaaaac cagcctgtct ccaaactggc ccgtctcagg gactgggggc     180
ctttaccccc agtgaaagat gcagacttta cagcgctgca gtacagtaga gtcaagtgac     240
tccttcagat agttggatgg gtctctcgat cattcctgat aataacattt tgcctatgtt     300
aagtgctttc cacctatcat gttaccttct aactactccc ttggttggat acaggtatta     360
gccccatttc acaattaaga aattgaggct taaaaggatt aaagagtttt ttagaggaga     420
aacagctctt ccttacagaa ggatcccaa                                      449

<210> SEQ ID NO 76
```

<211> LENGTH: 79
<212> TYPE: PRT
<213> ORGANISM: Homo sapiens

<400> SEQUENCE: 76

Arg Ser His Leu Thr Leu Leu Tyr Cys Ser Ala Val Lys Ser Ala Ser
1               5                   10                  15

Phe Thr Gly Gly Lys Gly Pro Gln Ser Leu Arg Arg Ala Ser Leu Glu
            20                  25                  30

Thr Gly Trp Phe Phe Leu Cys Ser Pro Glu Ser Pro Ser Asp Glu Lys
        35                  40                  45

Gly Gly Leu Glu Thr Glu Cys Gln Lys Pro Ile Lys Gly Thr Ala Leu
    50                  55                  60

His Phe Arg Glu Gly Ala Gly Leu Glu Lys Asn Gln Arg Ser Ser
65                  70                  75

<210> SEQ ID NO 77
<211> LENGTH: 3067
<212> TYPE: DNA
<213> ORGANISM: Homo sapiens

<400> SEQUENCE: 77

| | | | | | |
|---|---|---|---|---|---|
| ggcacgagca | atgggactta | tcgctgctga | tgttaacctt | gatctcttgg | ttcaggtggt | 60 |
| gcctgccagc | tgtctccact | gtggagttac | tattttcct | tttccccatt | ttattcatca | 120 |
| gaagccagtc | actaagcgag | gtcaaactcc | aggacagggg | aattaagtgc | caccttctgg | 180 |
| agagggagca | ttcacattta | ttacttggga | tccttctgta | aggaagagct | gtttctcctc | 240 |
| taaaaaactc | tttaatcctt | ttaagcctca | atttcttaat | tgtgaaatgg | ggctaatacc | 300 |
| tgtatccaac | caagggagta | gttagaaggt | aacatgatag | gtggaaagca | cttaacatag | 360 |
| gcaaaatgtt | attatcagga | atgatcgaga | gacccatcca | actatctgaa | ggagtcactt | 420 |
| aactctactg | tactgcagcg | ctgtaaagtc | tgcatctttc | actggggta | aaggcccca | 480 |
| gtccctgaga | cgggccagtt | tggagacagg | ctggttttt | ctctgttctc | ctgagagccc | 540 |
| ttcagatgag | aagggaggtc | tggagacaga | atgccaaaag | cccattaaag | gcacggcctt | 600 |
| gcatttcaga | gagggagcag | gtctagagaa | gaaccagagg | agctcagctg | agatatggtg | 660 |
| tatggattgg | atttttggtag | aagatgggaa | gaaccaaaca | cctgagaaac | cactttgaag | 720 |
| atcggggtca | gagtaaggcc | taacacatag | ttggctccca | gtaattattg | gttgattgaa | 780 |
| cagctcaaag | agcaactcga | ccaagaacac | tggactggga | gtccagttac | ttggatcttg | 840 |
| cattcctgat | ttattttat | tttatatgta | ttttttctat | tttttgaga | cgaagtctca | 900 |
| ctcactctgt | cgcccaggct | ggactacaat | ggcacgatct | cggctcactg | caaactctgc | 960 |
| ctcccaggtt | caagcgattc | tcctgcctca | gcctctcgag | tagctaggat | tacaggcatg | 1020 |
| caccaccacg | ctggctaatt | tttgtatttt | tagtagagac | ggggttttgc | catgttggcc | 1080 |
| atgctggtgt | ccacctcctg | acctcagttg | atcttcctgc | ctcagccttc | caaaatgttg | 1140 |
| ggattacagg | cgtgagccac | cgtgcctggc | cgtgatttat | tttttttgtg | tatgtttgtt | 1200 |
| tttgtcaact | tgctgtgtga | ccttaagcaa | gttacttaac | ttctctgggc | ttcactttcc | 1260 |
| atggatgaac | attgtaaaga | ggctggagag | agatgaggac | taggtacagg | ctttagagga | 1320 |
| gagccaccgc | cccggacttc | tccctctgtc | accccgcttt | ccatgaccct | ccttgcctga | 1380 |
| ctttgtgact | ccttgcctcg | ctatcaaaac | aagtgctgca | atctcagtgc | tttccaagag | 1440 |
| ccctgcattg | ttagaaaactt | cccagcacgc | agcaaaggct | gctgcaatac | tcgctctgcc | 1500 |

-continued

```
tgcctttgcc ctgcgcttcc tacttaccct ccttttgttt ctcccaaaca tctgtccctg    1560
actatgctca tctcatgttt gtcctcagct gctgaaaggg ccacgtttgt tttcattaca    1620
aataagacca ccgagtgggc tcctggcgtg ggggcgggag cagccgcgcg cagtcttcag    1680
aggcagcccc ccaggctgtc tctggagggt gtgtctctgc ttccctttcc ccgtgtttat    1740
tttcagacga agccaagtgg cccgggggga ccctccggac tcccagcctt cagagaggag    1800
ggcagctcgg gctttcgccg cagtgcttcc tgcccgtcac gtgtgtgctc ctagccgggg    1860 tcggggagc tggtatcttg gcccttctgg gaggacgcgc acagcccgag gaggcagagc     1920
cccagacggg aatgggcttt tcagaggtgg ggtgcgggcg aggggacgat gcattatttt    1980
taatatttga tttattttc caactggact tcttcccggg gctctttctg ggcccagctg     2040
cctttgtgat cccgcgcccc ggtcctcggc ctctcacctc cagcgccggg gcgcccctg     2100 ctgtcggaag cggctgtgac cgggcagagg tgctatctgg gactctgggt tctcagcccg    2160
gggacagcga accgaggggc agatgatcca tcagaaaaga gccggcactg cccagccccg    2220 cgccctgcc cctgccttt tccggagcg cgccgcgccg caccgctac ggccgcttga        2280 ccccatcttt gagcccggcc ccaagctctg gaccgtcgt gccctcatc aaggaagagc     2340 caaggacccc aaggagaagg tcaggagcgg cggtgtggat gtcccttggc tgcaggcccc    2400
gccgcgcact cccttcagtc cttcccttct ctagggacca ggtagcatca gtgcctggat    2460
ctcggccttg tgtgccctgc tccctgcccc acctactaag aaccaagtct ggttcaccgg    2520
ctcccaagag ctggaaccca ttctcagcta gctgggggcc caggccaccc cttccctcca    2580
gacctgtgtg ccttctgccc tggctccagg gccccccaca ccgtgaccag gcgggatcc    2640 ctatggggct ggccagtcgg caccgtgcca ggcccacagt gccctgggcg tccatggaag    2700
tcgttctgtg tctttaaaat cagaaggaag acattaacct ttaggctgaa gaaaatgttt    2760
tagtacacag caataactta tttgtcttta ccaacagcc ataaaatata actttaaata    2820
ttctattgat agagaaagga gttcatgaag gcagaaatgc ctggggccca cgaacatccc    2880
agtgtggccc tggacgggac atcatgctgg gcaacacagc taaaatgcgg gtgaagacca    2940
gatttcttgc acatggcggt gacgggatgc tccctagaga gcttcaagtg gattctttgc    3000 ttttattt ctctcttaat aaaaatgtat gatgtttaca ttgtcagaga aaaaaaaaa      3060 aaaaaaa                                                             3067
```

<210> SEQ ID NO 78
<211> LENGTH: 554
<212> TYPE: DNA
<213> ORGANISM: Homo sapiens
<220> FEATURE:
<221> NAME/KEY: modified_base
<222> LOCATION: (1)..(554)
<223> OTHER INFORMATION: n = g, a, c or t

<400> SEQUENCE: 78

```
aaagcgaatt catactataa cagcagaaac aaaacttcag atttcagaat ttgttattgg     60
caaaatttat tctcattata cctgcttcat atgggtatat tactattaaa acagaatacc    120
atagagtaat tgcattattt gaaaattctn tcattttaca atgcacttca ccaatgaaac    180
agntaatttc cattttgaaa attaaaagaa aacagcacag agaagttaaa tgcggtgtag    240
caaagttatg gggtctgctt gagggcacta acctcaacag attattcctc ctctccttag    300
aataaccatg aaaatacaaa tttacttagc acatttttgc ttttttaagta gctggttcat    360 tttctgaatt tcccacattc agagttccag tcattattgt tacatcatgt ttgcagaaac    420
```

```
cttgtcttat ttagtgtcta tttgcatata accctgaaaa cattattatt tgaaaacttt      480
tctatatctc aaattaatat acattttcat aacctacctt tgnattaaga cttgcaattt      540
tatcaatcta ttat                                                       554
```

<210> SEQ ID NO 79
<211> LENGTH: 3243
<212> TYPE: DNA
<213> ORGANISM: Homo sapiens

<400> SEQUENCE: 79

```
ccgcagcctc cgcgggtggc aagcgggctg gggagagccg agggccaaag gaagagaaaa       60
tcgcggggag tctctggccg ggagagtcca ggtagcgctc ggcgggcagc agtgcgcagg      120
cccctcggct tcaaccgcca caatgctgcc agcagcgcca ggcaaggggc ttgggagccc      180
ggaccccgcc ccctgcggcc cagcgccccc aggaaataca aaagatataa taatgatata      240
tgaagaagat gctgaggaat gggctctgta cttgacagaa gtattttttac atgttgtgaa      300 aagggaagcc atcctgttat atcgcttgga gaatttctct tttcggcatt tggagttgct      360
gaacttaacg tcttacaaat gtaaactttt gatattatca aatagcctgc ttagagacct      420
aactccaaag aaatgtcagt ttctggaaaa gatacttcat tcaccaaaaa gtgtagttac      480
tttgctttgt ggagtgaaga gttcagatca gctctatgaa ttactaaata tctctcaaag      540
cagatgggag atctcaactg aacaggaacc tgaagactac atctctgtaa tccagagtat      600
catattcaaa gattctgaag actactttga ggtcaacatt ccaacagacc tacgagcaaa      660
acattctggg gaaataagtg agagaaagga aattgaagaa ctatcagaag cttcaagaaa      720
caccatacca ctagcagtgg tgcttcccac tgaaattcca tgtgagaatc ctggtgaaat      780
attcataatt ttgagagatg aagtaattgg tgatactgta gaggttgaat ttacatcaag      840
taataagcgc attagaacac ggccagccct ttggaataag aaagtctggt gcatgaaagc      900
tttagagttt cctgctggtt cagtccatgt caatgtctac tgtgatggaa tcgttaaagc      960
tacaaccaaa attaagtact acccaacagc aaaggcaaag gaatgcctat tcagaatggc     1020
agattcagga gagagtttgt gccagaatag cattgaagaa cttgatggtg tccttacatc     1080
catattcaaa catgagatac catattatga gttccagtct cttcaaactg aaatttgttc     1140
tcaaaacaaa tatactcatt tcaaagaact tccaactctt ctccactgtg cagcaaaatt     1200
tggcttaaag aacctggcta ttcatttgct tcaatgttca ggagcaacct gggcatctaa     1260
gatgaaaaat atggagggtt cagacccgc acatattgct gaaaggcatg gtcacaaaga      1320
actcaagaaa atcttcgaag acttttcaat ccaagaaatt gacataaata atgagcaaga     1380
aaatgattat gaagaggata ttgcctcatt ttccacatat attccttcca cacagaaccc     1440
agcatttcat catgaaagca gaagacata cgggcagagt gcagatggag ctgaggcaaa     1500
tgaaatggaa ggggaaggaa acagaatgg atcaggcatg gagaccaaac acagcccact      1560
agaggttggc agtgagagtt ctgaagacca gtatgatgac ttgtatgtgt tcattcctgg      1620
tgctgatcca gaaaataatt cacaagagcc actcatgagc agcagacctc ctctccccc      1680 gccgcgacct gtagctaatg ccttccaact ggaaagacct cacttcacct taccagggac      1740
aatggtggaa ggccaaatgg aaagaagtca aaactggggt catcctggtg ttagacaaga     1800
aacaggagat gaaccaaag gagaaaaaga gaagaaagaa gaggaaaaag agcaggagga      1860
ggaagaagac ccatatactt tgctgagat tgatgacagt gaatatgaca tgatattggc     1920
```

```
caatctgagt ataagaaaaa aaactgggag tcggtctttc attataaata gacctcctgc    1980
ccccacaccc cgacccacaa gtatacctcc aaaagaggaa actacacctt acatagctca    2040
agtgtttcaa caaaagacag ccagaagaca atctgatgat gacaagttcc gtggtcttcc    2100
taagaaacaa gacagagctc ggatagagag tccagccttt tctactctca ggggctgtct    2160
aactgatggt caggaagaac tcatcctcct gcaggagaaa gtaaagaatg ggaaaatgtc    2220
tatggatgaa gctctggaga aatttaaaca ctggcagatg ggaaaagtg gcctggaaat     2280 gattcagcag gagaaattac gacaactacg agactgcatt attgggaaaa ggccagaaga    2340
agaaaatgtc tataataaac tcaccattgt gcaccatcca ggtggtaagg aaactgccca    2400
caatgaaaat aagttttata atgtacactt cagcaataag cttcctgctc gaccccaagt    2460
tgaaaaggaa tttggtttct gttgcaagaa agatcattaa agaaggttat tataatgaaa    2520
ctcacgaatc tacggacatt ttgctttcag ggtgaagcaa gcttgaattt ggattgcctg    2580
cttttcttta agcgaattca tactataaca gcagaaacaa aacttcgat ttcagaattt      2640 gttattggca aaatttattc tcattatacc tgcttcatat gggtatatta ctattaaaac    2700
agaataccat agagtaattg cattatttga aaattctctc atttacaat gcacttcacc     2760 aatgaaacag ctaatttcca ttttgaaaat taaaagaaaa cagcacagag aagttaaatg    2820
cggtgtagca agttatggg gtctgcttga gggcactaac ctcaacagat tattcctcct      2880
ctccttagaa taaccatgaa atacaaatt tacttagcac attttgctt tttaagtagc      2940 tggttcattt tctgaatttc tcacattcag agttccagtc attattgtta catcatgttt    3000
gcagaaacct tgtcttattt agtgtctatt tgcatataac cctgaaaaca ttattatttg    3060
aaaacttttc tatatctcaa attaatatac attttcataa cctaccttg tattaagact      3120 tgcaatttta tcaatctatt atttcttaga aacaatttac tagcttagaa tagaaagcaa    3180
tgttatcgtc atataatttt catgtacaaa tgccacaaat aaattgaatg tttaaagcta    3240
aaa                                                                  3243
```

<210> SEQ ID NO 80
<211> LENGTH: 755
<212> TYPE: PRT
<213> ORGANISM: Homo sapiens

<400> SEQUENCE: 80

```
Met Ile Tyr Glu Glu Asp Ala Glu Glu Trp Ala Leu Tyr Leu Thr Glu
  1               5                  10                  15

Val Phe Leu His Val Val Lys Arg Glu Ala Ile Leu Leu Tyr Arg Leu
                 20                  25                  30

Glu Asn Phe Ser Phe Arg His Leu Glu Leu Leu Asn Leu Thr Ser Tyr
             35                  40                  45

Lys Cys Lys Leu Leu Ile Leu Ser Asn Ser Leu Leu Arg Asp Leu Thr
         50                  55                  60

Pro Lys Lys Cys Gln Phe Leu Glu Lys Ile Leu His Ser Pro Lys Ser
     65                  70                  75                  80

Val Val Thr Leu Leu Cys Gly Val Lys Ser Ser Asp Gln Leu Tyr Glu
                 85                  90                  95

Leu Leu Asn Ile Ser Gln Ser Arg Trp Glu Ile Ser Thr Glu Gln Glu
            100                 105                 110

Pro Glu Asp Tyr Ile Ser Val Ile Gln Ser Ile Ile Phe Lys Asp Ser
        115                 120                 125

Glu Asp Tyr Phe Glu Val Asn Ile Pro Thr Asp Leu Arg Ala Lys His
```

-continued

```
            130                 135                 140
Ser Gly Glu Ile Ser Glu Arg Lys Glu Ile Glu Glu Leu Ser Glu Ala
145                 150                 155                 160

Ser Arg Asn Thr Ile Pro Leu Ala Val Val Leu Pro Thr Glu Ile Pro
                165                 170                 175

Cys Glu Asn Pro Gly Glu Ile Phe Ile Ile Leu Arg Asp Glu Val Ile
                180                 185                 190

Gly Asp Thr Val Glu Val Glu Phe Thr Ser Ser Asn Lys Arg Ile Arg
                195                 200                 205

Thr Arg Pro Ala Leu Trp Asn Lys Lys Val Trp Cys Met Lys Ala Leu
210                 215                 220

Glu Phe Pro Ala Gly Ser Val His Val Asn Val Tyr Cys Asp Gly Ile
225                 230                 235                 240

Val Lys Ala Thr Thr Lys Ile Lys Tyr Tyr Pro Thr Ala Lys Ala Lys
                245                 250                 255

Glu Cys Leu Phe Arg Met Ala Asp Ser Gly Glu Ser Leu Cys Gln Asn
                260                 265                 270

Ser Ile Glu Glu Leu Asp Gly Val Leu Thr Ser Ile Phe Lys His Glu
                275                 280                 285

Ile Pro Tyr Tyr Glu Phe Gln Ser Leu Gln Thr Glu Ile Cys Ser Gln
290                 295                 300

Asn Lys Tyr Thr His Phe Lys Glu Leu Pro Thr Leu Leu His Cys Ala
305                 310                 315                 320

Ala Lys Phe Gly Leu Lys Asn Leu Ala Ile His Leu Leu Gln Cys Ser
                325                 330                 335

Gly Ala Thr Trp Ala Ser Lys Met Lys Asn Met Glu Gly Ser Asp Pro
                340                 345                 350

Ala His Ile Ala Glu Arg His Gly His Lys Glu Leu Lys Lys Ile Phe
                355                 360                 365

Glu Asp Phe Ser Ile Gln Glu Ile Asp Ile Asn Asn Glu Gln Glu Asn
                370                 375                 380

Asp Tyr Glu Glu Asp Ile Ala Ser Phe Ser Thr Tyr Ile Pro Ser Thr
385                 390                 395                 400

Gln Asn Pro Ala Phe His His Glu Ser Arg Lys Thr Tyr Gly Gln Ser
                405                 410                 415

Ala Asp Gly Ala Glu Ala Asn Glu Met Glu Gly Glu Gly Lys Gln Asn
                420                 425                 430

Gly Ser Gly Met Glu Thr Lys His Ser Pro Leu Glu Val Gly Ser Glu
                435                 440                 445

Ser Ser Glu Asp Gln Tyr Asp Asp Leu Tyr Val Phe Ile Pro Gly Ala
450                 455                 460

Asp Pro Glu Asn Asn Ser Gln Glu Pro Leu Met Ser Ser Arg Pro Pro
465                 470                 475                 480

Leu Pro Pro Pro Arg Pro Val Ala Asn Ala Phe Gln Leu Glu Arg Pro
                485                 490                 495

His Phe Thr Leu Pro Gly Thr Met Val Glu Gly Gln Met Glu Arg Ser
                500                 505                 510

Gln Asn Trp Gly His Pro Gly Val Arg Gln Glu Thr Gly Asp Glu Pro
                515                 520                 525

Lys Gly Glu Lys Glu Lys Lys Glu Glu Lys Glu Gln Glu Glu Glu
                530                 535                 540

Glu Asp Pro Tyr Thr Phe Ala Glu Ile Asp Asp Ser Glu Tyr Asp Met
545                 550                 555                 560
```

```
Ile Leu Ala Asn Leu Ser Ile Lys Lys Thr Gly Ser Arg Ser Phe
                565                 570                 575
Ile Ile Asn Arg Pro Pro Ala Pro Thr Pro Arg Pro Thr Ser Ile Pro
            580                 585                 590
Pro Lys Glu Glu Thr Thr Pro Tyr Ile Ala Gln Val Phe Gln Gln Lys
        595                 600                 605
Thr Ala Arg Arg Gln Ser Asp Asp Lys Phe Arg Gly Leu Pro Lys
    610                 615                 620
Lys Gln Asp Arg Ala Arg Ile Glu Ser Pro Ala Phe Ser Thr Leu Arg
625                 630                 635                 640
Gly Cys Leu Thr Asp Gly Gln Glu Glu Leu Ile Leu Leu Gln Glu Lys
                645                 650                 655
Val Lys Asn Gly Lys Met Ser Met Asp Glu Ala Leu Glu Lys Phe Lys
                660                 665                 670
His Trp Gln Met Gly Lys Ser Gly Leu Glu Met Ile Gln Gln Glu Lys
            675                 680                 685
Leu Arg Gln Leu Arg Asp Cys Ile Ile Gly Lys Arg Pro Glu Glu Glu
    690                 695                 700
Asn Val Tyr Asn Lys Leu Thr Ile Val His His Pro Gly Gly Lys Glu
705                 710                 715                 720
Thr Ala His Asn Glu Asn Lys Phe Tyr Asn Val His Phe Ser Asn Lys
                725                 730                 735
Leu Pro Ala Arg Pro Gln Val Glu Lys Glu Phe Gly Phe Cys Cys Lys
                740                 745                 750
Lys Asp His
        755

<210> SEQ ID NO 81
<211> LENGTH: 3195
<212> TYPE: DNA
<213> ORGANISM: Homo sapiens

<400> SEQUENCE: 81
ggaagagaaa atcgcgggga gtctctggcc gggagagtcc aggtagcgct cggcgggcag      60
cagtgcgcag gccccctcggc ttcaaccgcc acaatgctgc cagcagcgcc aggcaagggg    120
cttgggagcc cggaccccgc ccctgcggc ccagcgcccc caggaaatac aaaagatata     180
ataatgatat atgaagaaga tgctgaggaa tgggctctgt acttgacaga agtattttta    240
catgttgtga aagggaagc catcctgtta tatcgcttgg agaatttctc ttttcggcat     300
ttggagttgc tgaacttaac gtcttacaaa tgtaaacttt tgatattatc aaatagcctg   360
cttagagacc taactccaaa gaatgtcag tttctggaaa agatacttca ttcaccaaaa    420
agtgtagtta ctttgctttg tggagtgaag agttcagatc agctctatga attactaaat   480
atctctcaaa gcagatggga gatctcaact gaacaggaac ctgaagacta catctctgta   540
atccagagta tcatattcaa agattctgaa gactactttg aggtcaacat tccaacagac   600
ctacgagcaa acattctgg ggaaataagt gagagaaagg aaattgaaga actatcagaa    660
gcttcaagaa acaccatacc actagcagtg gtgcttccca ctgaaattcc atgtgagaat   720
cctggtgaaa tattcataat tttgagagat gaagtaattg gtgatactgt agaggttgaa   780
tttacatcaa gtaataagcg cattagaaca cggccagccc tttggaataa gaaagtctgg   840
tgcatgaaag ctttagagtt tcctgctggt tcagtccatg tcaatgtcta ctgtgatgga   900
atcgttaaag ctacaaccaa aattaagtac tacccaacag caaaggcaaa ggaatgccta   960
```

```
ttcagaatgg cagattcagg agagagtttg tgccagaata gcattgaaga acttgatggt    1020
gtccttacat ccatattcaa acatgagata ccatattatg agttccagtc tcttcaaact    1080
gaaatttgtt ctcaaaacaa atatactcat ttcaaagaac ttccaactct tctccactgt    1140
gcagcaaaat ttggcttaaa gaacctggct attcatttgc ttcaatgttc aggagcaacc    1200
tgggcatcta agatgaaaaa tatggagggt tcagaccccg cacatattgc tgaaaggcat    1260
ggtcacaaag aactcaagaa aatcttcgaa gactttccaa tccaagaaat tgacataaat    1320
aatgagcaag aaaatgatta tgaagaggat attgcctcat tttccacata tattccttcc    1380
acacagaacc cagcatttca tcatgaaagc agaaagacat acgggcagag tgcagatgga    1440
gctgaggcaa atgaaatgga aggggaagga aaacagaatg gatcaggcat ggagaccaaa    1500
cacagcccac tagaggttgg cagtgagagt tctgaagacc agtatgatga cttgtatgtg    1560
ttcattcctg gtgctgatcc agaaaataat tcacaagagc cactcatgag cagcagacct    1620
cctctccccc cgccgcgacc tgtagctaat gccttccaac tggaaagacc tcacttcacc    1680
ttaccaggga caatggtgga aggccaaatg gaaagaagtc aaaactgggg tcatcctggt    1740
gttagacaag aaacaggaga tgaacccaaa ggagaaaaag agaagaaaga gaggaaaaa    1800 gagcaggagg aggaagaaga cccatatact tttgctgaga ttgatgacag tgaatatgac    1860
atgatattgg ccaatctgag tataaagaaa aaaactggga gtcggtcttt cattataaat    1920
agacctcctg cccccacacc ccgacccaca agtataccctc caaagaggga aactacacct    1980
tacatagctc aagtgtttca acaaaagaca gccagaagac aatctgatga tgacaagttc    2040
cgtggtcttc ctaagaaaca agacagagct cggatagaga gtccagcctt ttctactctc    2100
aggggctgtc taactgatgg tcaggaagaa ctcatcctcc tgcaggagaa agtaaagaat    2160
gggaaaatgt ctatggatga agctctggag aaatttaaac actggcagat gggaaaaagt    2220
ggcctggaaa tgattcagca ggagaaatta cgacaactac gagactgcat tattgggaaa    2280
aggccagaag aagaaaatgt ctataataaa ctcaccattg tgcaccatcc aggtggtaag    2340
gaaactgccc acaatgaaaa taagttttat aatgtacact tcagcaataa gcttcctgct    2400
cgaccccaag ttgaaaagga atttggtttc tgttgcaaga aagatcatta agaaggtta    2460 ttataatgaa actcacgaat ctacggacat tttgctttca gggtgaagca agcttgaatt    2520
tggattgcct gctttcttta aagcgaattc atactataac agcagaaaca aaacttcaga    2580
tttcagaatt tgttattggc aaaatttatt ctcattatac ctgcttcata tgggtatatt    2640
actattaaaa cagaatacca tagagtaatt gcattatttg aaaattctct cattttacaa    2700
tgcacttcac caatgaaaca gctaatttcc attttgaaaa ttaaaagaaa acagcacaga    2760
gaagttaaat gcggtgtagc aaagttatgg ggtctgcttg agggcactaa cctcaacaga    2820
ttattcctcc tctccttaga ataaccatga aaatacaaat ttacttagca cattttgct    2880 ttttaagtag ctggttcatt ttctgaattt ctcacattca gagttccagt cattattgtt    2940
acatcatgtt tgcagaaacc ttgtcttatt tagtgtctat ttgcatataa ccctgaaaac    3000
attattattt gaaaactttt ctatatctca aattaatata cattttcata acctaccttt    3060
gtattaagac ttgcaatttt atcaatctat tatttcttag aaacaattta ctagcttaga    3120
atagaaagca atgttatcgt catataattt tcatgtacaa atgccacaaa taaattgaat    3180
gtttaaagct aaaaa                                                    3195
```

<210> SEQ ID NO 82

<211> LENGTH: 816
<212> TYPE: PRT
<213> ORGANISM: Homo sapiens

<400> SEQUENCE: 82

```
Gly Arg Glu Asn Arg Gly Glu Ser Leu Ala Gly Arg Val Gln Val Ala
1               5                   10                  15

Leu Gly Gly Gln Gln Cys Ala Gly Pro Ser Ala Ser Thr Ala Thr Met
            20                  25                  30

Leu Pro Ala Ala Pro Gly Lys Gly Leu Gly Ser Pro Asp Pro Ala Pro
        35                  40                  45

Cys Gly Pro Ala Pro Gly Asn Thr Lys Asp Ile Ile Met Ile Tyr
    50                  55                  60

Glu Glu Asp Ala Glu Glu Trp Ala Leu Tyr Leu Thr Glu Val Phe Leu
65                  70                  75                  80

His Val Val Lys Arg Glu Ala Ile Leu Leu Tyr Arg Leu Glu Asn Phe
                85                  90                  95

Ser Phe Arg His Leu Glu Leu Leu Asn Leu Thr Ser Tyr Lys Cys Lys
            100                 105                 110

Leu Leu Ile Leu Ser Asn Ser Leu Leu Arg Asp Leu Thr Pro Lys Lys
        115                 120                 125

Cys Gln Phe Leu Glu Lys Ile Leu His Ser Pro Lys Ser Val Val Thr
    130                 135                 140

Leu Leu Cys Gly Val Lys Ser Ser Asp Gln Leu Tyr Glu Leu Leu Asn
145                 150                 155                 160

Ile Ser Gln Ser Arg Trp Glu Ile Ser Thr Glu Gln Glu Pro Glu Asp
                165                 170                 175

Tyr Ile Ser Val Ile Gln Ser Ile Ile Phe Lys Asp Ser Glu Asp Tyr
            180                 185                 190

Phe Glu Val Asn Ile Pro Thr Asp Leu Arg Ala Lys His Ser Gly Glu
        195                 200                 205

Ile Ser Glu Arg Lys Glu Ile Glu Glu Leu Ser Glu Ala Ser Arg Asn
    210                 215                 220

Thr Ile Pro Leu Ala Val Val Leu Pro Thr Glu Ile Pro Cys Glu Asn
225                 230                 235                 240

Pro Gly Glu Ile Phe Ile Ile Leu Arg Asp Glu Val Ile Gly Asp Thr
                245                 250                 255

Val Glu Val Glu Phe Thr Ser Ser Asn Lys Arg Ile Arg Thr Arg Pro
            260                 265                 270

Ala Leu Trp Asn Lys Lys Val Trp Cys Met Lys Ala Leu Glu Phe Pro
        275                 280                 285

Ala Gly Ser Val His Val Asn Val Tyr Cys Asp Gly Ile Val Lys Ala
    290                 295                 300

Thr Thr Lys Ile Lys Tyr Tyr Pro Thr Ala Lys Ala Lys Glu Cys Leu
305                 310                 315                 320

Phe Arg Met Ala Asp Ser Gly Glu Ser Leu Cys Gln Asn Ser Ile Glu
                325                 330                 335

Glu Leu Asp Gly Val Leu Thr Ser Ile Phe Lys His Glu Ile Pro Tyr
            340                 345                 350

Tyr Glu Phe Gln Ser Leu Gln Thr Glu Ile Cys Ser Gln Asn Lys Tyr
        355                 360                 365

Thr His Phe Lys Glu Leu Pro Thr Leu Leu His Cys Ala Ala Lys Phe
    370                 375                 380

Gly Leu Lys Asn Leu Ala Ile His Leu Leu Gln Cys Ser Gly Ala Thr
```

```
        385                 390                 395                 400
Trp Ala Ser Lys Met Lys Asn Met Glu Gly Ser Asp Pro Ala His Ile
                405                 410                 415

Ala Glu Arg His Gly His Lys Glu Leu Lys Lys Ile Phe Glu Asp Phe
            420                 425                 430

Ser Ile Gln Glu Ile Asp Ile Asn Glu Gln Glu Asn Asp Tyr Glu
        435                 440                 445

Glu Asp Ile Ala Ser Phe Ser Thr Tyr Ile Pro Ser Thr Gln Asn Pro
    450                 455                 460

Ala Phe His His Glu Ser Arg Lys Thr Tyr Gly Gln Ser Ala Asp Gly
465                 470                 475                 480

Ala Glu Ala Asn Glu Met Gly Glu Gly Lys Gln Asn Gly Ser Gly
            485                 490                 495

Met Glu Thr Lys His Ser Pro Leu Glu Val Gly Ser Glu Ser Ser Glu
                500                 505                 510

Asp Gln Tyr Asp Asp Leu Tyr Val Phe Ile Pro Gly Ala Asp Pro Glu
        515                 520                 525

Asn Asn Ser Gln Glu Pro Leu Met Ser Ser Arg Pro Pro Leu Pro Pro
    530                 535                 540

Pro Arg Pro Val Ala Asn Ala Phe Gln Leu Glu Arg Pro His Phe Thr
545                 550                 555                 560

Leu Pro Gly Thr Met Val Glu Gly Gln Met Glu Arg Ser Gln Asn Trp
                565                 570                 575

Gly His Pro Gly Val Arg Gln Glu Thr Gly Asp Glu Pro Lys Gly Glu
            580                 585                 590

Lys Glu Lys Lys Glu Glu Lys Glu Gln Glu Glu Glu Asp Pro
        595                 600                 605

Tyr Thr Phe Ala Glu Ile Asp Asp Ser Glu Tyr Asp Met Ile Leu Ala
    610                 615                 620

Asn Leu Ser Ile Lys Lys Lys Thr Gly Ser Arg Ser Phe Ile Ile Asn
625                 630                 635                 640

Arg Pro Pro Ala Pro Thr Pro Arg Pro Thr Ser Ile Pro Pro Lys Glu
                645                 650                 655

Glu Thr Thr Pro Tyr Ile Ala Gln Val Phe Gln Gln Lys Thr Ala Arg
            660                 665                 670

Arg Gln Ser Asp Asp Lys Phe Arg Gly Leu Pro Lys Lys Gln Asp
        675                 680                 685

Arg Ala Arg Ile Glu Ser Pro Ala Phe Ser Thr Leu Arg Gly Cys Leu
    690                 695                 700

Thr Asp Gly Gln Glu Glu Leu Ile Leu Leu Gln Glu Lys Val Lys Asn
705                 710                 715                 720

Gly Lys Met Ser Met Asp Glu Ala Leu Glu Lys Phe Lys His Trp Gln
                725                 730                 735

Met Gly Lys Ser Gly Leu Glu Met Ile Gln Gln Glu Lys Leu Arg Gln
            740                 745                 750

Leu Arg Asp Cys Ile Ile Gly Lys Arg Pro Glu Glu Glu Asn Val Tyr
        755                 760                 765

Asn Lys Leu Thr Ile Val His Pro Gly Gly Lys Glu Thr Ala His
    770                 775                 780

Asn Glu Asn Lys Phe Tyr Asn Val His Phe Ser Asn Lys Leu Pro Ala
785                 790                 795                 800

Arg Pro Gln Val Glu Lys Glu Phe Gly Phe Cys Cys Lys Lys Asp His
                805                 810                 815
```

<210> SEQ ID NO 83
<211> LENGTH: 3544
<212> TYPE: DNA
<213> ORGANISM: Homo sapiens

<400> SEQUENCE: 83

```
attttggttt ctcttcaaga attaacaaac cacttactct tgaattctct tctagttaac      60
acaggcatca ctacttccaa ttgatctcag gatgtgggat cctcatacac attttgaaca     120
aaatcctctg tttcagcaag gaattcatat ttgcatatgg tgaagatggt ttctgaagtg     180
agatcagaag tagagcttct aatgacccc agaagcactg agtgaccaag tgacatacct      240
gccaggccca ttgtgtccat cgctctcaga gcagctgggg attgtgcttg gctcccagag     300
ctatggtgca aaaggcgggg tcgctagggc cactcaggga agagaaccc agaaacatgg      360
catgctgaca aaaggtagtc cctgcttatc cagcttcact ttctgctgat ttagttaccc     420
atggtcaact gccatctgaa aataggaaat acaaaagata taataatgat atatgaagaa     480
gatgctgagg aatgggctct gtacttgaca gaagtatttt tacatgttgt gaaaagggaa     540
gccatcctgt tatatcgctt ggagaatttc tcttttcggc atttggagtt gctgaactta     600
acgtcttaca aatgtaaact tttgatatta tcaaatagcc tgcttagaga cctaactcca     660
aagaaatgtc agtttctgga aaagatactt cattcaccaa aaagtgtagt tactttgctt     720
tgtggagtga agagttcaga tcagctctat gaattactaa atatctctca aagcagatgg     780
gagatctcaa ctgaacagga acctgaagac tacatctctg taatccagag tatcatattc     840
aaagattctg aagactactt tgaggtcaac attccaacag acctacgagc aaaacattct     900
ggggaaataa gtgagagaaa ggaaattgaa gaactatcag aagcttcaag aaacaccata     960
ccactagcag tggtgcttcc cactgaaatt ccatgtgagg atcctggtga atattcata    1020
attttgagag atgaagtaat tggtgatact gtagaggttg aatttacatc aagtaataag    1080
cgcattagaa cacggccagc cctttggaat aagaaagtct ggtgcatgaa agctttagag    1140
tttcctgctg gttcagtcca tgtcaatgtc tactgtgatg gaatcgttaa agctacaacc    1200
aaaattaagt actacccaac agcaaaggca aaggaatgcc tattcagaat ggcagattca    1260
ggagagagtt tgtgccagaa tagcattgaa gaacttgatg gtgtccttac atccatattc    1320
aaacatgaga taccatatta tgagttccag tctcttcaaa ctgaaatttg ttctcaaaac    1380
aaatatactc atttcaaaga acttccaact cttctccact gtgcagcaaa atttggctta    1440
aagaacctgg ctattcattt gcttcaatgt tcaggagcaa cctgggcatc taagatgaaa    1500
aatatggagg gttcagaccc cacacatatt gctgaaaggc atggtcacaa agaactcaag    1560
aaaatcttcg aagactttc aatccaagaa attgacataa ataatgagca gaaaatgat    1620
tatgaagagg atattgcctc attttccaca tatattcctt ccacacagaa cccagcattt    1680
catcatgaaa gcaggaagac atacgggcag agtgcagatg gagctgaggc aaatgaaatg    1740
gaaggggaag gaaaacagaa tggatcaggc atggagacca acacagccc actagaggtt    1800
ggcagtgaga gttctgaaga ccagtatgat gacttgtatg tgttcattcc tggtgctgat    1860
ccagaaaata attcacaaga gccactcatg agcagcagac ctcctctccc cccgccgcga    1920
cctgtagcta atgccttcca actggaaaga cctcacttca ccttaccagg acaatggtg    1980
gaaggccaaa tggaaagaag tcaaaactgg ggtcatcctg gtgttagaca agaaacagga    2040
gatgaaccca aggagaaaaa agagaagaaa gaagaggaaa aagagcagga ggaggaagaa    2100
```

```
gacccatata cttttgctga gattgatgac agtgaatatg acatgatatt ggccaatctg    2160
agtataaaga aaaaaactgg gagtcggtct ttcattataa atagacctcc tgccccaca     2220 ccccgaccca caagtatacc tccaaaagag gaaactacgc cttacatagc tcaagtgttt    2280
caacaaaaga cagccagaag acaatctgat gatgacaagt tccgtggtct tcctaagaaa    2340
caagacagag ctcggataga gagtccagcc ttttctactc tcaggggctg tctaactgat    2400
ggtcaggaag aactcatcct cctgcaggag aaagtaaaga atgggaaaat gtctatggat    2460
gaagctctgg agaaatttaa acactggcag atgggaaaaa gtggcctgga aatgattcag    2520
caggagaaat tacgacaact acgagactgc attattggga aaaggccaga agaagaaaat    2580
gtctataata aactcaccat tgtgcaccat ccaggtggta aggaaactgc ccacaatgaa    2640
aataagtttt ataatgtaca cttcagcaat aagcttcctg ctcgaccca  agttgaaaag    2700 gaatttggtt tctgttgcaa gaaagatcat taaagaaggt tattataatg aaactcacga    2760
atctacggac attttgcttt cagggtgaag caagcttgaa tttggattgc ctgctctctt    2820
taaagcgaat tcatactatg acagcagaaa caaaacttca gatttcagaa tttgttattg    2880
gcaaaattta ttctcattat acctgcttca tatgggtata ttactattaa aacagaatac    2940
catagagtaa ttgcattatt tgaaaattct ctcattttac aatgcacttc accaatgaaa    3000
cagctaattt ccattttgaa aattaaaaga aaacagcaca gagaagttaa atgcggtgta    3060
gcaaagttat ggggtctgct tgagggcact aacctcaaca gattattcct ccctccttaa    3120
gaataaccat gaaaatacaa atttacttag cacatttctg cttttttaagt agctggttca    3180 ttttctgaat ttctcacatt cagagttcca gtcattattg ttacatcatg tttgcagaaa    3240
ccttgtctta tttagtgtct atttgcatat aaccctgaaa acattattat ttgaaaactt    3300
ttctatatct caaattaata tacattttca taacctacct ttgtattaag acttgcaatt    3360
ttatcaatct attatttctt agaaacaatt tactagctta gaatagaaag caatgttatc    3420
gtcatataat tttcatgtac aaatgccaca aataaattga atgtttaaag ctatgtctga    3480
gtttttaaag taaatttata agaattagcc aataaaattg cttctcggcc ttttggctaa    3540
gatc                                                                 3544
```

<210> SEQ ID NO 84
<211> LENGTH: 770
<212> TYPE: PRT
<213> ORGANISM: Homo sapiens

<400> SEQUENCE: 84

Met Val Asn Cys His Leu Lys Ile Gly Asn Thr Lys Asp Ile Ile Met
1               5                   10                  15

Ile Tyr Glu Glu Asp Ala Glu Glu Trp Ala Leu Tyr Leu Thr Glu Val
            20                  25                  30

Phe Leu His Val Val Lys Arg Glu Ala Ile Leu Leu Tyr Arg Leu Glu
        35                  40                  45

Asn Phe Ser Phe Arg His Leu Glu Leu Leu Asn Leu Thr Ser Tyr Lys
    50                  55                  60

Cys Lys Leu Leu Ile Leu Ser Asn Ser Leu Leu Arg Asp Leu Thr Pro
65                  70                  75                  80

Lys Lys Cys Gln Phe Leu Glu Lys Ile Leu His Ser Pro Lys Ser Val
                85                  90                  95

Val Thr Leu Leu Cys Gly Val Ser Ser Asp Gln Leu Tyr Glu Leu
                100                 105                 110

-continued

Leu Asn Ile Ser Gln Ser Arg Trp Glu Ile Ser Thr Glu Gln Glu Pro
            115                 120                 125
Glu Asp Tyr Ile Ser Val Ile Gln Ser Ile Ile Phe Lys Asp Ser Glu
130                 135                 140
Asp Tyr Phe Glu Val Asn Ile Pro Thr Asp Leu Arg Ala Lys His Ser
145                 150                 155                 160
Gly Glu Ile Ser Glu Arg Lys Glu Ile Glu Glu Leu Ser Glu Ala Ser
                165                 170                 175
Arg Asn Thr Ile Pro Leu Ala Val Val Leu Pro Thr Glu Ile Pro Cys
            180                 185                 190
Glu Asp Pro Gly Glu Ile Phe Ile Ile Leu Arg Asp Glu Val Ile Gly
        195                 200                 205
Asp Thr Val Glu Val Glu Phe Thr Ser Ser Asn Lys Arg Ile Arg Thr
    210                 215                 220
Arg Pro Ala Leu Trp Asn Lys Lys Val Trp Cys Met Lys Ala Leu Glu
225                 230                 235                 240
Phe Pro Ala Gly Ser Val His Val Asn Val Tyr Cys Asp Gly Ile Val
                245                 250                 255
Lys Ala Thr Thr Lys Ile Lys Tyr Tyr Pro Thr Ala Lys Ala Lys Glu
            260                 265                 270
Cys Leu Phe Arg Met Ala Asp Ser Gly Glu Ser Leu Cys Gln Asn Ser
        275                 280                 285
Ile Glu Glu Leu Asp Gly Val Leu Thr Ser Ile Phe Lys His Glu Ile
    290                 295                 300
Pro Tyr Tyr Glu Phe Gln Ser Leu Gln Thr Glu Ile Cys Ser Gln Asn
305                 310                 315                 320
Lys Tyr Thr His Phe Lys Glu Leu Pro Thr Leu Leu His Cys Ala Ala
                325                 330                 335
Lys Phe Gly Leu Lys Asn Leu Ala Ile His Leu Leu Gln Cys Ser Gly
            340                 345                 350
Ala Thr Trp Ala Ser Lys Met Lys Asn Met Glu Gly Ser Asp Pro Thr
        355                 360                 365
His Ile Ala Glu Arg His Gly His Lys Glu Leu Lys Lys Ile Phe Glu
    370                 375                 380
Asp Phe Ser Ile Gln Glu Ile Asp Ile Asn Asn Glu Gln Glu Asn Asp
385                 390                 395                 400
Tyr Glu Glu Asp Ile Ala Ser Phe Ser Thr Tyr Ile Pro Ser Thr Gln
                405                 410                 415
Asn Pro Ala Phe His His Glu Ser Arg Lys Thr Tyr Gly Gln Ser Ala
            420                 425                 430
Asp Gly Ala Glu Ala Asn Glu Met Glu Gly Glu Gly Lys Gln Asn Gly
        435                 440                 445
Ser Gly Met Glu Thr Lys His Ser Pro Leu Glu Val Gly Ser Glu Ser
    450                 455                 460
Ser Glu Asp Gln Tyr Asp Asp Leu Tyr Val Phe Ile Pro Gly Ala Asp
465                 470                 475                 480
Pro Glu Asn Asn Ser Gln Glu Pro Leu Met Ser Ser Arg Pro Pro Leu
                485                 490                 495
Pro Pro Pro Arg Pro Val Ala Asn Ala Phe Gln Leu Glu Arg Pro His
            500                 505                 510
Phe Thr Leu Pro Gly Thr Met Val Glu Gly Gln Met Glu Arg Ser Gln
        515                 520                 525
Asn Trp Gly His Pro Gly Val Arg Gln Glu Thr Gly Asp Glu Pro Lys

```
                530               535                540
Gly Glu Lys Glu Lys Lys Glu Glu Lys Glu Gln Glu Glu Glu
545                 550                 555                 560

Asp Pro Tyr Thr Phe Ala Glu Ile Asp Asp Ser Glu Tyr Asp Met Ile
                565                 570                 575

Leu Ala Asn Leu Ser Ile Lys Lys Thr Gly Ser Arg Ser Phe Ile
                580                 585                 590

Ile Asn Arg Pro Pro Ala Pro Thr Pro Arg Pro Thr Ser Ile Pro Pro
                595                 600                 605

Lys Glu Glu Thr Thr Pro Tyr Ile Ala Gln Val Phe Gln Gln Lys Thr
                610                 615                 620

Ala Arg Arg Gln Ser Asp Asp Lys Phe Arg Gly Leu Pro Lys Lys
625                 630                 635                 640

Gln Asp Arg Ala Arg Ile Glu Ser Pro Ala Phe Ser Thr Leu Arg Gly
                645                 650                 655

Cys Leu Thr Asp Gly Gln Glu Glu Leu Ile Leu Leu Gln Glu Lys Val
                660                 665                 670

Lys Asn Gly Lys Met Ser Met Asp Glu Ala Leu Glu Lys Phe Lys His
                675                 680                 685

Trp Gln Met Gly Lys Ser Gly Leu Glu Met Ile Gln Gln Glu Lys Leu
                690                 695                 700

Arg Gln Leu Arg Asp Cys Ile Ile Gly Lys Arg Pro Glu Glu Asn
705                 710                 715                 720

Val Tyr Asn Lys Leu Thr Ile Val His His Pro Gly Gly Lys Glu Thr
                725                 730                 735

Ala His Asn Glu Asn Lys Phe Tyr Asn Val His Phe Ser Asn Lys Leu
                740                 745                 750

Pro Ala Arg Pro Gln Val Glu Lys Glu Phe Gly Phe Cys Cys Lys Lys
                755                 760                 765

Asp His
    770

<210> SEQ ID NO 85
<211> LENGTH: 564
<212> TYPE: DNA
<213> ORGANISM: Homo sapiens

<400> SEQUENCE: 85
cctctcagaa aactgagcat actagcaaga cagctcttct tgaaaaaaaa aatatgtata      60
cacaaatata tacgtatatc tatatatacg tatgtatata cacacatgta tattcttcct    120
tgattgtgta gctgtccaaa ataataacat atatagaggg agctgtattc ctttatacaa    180
atctgatggc tcctgcagca cttttttcctt ctgaaaatat ttcattttg ctaacctagt     240 ttgttacttt aaaaatcagt tttgatgaaa ggagggaaaa gcagatggac ttgaaaaaga    300
tccaagctcc tattagaaaa ggtatgaaaa tcttttatagt aaaatttttt ataaactaaa    360
gttgtacctt ttaatatgta gtaaactctc atttatttgg ggttcgctct tggatctcat    420
ccatccattg tgttctcttt aatgctgcct gccttttgag gcattcactg ccctagacaa    480
tgccaccaga gatagtgggg gaaatgccag atgaaaccaa ctcttgctct cactagttgt    540
cagcttctct ggataagtga ccac                                           564

<210> SEQ ID NO 86
<211> LENGTH: 5024
<212> TYPE: DNA
```

<213> ORGANISM: Homo sapiens

<400> SEQUENCE: 86

```
agcggagtgg gtcctgcctg tgacgcgcgg cggcggtcgg tcctgcctgt aacggcggcg      60
gcggctgctg ctccagacac ctgcggcggc ggcggcgacc acgcggcggg cgcggagatg     120
tggcccctgg tagcggcgct gttgctgggc tcggcgtgct gcggatcagc tcagctacta     180
tttaataaaa caaaatctgt agaattcacg ttttgtaatg acactgtcgt cattccatgc     240
tttgttacta atatggaggc acaaaacact actgaagtat acgtaaagtg gaaatttaaa     300
ggaagagata tttacacctt tgatggagct ctaaacaagt ccactgtccc cactgacttt     360
agtagtgcaa aaattgaagt ctcacaatta ctaaaaggag atgcctcttt gaagatggat     420
aagagtgatg ctgtctcaca cacaggaaac tacacttgtg aagtaacaga attaaccaga     480
gaaggtgaaa cgatcatcga gctaaaatat cgtgttgttt catggttttc tccaaatgaa     540
aatattctta ttgttatttt cccaattttt gctatactcc tgttctgggg acagtttggt     600
attaaaacac ttaaatatag atccggtggt atggatgaga aaacaattgc tttacttgtt     660
gctggactag tgatcactgt cattgtcatt gttggagcca ttcttttcgt cccaggtgaa     720
tattcattaa agaatgctac tggccttggt ttaattgtga cttctacagg gatattaata     780
ttacttcact actatgtgtt tagtacagcg attggattaa cctccttcgt cattgccata     840
ttggttattc aggtgatagc ctatatcctc gctgtggttg gactgagtct ctgtattgcg     900
gcgtgtatac caatgcatgg ccctcttctg atttcaggtt tgagtatctt agctctagca     960
caattacttg gactagttta tatgaaattt gtggcttcca atcagaagac tatacaacct    1020
cctaggaata actgaagtga agtgatggac tccgatttgg agagtagtaa gacgtgaaag    1080
gaatacactt gtgtttaagc accatggcct tgatgattca ctgttgggga gaagaaacaa    1140
gaaaagtaac tggttgtcac ctatgagacc cttacgtgat tgttagttaa gttttattc    1200
aaagcagctg taatttagtt aataaaataa ttatgatcta tgttgtttgc ccaattgaga    1260
tccagttttt tgttgttatt tttaatcaat taggggcaat agtagaatgg acaatttcca    1320
agaatgatgc ctttcaggtc ctagggcctc tggcctctag gtaaccagtt taaattggtt    1380
cagggtgata actacttagc actgccctgg tgattaccca gagatatcta tgaaaaccag    1440
tggcttccat caaaccttg ccaactcagg ttcacagcag ctttgggcag ttatggcagt    1500
atggcattag ctgagaggtg tctgccactt ctgggtcaat ggaataataa attaagtaca    1560
ggcaggaatt tggttgggag catcttgtat gatctccgta tgatgtgata ttgatggaga    1620
tagtggtcct cattcttggg ggttgccatt cccacattcc cccttcaaca aacagtgtaa    1680
caggtccttc ccagatttag ggtacttta ttgatggata tgttttcctt ttattcacat    1740
aacccttga aaccctgtct tgtcctcctg ttacttgctt ctgctgtaca agatgtagca    1800
ccttttctcc tctttgaaca tggtctagtg acacggtagc accagttgca ggaaggagcc    1860
agacttgttc tcagagcact gtgttcacac ttttcagcaa aaatagctat ggttgtaaca    1920
tatgtattcc cttcctctga tttgaaggca aaaatctaca gtgtttcttc acttcttttc    1980
tgatctgggg catgaaaaaa gcaagattga aatttgaact atgagtctcc tgcatggcaa    2040
caaaatgtgt gtcaccatca ggccaacagg ccagcccttg aatggggatt tattactgtt    2100
gtatctatgt tgcatgataa acattcatca ccttcctcct gtagtcctgc ctcgtactcc    2160
ccttccccta tgattgaaaa gtaaacaaaa cccacatttc ctatcctggt tagaagaaaa    2220
ttaatgttct gacagttgtg atcgcctgga gtactttag acttttagca ttcgtttttt    2280
```

-continued

```
acctgtttgt ggatgtgtgt ttgtatgtgc atacgtatga gataggcaca tgcatcttct    2340
gtatggacaa aggtggggta cctacaggag agcaaaggtt aattttgtgc ttttagtaaa    2400
aacatttaaa tacaaagttc tttattgggt ggaattatat ttgatgcaaa tatttgatca    2460
cttaaaactt ttaaaacttc taggtaattt gccacgcttt ttgactgctc accaataccc    2520
tgtaaaaata cgtaattctt cctgtttgtg taataagata ttcatatttg tagttgcatt    2580
aataatagtt atttcttagt ccatcagatg ttcccgtgtg cctctttat gccaaattga     2640 ttgtcatatt tcatgttggg accaagtagt tgcccatgg caaacctaaa tttatgacct     2700
gctgaggcct ctcagaaaac tgagcatact agcaagacag ctcttcttga aaaaaaaat     2760 atgtatacac aaatatatac gtatatctat atacgtat gtatatacac acatgtatat      2820
tcttccttga ttgtgtagct gtccaaaata ataacatata tagagggagc tgtattcctt    2880
tatacaaatc tgatggctcc tgcagcactt tttccttctg aaaatattta cattttgcta    2940
acctagtttg ttactttaaa aatcagtttt gatgaaagga gggaaaagca gatggacttg    3000
aaaaagatcc aagctcctat tagaaaaggt atgaaaatct ttatagtaaa attttttata   3060
aactaaagtt gtacctttta atatgtagta aactctcatt tatttggggt tcgctcttgg    3120
atctcatcca tccattgtgt tctctttaat gctgcctgcc ttttgaggca ttcactgccc    3180
tagacaatgc caccagagat agtgggggaa atgccagatg aaaccaactc ttgctctcac   3240
tagttgtcag cttctctgga taagtgacca cagaagcagg agtcctcctg cttgggcatc    3300
attgggccag ttccttctct ttaaatcaga tttgtaatgg ctcccaaatt ccatcacatc    3360
acatttaaat tgcagacagt gttttgcaca tcatgtatct gttttgtccc ataatatgct    3420
ttttactccc tgatcccagt ttctgctgtt gactcttcca ttcagttta tttattgtgt     3480 gttctcacag tgacaccatt tgtccttttc tgcaacaacc tttccagcta cttttgccaa    3540
attctatttg tcttctcctt caaaacattc tcctttgcag ttcctcttca tctgtgtagc    3600
tgctcttttg tctcttaact taccattcct atagtacttt atgcatctct gcttagttct    3660
attagttttt tggccttgct cttctccttg attttaaaat tccttctata gctagagctt    3720
ttctttcttt cattctctct tcctgcagtg ttttgcatac atcagaagct aggtacataa    3780
gttaaatgat tgagagttgg ctgtatttag atttatcact ttttaatagg gtgagcttga   3840
gagttttctt tctttctgtt ttttttttt ttttttttga ctaatttcac atgctctaaa     3900
aaccttcaaa ggtgattatt tttctcctgg aaactccagg tccattctgt ttaaatccct    3960
aagaatgtca gaattaaaat aacagggcta tcgcgtaatt ggaaatattt cttttttcag    4020
gatgctatag tcaatttagt aagtgaccac caaattgtta tttgcactaa caaagctcaa    4080
aacacgataa gtttactcct ccatctcagt aataaaaatt aagctgtaat caaccttcta    4140
ggtttctctt gtcttaaaat gggtattcaa aaatggggat ctgtggtgta tgtatggaaa    4200
cacatactcc ttaatttacc tgttgttgga aactggagaa atgattgtcg ggcaaccgtt    4260
tattttttat tgtatttat ttggttgagg gattttttta taaacagttt tacttgtgtc     4320
atattttaaa attactaact gccatcacct gctgggtcc tttgttaggt cattttcagt     4380
gactaatagg gataatccag gtaacttga agagatgagc agtgagtgac caggcagttt     4440
ttctgccttt agctttgaca gttcttaatt aagatcattg aagaccagct ttctcataaa    4500
tttctctttt tgaaaaaaag aaagcatttg tactaagctc ctctgtaaga caacatctta    4560
aatcttaaaa gtgttgttat catgactggt gagagaagaa aacatttttgt ttttattaaa    4620
```

```
tggagcatta tttacaaaaa gccattgttg agaattagat cccacatcgt ataaatatct    4680
attaaccatt ctaaataaag agaactccag tgttgctatg tgcaagatcc tctcttggag    4740 ctttttttgca tagcaattaa aggtgtgcta tttgtcagta gccattttt tgcagtgatt    4800 tgaagaccaa agttgtttta cagctgtgtt accgttaaag gttttttttt ttatatgtat    4860
taaatcaatt tatcactgtt taaagctttg aatatctgca atctttgcca aggtactttt    4920
ttatttaaaa aaaaacataa ctttgtaaat attaccctgt aatattatat atacttaata    4980
aaacatttta agctaaaaaa aaaaaaacaa aaaaaaaaa aaaa                      5024

<210> SEQ ID NO 87
<211> LENGTH: 305
<212> TYPE: PRT
<213> ORGANISM: Homo sapiens

<400> SEQUENCE: 87

Met Trp Pro Leu Val Ala Ala Leu Leu Leu Gly Ser Ala Cys Cys Gly
  1               5                  10                  15

Ser Ala Gln Leu Leu Phe Asn Lys Thr Lys Ser Val Glu Phe Thr Phe
                 20                  25                  30

Cys Asn Asp Thr Val Val Ile Pro Cys Phe Val Thr Asn Met Glu Ala
             35                  40                  45

Gln Asn Thr Thr Glu Val Tyr Val Lys Trp Lys Phe Lys Gly Arg Asp
         50                  55                  60

Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300
```

Asn
305

<210> SEQ ID NO 88
<211> LENGTH: 6790
<212> TYPE: DNA
<213> ORGANISM: Homo sapiens

<400> SEQUENCE: 88

| | | | | | |
|---|---|---|---|---|---|
| ggagatattt | tcttgttcaa | tttaaggaga | ggtaaatttg | gtatcaatag | aaaaaatgtt | 60 |
| tctgaaaaat | ttaaaccctg | gaaatgtatt | tatggcatgg | agtcagatgt | ttcagggaga | 120 |
| gaagaacaaa | tcaagaagca | ttgcaagtat | gctcatatgg | aatgcttaag | gcttgtggtt | 180 |
| aaaaaatata | tatatatggc | tgtcaatgtc | ttaggctcat | ggtagcagca | gaaatcgtaa | 240 |
| taattctttt | gtcacatggg | ttatatccat | attggagaga | attaactcag | gtgaaattaa | 300 |
| cttgtacact | gtttggtttt | ataatattta | gagggatcac | aactgactga | tgtccctttg | 360 |
| aagtaccatt | cttcataaat | cttttttttt | tcagaatggg | ccagccaact | gtgacatccc | 420 |
| ttggatcgga | gatttagaac | tagaaagtat | tctttctaca | ttattaggga | agaaaaggag | 480 |
| ttacttggcg | gttagcaata | ttctattttg | ttttgttttg | ttttagaga | cagggtctca | 540 |
| ttatgttgac | caggctggcc | tcgagctcct | gggctcaagc | aatgctccca | cctcagcctc | 600 |
| ccaagtagct | gggactacgg | gcatgtgcca | ctacacctgg | cagtgtttat | tctgataaat | 660 |
| acatttatga | gctcaaaaat | gtaactctaa | aaccttatct | ctgaacttcc | atattaccat | 720 |
| cagaaattta | gatagttgtt | tagttctctt | tttctttgta | gaacatagat | ataaggcatg | 780 |
| gtttcattga | agtcagttgt | atatacatgt | aactatcctg | atgttcccaa | ataaagctct | 840 |
| gtatttatgc | ttagtttatt | ggggaggctg | ctaaatgtag | tgcatcccaa | cccattttac | 900 |
| cctgttctac | tttaaaaga | ggttggcttc | ttgtttggat | acaaggacca | agtcactccc | 960 |
| ccaggttcct | ccacagtaag | ggaggcctat | ttaaagccgc | ccatggcact | aacagaaact | 1020 |
| ggactcctat | gagctcagat | acataactgg | gcctcacagg | ggtgggacag | tatgtagtct | 1080 |
| aggaattgga | aggatccatt | ccatatcaaa | gaactgaagc | atcgtgttgc | cctctcagca | 1140 |
| gcaagagtaa | ggtgatgccc | ctgtcagtta | tagttcctga | gttcctctgt | ctttgattct | 1200 |
| ttgcctatta | gccagctagc | tcaccctctt | gtttatgcca | ctgtttttta | tcctattcat | 1260 |
| gccttctcac | agacaacttt | tcttacctac | agctttggac | tcatccttgt | ctcctttctg | 1320 |
| tttctttttc | actttccctt | cccatcacca | actttctggg | ttttttctg | tttcttctta | 1380 |
| gagtccagtg | gcagggagaa | acttgtcagt | ccagtctgtt | gccatttttc | ctgtttgaga | 1440 |
| aagactcacc | agcttttggc | tggctcacag | attggctttc | cttgggtcag | gacccaccct | 1500 |
| tttccctgcc | agctttggaa | gcttgacaga | attcgagtgt | gcagtggtgg | taaataaata | 1560 |
| gtaaggaaca | cagagcagtc | ctggaggcgt | gcctccatct | gctgatgaga | aaatccagtg | 1620 |
| ctgtcatcca | gccaggtcc | cagcggaatg | ggctctctg | ttcagtagga | tccccctcct | 1680 |
| gctgagtggt | tcatggcatg | tttctgttca | acgcttttcc | atctgtagga | ttcttattct | 1740 |
| gtatttattt | gtttttttgg | gtttttttat | tttttgagat | ggagtctcgc | tctgtcgccc | 1800 |
| aggctggagt | gcagtggcac | gaccccagct | cgctgcagcc | tctgcctccc | aggacgaggg | 1860 |
| agatcctccc | acctcagcct | tccacgtagc | tgggactaca | ggcatgcacc | acaggcatgc | 1920 |
| accaccacgc | cagctaattt | ttgtattttt | ggtagagaca | gggttgcatc | atgttgccca | 1980 |
| ggctggtctt | gaatgcctga | gctcaagcaa | tctatttgcc | ttggcctccc | aaagtgctgg | 2040 |

-continued

```
gattacaggc atgagccacc acggccagcc ttctcatttg ttttttttat aaggaagcta    2100
tctcttcttc cctccccaac tagggtattc ttttttcctt tcgtcacttt gctcatgtac    2160
tgtattcctt caacttcatt aatgaatcca tttggaagca gtgaaaaagg caactcagaa    2220
agctaagaag aaatagatag aggaatactc agagctatct gagtattttc tttagtttgt    2280
tagctctttg gagctttgaa actggaaaga cccagggagt gatgtggaga aagagactga    2340
gcttgtaaga cacaggagca gtgagctaag ggagatggag tagtggggac aaattctggc    2400
acattctgtc tacactctgg gtagatagag gagggaggat ggagcaccca tggtggggt     2460 atgttggtga cagcattttc ccaccagcca gtgtaacaag tggctgattt ggggaaaga    2520 tggcataaac aaatgagaga atgtgtttac tatttgatgt agatgggtta tttgcttcat    2580
ttttcaaatc agtgtatata atcaagaata ttcagcatgt ttgaatagac tgtcagagct    2640
ggaactcttt cattaacatc tctggcacct ttagttttag ccctgaacat tttatcttaa    2700
aattaaacat taccaaatgc cttagtttat ttcatttatt aaattatat tcttatttgt     2760 tatttatatc agcttccaat cagaagacta tacaacctcc taggaataac tgaagtgaag    2820
tgatggactc cgatttggag agtagtaaga cgtgaaagga atacacttgt gtttaagcac    2880
catggccttg atgattcact gttggggaga agaaacaaga aaagtaactg gttgtcacct    2940
atgagaccct tacgtgattg ttagttaagt ttttattcaa agcagctgta atttagttaa    3000
taaaataatt atgatctatg ttgtttgccc aattgagatc cagttttttg ttgttatttt    3060
taatcaatta ggggcaatag tagaatggac aatttccaag aatgatgcct tcaggtcct    3120 agggcctctg gcctctaggt aaccagttta aattggttca gggtgataac tacttagcac    3180
tgcccctggt gattacccca gagatatcta tgaaaaccag tggcttccat caaacctttg    3240
ccaactcagg ttcacagcag ctttgggcag ttatggcagt atggcattag ctgagaggtg    3300
tctgccactt ctgggtcaat ggaataataa attaagtaca ggcaggaatt tggttgggag    3360
catcttgtat gatctccgta tgatgtgata ttgatggaga tagtggtcct cattcttggg    3420
ggttgccatt cccacattcc cccttcaaca aacagtgtaa caggtccttc ccagatttag    3480
ggtactttta ttgatggata tgttttcctt ttattcacat aaccccttga aaccctgtct    3540
tgtcctcctg ttacttgctt ctgctgtaca agatgtagca ccttttctcc tctttgaacg    3600
tggtctagtg acacggtagc accagttgca ggaaggagcc agacttgttc tcagagcact    3660
gtgttcacac ttttcagcaa aaatagctat ggttgtaaca tatgtattcc cttcctctga    3720
tttgaaggca aaaatctaca gtgtttcttc acttcttttc tgatctgggg catgaaaaaa    3780
gcaagattga aatttgaact atgagtctcc tgcatggcaa caaaatgtgt gtcaccatca    3840
ggccaacagg ccagcccttg aatggggatt tattactgtt gtatctatgt tgcatgataa    3900
acattcatca ccttcctcct gtagtcctgc ctcgtactcc ccttccccta tgattgaaaa    3960
gtaaacaaaa cccacatttc ctatcctggt tagaagaaaa taaatgttct gacagttgtg    4020
atcgcctgga gtacttttag acttttagca ttcgtttttt acctgtttgt ggatgtgtgt    4080
ttgtatgtgc atacgtatga gataggcaca tgcatcttct gtatggacaa aggtggggta    4140
cctacaggag agcaaaggtt aattttgtgc ttttagtaaa aacatttaaa tacaaagttc    4200
tttattgggc ggaattatat ttgatgcaaa tatttgatca cttaaaactt ttaaaacttc    4260
taggtaattt gccacgcttt ttgactgctc accaataccc tgtaaaaata cgtaattctt    4320
cctgtttgtg taataagata ttcatatttg tagttgcatt aataatagtt atttcttagt    4380
ccatcagatg ttcccgtgtg cctctttttat gccaaattga ttgtcatatt tcatgttggg    4440
```

```
accaagtagt tgcccatgg caaacctaaa tttatgacct gctgaggcct ctcagaaaac    4500
tgagcatact agcaagacag ctcttcttga aaaaaaaaat atgtatacac aaatatatac    4560
gtatatctat atatacgtat gtatatacac acatgtatat tcttccttga ttgtgtagct    4620
gtccaaaata ataacatata tagagggagc tgtattcctt tatacaaatc tgatggctcc    4680
tgcagcactt tttccttctg aaaatattta cattttgcta acctagtttg ttactttaaa    4740
aatcagtttt gatgaaagga gggaaaagca gatggacttg aaaagatcc aagctcctat    4800 tagaaaaggt atgaaaatct ttatagtaaa attttttata aactaaagtt gtacctttta    4860
atatgtagta aactctcatt tatttggggt tcgctcttgg atctcatcca tccattgtgt    4920
tctctttaat gctgcctgcc ttttgaggca ttcactgccc tagacaatgc caccagagat    4980
agtgggggaa atgccagatg aaaccaactc ttgctctcac tagttgtcag cttctctgga    5040
taagtgacca cagaagcagg agtcctcctg cttgggcatc attgggccag ttccttctct    5100
ttaaatcaga tttgtaatgg ctcccaaatt ccatcacatc acatttaaat tgcagacagt    5160
gttttgcaca tcatgtatct gttttgtccc ataatatgct ttttactccc tgatcccagt    5220
ttctgctgtt gactcttcca ttcagtttta ttaattgtgt gttctcacag tgacaccatt    5280
tgtccttttc tgcaacaacc tttccagcta cttttgccaa attctatttg tcttctcctt    5340
caaaacattc tcctttgcag ttcctcttca tctgtgtagc tgctcttttg tctcttaact    5400
taccattcct atagtacttt atgcatctct gcttagttct attagttttt tggccttgct    5460
cttctccttg attttaaaat tccttctata gctagagctt ttctttcttt cattctctct    5520
tcctgcagtg tttttgcatac atcagaagct aggtacataa gttaaatgat tgagagttgg    5580
ctgtatttag atttatcact ttttaatagg gtgagcttga gagttttctt tctttctggt    5640
tttttttttt tttttttttt tttttgact aatttcacat gctctaaaaa ccttcaaagg    5700
tgattatttt tctcctggaa actccaggtc cattctgttt aaatccctaa gaatgtcaga    5760
attaaaataa cagggctatc ccgtaattgg aaatattct ttttttcagga tgctatagtc    5820 aatttagtaa gtggccacca aattgttatt tgcactaaca aagctcaaaa cacgataagt    5880
ttactcctcc atctcagtaa taaaaattaa gctgtaatca accttctagg tttctcttgt    5940
cttaaaatgg gtattcaaaa atggggatct gtggtgtatg tatggaaaca catactcctt    6000
aatttacctg ttgttggaaa ctggagaaat gattgtcggg caaccgttta tttttttattg    6060 tattttattt ggttgaggga tttttttata aacagtttta cttgtgtcat attttaaaat    6120
tactaactgc catcacctgc tggggtcctt tgttaggtca ttttcagtga ctaatagga    6180 taatccaggt aactttgaag agatgagcag ggagtgacca ggcagttttc ttgcctttag    6240
ctttgacagt tcttaattaa gatcattgaa gaccagcttt tcataaatt tctctttttg    6300 aaaaaagaaa gcatttgtac taagctcctc tgtaagacaa catcttaaat cttaaaagtg    6360
ttgttatcat gactggtgag agaagaaaac gttttgtttt tattaaatgg agcattattt    6420
acaaaaagcc attgttgaga attagatccc acatcgtata aatatctatt aaccattcta    6480
aataaagaga actccagtgt tgctatgtgc aagatcctct cttggagctt ttttgcatag    6540
caattaaagg tgtgctattt gtcagtagcc attttttgc agtgatttga agaccaaagt    6600
tgttttacag ctgtgttacc gttaaaggtt ttttttttta tatgtattaa atcaatttat    6660
cactgtttaa agctttgaat atctgcaatc tttgccaagg tactttttta tttaaaaaaa    6720
aacataactt tgtaaatatt accctgtaat attatatata cttaataaaa cattttaagc    6780
```
tataaaaaaa 6790

<210> SEQ ID NO 89
<211> LENGTH: 2538
<212> TYPE: DNA
<213> ORGANISM: Homo sapiens

<400> SEQUENCE: 89

| | | | | | |
|---|---|---|---|---|---|
| ttttaaaact | tctaggtaat | ttgccacgct | ttttgactgc | tcaccaatac | cctgtaaaaa | 60 |
| tacgtaattc | ttcctgtttg | tgtaataaga | tattcatatt | tgtagttgca | ttaataatag | 120 |
| ttatttctta | gtccatcaga | tgttcccgtg | tgcctctttt | atgccaaatt | gattgtcata | 180 |
| tttcatgttg | ggaccaagta | gtttgcccat | ggcaaaccta | aatttatgac | ctgctgaggc | 240 |
| ctctcagaaa | actgagcata | ctagcaagac | agctcttctt | gaaaaaaaaa | atatgtatac | 300 |
| acaaatatat | acgtatatct | atatatacgt | atgtatatac | acacatgtat | attcttcctt | 360 |
| gattgtgtag | ctgtccaaaa | taataacata | tatagaggga | gctgtattcc | tttatacaaa | 420 |
| tctgatggct | cctgcagcac | ttttccttc | tgaaaatatt | tacattttgc | taacctagtt | 480 |
| tgttacttta | aaaatcagtt | ttgatgaaag | gagggaaaag | cagatggact | tgaaaaagat | 540 |
| ccaagctcct | attagaaaag | gtatgaaaat | ctttatagta | aaattcttta | taaactaaag | 600 |
| ttgtaccttt | taatatgtag | taaactctca | tttatttggg | gttcgctctt | ggatctcatc | 660 |
| catccattgt | gttctcttta | atgctgcctg | ccttttgagg | cattcactgc | cctagacaat | 720 |
| gccaccagag | atagtggggg | aaatgccaga | tgaaaccaac | tcttgctctc | actagttgtc | 780 |
| agcttctctg | gataagtgac | cacagaagca | ggagtcctcc | tgcttgggca | tcattgggcc | 840 |
| agttccttct | ctttaaatca | gatttgtaat | ggctcccaaa | ttccatcaca | tcacatttaa | 900 |
| attgcagaca | gtgttttgca | catcatgtat | ctgttttgtc | ccataaatatg | cttttactc | 960 |
| cctgatccca | gtttctgctg | ttgactcttc | cattcagttt | tatttattgt | gtgttctcac | 1020 |
| agtgacacca | tttgtccttt | tctgcaacaa | ccttttccagc | tacttttgcc | aaattctatt | 1080 |
| tgtcttctcc | ttcaaaacat | tctcctttgc | agttcctctt | catctgtgta | gctgctcttt | 1140 |
| tgtctcttaa | cttaccattc | ctatagtact | ttatgcatct | ctgcttagtt | ctattagttt | 1200 |
| tttggccttg | ctcttctcct | tgattttaaa | attccttcta | tagctagagc | ttttctttct | 1260 |
| ttcattctct | cttcctgcag | tgtttttgcat | acatcagaag | ctaggtacat | aagttaaatg | 1320 |
| attgagagtt | ggctgtattt | agatttatca | ctttttaata | gggtgagctt | gagagttttc | 1380 |
| tttctttctg | tttttttttt | tttttttttt | tttttttttt | ttgactaatt | tcacatgctc | 1440 |
| taaaaacctt | caaaggtgat | tatttttctc | ctggaaactc | caggtccatt | ctgtttaaat | 1500 |
| ccctaagaat | gtcagaatta | aaataacagg | gctatcccgt | aattggaaat | atttcttttt | 1560 |
| tcaggatgct | atagtcaatt | tagtaagtga | ccaccaaatt | gttatttgca | ctaacaaagc | 1620 |
| tcaaaacacg | ataagtttac | tccttcatct | cagtaataaa | aattaagctg | taatcaacct | 1680 |
| tctaggtttc | tcttgtctta | aaatgggtat | tcaaaaatgg | ggatctgtgg | tgtatgtatg | 1740 |
| gaaacacata | ctccttaatt | tacctgttgt | tggaaactgg | agaaatgatt | gtcgggcaac | 1800 |
| cgtttatttt | ttattgtatt | ttatttggtt | gagggatttt | tttataaaca | gttttacttg | 1860 |
| tgtcatattt | taaaattact | aactgccatc | acctgctggg | gtcctttgtt | aggtcatttt | 1920 |
| cagtgactaa | tagggataat | ccaggtaact | ttgaagagat | gagcagtgag | tgaccaggca | 1980 |
| gttttctgc | cttagctttt | gacagttctt | aattaagatc | attgaagacc | agcttttctca | 2040 |
| taaatttctc | ttttttgaaaa | aaagaaagca | tttgtactaa | gctcctctgt | aagacaacat | 2100 |

```
cttaaatcctt aaaagtgttg ttatcatgac tggtgagaga agaaaacatt ttgttttttat   2160 taaatggagc attatttaca aaaagccatt gttgagaatt agatcccaca tcgtataaat     2220
atctattaac cattctaaat aaagagaact ccagtgttgc tatgtgcaag atcctctctt     2280 ggagctttt  tgcatagcaa ttaaaggtgt gctatttgtc agtagccatt tttttgcagt     2340
gatttgaaga ccaaagttgt tttacagctg tgttaccgtt aaaggttttt ttttttatat     2400
gtattaaatc aatttatcac tgtttaaagc tttgaatatc tgcaatcttt gccaaggtac     2460
ttttttattt aaaaaaaaac ataactttgt aaatattacc ctgtaatatt atatatactt     2520
aataaaacat tttaagct                                                    2538

<210> SEQ ID NO 90
<211> LENGTH: 550
<212> TYPE: DNA
<213> ORGANISM: Homo sapiens
<220> FEATURE:
<221> NAME/KEY: modified_base
<222> LOCATION: (1)..(550)
<223> OTHER INFORMATION: n = g, a, c or t

<400> SEQUENCE: 90
ccatatcatg taccaaaagt tgctgaagtt tctcttctag ctggtaaagt aggagtttgc      60
atgacttcac actttttttg cgtagtttct tctgttgtat gatggcgtga gtgtgtgtct     120
tgggtaccgc tgtgtactac tgtgtgccta gattccatgc actctcgttg tgtttgaagt     180
aaatattgga gaccggaggg taacaggttg gcctgttgat tacagctagt aatcgctgtg     240
tcttgttccg cccccctccct gacaccccag cttcccagga tgtggaaagc ctggatctca     300
gctccttgcc ccatatccct tctgtaattt gtacctaaag agtgtgatta tcctaattca     360
agagtcacta aaactcatca cattatcatt gcatatcagc aaagggtaaa gtcctagcac     420
caattgcttc ataccagc atgttccatt tccaatttag aattagccac ataataaaat      480
cttagaatct tccttgagaa agagctgcct gagatgtagt tttgntatat ggntccccac     540
cgaccatttt                                                            550

<210> SEQ ID NO 91
<211> LENGTH: 1209
<212> TYPE: DNA
<213> ORGANISM: Homo sapiens

<400> SEQUENCE: 91
ccatatcatg taccaaaagt tgctgaagtt tctcttctag ctggtaaagt aggagtttgc      60
atgacttcac actttttttg cgtagtttct tctgttgtat gatggcgtga gtgtgtgtct     120
tgggtaccgc tgtgtactac tgtgtgccta gattccatgc actctcgttg tgtttgaagt     180
aaatattgga gaccggaggg taacaggttg gcctgttgat tacagctagt aatcgctgtg     240
tcttgttccg cccccctccct gacaccccag cttcccagga tgtggaaagc ctggatctca     300
gctccttgcc ccatatccct tctgtaattt gtacctaaag agtgtgatta tcctaattca     360
agagtcacta aaactcatca cattatcatt gcatatcagc aaagggtaaa gtcctagcac     420
caattgcttc ataccagc atgttccatt tccaatttag aattagccac ataataaaat      480
cttagaatct tccttgagaa agagctgcct gagatgtagt tttgttatat ggttccccac     540
cgaccatttt tgtgcttttt tcttgttttg ttttgttttg actgcactgt gagttttgta     600
gtgtcctctt cttgccaaaa caaacgcgag atgaactgga cttatgtaga caaatcgtga     660
```

```
tgccagtgta tccttccttt cttcagttcc agcaataatg aatggtcaac ttttttaaaa      720
tctagatctc tctcattcat ttcaatgtat ttttacttta agatgaacca aaattattag      780
acttatttaa gatgtacagg catcagaaaa aagaagcaca taatgctttt ggtgcgatgg      840
cactcactgt gaacatgtgt aaccacatat taatatgcaa tattgttttcc aatactttct     900 aatacagttt tttataatgt tgtgtgtggt gattgttcag gtcgaatctg ttgtatccag      960
tacagcttta ggtcttcagc tgcccttctg gcgagtacat gcacaggatt gtaaatgaga     1020
aatgcagtca tatttccagt ctgcctctat gatgatgtta aattattgct gtttagctgt     1080
gaacaaggga tgtaccactg gaggaataga gtatccttt gtacacattt tgaaatgctt     1140
cttctgtagt gatagaacaa ataaatgcaa cgaatactct gtcaaaaaaa aaaaaaaaaa    1200
aaaaaaaaa                                                              1209

<210> SEQ ID NO 92
<211> LENGTH: 1661
<212> TYPE: DNA
<213> ORGANISM: Homo sapiens

<400> SEQUENCE: 92
ccatatcatg taccaaaagt tgctgaagtt tctcttctag ctggtaaagt aggagtttgc       60
atgacttcac acttttttg cgtagtttct tctgttgtat gatggcgtga gtgtgtgtct      120
tgggtaccgc tgtgtactac tgtgtgccta gattccatgc actctcgttg tgtttgaagt     180
aaatattgga gaccggaggg taacaggttg gcctgttgat tacagctagt aatcgctgtg      240
tcttgttccg cccctccct gacaccccag cttcccagga tgtggaaagc ctggatctca     300
gctccttgcc ccatatccct tctgtaattt gtacctaaag agtgtgatta tcctaattca      360
agagtcacta aaactcatca cattatcatt gcatatcagc aaagggtaaa gtcctagcac     420
caattgcttc acataccagc atgttccatt tccaatttag aattagccac ataataaaat     480
cttagaatct tccttgagaa agagctgcct gagatgtagt tttgttatat ggttccccac     540
cgaccatttt tgtgcttttt tcttgttttg tttgtttg actgcactgt gagttttgta     600
gtgtcctctt cttgccaaaa caaacgcgag atgaactgga cttatgtaga caaatcgtga     660
tgccagtgta tccttccttt cttcagttcc agcaataatg aatggtcaac ttttttaaaa      720
tctagatctc tctcattcat ttcaatgtat ttttacttta agatgaacca aaattattag      780
acttatttaa gatgtacagg catcagaaaa aagaagcaca taatgctttt ggtgcgatgg      840
cactcactgt gaacatgtgt aaccacatat taatatgcaa tattgttttcc aatactttct     900 aatacagttt tttataatgt tgtgtgtggt gattgttcag gtcgaatctg ttgtatccag      960
tacagcttta ggtcttcagc tgcccttctg gcgagtacat gcacaggatt gtaaatgaga     1020
aatgcagtca tatttccagt ctgcctctat gatgatgtta aattattgct gtttagctgt     1080
gaacaaggga tgtaccactg gaggaataga gtatccttt gtacacattt tgaaatgctt     1140
cttctgtagt gatagaacaa ataaatgcaa cgaatactct gtctgcccta tcccgtgaag    1200
tccacactgg cgtaagagaa ggcccagcag agcaggaatc tgcctagact ttctcccaat    1260
gagatcccaa tatgagaggg agaagagatg ggcctcagga cagctgcaat accacttggg    1320
aacacatgtg gtgtcttgat gtggccagcg cagcagttca gcacaacgta cctcccatct    1380
acaacagtgc tggacgtggg aattctaagt cccagtcttg agggtgggtg gagatggagg    1440
gcaacaagag atacatttcc agttctccac tgcagcatgc ttcagtcatt ctgtgagtgg    1500
ccggggccag ggccctcaca atttcactac cttgtcttta catagtcata agaattatcc    1560
```

```
tcaacatagc cttttgacgc ttgtaaatct tgagtattca atttaacccct tttctgaatc   1620 tccctggaaa caggtgcctg cctggattgc cttcttcttc c                        1661

<210> SEQ ID NO 93
<211> LENGTH: 6400
<212> TYPE: DNA
<213> ORGANISM: Homo sapiens

<400> SEQUENCE: 93
gaattccggc gtcgcggacg catcccagtc tgggcgggac gctcggccgc ggcgaggcgg     60
gcaagcctgg cagggcagag ggagccccgg ctccgaggtt gctcttcgcc cccgaggatc    120
agtcttggcc ccaaagcgcg acgcacaaat ccacataacc tgaggaccat ggatgctgat    180
gagggtcaag acatgtccca gtttcaggg aaggaaagcc cccctgtaag cgatactcca    240
gatgagggcg atgagcccat gccgatcccc gaggacctct ccaccacctc gggaggacag    300
caaagctcca agagtgacag agtcgtggcc agtaatgtta agtagagac tcagagtgat    360 gaagagaatg ggcgtgcctg tgaaatgaat ggggaagaat gtgcggagga tttacgaatg    420
cttgatgcct cggagagaa atgaatggc tcccacaggg accaaggcag ctcggctttg    480
tcgggagttg gaggcattcg acttcctaac ggaaaactaa agtgtgatat ctgtgggatc    540
atttgcatcg ggcccaatgt gctcatggtt cacaaaagaa gccacactgg agaacgccc    600 ttccagtgca atcagtgcgg ggcctcattc acccagaagg gcaacctgct ccggcacatc    660
aagctgcatt ccggggagaa gcccttcaaa tgccacctct gcaactacgc ctgccgccgg    720
agggacgccc tcactggcca cctgaggacg cactccgttg gtaaacctca caaatgtgga    780
tattgtggcc gaagctataa acagcgaagc tctttagagg aacataaaga gcgctgccac    840
aactacttgg aaagcatggg ccttccgggc acactgtacc cagtcattaa agaagaaact    900
aatcacagtg aaatggcaga agacctgtgc aagataggat cagagagatc tctcgtgctg    960
gacagactag caagtaacgt cgccaaacgt aagagctcta tgcctcagaa atttcttggg   1020
gacaagggcc tgtccgacac gccctacgac agcagcgcca gctacgagaa ggagaacgaa   1080
atgatgaagt cccacgtgat ggaccaagcc atcaacaacg ccatcaacta cctgggggcc   1140
gagtccctgc gcccgctggt gcagacgccc cgggcggtt ccgaggtggt cccggtcatc   1200
agcccgatgt accagctgca caagccgctc gcggagggca cccccgcgctc caaccactcg   1260 gcccaggaca gcgccgtgga aacctgctg ctgctctcca aggccaagtt ggtgccctcg   1320
gagcgcgagg cgtccccgag caacagctgt caagactcca cggacaccga gagcaacaac   1380
gaggagcagc gcagcggtct catctacctg accaaccaca tcgccccgca cgcgcgcaac   1440
ggcttgtcgc tcaaggagga gcaccgcgcc tacgacctgc tgcgcgccgc ctccgagaac   1500
tcgcaggacg cgctccgcgt ggtcagcacc agcgggagc agatgaaggt gtacaagtgc   1560
gaacactgcc gggtgctctt cctggatcac gtcatgtaca ccatccacat gggctgccac   1620
ggcttccgtg atccttttga gtgcaacatg tgcggctacc acagccagga ccggtacgag   1680
ttctcgtcgc acataacgcg aggggagcac cgcttccaca tgagctaaag ccctcccgcg   1740
cccccacccc agacccgag ccaccccagg aaaagcacaa ggactgccgc cttctcgctc   1800
ccgccagcag catagactgg actggaccag acaatgttgt gtttggattt gtaactgttt   1860
tttgtttttt gtttgagttg gttgattggg gtttgatttg cttttgaaaa gattttttatt   1920 tttagaggca gggctgcatt gggagcatcc agaactgcta ccttcctaga tgtttcccca   1980
```

```
gaccgctggc tgagattccc tcacctgtcg cttcctagaa tccccttctc caaacgatta   2040
gtctaaattt tcagagagaa atagataaaa cacgccacag cctgggaagg agcgtgctct   2100
accctgtgct aagcacgggg ttcgcgcacc aggtgtcttt ttccagtccc cagaagcaga   2160
gagcacagcc cctgctgtgt gggtctgcag gtgagcagac aggacaggtg tgccgccacc   2220
caagtgccaa gacacagcag ggccaacaac ctgtgcccag gccagcttcg agctacatgc   2280
atctagggcg gagaggctgc acttgtgaga gaaatacttt atttcaagtc atattctgcg   2340
gtaggaaaat gattgggttg gggaaagtcg gtgtctgtca gactgccctg ggtggaggga   2400
gacgccgggt tagagccttt gggatcgtcc tggattcact ggcttggggg aggctgttca   2460
gatggcctga gcctcccgag gcttgctgcc ccgtaggagg agactgtctt cccgtgggca   2520
tatctgggga gccctgttcc ccgcttttc actcccatac ctttaatggc ccccaaaatc   2580
tgtcactaca atttaaacac cagtcccgaa atttggatct tctttctttt tgaatctctc   2640
aaacggcaac attcctcaga aaccaaagct ttatttcaaa tctcttcctt ccctggctgg   2700
ttccatctag taccagaggc ctcttttcct gaagaaatcc aatcctagcc ctcattttaa   2760
ttatgtacat ctgcttgtag ccacaagcct gaatttctca gtgttggtaa gtttctttac   2820
ctaccctcac tatatattat tctcgtttta aacccataa aggagtgatt tagaacagtc   2880
attaattttc caactcaatg aaaatatgtg aagcccagca tctctgttgc taacacacag   2940
agctcacctg tttgaaacca agcttttcaaa catgttgaag ctctttactg taaaggcaag   3000
ccagcatgtg tgtccacaca tacataggat ggctggctct gcacctgtag gatattggaa   3060
tgcacagggc aattgaggga ctgagccaga ccttcggaga gtaatgccac cagatcccct   3120
aggaaagagg aggcaaatgg cactgcaggt gagaaccccg cccatccgtg ctatgacatg   3180
gaggcactga agcccgagga aggtgtgtgg agattctaat cccaacaagc aagggtctcc   3240
ttcaagatta atgctatcaa tcattaaggt cattactctc aaccacctag gcaatgaaga   3300
atataccatt tcaaatattt acagtacttg tcttcaccaa cactgtccca aggtgaaatg   3360
aagcaacaga gaggaaattg tacataagta cctcagcatt taatccaaac aggggttctt   3420
agtctcagca ctatgacatt tgggctgac tacttatttg ttaggcggga gctctcctgt   3480
gcattgtagg ataattagca gtatccctgg tggctaccca atagacgcca gtagcacccc   3540
gaattgacaa cccaaaactct ccagacatca ccaactgtcc cctgcgagga gaaatcactc   3600
ctgggggaga accactgacc caaatgaatt ctaaaccaat caaatgtctg ggaagccctc   3660
caagaaaaaa aatagaaaag cacttgaaga atattcccaa tattcccggt cagcagtatc   3720
aaggctgact tgtgttcatg tggagtcatt ataaattcta taaatcaatt attccccttc   3780
ggtcttcaaa aatatatttc ctcataaaca tttgagtttt gttgaaaaga tggagtttac   3840
aaagatacca ttcttgagtc atggatttct ctgctcacag aagggtgtgg catttggaaa   3900
cgggaataaa caaaattgct gcaccaatgc actgagtgaa ggaagagaga cagaggatca   3960
agggctttag acagcactcc ttcaatatgc aatcacagag aaagatgcgc cttatccaag   4020
ttaatatctc taaggtgaga gccttcttag agtcagtttg ttgcaaattt cacctactct   4080
gttcttttcc atccatcccc ctgagtcagt tggttgaagg gagttatttt tcaagtgga   4140 attcaaacaa agctcaaacc agaactgtaa atagtgattg caggaattct tttctaaact   4200
gctttgccct ttcctctcac tgccttttat agccaatata aatgtctctt tgcacacctt   4260
ttgttgtggt tttatattgt aacaccattt ttcctttgaaa ctattgtatt taaagtaagg   4320
tttcatatta tgtcagcaag taattaactt atgtttaaaa ggtggccata tcatgtacca   4380
```

```
aaagttgctg aagtttctct tctagctggt aaagtaggag tttgcatgac ttcacacttt    4440
ttttgcgtag tttcttctgt tgtatgatgg cgtgagtgtg tgtcttgggt accgctgtgt    4500
actactgtgt gcctagattc catgcactct cgttgtgttt gaagtaaata ttggagaccg    4560
gagggtaaca ggttggcctg ttgattacag ctagtaatcg ctgtgtcttg ttccgccccc    4620
tccctgacac cccagcttcc caggatgtgg aaagcctgga tctcagctcc ttgccccata    4680
tcccttctgt aatttgtacc taaagagtgt gattatccta attcaagagt cactaaaact    4740
catcacatta tcattgcata tcagcaaagg gtaaagtcct agcaccaatt gcttcacata    4800
ccagcatgtt ccatttccaa tttagaatta gccacataat aaaatcttag aatcttcctt    4860
gagaaagagc tgcctgagat gtagttttgt tatatggttc cccaccgacc attttgtgc     4920 ttttttcttg ttttgttttg tttgactgc actgtgagtt ttgtagtgtc ctcttcttgc     4980
caaaacaaac gcgagatgaa ctggacttat gtagacaaat cgtgatgcca gtgtatcctt    5040
cctttcttca gttccagcaa taatgaatgg tcaacttttt taaaatctag atcattggag    5100
accggagggt aacaggttgg cctgttgatt acagctagta atcgctgtgt cttgttccgc    5160
cccctccctg acaccccagc ttcccaggat gtggaaagcc tggatctcag ctccttgccc    5220
catatccctt ctgtaatttg tacctaaaga gtgtgattat cctaattgat ctctctcatt    5280
catttcaatg tattttttact ttaagatgaa ccaaaattat tagacttatt taagatgtac   5340
aggcatcaga aaaagaagc acataatgct tttggtgcga tggcactcac tgtgaacatg     5400
tgtaaccaca tattaatatg caatattgtt tccaatactt tctaatacag ttttttataa    5460
tgttgtgtgt ggtgattgtt caggtcgaat ctgttgtatc cagtacagct ttaggtcttc    5520 agctgcccctt ctggcgagta catgcacagg attgtaaatg agaaatgcag tcatatttcc   5580
agtctgcctc tatgatgatg ttaaattatt gctgtttagc tgtgaacaag ggatgtacca    5640
ctggaggaat agagtatcct tttgtacaca ttttgaaatg cttcttctgt agtgatagaa    5700
caaataaatg caacgaatac tctgtctgcc ctatcccgtg aagtccacac tggcgtaaga    5760
gaaggcccag cagagcagga atctgcctag actttctccc aatgagatcc caatatgaga    5820
gggagaagag atgggcctca ggacagctgc aataccactt gggaacacat gtggtgtctt    5880
gatgtggcca gcgcacgagt tcagcacaac gtacctccca tctacaacag tgctggacgt    5940
gggaattcta agtcccagtc ttgagggtgg gtggagatgg agggcaacaa gagatacatt    6000
tccagttctc cactgcagca tgcttcagtc attctgtgag tggccgggcc cagggccctc    6060
acaatttcac taccttgtct tttacatagt cataagaatt atcctcaaca tagccttttg    6120
acgctgtaaa tcttgagtat tcatttaccc ttttctgatc tcctggaaac agctgcctgc    6180
ctgcattgca cttctcttcc cgaggagtgg ggtaaattta aaagtcaagt tatagtttgg    6240
atgttagtat agaattttga aattgggaat taaaaatcag gactggggac tgggagacca    6300
aaaatttctg atcccatttc tgatggatgt gtcacacctt ttctgtcaaa ataaaatgtc    6360
ttggaggtta tgactccttg gtgaaaaaaa aaaaaaaaa                           6400
```

<210> SEQ ID NO 94
<211> LENGTH: 1364
<212> TYPE: DNA
<213> ORGANISM: Homo sapiens

<400> SEQUENCE: 94

```
aatcaaaggt gggaggattt tccctaaact gacttagcag gactcttgtt acaattggac       60
```

| | |
|---|---|
| taggcaggct gaagacagga tgcaaggaca aagcttgttg aaaagaggcc tcagaggagc | 120 |
| tcatctaaaa tttggtcaag gggagggtct ttcttggtcc ctcctcttgt tcaagggaaa | 180 |
| aagagacatt cttctttcct tgaacaata taagtcaatt tctcattggt ggcctttttt | 240 |
| tcattaagga caagctgagc ccctgctga aacttggtag cagggcagcc agttgagaag | 300 |
| atttctagat gtcaaggcat ctttagatga tggggtgagg actgcagtgg ccatcccaga | 360 |
| tcatggattt tctggtttgc agtttgaatg tccttggtga tggcatagac atcagtgtca | 420 |
| cagtcatggt tattttccg agcagagtgt agaagtgtcc aacttcatct tgaagggctt | 480 |
| ctttagrcag tcacaataaa gatctgggaa gttaggtttt agttctcagt gatgccaaat | 540 |
| caggacagtg ggagaaaaat taaaaacctc agtttggaga gtggtagcca gatagtaaag | 600 |
| ggaactagaa gaactgagaa tttggtaagg actgacaagc tgtgcatgat gacaggatcc | 660 |
| cgttcaattt acaagtagat aacaaaacct gaaagacaag tacaggacca gaataataac | 720 |
| ccataagaag gtgctatagt ttttataaaa tatctttcta cagtcatccc cctttttga | 780 |
| tccaaattaa ccaaagtaag attattcttg tttacaaaat aagtcttgtc tcattatatt | 840 |
| tgacttactt atttgcataa ttgcagcaag aatggcaact gaccaggtag gcttatttaa | 900 |
| gtttgcattg ctggaactt ttacaagtaa tctcagatta tgctttcaag agttcttgaa | 960 |
| gctataaagc caagtcaagc accaccaggc cttatctgca atgcctagag attccagatg | 1020 |
| ggttcttctc ttcttgaggt cctaaaaaca tcctgagttt ctttggcctg ccagaaagtc | 1080 |
| accttcctga ctcacctgta aggctgggaa ctccataatc caggtaccag gcagactttc | 1140 |
| cgggagggct tcatatgcat tggctccata aagttaacct tagttcctca aaactgtctg | 1200 |
| ttcatatgtg attttatgtc ttattctcag ttggaaatgc agaaatcacc tgtcttctgc | 1260 |
| gtcgatcagg ctgggagctg cagaccggag ctgttcctat tcggccatct tggaatggac | 1320 |
| ccccatgtct tattctcaaa taaaacattt tggtcaaaaa aaaa | 1364 |

<210> SEQ ID NO 95
<211> LENGTH: 411
<212> TYPE: DNA
<213> ORGANISM: Homo sapiens

<400> SEQUENCE: 95

| | |
|---|---|
| cctaatatga cattatttca aagcttatta taaaggaaca gtaatcaaac tagtgcaatt | 60 |
| ttggcataaa gttagaaaaa cagatcaatg aagcagaaga gagagtccag aaacagaact | 120 |
| gcacatttat gtgttggtga atgccaggga ttcagcttag gtctgattgc tcaccacaca | 180 |
| gaaagccaat cactgagaca acaagtactg ccaggaagaa aggctttatt gctggtgatg | 240 |
| ccagccagga tatgggagac aagtctaaaa tctgtctctg taaccaataa agttaggagt | 300 |
| ttatgtagga gttgctcaac aggcagtagg tagttgaatc agggttctgg caccttgctg | 360 |
| ttaggatgca gcgatctgga aatcttcagc tttctgatac tatctgggag g | 411 |

<210> SEQ ID NO 96
<211> LENGTH: 1632
<212> TYPE: DNA
<213> ORGANISM: Homo sapiens
<220> FEATURE:
<221> NAME/KEY: modified_base
<222> LOCATION: (1)..(1632)
<223> OTHER INFORMATION: n = g, a, c or t

<400> SEQUENCE: 96

| | |
|---|---|
| gtgccagtta taaaatatct tatattttct tataatgcct ccatagtttt attatatatt | 60 |

-continued

```
cactcaatac atcatttttc tatgtggtat gaggtaagaa tctaactttt actgatttta      120
tctttatgca ttttttttaa tttaaaatgt ggggtaggga tctaactttt ttcaaacaca      180
tataaatgtg cactactatt tatttaaata gtctgttctt ttccttttta ttattatgct      240
atcttatctc acttgaattc aacctaagcc tgttttagac tccaactaat actacagatc      300
ttcctaccac tcttccccct gcataattaa cttcaagcac attagcctcc gggttcctca      360
agcacaccaa atttagtccc agctcaggaa ctctgtactt tctatttcca tgctttaatg      420
ttctttctct tgatatcctt gttttcttat ttccttcatt tgcatttctg ctttgatttt      480
ctgtttctgg tccatggaca tttttatttt ctttttatag aacaaacaca gcttttttac      540
attttgtatt tttcctgcca ttgctatgtg cttggagctc agggagggcc tcaaaggatg      600
aaattggagt atggtgtgat cagaagtttg aacttctttg tattgtatga tcatcccttt      660
accttaatac tcacatgaaa tgctatctat ggcttcttac attccacttc ttcttaatca      720
atttctttct tcatgaactt aaacgttccc atcatttttg atagggtctg tgagtttatt      780
tgtccaaaaa gcccaaaagc agaatttaag attgatagca tagctttgtg ctcaacagtt      840
gtaatatttt tttccatggt cgtctagctt cttctgtttt ctttgagaaa tctatgtaat      900
tgttgtttct ttataattaa tctatctttt ctctccagtt gcctttaaga cttttatat       960 ttgatattat gcaatttcac tatgatttgt ctaaatgtgc atttattttg ctagagatta     1020
ataactcaag tctaaggtat catgtctttt ttcaagttta gaaaatattt ggctattatc     1080
tctttattat catgctgcta cagcattatt tgaattcttt ccctcagaaa tttatattag     1140
aagtttgcta gacttcattc tagtctcatg actcttaatt agtcttgcaa aattttcatt     1200
tcattatcac ttattgcatt ttaggtaatt tcttaatctc tgtcttccag tttactggtt     1260
ctttcttcag ctgtatctat tttattgttt aacctattta ttttctattt caatgattac     1320
attttttgag attttattag caaaatggtt aaaagcatgg tttcagagga ttgtctggat     1380
ttacattttg cctccattat ttactagctc tccagttttg gttaaattaa ttaaccttt     1440 gtgcttcttg gtgtgtaaaa ttgaagtaac aattgtatat aaatatagtg ttttttggta     1500
attaattaaa attatttgca taaaatgctt aagacagggc ctgaaatgac attgagtcct     1560
caaaaaataa attattatta tcattccttc aaaaaaaaaa aaaaaaaaaa aaaaaaana     1620 aaaaaaanac ca                                                         1632
```

<210> SEQ ID NO 97
<211> LENGTH: 2378
<212> TYPE: DNA
<213> ORGANISM: Homo sapiens

<400> SEQUENCE: 97

```
tctaaaagct gcggaattcc tcgagcactg ttggcctttg gtagatgccc ctctgggaga       60
gatccccagg ggtgacagcc atgggccctg aagggcctg ggctaggac agggaccaga       120 gccagtccag ggagaggaca gagccaatgg actggggtgt actgtaacag ccctgctggc      180
gagagggacc agggcaccgt cctccaggga gcccatgctg caagtcgggc cagaggtgcc      240
cctgaacctg aaggccaatg agacccaaga caggccaagt gggttgtgag accctgagg      300 agctgggccc tggtcccagg cagcgctggc ccctgctgct gctgggtctg gccatggtcg      360
cccatggcct gctgcgccca atggttcac cgcaaagcgg ggaccagac cctggagcct      420 cagttggaag cagccgatcc agcctgcgga gcctgtgggg caggtaaggg gcaagagata     480
```

```
tgtggggtc ctgcagcaga gctgggaaag ggtgaccaag gggggacaag ccagaggagt    540
gaggaggaag gttaacccct aagaggggcc tgggctgaca ctggctttag taatggttg     600 atattttgtc catcacagat ttgtttgatt tactgttttt aatatcatat tacgatatta    660
tttttcttca tttctgagtt ttctggcgcc acttaaattt tcaccagggt cagtgcctca    720
atcacctagt cctagtcctc tgggtaggga aggaacagag gcagggacag gacatccaca    780
gggggtggtg gccactgtcc ccacagggtg cccaggcctg ttcctccccc tcctcctctc    840
tgcccatgtg cctcctgccc agtgagggca ggggccactc cctggagaag gcagcaaggg    900
cttggtttgg tctcccccaa ggctgtctgt tcaccaactt gcacataaat acttactggg    960
gccaggctca aggacacagg gagggtggga tgaaccgagg ggagctgtcc agtcattgga   1020
acaggcccac ggcccatgtt tgcagcaatg aagggagagg gcatctccct ctgggatgat   1080
gcccaggctg gtctcacaga tcgaggggca ctggctggtg atgggtgccc ccaaaagaca   1140
gagcagtgtc agaggagagg agagcacagg atgaggctgg gagctcctgg gtgactggga   1200
aggggaggca agaagaccat agggtccgtg caccattccc agtccaggac gagtccttgg   1260
atggatttag gtagattgat tatcagagtc agatttgtgt ttttggaaaa atcagcaccg   1320
gattggaggc tgatgcgacg cccaattaga ggagggagga gaggggtga tggccaagtc    1380 cagggtaggt ggggatcctg gaggaagccg tgccttgggg atggggagga cactcagatt   1440
cagagcaccc aggggcccag tttcctatga aatgggagca tgaggttgaa gtgagggctg   1500
agcagagggg agcagacacg ctcggggact gtctatgggc attgaaaatg tataaccatt   1560
ttagcaacag gcggcgagtc aaacccaag gtgtgtttat ctaaactggg caattcctct    1620
tctaggaatt tatcctaagg gttggttggg ggaataatca aagctgaaac caaatcttta   1680
taacaagggt ggttaggtca gcattcttag tgatgggaga aaactggaaa aaatccaaat   1740
atctaccaga aagggtgtga aaaacacaa ttgtatttgg gggactgttg ttgattttgt    1800
tttgaaacag tcttgatctg ttgctcaggc tggagtacag tggcgtggcc acagctcact   1860
gcagcctcaa cctccagggc tcaaaagatc ctccagcctc agcctcctga gtagttagga   1920
ctacagatgc aggccactac acctggctaa ttttgattag gattatcatt agtttagaga   1980
cagagcctcg ctatattgct caggcctgtc tcaaattcct aagctcaagc aatctttctg   2040
cctcagtttc ccacgtgctg gaattacagg cgtgagccac tgcacctgac ccaactgtgt   2100
ttttaaagta tatatgcatt ttcaaaaacc tgtcagaaaa tatagaaaaa tgtcaatggt   2160
gtgtctggct ggctgatggg atttcaccta atttttaatgt ggctttataa ttttctggtt   2220
ttgtgaagtt gttcacaaaa agagacattt cttctaatat aattttttaat acaacagtaa   2280 tgtactcatg tgcattactc tttttgtaat gagtatatta caaatgtaa tgacttttgt     2340 acattactct tttttcttgc caaaaaaaaa aaaaaaa                             2378
```

<210> SEQ ID NO 98
<211> LENGTH: 313
<212> TYPE: DNA
<213> ORGANISM: Homo sapiens
<220> FEATURE:
<221> NAME/KEY: modified_base
<222> LOCATION: (1)..(313)
<223> OTHER INFORMATION: n = g, a, c or t

<400> SEQUENCE: 98

```
ccacaaaata aggtctaatt caataaatta tagtaaatta atgtaatata atattacatg     60
ccactaaaaa gaataaggta gctgtatatt tcctggtatg gaaaaaacat attaatatgt    120
```

```
tataaactat taggttggtg caaaactaat tgtggttttt gccattgaaa tggcattgaa    180
ataaaagtgt aaagaaatct ataccagatg tagtaacagt ggtttggttc tgggaggttg    240
gattacaggg agcatttgat ttctatgttg ngtatttcta tantgtttga attgtttaga    300
atgaatctgt ntt                                                       313

<210> SEQ ID NO 99
<211> LENGTH: 317
<212> TYPE: DNA
<213> ORGANISM: Homo sapiens

<400> SEQUENCE: 99
ccagtatgga atccagaagg accgagtgga taagagcgct gtcggcttca atgaaatgga     60
ggccccgacc acagcttata agaagacgac gcccatagaa ccgcttcta gtggtgcccg    120 tgggctgaag gcgaaatttg agtccatggc tgaggagaag aggaagcgag aggaagagga    180
gaaggcacag caggtggcca ggaggcaaca ggagcgaaag gctgtgacaa agaggagccc    240
tgaggctcca cagccagtga tagctatgga agagccagca gtaccggccc cactgcccaa    300
gaaaatctcc tcagagg                                                   317

<210> SEQ ID NO 100
<211> LENGTH: 1968
<212> TYPE: DNA
<213> ORGANISM: Homo sapiens

<400> SEQUENCE: 100
aattccgccg ggcgcttaga acagaggctt gcacaggtgg agatgtggaa gtctgtagtg     60
ggccatgatg tgtctgtttc cgtggagacc cagggtgatg attgggacac agatcctgac    120
tttgtgaatg acatctctga aaaggagcaa cgatggggag ccaagaccat cgaggggtct    180
ggacgcacag aacacatcaa catccaccag ctgaggaaca agtatcaga ggagcatgat    240 gttctcagga agaaagagat ggagtcaggg cccaaagcat cccatggcta tggaggtcgg    300
tttggagtag aaagagaccg aatggacaag agtgcagtgg gccatgagta tgttgccgag    360
gtggagaagc actcttctca gacggatgct gccaaaggct tgggggcaa gtacggagtt    420 gagagggaca gggcagacaa gtcagcagtc ggctttgatt ataaaggaga agtggagaag    480
catacatctc agaaagatta ctctcgtggc tttggtggcc ggtacggggt ggagaaggat    540
aaatgggaca aagcagctct gggatatgac tacaagggag agacggagaa acacgagtcc    600
cagagagatt atgccaaggg ctttggtggc agtatggaa tccagaagga ccgagtggat    660
aagagcgctg tcggcttcaa tgaaatggag gccccgacca cagcttataa gaagacgacg    720
cccatagaag ccgcttctag tggtgcccgt gggctgaagg cgaaatttga gtccatggct    780
gaggagaaga ggaagcgaga ggaagaggag aaggcacagc aggtggccag gaggcaacag    840
gagcgaaagg ctgtgacaaa gaggagccct gaggctccac agccagtgat agctatggaa    900
gagccagcag taccggcccc actgcccaag aaaatctcct cagaggcctg gcctccagtt    960
gggactcctc catcatcaga gtctgagcct gtgagaacca gcaggaaca cccagtgccc   1020 ttgctgccca ttaggcagac tctcccggag gacaatgagg agcccccagc tctgccccct   1080
aggactctgg aaggcctcca ggtggaggaa gagccagtgt acgaagcaga gcctgagcct   1140 gagcccagc ctgagcccga gcctgagaat gactatgagg acgttgagga gatgacagg   1200 catgagcagg aggatgaacc agaggggac tatgaggagg tgctcgagcc tgaagattct   1260
```

-continued

```
tcttttctt ctgctctggc tggatcatca ggctgcccgg ctggggctgg ggctggggct    1320
gtggctctgg ggatctcagc tgtggctcta tatgattacc aaggagaggg aagtgatgag    1380
ctttcctttg atccggacga cgtaatcact gacattgaga tggtggacga gggctggtgg    1440
cggggacgtt gccatggcca ctttggactc ttccctgcaa attatgtcaa gcttctggag    1500
tgactagagc tcactgtcta ctgcaactgt gatttcccat gtccaaagtg gctctgctcc    1560
accccctccc tattcctgat gcaaatgtct aaccagatga gtttctggac agacttccct    1620
ctcctgcttc attaagggct tggggcagag acagcatggg gaaggaggtc cccttcccca    1680
agagtccctct ctatcctgga tgagctcatg aacatttctc ttgtgttcct gactccttcc    1740
caatgaacac ctctctgcca ccccaagctc tgctctcctc ctctgtgagc tctgggcttc    1800
ccagtttgtt tacccgggaa agtacgtcta gattgtgtgg tttgcctcat tgtgctattt    1860
gcccactttc cttccctgaa gaaatatctg tgaaccttct ttctgttcag tcctaaaatt    1920
cgaaataaag tgagactatg gttcacctgt aaaaaaaaaa aaggaatt              1968
```

<210> SEQ ID NO 101
<211> LENGTH: 486
<212> TYPE: PRT
<213> ORGANISM: Homo sapiens

<400> SEQUENCE: 101

```
Met Trp Lys Ser Val Val Gly His Asp Val Ser Val Ser Val Glu Thr
  1               5                  10                  15

Gln Gly Asp Asp Trp Asp Thr Asp Pro Asp Phe Val Asn Asp Ile Ser
              20                  25                  30

Glu Lys Glu Gln Arg Trp Gly Ala Lys Thr Ile Glu Gly Ser Gly Arg
          35                  40                  45

Thr Glu His Ile Asn Ile His Gln Leu Arg Asn Lys Val Ser Glu Glu
      50                  55                  60

His Asp Val Leu Arg Lys Lys Glu Met Glu Ser Gly Pro Lys Ala Ser
  65                  70                  75                  80

His Gly Tyr Gly Gly Arg Phe Gly Val Glu Arg Asp Arg Met Asp Lys
              85                  90                  95

Ser Ala Val Gly His Glu Tyr Val Ala Glu Val Glu Lys His Ser Ser
             100                 105                 110

Gln Thr Asp Ala Ala Lys Gly Phe Gly Gly Lys Tyr Gly Val Glu Arg
         115                 120                 125

Asp Arg Ala Asp Lys Ser Ala Val Gly Phe Asp Tyr Lys Gly Glu Val
     130                 135                 140

Glu Lys His Thr Ser Gln Lys Asp Tyr Ser Arg Gly Phe Gly Gly Arg
145                 150                 155                 160

Tyr Gly Val Glu Lys Asp Lys Trp Asp Lys Ala Ala Leu Gly Tyr Asp
                 165                 170                 175

Tyr Lys Gly Glu Thr Glu Lys His Glu Ser Gln Arg Asp Tyr Ala Lys
             180                 185                 190

Gly Phe Gly Gly Gln Tyr Gly Ile Gln Lys Asp Arg Val Asp Lys Ser
         195                 200                 205

Ala Val Gly Phe Asn Glu Met Glu Ala Pro Thr Thr Ala Tyr Lys Lys
     210                 215                 220

Thr Thr Pro Ile Glu Ala Ala Ser Ser Gly Ala Arg Gly Leu Lys Ala
225                 230                 235                 240

Lys Phe Glu Ser Met Ala Glu Glu Lys Arg Lys Arg Glu Glu Glu Glu
                 245                 250                 255
```

Lys Ala Gln Gln Val Ala Arg Arg Gln Glu Arg Lys Ala Val Thr
            260                 265                 270

Lys Arg Ser Pro Glu Ala Pro Gln Pro Val Ile Ala Met Glu Glu Pro
        275                 280                 285

Ala Val Pro Ala Pro Leu Pro Lys Lys Ile Ser Ser Glu Ala Trp Pro
        290                 295                 300

Pro Val Gly Thr Pro Ser Ser Glu Ser Glu Pro Val Arg Thr Ser
305                 310                 315                 320

Arg Glu His Pro Val Pro Leu Leu Pro Ile Arg Gln Thr Leu Pro Glu
                325                 330                 335

Asp Asn Glu Glu Pro Pro Ala Leu Pro Pro Arg Thr Leu Glu Gly Leu
            340                 345                 350

Gln Val Glu Glu Glu Pro Val Tyr Glu Ala Glu Pro Glu Pro Glu Pro
        355                 360                 365

Glu Pro Glu Pro Glu Pro Glu Asn Asp Tyr Glu Asp Val Glu Glu Met
    370                 375                 380

Asp Arg His Glu Gln Glu Asp Glu Pro Glu Gly Asp Tyr Glu Glu Val
385                 390                 395                 400

Leu Glu Pro Glu Asp Ser Ser Phe Ser Ser Ala Leu Ala Gly Ser Ser
                405                 410                 415

Gly Cys Pro Ala Gly Ala Gly Ala Gly Ala Val Ala Leu Gly Ile Ser
            420                 425                 430

Ala Val Ala Leu Tyr Asp Tyr Gln Gly Glu Gly Ser Asp Glu Leu Ser
        435                 440                 445

Phe Asp Pro Asp Asp Val Ile Thr Asp Ile Glu Met Val Asp Glu Gly
    450                 455                 460

Trp Trp Arg Gly Arg Cys His Gly His Phe Gly Leu Phe Pro Ala Asn
465                 470                 475                 480

Tyr Val Lys Leu Leu Glu
                485

<210> SEQ ID NO 102
<211> LENGTH: 96
<212> TYPE: DNA
<213> ORGANISM: Homo sapiens

<400> SEQUENCE: 102
ctgacagcat ctggctttca gttcctcagt caccactact ttgtaccaaa ttcactgttt    60
tggctctgaa atctaatttt gagtttagca aggatg                              96

<210> SEQ ID NO 103
<211> LENGTH: 349
<212> TYPE: DNA
<213> ORGANISM: Homo sapiens

<400> SEQUENCE: 103
ccagagtgca ggatacatca ttggcaccaa gggtcttttt caattcttgg tcaatcctct    60
gcagcaagca cccccggatg acgtcctcat agatgccctc agtggtcaga gcctggctgc   120
ccacggcaag gacatccccc tcgaactcag gcagctcctg tttgcagcct ggctcgagtt   180
ggctcagcac aaaaggtaaa aagatgcaga gaccccagcc tcggatgaac ctcctctgcg   240
ccaacccgct gtccgatttg aatttcttca gcacgcgccc cctgactctc tccagcctct   300
gggcagcctg gtcacagttg agggccgtcg tcagacactg gtcagccag               349

```
<210> SEQ ID NO 104
<211> LENGTH: 116
<212> TYPE: PRT
<213> ORGANISM: Homo sapiens

<400> SEQUENCE: 104

Leu Ala Asp Gln Cys Leu Thr Thr Ala Leu Asn Cys Asp Gln Ala Ala
  1               5                  10                  15

Gln Arg Leu Glu Arg Val Arg Gly Arg Val Leu Lys Lys Phe Lys Ser
             20                  25                  30

Asp Ser Gly Leu Ala Gln Arg Phe Ile Arg Gly Trp Gly Leu Cys
         35                  40                  45

Ile Phe Leu Pro Phe Val Leu Ser Gln Leu Glu Pro Gly Cys Lys Lys
     50                  55                  60

Glu Leu Pro Glu Phe Glu Gly Asp Val Leu Ala Val Gly Ser Gln Ala
 65                  70                  75                  80

Leu Thr Thr Glu Gly Ile Tyr Glu Asp Val Ile Arg Gly Cys Leu Leu
                 85                  90                  95

Gln Arg Ile Asp Gln Glu Leu Lys Lys Thr Leu Gly Ala Asn Asp Val
            100                 105                 110

Ser Cys Thr Leu
        115

<210> SEQ ID NO 105
<211> LENGTH: 311
<212> TYPE: DNA
<213> ORGANISM: Homo sapiens
<220> FEATURE:
<221> NAME/KEY: modified_base
<222> LOCATION: (1)..(311)
<223> OTHER INFORMATION: n = g, a, c or t

<400> SEQUENCE: 105
ctgcaagaca gcagagaanc tgccaatatc cagttagcag atgactttgc tggcaagcag      60
aggaagncgg taaaagcttg tctcccagcc aggaaacttg acaccaagnt aagatttgga     120
gctaggaaac aaacccaaaa ggctcacagc aagcggagaa aaaaacccca aaatctgtaa     180
cctgtatcac aaagcgttca tatccttcag atataaagag ttattagata tcaataagaa     240
aaatgcaaac actcctgaaa agtagaaaaa agctatgaac aggcaattca ctgaaattaa     300
aaaaaaaaaa a                                                          311

<210> SEQ ID NO 106
<211> LENGTH: 5107
<212> TYPE: DNA
<213> ORGANISM: Homo sapiens

<400> SEQUENCE: 106
cgcaggcggt ggtcgtgggg aagggaagag gagccccggg agacgacagc agcatgggtg      60
ggcggccttc gagccctctg acaagcagc agcggcagca cctaagggg caggtggaca     120 ccctgctgag gaacttcctg ccttgctacc gtgggcagct ggcagcgtct gtcctgcggc     180
agatctctcg agagctgggc cctcaggagc cgaccggaag ccagttgcta cgcagcaaaa     240
agctgccccg agtccgtgag caccgaggac ccctgaccca gcttcgggc cacccacccc     300 ggtggcagcc gatcttctgt gttctgcgtg gggacggccg cctagagtgg ttcagccaca     360
aggaggaata tgaaaacggg ggccactgcc ttggctcaac agccctgaca ggatacacgc     420
tcctgacttc ccagcgagaa tatctccgcc ttttggatgc tctctgccct gaatccttgg     480
```

```
gagaccatac tcaggaagag cctgactccc tcttggaagt gcctgtgagc ttcccgctgt    540
tcctgcagca ccccttccgc cggcacctct gcttctctgc agccaccagg gaggcacagc    600
atgcctggag gctggccctg cagggtggca tccggcttca gggcacagtc ctgcagcgaa    660
gccaggcccc tgctgcccgg gccttcctgg acgccgtccg actctaccgg cagcaccaag    720
gccactttgg cgacgacgac gtgaccctag gctcagacgc cgaggtgctg accgcggtgc    780
tgatgcggga gcaacttccc cgcgctgcgag cccagaccct tcctggcctg cgggggggcag   840 gccgcgcccg cgcctgggcc tggaccgagc ttctagacgc cgttcacgca gctgtcctgg    900
ccggggcctc cgccgggctc tgcgccttcc agcccgaaaa ggacgagctg cttgcgtcgc    960
tggagaagac gatccgcccg gacgtggacc agctgctgcg gcagcgggcg cgtgtggcgg   1020
ggcggctgag gacggatatc aggggaccgc tcgagtcgtg cctgcgccgg gaggtggacc   1080
cgcagctgcc ccgggtcgtg cagaccctgc tgcgcaccgt ggaagcctcg ctcgaggcgg   1140
tgcggaccct cctggctcaa ggcatggacc gactgtccca ccgcctgcgc cagagcccct   1200
cgggcacgcg gctgcgcagg gaggtttact catttgggga gatgccgtgg gacttggcgc   1260
tgatgcagac atgctaccgt gaggccgagc ggagccgggg gcgcttgggg cagctggcag   1320
caccgtttgg ctttctgggg atgcagagcc tcgtgtttgg ggcccaagat cttgcacagc   1380
agctcatggc tgacgccgtg gccaccttcc tgcagctggc tgaccagtgt ctgacgacgg   1440
ccctcaactg tgaccaggct gcccagaggc tggagagagt caggggggcgc gtgctgaaga   1500 aattcaaatc ggacagcggg ttggcgcaga ggaggttcat ccgaggctgg ggtctctgca   1560 tcttttttacc ttttgtgctg agccaactcg agccaggctg caaaaagacg gagtctcgct   1620
ctgtcgccca ggctgtagtg cagtggtgtg atcttggctc gctgcggcct ccacctccta   1680
ggttcaagcg atcctcccat ctcggcctcc caagtagctg ggattacagg cacccgctat   1740
agggaccagc cccacagggt cggtgggtct ctccctgtgt gcagagacaa gagagtgtag   1800
aaataaagac acaagacaaa gagataaaag aaaagacagc tgggcccggg ggaccactac   1860
taccaagttg cggagaccgg tagtggcccc gaatgtctgg ctgcgctgtt atttattgga   1920
tacaaagcaa aaggggcagg gtaaagagtg tgagtcatct ccaatgatag gtaaggtcac   1980
gtgggtcatg tgtccactgg acaggggggcc cctccctgcc tggcagctga ggcagagaga   2040
gagaggagac aaagagaaag acagcttaag ccattatttc tgcatatcag agactttag    2100 tactttcact aactgactac tgctatctag aaggcagagc caggtgtaca ggatggaaca   2160
cgaaggcgga ctaggagcga gaccactgaa gcacagcatc acaggagac ggttaggtct    2220 ctggataact gtgggcaagc ctgactgata tcaggccctc cacaagaggt ggaggagcag   2280
agtcttctct aaactccccc ggagaaaagg agactcccctt tcccggtctg ctaagtagcc   2340 ggtgttttc cttgacactt ttcgctaccg ctagaccacg gtctgcctgg caacaggcat    2400
cttcccagac gctggcgtca ccgctagacc aaggagccct tctgctggcc ctgtccgggc   2460
ataacagaag gctcgcactc ttgtcttctg gtcataccctc actatgcccc ctcagctcct   2520
atctctgtat ggcctggttt ttcctaggtt atgattgtag agtgaggatt attataatat   2580
tggaataaag agtaactgct accaactaat cattaatgat attcatatat aatcatatct   2640
aatatctata tctggtataa ctattcttgt tttatatttt gttatactgg aacagctcat   2700
gtcctcggtc tcttgcctca gcacctgggt ggcttgccgc ccacaacccg ccaccacgcc   2760
cagctaattt ttgtactttt ggtagagacg gtggtttcac catgttggtc aggctggtct   2820
tgaactcctg acctcatgat ccgcccacct cagccaacca aagtgctggg attacaggca   2880
```

```
tgagccaccg cacccggcct gtttatttta aataaaaat atttaaaaat aaagataagg    2940
aaactaaggc ccaagccccg ccccccaacc ccacagctaa tcaggcccag ggctagggca    3000
gaagcctgtg ttgtaggcct ctagaggggc cctcctctcc atccgagccc ctaacccgcc    3060
atggttccag gagctgcctg agttcgaggg ggatgtcctt gccgtgggca gccaggctct    3120
gaccactgag ggcatctatg aggacgtcat ccggggtgc ttgctgcaga ggattgacca    3180
agacccttgg tgccaatgat gtatcctgca ctctggacgg ctgcttggag gtcccatggg    3240
aacaggaggg agcagatgag gaaactgagg ctgagcggga aggaggggct tgtcccaggc    3300
agccagactc tggtgcccag atccagccac tctgcccacc gccttctcca ggaacattcc    3360
ggagctgaat cttcacccac atctatcttg tttctattgg ataaatgtct acaagtggaa    3420
tttctgggcc aaaacggatg tgccatcttt aggcttttgt aaccctgca acttcagaaa    3480 actgtaccat tttatactcc aagcagcagc atttatttgt gtattttccc caaggctttc    3540
tttattttaa tttttttttt tttttttgag actgggtctt gctctgtcac ccgggctggg    3600
gtgcagtggc aggatctcgg ctcactgcga cctccgcctc ccgggttcaa gcgattctcc    3660
tgcctcagcc tcccgagtag ctgggatttc aggcacccgc caccatgcct ggttaattgt    3720 gttttggta gagatgggt tcgccgtgt tggccaggct ggtctcgaac tcctgtcctt    3780
aggtggtctg cccgcctcag cctcccggag tgctgggatt gcaggtgtga gccaccacac    3840
gtggcctaat tttttttttt taaataatag agacaaggtc tcgctatgct gcccaggctg    3900
atctcaaact cctggactca agcaatcctc ctgccttggc ctcccaaagt gctaggatta    3960
taggagtgat ccactatgtc cagcctccaa atcctttcta aacactagga cttttcatga    4020
aaagaaaaaa gctatgccag ttagacacac acagaaatct catgatttta ttttgaattt    4080
ctttgactaa attgaactta caaataagtt tattatggcc gggcgtggcg gtgcacacct    4140
gtggtcccgg cactttggga ggctgaggcg ggcagatcac ttgagctcag gagttcggga    4200
ccagcctggc ggacgtggtg ggacctcatc tctacaaaaa atacaaaatt agcggccggg    4260
agtggtggct cacgcctgtc atcccagcac tttgggaggc tgagacaggt ggattgcttg    4320
agccaaggag ttttgaggcc agcttgggca atgtggtgaa acctgtctct actaaaaaat    4380 aaaataaaata aataaataaa taaataaata aataaataaa taaatttaa aagaagctgg    4440 gctgagatgg gagatttgcc tgagcctggg aactcaaggc tgcagtgagt ggtgattgca    4500
ccactgcact ccagcctggg tgatgggagt gagaccctgt ctcaaaaaac aaaatccaaa    4560
tatgttgatt agccatttac atgttgtag tttttttttt tttaattca gtgaattgcc    4620 tgttcatagc ttttttctac ttttcaggag tgtttgcatt tttcttattg atatctaata    4680
actctttata tctgaaggat atgaacgctt tgtgatacag gttacagatt ttggggtttt    4740
tttctccgct tgctgtgagc cttttgggtt tgtttcctag ctccaaatct taacttggtg    4800
tcaagtttcc tggctgggag acaagctttt accgacttcc tctgcttgcc agcaaagtca    4860
tctgctaact ggatattggc agcttctctg ctgtcttgca gctgcttccg gagtgggttc    4920
cacagggatt cccgtgtgtt cttggttcag cttgcagagg gactttcaca ctccctggag    4980
accgtttcct cccattctgt ctggagtttt cggcctaccc caagacaatg agatattcct    5040 gaccttcca cctatttccc tccaaccca ccttccaaaa tacatttgct caatacattt    5100
gcacttc                                                                5107
```

<210> SEQ ID NO 107

<211> LENGTH: 579
<212> TYPE: PRT
<213> ORGANISM: Homo sapiens

<400> SEQUENCE: 107

```
Gln Ala Val Val Gly Lys Gly Arg Gly Pro Gly Asp Asp Ser
  1               5                  10                  15

Ser Met Gly Gly Arg Pro Ser Pro Leu Asp Lys Gln Gln Arg Gln
             20                  25                  30

His Leu Arg Gly Gln Val Asp Thr Leu Leu Arg Asn Phe Leu Pro Cys
         35                  40                  45

Tyr Arg Gly Gln Leu Ala Ala Ser Val Leu Arg Gln Ile Ser Arg Glu
     50                  55                  60

Leu Gly Pro Gln Glu Pro Thr Gly Ser Gln Leu Leu Arg Ser Lys Lys
 65                  70                  75                  80

Leu Pro Arg Val Arg Glu His Arg Gly Pro Leu Thr Gln Leu Arg Gly
                 85                  90                  95

His Pro Pro Arg Trp Gln Pro Ile Phe Cys Val Leu Arg Gly Asp Gly
            100                 105                 110

Arg Leu Glu Trp Phe Ser His Lys Glu Glu Tyr Glu Asn Gly Gly His
        115                 120                 125

Cys Leu Gly Ser Thr Ala Leu Thr Gly Tyr Thr Leu Leu Thr Ser Gln
130                 135                 140

Arg Glu Tyr Leu Arg Leu Leu Asp Ala Leu Cys Pro Glu Ser Leu Gly
145                 150                 155                 160

Asp His Thr Gln Glu Glu Pro Asp Ser Leu Leu Glu Val Pro Val Ser
                165                 170                 175

Phe Pro Leu Phe Leu Gln His Pro Phe Arg Arg His Leu Cys Phe Ser
            180                 185                 190

Ala Ala Thr Arg Glu Ala Gln His Ala Trp Arg Leu Ala Leu Gln Gly
        195                 200                 205

Gly Ile Arg Leu Gln Gly Thr Val Leu Gln Arg Ser Gln Ala Pro Ala
    210                 215                 220

Ala Arg Ala Phe Leu Asp Ala Val Arg Leu Tyr Arg Gln His Gln Gly
225                 230                 235                 240

His Phe Gly Asp Asp Val Thr Leu Gly Ser Asp Ala Glu Val Leu
                245                 250                 255

Thr Ala Val Leu Met Arg Glu Gln Leu Pro Ala Leu Arg Ala Gln Thr
            260                 265                 270

Leu Pro Gly Leu Arg Gly Ala Gly Arg Ala Arg Ala Trp Ala Trp Thr
        275                 280                 285

Glu Leu Leu Asp Ala Val His Ala Ala Val Leu Ala Gly Ala Ser Ala
    290                 295                 300

Gly Leu Cys Ala Phe Gln Pro Glu Lys Asp Glu Leu Leu Ala Ser Leu
305                 310                 315                 320

Glu Lys Thr Ile Arg Pro Asp Val Asp Gln Leu Leu Arg Gln Arg Ala
                325                 330                 335

Arg Val Ala Gly Arg Leu Arg Thr Asp Ile Arg Gly Pro Leu Glu Ser
            340                 345                 350

Cys Leu Arg Arg Glu Val Asp Pro Gln Leu Pro Arg Val Val Gln Thr
        355                 360                 365

Leu Leu Arg Thr Val Glu Ala Ser Leu Glu Ala Val Arg Thr Leu Leu
    370                 375                 380

Ala Gln Gly Met Asp Arg Leu Ser His Arg Leu Arg Gln Ser Pro Ser
```

```
                385                 390                 395                 400
            Gly Thr Arg Leu Arg Arg Glu Val Tyr Ser Phe Gly Glu Met Pro Trp
                            405                 410                 415
            Asp Leu Ala Leu Met Gln Thr Cys Tyr Arg Glu Ala Glu Arg Ser Arg
                            420                 425                 430
            Gly Arg Leu Gly Gln Leu Ala Ala Pro Phe Gly Phe Leu Gly Met Gln
                        435                 440                 445
            Ser Leu Val Phe Gly Ala Gln Asp Leu Ala Gln Leu Met Ala Asp
                    450                 455                 460
            Ala Val Ala Thr Phe Leu Gln Leu Ala Asp Gln Cys Leu Thr Thr Ala
            465                 470                 475                 480
            Leu Asn Cys Asp Gln Ala Ala Gln Arg Leu Glu Arg Val Arg Gly Arg
                            485                 490                 495
            Val Leu Lys Lys Phe Lys Ser Asp Ser Gly Leu Ala Gln Arg Arg Phe
                        500                 505                 510
            Ile Arg Gly Trp Gly Leu Cys Ile Phe Leu Pro Phe Val Leu Ser Gln
                    515                 520                 525
            Leu Glu Pro Gly Cys Lys Lys Thr Glu Ser Arg Ser Val Ala Gln Ala
                530                 535                 540
            Val Val Gln Trp Cys Asp Leu Gly Ser Leu Arg Pro Pro Pro Arg
            545                 550                 555                 560
            Phe Lys Arg Ser Ser His Leu Gly Leu Pro Ser Ser Trp Asp Tyr Arg
                            565                 570                 575
            His Pro Leu

<210> SEQ ID NO 108
<211> LENGTH: 2917
<212> TYPE: DNA
<213> ORGANISM: Homo sapiens

<400> SEQUENCE: 108
ctagaatgct aattgcactt aggcctcatg gttctagtaa acggcagctg tgggcccttt      60
tgcctcttcc cctgttcttg gcctcacatc tccagctgag ctgccggtct ggcttcctg     120 gtcgcctctg tcccagagat ggtcccaggg agccatccta gggcaggtag cactgaggct    180
cctgtggaaa caggagccac ctgctcagga gacccctttc ctgaggaagt ccttacctct    240
ccccttgaga tgtaaaaatg gtccagcaga acaagctcc cgtggaaaac agacaggagc    300
atgggggcag ctgtcatggc tgtggcgggc acttttcctc agagtttctg ccttgcgctg    360
gtccaggagc cattttgcac caaggacttg gtaggcagag gcagccccac tgtaaagaag    420
ggtcagatta aacaaaaaaa ctgccaaaag catcccctct gcccccccatg tggcactggc   480 atcattctct gcttccctgg gaggaatttt ttcaccatgt tattgaaggg gatggttcat    540
taaggactcc acccctcaga gctcactcag accccaagga cagaggtgac tggggcttgg    600
tgacttgttc actcctttt tcccaggtat actgaagggg tgacagagag aggtcttcat    660
ggcagaccag gccttcacag ctaatgggga gaggaactca tgttacctct gcaggcctgg    720
ggtcctgagg gggtcttttg gcttcagcct gttcccccag aggcttgatc atcccacatt    780
gtcccttcag ctcagctgct cttctccccc acccaccctg gatgtgggt gctctgggct    840 gaaccaaggc tatgacttct ggagagaggc tcaggggttg gtctgagagg cctgccatcc    900 accccctcagg gagctaggtt ttctcagagg ctcagctgga cagcactttt tagaaaagtt    960
tgtagcatta agctggttta aaatatgaag ttggttttgt tggatggctc ctgagctgac   1020
```

```
tgactgatgt ctgaagtttg agacgaggga ttatttcagg gtggggccca atgtgatcta    1080
atgcccagct ggggacaatt gtgcctcatc atttgctcaa attcctgggc ccccaagtta    1140
gccccctccc aggagtggtc agcgggtcac agctgccccc actctataag cagggctaat    1200
tgtgtacccct ttgcagaaat gcttttggtc tcctacccaa atactcacaa gggtcttatc   1260
agacgcccgt cttaaagtcc agcatgctca gggaccctgt gtaggatctc gtttgtggtg    1320
agtgggctgc tctgaggtct ccactgggct gccatttagc catgtgccat ctctgaagtc    1380
agaggtgttt gactcccatt ccttgggctc tggagctttc cccaagaatt acatcagaga    1440
aaaggaagaa ggggcctgca ggacccattg ggaatgagtt taatactgaa gtctggaatg    1500
taagctcatg cccctagaggc ctctccatat ggctggtcag gggagctgcc ttcaggcttg   1560
tgccccgtgt gctcagcagc tgcctctgtc ccctctact gtcccttttca ccttgcct      1620
ggccaagggg ctagacctcc caggctaagc ctcagattca gtgcaggaca caagctcatg    1680
cccccgtctt gccagtgaca cttgaagcct cccgacttcc acagagtgct tcaggacaca    1740
ttttgagtgg tattttcttt tctttttttc ttctttttttt ttttttgag atggagtctc    1800
gctctgttgc ccaggctgga gtgcagtggc ctgatctcgg ctcactgcaa cctctgcctc    1860
ccaggttcaa gcgattcttc tgcctcagcc tccagagtag ctgggactat agacatgcac    1920
caccacgccc ggctaatttt gtattttttgg tcgagacggg gttttgccat gttagtcagg    1980
ctggtcttga actcctgacc tcaagtgatc caccacctcg gcctcccaaa gtgttgagat    2040
gacaggcacg agccaccagg cccagcctga gtggtatttt ctttagggac caggtagact    2100
ttaaaacgag ggtaagagaa aagccagtgt ctttctgagg taaataattt ctgccaggaa    2160
acttcccagc cccaccagca gcccccctaa aaaaatcact cgtgtcccca gggacttcta    2220
aagcttgggg ctccaggaaa tcatccagta gagttggaga ttcagagatt tcttgaagcc    2280
agggacatgc tcctaactcc tttcccatta aaggtgttag aatagaccag agggtgtccc    2340
ttttccacag taatgggatc ggctggtgtg ccttcaggga ggaagaggga ggtggtcaag    2400
cttgaaaaac tggctttagg atggttctga ctttgttctc cctccccaag tgttctcaac    2460
ctccattctg cagtgttcag agttttaggg aaagggtttg ggtgccccag catccaggtg    2520
ttgtgtggct tagcgcatgt gaagtgaaaa ccttctgggg ttgtttggaa gcagctttct    2580
ggttcttgtg attgtatcct gaggtcccag aaccctattc tcccacgagg atcctcagtg    2640
accatggtgg ccacacgcct ggccagcctg ctggctcctg ggtgagctga agaaccttgc    2700
ctgtggcact tttcgagggt gagctggaac cgagagaaca tggtccccgt gctgggactc    2760
atgcgggtca tttcctgccg gcctggtttc gcctggtcgt gtctttatga gcaccatgta    2820
agcctccttg tattgagata attgggcatt aaacattaaa ctgcagctct gggaaaaaaa    2880
aaaaaaaaaa aaaaaaaaa aaaaaaaaa aaaaaac                               2917
```

<210> SEQ ID NO 109
<211> LENGTH: 83
<212> TYPE: PRT
<213> ORGANISM: Homo sapiens

<400> SEQUENCE: 109

Met Glu Ser Arg Ser Val Ala Gln Ala Gly Val Gln Trp Pro Asp Leu
 1               5                  10                  15

Gly Ser Leu Gln Pro Leu Pro Pro Arg Phe Lys Arg Phe Phe Cys Leu
            20                  25                  30

Ser Leu Gln Ser Ser Trp Asp Tyr Arg His Ala Pro Pro Arg Pro Ala

```
                35                  40                  45
Asn Phe Val Phe Leu Val Glu Thr Gly Phe Cys His Val Ser Gln Ala
         50                  55                  60
Gly Leu Glu Leu Leu Thr Ser Ser Asp Pro Pro Arg Pro Pro Lys
 65                  70                  75                  80

Val Leu Arg

<210> SEQ ID NO 110
<211> LENGTH: 509
<212> TYPE: DNA
<213> ORGANISM: Homo sapiens
<220> FEATURE:
<221> NAME/KEY: modified_base
<222> LOCATION: (467)
<223> OTHER INFORMATION: n = g, a, c or t

<400> SEQUENCE: 110
aaaccttaag aaccacataa tactatataa tgcttttctg tacaaatctc aagaaacact      60
ttcattcatt aaaacatcat gaaaatcctt aaatgtgtta aatggaaaaa aatgaaacca     120
tgaacaaaaa agctatacat gtaggtgcat atttatctcc tcctgagttg ggagaaatct     180
ttctaagcat agaaacaatg gtagcaaaag agaagaatga atttggctgg attaacaata     240
aaaaatttct gccagaaata tgaaaattca atttagacaa aattcaatat aaacaaaatt     300
aatatagaca aaggtggtaa acaggtggtt ctcagagaag ataaatacat gattatttaa     360
cataaaaaga aatgttcaat gtttctagaa gacaaataat tacaaaccta aacaaattgt     420
atatttgtta gattggcata aattataata atccaacatt gagttangtg gaatataaat     480
tggtaaaata tttctggaag acaatttgg                                       509

<210> SEQ ID NO 111
<211> LENGTH: 525
<212> TYPE: DNA
<213> ORGANISM: Homo sapiens

<400> SEQUENCE: 111
agaagtgatt atgggattaa agaatacat aattacagtg ttttgggatt gggctctttt       60
ttttcttaat agaaaagcag aaacttcata ataatagct gtgctttaga taccagataa      120
caaatattgt ttccctgaa gatatgacct actagaacta ctcacatata tagtccaata     180
attgctgact taataggtat ggtaaaatag ctgataataa gtcagactct caagagtttc     240
tgtaccttga ttattgacaa attcattgtt ttacatccta ctaaagaaca tgtgtgtggg     300
gaggggtggg ggaactggtt cacaacataa tctgaaggag atcaaacatc tgtaaggaca     360
ggtacccagt gatgataata tatctgaaaa cacaagccat ttttattctt tatcccaatt     420
aacttgaggt actctaatga tgaagcactc gattgcacta tgacctcctt gagtgatggg     480
cagcttggtt cctctctcac tttttgtttc tttttaatat gcaaa                    525

<210> SEQ ID NO 112
<211> LENGTH: 183
<212> TYPE: DNA
<213> ORGANISM: Homo sapiens
<220> FEATURE:
<221> NAME/KEY: modified_base
<222> LOCATION: (1)..(183)
<223> OTHER INFORMATION: n = g, a, c or t

<400> SEQUENCE: 112
aaaaaaagac aatttgagca ggacgaccct ctccaatctg ggtagcatgg ttagcctgtg       60
```

```
cagtaacaac gtaggcttgg aggatgggtn caatgaaaat gattctgatt cggaaacgtt      120
ttgactttgg actgtanaag cttttctttg atcacctgtg ntggaggaaa ggaaagaagc      180
ctt                                                                    183
```

<210> SEQ ID NO 113
<211> LENGTH: 1750
<212> TYPE: DNA
<213> ORGANISM: Homo sapiens

<400> SEQUENCE: 113

```
cagctctctg tcagaatggc caccatggta ccatccgtgt tgtggcccag ggcctgctgg       60
actctgctgg tctgctgtct gctgacccca ggtgtccagg ggcaggagtt ccttttgcgg      120
gtggagcccc agaaccctgt gctctctgct ggagggtccc tgtttgtgaa ctgcagtact      180
gattgtccca gctctgagaa atcgccttg gagacgtccc tatcaaagga gctggtggcc       240
agtggcatgg gctgggcagc cttcaatctc agcaacgtga ctggcaacag tcggatcctc      300
tgctcagtgt actgcaatgg ctcccagata acaggctcct ctaacatcac cgtgtacggg      360
ctcccggagc gtgtggagct ggcacccctg cctccttggc agccggtggg ccagaacttc      420
accctgcgct gccaagtgga gggtgggtcg ccccggacca gcctcacggt ggtgctgctt      480
cgctgggagg aggagctgag ccggcagccc gcagtggagg agccagcgga ggtcactgcc      540
actgtgctgg ccagcagaga cgaccacgga gccccttttct catgccgcac agaactggac      600
atgcagcccc aggggctggg actgttcgtg aacacctcag ccccccgcca gctccgaacc      660
tttgtcctgc ccgtgacccc cccgcgcctc gtggccccc ggttcttgga ggtggaaacg       720
tcgtggccgg tggactgcac cctagacggg cttttttccag cctcagaggc ccaggtctac     780
ctggcgctgg gggaccagat gctgaatgcg acagtcatga ccacgggga cacgctaacg      840 gccacagcca cagccacggc gcgcgcggat caggagggtg cccggagat cgtctgcaac      900 gtgaccctag ggggcgagag acgggaggcc cgggagaact tgacggtctt tagcttccta     960
ggacccattg tgaacctcag cgagcccacc gcccatgagg ggtccacagt gaccgtgagt    1020
tgcatggctg gggctcgagt ccaggtcacg ctggacgag ttccggccgc ggccccgggg     1080
cagccagctc aacttcagct aaatgctacc gagagtgacg acggacgcag cttcttctgc    1140
agtgccactc tcgaggtgga cggcgagttc ttgcacagga acagtagcgt ccagctgcga    1200
gtcctgtatg gtcccaaaat tgaccgagcc acatgccccc agcacttgaa atggaaagat    1260
aaaacgagac acgtcctgca gtgccaagcc agggggcaacc cgtaccccga gctgcggtgt    1320
ttgaaggaag gctccagccg ggaggtgccg gtggggatcc cgttcttcgt caacgtaaca    1380
cataatggta cttatcagtg ccaagcgtcc agctcacgag gcaaatacac cctggtcgtg    1440
gtgatggaca ttgaggctgg gagctcccac tttgtccccg tcttcgtggc ggtgttactg    1500
accctgggcg tggtgactat cgtactggcc ttaatgtacg tcttcaggga gcaccaacgg    1560
agcggcagtt accatgttag ggaggagagc acctatctgc ccctcacgtc tatgcagccg    1620
acagaagcaa tgggggaaga accgtccaga gctgagtgac gctgggatcc gggatcaaag    1680 ttggcgggg cttggctgtg ccctcagatt ccgcaccaat aaagccttca aactccctaa    1740
aaaaaaaaaa                                                          1750
```

<210> SEQ ID NO 114
<211> LENGTH: 547
<212> TYPE: PRT

<213> ORGANISM: Homo sapiens

<400> SEQUENCE: 114

```
Met Ala Thr Met Val Pro Ser Val Leu Trp Pro Arg Ala Cys Trp Thr
  1               5                  10                  15
Leu Leu Val Cys Cys Leu Leu Thr Pro Gly Val Gln Gly Gln Glu Phe
             20                  25                  30
Leu Leu Arg Val Glu Pro Gln Asn Pro Val Leu Ser Ala Gly Gly Ser
         35                  40                  45
Leu Phe Val Asn Cys Ser Thr Asp Cys Pro Ser Ser Glu Lys Ile Ala
     50                  55                  60
Leu Glu Thr Ser Leu Ser Lys Glu Leu Val Ala Ser Gly Met Gly Trp
 65                  70                  75                  80
Ala Ala Phe Asn Leu Ser Asn Val Thr Gly Asn Ser Arg Ile Leu Cys
                 85                  90                  95
Ser Val Tyr Cys Asn Gly Ser Gln Ile Thr Gly Ser Ser Asn Ile Thr
            100                 105                 110
Val Tyr Gly Leu Pro Glu Arg Val Glu Leu Ala Pro Leu Pro Pro Trp
        115                 120                 125
Gln Pro Val Gly Gln Asn Phe Thr Leu Arg Cys Gln Val Glu Gly Gly
    130                 135                 140
Ser Pro Arg Thr Ser Leu Thr Val Val Leu Arg Trp Glu Glu Glu
145                 150                 155                 160
Leu Ser Arg Gln Pro Ala Val Glu Glu Pro Ala Glu Val Thr Ala Thr
                165                 170                 175
Val Leu Ala Ser Arg Asp Asp His Gly Ala Pro Phe Ser Cys Arg Thr
            180                 185                 190
Glu Leu Asp Met Gln Pro Gln Gly Leu Gly Leu Phe Val Asn Thr Ser
        195                 200                 205
Ala Pro Arg Gln Leu Arg Thr Phe Val Leu Pro Val Thr Pro Pro Arg
    210                 215                 220
Leu Val Ala Pro Arg Phe Leu Glu Val Glu Thr Ser Trp Pro Val Asp
225                 230                 235                 240
Cys Thr Leu Asp Gly Leu Phe Pro Ala Ser Glu Ala Gln Val Tyr Leu
                245                 250                 255
Ala Leu Gly Asp Gln Met Leu Asn Ala Thr Val Met Asn His Gly Asp
            260                 265                 270
Thr Leu Thr Ala Thr Ala Thr Ala Thr Ala Arg Ala Asp Gln Glu Gly
        275                 280                 285
Ala Arg Glu Ile Val Cys Asn Val Thr Leu Gly Gly Glu Arg Arg Glu
    290                 295                 300
Ala Arg Glu Asn Leu Thr Val Phe Ser Phe Leu Gly Pro Ile Val Asn
305                 310                 315                 320
Leu Ser Glu Pro Thr Ala His Glu Gly Ser Thr Val Thr Val Ser Cys
                325                 330                 335
Met Ala Gly Ala Arg Val Gln Val Thr Leu Asp Gly Val Pro Ala Ala
            340                 345                 350
Ala Pro Gly Gln Pro Ala Gln Leu Gln Leu Asn Ala Thr Glu Ser Asp
        355                 360                 365
Asp Gly Arg Ser Phe Phe Cys Ser Ala Thr Leu Glu Val Asp Gly Glu
    370                 375                 380
Phe Leu His Arg Asn Ser Ser Val Gln Leu Arg Val Leu Tyr Gly Pro
385                 390                 395                 400
```

```
Lys Ile Asp Arg Ala Thr Cys Pro Gln His Leu Lys Trp Lys Asp Lys
                405                 410                 415

Thr Arg His Val Leu Gln Cys Gln Ala Arg Gly Asn Pro Tyr Pro Glu
            420                 425                 430

Leu Arg Cys Leu Lys Glu Gly Ser Ser Arg Glu Val Pro Val Gly Ile
        435                 440                 445

Pro Phe Phe Val Asn Val Thr His Asn Gly Thr Tyr Gln Cys Gln Ala
    450                 455                 460

Ser Ser Ser Arg Gly Lys Tyr Thr Leu Val Val Met Asp Ile Glu
465                 470                 475                 480

Ala Gly Ser Ser His Phe Val Pro Val Phe Ala Val Leu Leu Thr
                485                 490                 495

Leu Gly Val Val Thr Ile Val Leu Ala Leu Met Tyr Val Phe Arg Glu
        500                 505                 510

His Gln Arg Ser Gly Ser Tyr His Val Arg Glu Glu Ser Thr Tyr Leu
    515                 520                 525

Pro Leu Thr Ser Met Gln Pro Thr Glu Ala Met Gly Glu Glu Pro Ser
    530                 535                 540

Arg Ala Glu
545

<210> SEQ ID NO 115
<211> LENGTH: 275
<212> TYPE: DNA
<213> ORGANISM: Homo sapiens

<400> SEQUENCE: 115
cctgatgccc gaatttcagt ttggcactta cagcgaatct gagaggaaaa ccgaggagta    60
cgatactcag gccatgaagt acttgtcata cctgctgtac cctctctgtg tcggggtgc   120 tgtctattca ctcctgaata tcaaatataa gagctggtac tcctggttaa tcaacagctt   180
cgtcaacggg gtctatgcct ttggtttcct cttcatgctg ccccagctct ttgtgaacta   240
caagttgaag tcagtggcac atctgccctg gaagg                              275

<210> SEQ ID NO 116
<211> LENGTH: 2040
<212> TYPE: DNA
<213> ORGANISM: Homo sapiens

<400> SEQUENCE: 116
cagctccttc accagcttgg tggtgggcgt gttcgtggtc tacgtggtgc acacctgctg    60
ggtcatgtac ggcatcgtct acacccgccc gtgctccggc gacgccaact gcatccagcc   120
ctacctggcg cggcggccca gctgcagct gagcgtgtac accacgacga ggtcccacct   180
gggtgctgag aacaacatcg acctggtctt gaatgtggaa gactttgatg tggagtccaa   240
atttgaaagg acagttaatg tttctgtacc aaagaaaacg agaaacaatg ggacgctgta   300
tgcctacatc ttcctccatc acgctggggt cctgccgtgg cacgacggga gcaggtgca   360 cctggtcagt cctctgacca cctacatggt ccccaagcca aagaaatca acctgctcac   420 cggggagtct gatacacagc agatcgaggc ggagaagaag ccgacgagtg ccctggatga   480
gccagtgtcc cactggcgac gcggctggc gctgaacgtg atggcggaca ctttgtctt   540 tgacgggtcc tccctgcctg ccgatgtgca tcggtacatg aagatgatcc agctggggaa   600
aaccgtgcat tacctgccca tcctgttcat cgaccagctc agcaaccgcg tgaaggacct   660
gatggtcata aaccgctcca ccaccgagct gccctcacc gtgtcctacg acaaggtctc   720
```

```
actgggcgg ctgcgcttct ggatccacat gcaggacgcc gtgtactccc tgcagcagtt    780
cgggttttca gagaaagatg ctgatgaggt gaaaggaatt tttgtagata ccaacttata    840
cttcctggcg ctgaccttct ttgtcgcagc gttccatctt ctctttgatt tcctggcctt    900
taaaaatgac atcagtttct ggaagaagaa gaagagcatg atcggcatgt ccaccaaggc    960
agtgctctgg cgctgcttca gcaccgtggt catctttctg ttcctgctgg acgagcagac   1020
gagcctgctg gtgctggtcc cggcgggtgt tggagccgcc attgagctgt ggaaagtgaa   1080
gaaggcattg aagatgacta ttttttggag aggcctgatg cccgaatttc agtttggcac   1140
ttacagcgaa tctgagagga aaaccgagga gtacgatact caggccatga agtacttgtc   1200
atacctgctg taccctctct gtgtcggggg tgctgtctat tcactcctga atatcaaata   1260
taagagctgg tactcctggt taatcaacag cttcgtcaac ggggtctatg cctttggttt   1320
cctcttcatg ctgccccagc tctttgtgaa ctacaagttg aagtcagtgg cacatctgcc   1380
ctggaaggcc ttcacctaca aggctttcaa caccttcatt gatgacgtct ttgccttcat   1440
catcaccatg cccacgtctc accggctggc ctgcttccgg gacgacgtgg tgtttctggt   1500
ctacctgtac cagcggtggc tttatcctgt ggataaacgc agagtgaacg agtttgggga   1560
gtcctacgag gagaaggcca cgcgggcgcc ccacacggac tgaaggccgc ccgggctgcc   1620
gccagccaag tgcaacttga attgtcaatg agtattttg gaagcatttg gaggaattcc    1680
tagacattgc gttttctgtg ttgccaaaat cccttcggac atttctcaga catctcccaa   1740
gttcccatca cgtcagattt ggagctggta gcgcttacga tgcccccacg tgtgaacatc   1800
tgtcttggtc acagagctgg gtgctgccgg tcaccttgag ctgtggtggc tcccggcaca   1860
cgagtgtccg gggttcggcc atgtcctcac gcgggcaggg gtgggagccc tcacaggcaa   1920
ggggggctgtt ggatttccat ttcaggtggt tttctaagtg ctccttatgt gaatttcaaa   1980
cacgtatgga attcattccg catggactct gggatcaaag gctctttcct cttttgtttg   2040
```

<210> SEQ ID NO 117
<211> LENGTH: 538
<212> TYPE: PRT
<213> ORGANISM: Homo sapiens

<400> SEQUENCE: 117

Met Trp Ser Gly Arg Ser Ser Phe Thr Ser Leu Val Val Gly Val Phe
1               5                   10                  15

Val Val Tyr Val Val His Thr Cys Trp Val Met Tyr Gly Ile Val Tyr
                20                  25                  30

Thr Arg Pro Cys Ser Gly Asp Ala Asn Cys Ile Gln Pro Tyr Leu Ala
            35                  40                  45

Arg Arg Pro Lys Leu Gln Leu Ser Val Tyr Thr Thr Arg Ser His
        50                  55                  60

Leu Gly Ala Glu Asn Asn Ile Asp Leu Val Leu Asn Val Glu Asp Phe
65                  70                  75                  80

Asp Val Glu Ser Lys Phe Glu Arg Thr Val Asn Val Ser Val Pro Lys
                85                  90                  95

Lys Thr Arg Asn Asn Gly Thr Leu Tyr Ala Tyr Ile Phe Leu His His
            100                 105                 110

Ala Gly Val Leu Pro Trp His Asp Gly Lys Gln Val His Leu Val Ser
        115                 120                 125

Pro Leu Thr Thr Tyr Met Val Pro Lys Pro Glu Glu Ile Asn Leu Leu
    130                 135                 140

Thr Gly Glu Ser Asp Thr Gln Gln Ile Glu Ala Glu Lys Lys Pro Thr
145                 150                 155                 160

Ser Ala Leu Asp Glu Pro Val Ser His Trp Arg Pro Arg Leu Ala Leu
            165                 170                 175

Asn Val Met Ala Asp Asn Phe Val Phe Asp Gly Ser Ser Leu Pro Ala
        180                 185                 190

Asp Val His Arg Tyr Met Lys Met Ile Gln Leu Gly Lys Thr Val His
    195                 200                 205

Tyr Leu Pro Ile Leu Phe Ile Asp Gln Leu Ser Asn Arg Val Lys Asp
210                 215                 220

Leu Met Val Ile Asn Arg Ser Thr Thr Glu Leu Pro Leu Thr Val Ser
225                 230                 235                 240

Tyr Asp Lys Val Ser Leu Gly Arg Leu Arg Phe Trp Ile His Met Gln
                245                 250                 255

Asp Ala Val Tyr Ser Leu Gln Gln Phe Gly Phe Ser Glu Lys Asp Ala
            260                 265                 270

Asp Glu Val Lys Gly Ile Phe Val Asp Thr Asn Leu Tyr Phe Leu Ala
        275                 280                 285

Leu Thr Phe Phe Val Ala Ala Phe His Leu Leu Phe Asp Phe Leu Ala
    290                 295                 300

Phe Lys Asn Asp Ile Ser Phe Trp Lys Lys Lys Ser Met Ile Gly
305                 310                 315                 320

Met Ser Thr Lys Ala Val Leu Trp Arg Cys Phe Ser Thr Val Val Ile
                325                 330                 335

Phe Leu Phe Leu Leu Asp Glu Gln Thr Ser Leu Leu Val Leu Val Pro
            340                 345                 350

Ala Gly Val Gly Ala Ala Ile Glu Leu Trp Lys Val Lys Lys Ala Leu
        355                 360                 365

Lys Met Thr Ile Phe Trp Arg Gly Leu Met Pro Glu Phe Gln Phe Gly
    370                 375                 380

Thr Tyr Ser Glu Ser Glu Arg Lys Thr Glu Glu Tyr Asp Thr Gln Ala
385                 390                 395                 400

Met Lys Tyr Leu Ser Tyr Leu Leu Tyr Pro Leu Cys Val Gly Gly Ala
                405                 410                 415

Val Tyr Ser Leu Leu Asn Ile Lys Tyr Lys Ser Trp Tyr Ser Trp Leu
            420                 425                 430

Ile Asn Ser Phe Val Asn Gly Val Tyr Ala Phe Gly Phe Leu Phe Met
        435                 440                 445

Leu Pro Gln Leu Phe Val Asn Tyr Lys Leu Lys Ser Val Ala His Leu
    450                 455                 460

Pro Trp Lys Ala Phe Thr Tyr Lys Ala Phe Asn Thr Phe Ile Asp Asp
465                 470                 475                 480

Val Phe Ala Phe Ile Ile Thr Met Pro Thr Ser His Arg Leu Ala Cys
                485                 490                 495

Phe Arg Asp Asp Val Val Phe Leu Val Tyr Leu Tyr Gln Arg Trp Leu
            500                 505                 510

Tyr Pro Val Asp Lys Arg Arg Val Asn Glu Phe Gly Glu Ser Tyr Glu
        515                 520                 525

Glu Lys Ala Thr Arg Ala Pro His Thr Asp
    530                 535

<210> SEQ ID NO 118
<211> LENGTH: 4217

<212> TYPE: DNA
<213> ORGANISM: Homo sapiens

<400> SEQUENCE: 118

```
cttcccggcc ccagccaagg ctgtcgttta cgtgtcggac attcaggagc tgtacatccg        60
tgtggttgac aaggtggaga ttgggaagac agtgaaggca tacgtccgcg tgctggactt       120
gcacaagaag cccttccttg ccaaatactt cccctttatg gacctgaagc tccgagcagc       180
ctccccgatc attacattgg tggcccttga tgaagccctt gacaactaca ccatcacatt       240
cctcatccgc ggtgtggcca tcggccagac cagtctaact gcaagtgtga ccaataaagc       300
tggacagaga atcaactcag ccccacaaca gattgaagtc tttcccccgt tcaggctgat       360
gcccaggaag gtgacactgc ttatcggggc cacgatgcag gtcacctccg agggcggccc       420
ccagcctcag tccaacatcc ttttctccat cagcaatgag agcgttgcgc tggtgagcgc       480
tgctgggctg gtacagggcc tcgccatcgg gaacggcact gtgtctgggc tcgtgcaggc       540
agtggatgca gagaccggca aggtggtcat catctctcag gacctcgtgc aggtggaggt       600
gctgctgcta agggccgtga ggatccgcgc cccccatcatg cggatgagga cgggcaccca       660
gatgcccatc tatgtcaccg gcatcaccaa ccaccagaac cctttctcct ttggcaatgc       720
cgtgccaggc ctgaccttcc actggtctgt caccaagcgg gacgtcctgg acctccgagg       780
gcggcaccac gaggcgtcga tccgactccc gtcacagtac aactttgcca tgaacgtgct       840
cggccgggta aaaggccgga ccgggctgag ggtggtggtc aaggctgtgg accccacatc       900
ggggcagctg tatggcctgg ccagagaact ctcggatgag atccaagtcc aggtgtttga       960
gaagctgcag ctgctcaacc ctgaaataga agcagaacaa atattaatgt cgcccaactc      1020
atatataaag ctgcagacaa acagggatgg tgcagcctct ctgagctacc gcgtcctgga      1080
tggacccgaa aaggttccag ttgtgcatgt tgatgagaaa ggctttctag catcagggtc      1140
tatgatcggg acatccacca tcgaagtgat tgcacaagag cccttggggg ccaaccaaac      1200
catcattgtt gctgtaaagg tatcccctgt ttcctacctg agggtttcca tgagccctgt      1260
cctgcacacc cagaacaagg aggccctggt ggccgtgcct ttgggaatga ccgtgacctt      1320
cactgtccac ttccacgaca actctggaga tgtcttccat gctcacagtt cggtcctcaa      1380
ctttgccact aacagagacg actttgtgca gatcgggaag gccccacca acaacacctg      1440
cgttgtccgc acagtcagcg tgggcctgac actgctccgt gtgtgggacg cagagcaccc      1500
gggcctctcg gacttcatgc ccctgcctgt cctacaggcc atctccccag agctgtctgg      1560
ggccatggtg gtgggggacg tgctctgtct ggccactgtt ctgaccagcc tggaaggcct      1620
ctcaggaacc tggagctcct cagccaacag catcctccac atcgacccca gacgggtgt      1680
ggctgtggcc cgggccgtgg gatccgtgac ggtttactat gaggtcgctg ggcacctgag      1740
gacctacaag gaggtggtgg tcagcgtccc tcagaggatc atggcccgtc acctccaccc      1800
catccagaca gcttccagg aggctacagc ctccaaagtg attgttgccg tgggagacag      1860
aagctctaac ctgagaggcg agtgcacccc cacccagagg gaagtcatcc aggccttgca      1920
cccagagacc ctcatcagct gccagtccca gttcaagccg gccgtctttg atttcccatc      1980
tcaagatgtg ttcaccgtgg agccacagtt tgacactgct ctcggccagt acttctgctc      2040
aatcacaatg cacaggctga cggacaagca gcggaagcac ctgagcatga agaagacagc      2100
tctggtggtc agtgcctccc tctccagcag ccacttctcc acagagcagg tggggccga      2160
ggtgcccttc agcccaggtc tcttcgccga ccaggctgaa atccttttga gcaaccacta      2220
```

```
caccagttcc gagatcaggg tctttggtgc cccggaggtt ctggagaact tggaggtgaa    2280
atccgggtcc ccggccgtgc tggcattcgc aaaggagaag tcttttgggt ggcccagctt    2340
catcacatac acggtcggcg tctcggaccc cgcggctggc agccaagggc tctgtccac     2400
taccctgacc ttctccagcc ccgtgaccaa ccaagccatt gccatcccag tgacagtggc    2460
ttttgtgatg gatcgccgtg ggcccggtcc ttatggagcc agcctcttcc agcacttcct    2520
ggattcctac caggtcatgt tcttcacgct cttcgccctg ttggctggga cagcggtcat    2580
gatcatagcc taccacactg tctgcacgcc ccgggatctt gctgtgcctg cagccctcac    2640
gcctcgagcc agccctggac acagccccca ctatttcgct gcctcatcac ccacatctcc    2700
caatgcattg cctcctgctc gcaaagccag ccctccctca gggctgtgga gcccagccta    2760
tgcctcccac taggccgcgt gaaggttccc ggaggatggg tctcagccga gcctcgtgca    2820
ccccaagat  ggaacatccc tgctgcattc acactggaac aagcccctcc agatgagtgc    2880
cccggcccca ggccagcttc actgccgtct cttcacacag agctgtagtt tcggctctgc    2940
ccattagctc attttatgta ggagttttaa atgtgtgttt ttttcctttc aagtcttaca    3000
aagctaagac ttttggctc  attccttttt gcatggttgt ctagggtttc tggacaatgt    3060
gctgttgcat ttttattttc ctagccttgc taaaatcttt cccttctcaa gactttgagc    3120
agttagaagt gctctttaga agttgtctgt gggtgatgtt actgtagtgg tctcagggaa    3180
aggattgtcc agttactta ggggttttt ggtgggtt tccccctgt gaaaacttac         3240
tttgccccta gtctggctgc tgctaggact tctgaggagc aatgggacat gagtgtccct    3300
gtatctgcgc cactgccgca agggaagcct caggaaccag cacctggagg ccaggatagc    3360
caagccctgg gtgagcgaga ggctggagaa cacaggagct cacccagggc tgctgcccaa    3420
ccatgggcca ctgtgaacag acttcagtcc tctgttttg  tttcataagc cgttgagaca    3480
tctgatggac ttggcttagg ccctgctggg acatcccacg tgtgatccct ttcactccat    3540
caggacacca ggactgtcct taggaaaatg tccttgagat ggcagcagga gtcatatttt    3600
ctgtgtgtgt gtttcggaaa gccgctgtgt cctgcctcag cacaaagacc cagtgtcatt    3660
tgctcctcct gttcctgtgc cactccagaa cctcagcaga tctgagccac cgcctgccag    3720
tgtgagaggc ggccactttc atggcagctt atcaggcgca gggccccaga cagcttccca    3780
gccgccccta gagcccggcc tgggccaatg atggagggcg ccaccagcc  cagggcctgc    3840
ccatccagaa gggactcccc agggcctggg ggaggagacc cttggaaaag tcctctcttc    3900
ccagctcctg attctggatc tgagattctc agatacacagg ccctgtgct ccaggccgag    3960
gctgggccac cctcagggag atccagagac tcatgcccat ggccatccat gcgtggacgc    4020
tgtgtggaga gtccaggatg acgggatccc gcacaagctc ccttcagtcc ttcagggctg    4080
ggccatgtgg ttgatttttc taaagctgga gaaaggaaga attgtgcctt gcatattact    4140
tgagcttaaa ctgacaacct ggatgtaaat aggagccttt ctactggttt atttaataaa    4200
gttctatgtg attttttt                                                   4217
```

<210> SEQ ID NO 119
<211> LENGTH: 923
<212> TYPE: PRT
<213> ORGANISM: Homo sapiens

<400> SEQUENCE: 119

Phe Pro Ala Pro Ala Lys Ala Val Val Tyr Val Ser Asp Ile Gln Glu
 1               5                   10                  15

```
Leu Tyr Ile Arg Val Val Asp Lys Val Glu Ile Gly Lys Thr Val Lys
             20                  25                  30

Ala Tyr Val Arg Val Leu Asp Leu His Lys Lys Pro Phe Leu Ala Lys
             35                  40                  45

Tyr Phe Pro Phe Met Asp Leu Lys Leu Arg Ala Ala Ser Pro Ile Ile
 50                  55                  60

Thr Leu Val Ala Leu Asp Glu Ala Leu Asp Asn Tyr Thr Ile Thr Phe
 65                  70                  75                  80

Leu Ile Arg Gly Val Ala Ile Gly Gln Thr Ser Leu Thr Ala Ser Val
                 85                  90                  95

Thr Asn Lys Ala Gly Gln Arg Ile Asn Ser Ala Pro Gln Gln Ile Glu
                100                 105                 110

Val Phe Pro Pro Phe Arg Leu Met Pro Arg Lys Val Thr Leu Leu Ile
            115                 120                 125

Gly Ala Thr Met Gln Val Thr Ser Glu Gly Gly Pro Gln Pro Gln Ser
        130                 135                 140

Asn Ile Leu Phe Ser Ile Ser Asn Glu Ser Val Ala Leu Val Ser Ala
145                 150                 155                 160

Ala Gly Leu Val Gln Gly Leu Ala Ile Gly Asn Gly Thr Val Ser Gly
                165                 170                 175

Leu Val Gln Ala Val Asp Ala Glu Thr Gly Lys Val Val Ile Ile Ser
            180                 185                 190

Gln Asp Leu Val Gln Val Glu Val Leu Leu Arg Ala Val Arg Ile
        195                 200                 205

Arg Ala Pro Ile Met Arg Met Arg Thr Gly Thr Gln Met Pro Ile Tyr
210                 215                 220

Val Thr Gly Ile Thr Asn His Gln Asn Pro Phe Ser Phe Gly Asn Ala
225                 230                 235                 240

Val Pro Gly Leu Thr Phe His Trp Ser Val Thr Lys Arg Asp Val Leu
                245                 250                 255

Asp Leu Arg Gly Arg His His Glu Ala Ser Ile Arg Leu Pro Ser Gln
            260                 265                 270

Tyr Asn Phe Ala Met Asn Val Leu Gly Arg Val Lys Gly Arg Thr Gly
        275                 280                 285

Leu Arg Val Val Val Lys Ala Val Asp Pro Thr Ser Gly Gln Leu Tyr
290                 295                 300

Gly Leu Ala Arg Glu Leu Ser Asp Glu Ile Gln Val Gln Val Phe Glu
305                 310                 315                 320

Lys Leu Gln Leu Leu Asn Pro Glu Ile Glu Ala Glu Gln Ile Leu Met
                325                 330                 335

Ser Pro Asn Ser Tyr Ile Lys Leu Gln Thr Asn Arg Asp Gly Ala Ala
            340                 345                 350

Ser Leu Ser Tyr Arg Val Leu Asp Gly Pro Glu Lys Val Pro Val Val
        355                 360                 365

His Val Asp Glu Lys Gly Phe Leu Ala Ser Gly Ser Met Ile Gly Thr
370                 375                 380

Ser Thr Ile Glu Val Ile Ala Gln Glu Pro Phe Gly Ala Asn Gln Thr
385                 390                 395                 400

Ile Ile Val Ala Val Lys Val Ser Pro Val Ser Tyr Leu Arg Val Ser
                405                 410                 415

Met Ser Pro Val Leu His Thr Gln Asn Lys Glu Ala Leu Val Ala Val
            420                 425                 430

Pro Leu Gly Met Thr Val Thr Phe Thr Val His Phe His Asp Asn Ser
```

```
                435                 440                 445
Gly Asp Val Phe His Ala His Ser Ser Val Leu Asn Phe Ala Thr Asn
450                     455                 460

Arg Asp Asp Phe Val Gln Ile Gly Lys Gly Pro Thr Asn Asn Thr Cys
465                     470                 475                 480

Val Val Arg Thr Val Ser Val Gly Leu Thr Leu Leu Arg Val Trp Asp
                    485                 490                 495

Ala Glu His Pro Gly Leu Ser Asp Phe Met Pro Leu Pro Val Leu Gln
                500                 505                 510

Ala Ile Ser Pro Glu Leu Ser Gly Ala Met Val Val Gly Asp Val Leu
                515                 520                 525

Cys Leu Ala Thr Val Leu Thr Ser Leu Glu Gly Leu Ser Gly Thr Trp
530                     535                 540

Ser Ser Ser Ala Asn Ser Ile Leu His Ile Asp Pro Lys Thr Gly Val
545                     550                 555                 560

Ala Val Ala Arg Ala Val Gly Ser Val Thr Val Tyr Tyr Glu Val Ala
                    565                 570                 575

Gly His Leu Arg Thr Tyr Lys Glu Val Val Ser Val Pro Gln Arg
                580                 585                 590

Ile Met Ala Arg His Leu His Pro Ile Gln Thr Ser Phe Gln Glu Ala
                595                 600                 605

Thr Ala Ser Lys Val Ile Val Ala Val Gly Asp Arg Ser Ser Asn Leu
610                     615                 620

Arg Gly Glu Cys Thr Pro Thr Gln Arg Glu Val Ile Gln Ala Leu His
625                     630                 635                 640

Pro Glu Thr Leu Ile Ser Cys Gln Ser Gln Phe Lys Pro Ala Val Phe
                    645                 650                 655

Asp Phe Pro Ser Gln Asp Val Phe Thr Val Glu Pro Gln Phe Asp Thr
                660                 665                 670

Ala Leu Gly Gln Tyr Phe Cys Ser Ile Thr Met His Arg Leu Thr Asp
                675                 680                 685

Lys Gln Arg Lys His Leu Ser Met Lys Lys Thr Ala Leu Val Val Ser
690                     695                 700

Ala Ser Leu Ser Ser Ser His Phe Ser Thr Glu Gln Val Gly Ala Glu
705                     710                 715                 720

Val Pro Phe Ser Pro Gly Leu Phe Ala Asp Gln Ala Glu Ile Leu Leu
                725                 730                 735

Ser Asn His Tyr Thr Ser Ser Glu Ile Arg Val Phe Gly Ala Pro Glu
                740                 745                 750

Val Leu Glu Asn Leu Glu Val Lys Ser Gly Ser Pro Ala Val Leu Ala
                755                 760                 765

Phe Ala Lys Glu Lys Ser Phe Gly Trp Pro Ser Phe Ile Thr Tyr Thr
770                     775                 780

Val Gly Val Ser Asp Pro Ala Gly Ser Gln Gly Pro Leu Ser Thr
785                     790                 795                 800

Thr Leu Thr Phe Ser Ser Pro Val Thr Asn Gln Ala Ile Ala Ile Pro
                    805                 810                 815

Val Thr Val Ala Phe Val Met Asp Arg Arg Gly Pro Gly Pro Tyr Gly
                820                 825                 830

Ala Ser Leu Phe Gln His Phe Leu Asp Ser Tyr Gln Val Met Phe Phe
                835                 840                 845

Thr Leu Phe Ala Leu Leu Ala Gly Thr Ala Val Met Ile Ile Ala Tyr
850                     855                 860
```

His Thr Val Cys Thr Pro Arg Asp Leu Ala Val Pro Ala Ala Leu Thr
865                 870                 875                 880

Pro Arg Ala Ser Pro Gly His Ser Pro His Tyr Phe Ala Ala Ser Ser
            885                 890                 895

Pro Thr Ser Pro Asn Ala Leu Pro Pro Ala Arg Lys Ala Ser Pro Pro
        900                 905                 910

Ser Gly Leu Trp Ser Pro Ala Tyr Ala Ser His
        915                 920

<210> SEQ ID NO 120
<211> LENGTH: 1270
<212> TYPE: PRT
<213> ORGANISM: Homo sapiens

<400> SEQUENCE: 120

Arg Asp Phe Gln Ser Glu Val Leu Leu Ser Ala Met Glu Leu Phe His
1               5                   10                  15

Met Thr Ser Gly Gly Asp Ala Ala Met Phe Arg Asp Gly Lys Glu Pro
            20                  25                  30

Gln Pro Ser Ala Glu Ala Ala Ala Pro Ser Leu Ala Asn Ile Ser
        35                  40                  45

Cys Phe Thr Gln Lys Leu Val Glu Lys Leu Tyr Ser Gly Met Phe Ser
    50                  55                  60

Ala Asp Pro Arg His Ile Leu Leu Phe Ile Leu Glu His Ile Met Val
65                  70                  75                  80

Val Ile Glu Thr Ala Ser Ser Gln Arg Asp Thr Val Leu Ser Thr Leu
            85                  90                  95

Tyr Ser Ser Leu Asn Lys Val Ile Leu Tyr Cys Leu Ser Lys Pro Gln
            100                 105                 110

Gln Ser Leu Ser Glu Cys Leu Gly Leu Leu Ser Ile Leu Gly Phe Leu
        115                 120                 125

Gln Glu His Trp Asp Val Val Phe Ala Thr Tyr Asn Ser Asn Ile Ser
130                 135                 140

Phe Leu Leu Cys Leu Met His Cys Leu Leu Leu Asn Glu Arg Ser
145                 150                 155                 160

Tyr Pro Glu Gly Phe Gly Leu Glu Pro Lys Pro Arg Met Ser Thr Tyr
            165                 170                 175

His Gln Val Phe Leu Ser Pro Asn Glu Asp Val Lys Glu Lys Arg Glu
        180                 185                 190

Asp Leu Pro Ser Leu Ser Asp Val Gln His Asn Ile Gln Lys Thr Val
    195                 200                 205

Gln Thr Leu Trp Gln Gln Leu Val Ala Gln Arg Gln Gln Thr Leu Glu
    210                 215                 220

Asp Ala Phe Lys Ile Asp Leu Ser Val Lys Pro Gly Glu Arg Glu Val
225                 230                 235                 240

Lys Ile Glu Glu Val Thr Pro Leu Trp Glu Glu Thr Met Leu Lys Ala
            245                 250                 255

Trp Gln His Tyr Leu Ala Ser Glu Lys Lys Ser Leu Ala Ser Arg Ser
        260                 265                 270

Asn Val Ala His His Ser Lys Val Thr Leu Trp Ser Gly Ser Leu Ser
    275                 280                 285

Ser Ala Met Lys Leu Met Pro Gly Arg Gln Ala Lys Asp Pro Glu Cys
290                 295                 300

Lys Thr Glu Asp Phe Val Ser Cys Ile Glu Asn Tyr Arg Arg Arg Gly

```
                305                 310                 315                 320
        Gln Glu Leu Tyr Ala Ser Leu Tyr Lys Asp His Val Gln Arg Arg Lys
                        325                 330                 335
        Cys Gly Asn Ile Lys Ala Ala Asn Ala Trp Ala Arg Ile Gln Glu Gln
                        340                 345                 350
        Leu Phe Gly Glu Leu Gly Leu Trp Ser Gln Gly Glu Thr Lys Pro
                        355                 360                 365
        Cys Ser Pro Trp Glu Leu Asp Trp Arg Glu Gly Pro Ala Arg Met Arg
        370                 375                 380
        Lys Arg Ile Lys Arg Leu Ser Pro Leu Glu Ala Leu Ser Ser Gly Arg
        385                 390                 395                 400
        His Lys Glu Ser Gln Asp Lys Asn Asp His Ile Ser Gln Thr Asn Ala
                        405                 410                 415
        Glu Asn Gln Asp Glu Leu Thr Leu Arg Glu Ala Glu Gly Glu Pro Asp
                        420                 425                 430
        Glu Val Gly Val Asp Cys Thr Gln Leu Thr Phe Phe Pro Ala Leu His
                        435                 440                 445
        Glu Ser Leu His Ser Glu Asp Phe Leu Glu Leu Cys Arg Glu Arg Gln
                        450                 455                 460
        Val Ile Leu Gln Glu Leu Leu Asp Lys Glu Lys Val Thr Gln Lys Phe
        465                 470                 475                 480
        Ser Leu Val Ile Val Gln Gly His Leu Val Ser Glu Gly Val Leu Leu
                        485                 490                 495
        Phe Gly His Gln His Phe Tyr Ile Cys Glu Asn Phe Thr Leu Ser Pro
                        500                 505                 510
        Thr Gly Asp Val Tyr Cys Thr Arg His Cys Leu Ser Asn Ile Ser Asp
                        515                 520                 525
        Pro Phe Ile Phe Asn Leu Cys Ser Lys Asp Arg Ser Thr Asp His Tyr
                        530                 535                 540
        Ser Cys Gln Cys His Ser Tyr Ala Asp Met Arg Glu Leu Arg Gln Ala
        545                 550                 555                 560
        Arg Phe Leu Leu Gln Asp Ile Ala Leu Glu Ile Phe Phe His Asn Gly
                        565                 570                 575
        Tyr Ser Lys Phe Leu Val Phe Tyr Asn Asn Asp Arg Ser Lys Ala Phe
                        580                 585                 590
        Lys Ser Phe Cys Ser Phe Gln Pro Ser Leu Lys Gly Lys Ala Thr Ser
                        595                 600                 605
        Glu Asp Thr Leu Asn Leu Arg Arg Tyr Pro Gly Ser Asp Arg Ile Met
        610                 615                 620
        Leu Gln Lys Trp Gln Lys Arg Asp Ile Ser Asn Phe Glu Tyr Leu Met
        625                 630                 635                 640
        Tyr Leu Asn Thr Ala Ala Gly Arg Thr Cys Asn Asp Tyr Met Gln Tyr
                        645                 650                 655
        Pro Val Phe Pro Trp Val Leu Ala Asp Tyr Thr Ser Glu Thr Leu Asn
                        660                 665                 670
        Leu Ala Asn Pro Lys Ile Phe Arg Asp Leu Ser Lys Pro Met Gly Ala
                        675                 680                 685
        Gln Thr Lys Glu Arg Lys Leu Lys Phe Ile Gln Arg Phe Lys Glu Val
                        690                 695                 700
        Glu Lys Thr Glu Gly Asp Met Thr Val Gln Cys His Tyr Tyr Thr His
        705                 710                 715                 720
        Tyr Ser Ser Ala Ile Ile Val Ala Ser Tyr Leu Val Arg Met Pro Pro
                        725                 730                 735
```

```
Phe Thr Gln Ala Phe Cys Ala Leu Gln Gly Gly Ser Phe Asp Val Ala
            740                 745                 750

Asp Arg Met Phe His Ser Val Lys Ser Thr Trp Glu Ser Ala Ser Arg
            755                 760                 765

Glu Asn Met Ser Asp Val Arg Glu Leu Thr Pro Glu Phe Phe Tyr Leu
            770                 775                 780

Pro Glu Phe Leu Thr Asn Cys Asn Gly Val Glu Phe Gly Cys Met Gln
785                 790                 795                 800

Asp Gly Thr Val Leu Gly Asp Val Gln Leu Pro Pro Trp Ala Asp Gly
            805                 810                 815

Asp Pro Arg Lys Phe Ile Ser Leu His Arg Lys Ala Leu Glu Ser Asp
            820                 825                 830

Phe Val Ser Ala Asn Leu His His Trp Ile Asp Leu Ile Phe Gly Tyr
            835                 840                 845

Lys Gln Gln Gly Pro Ala Ala Val Asp Ala Val Asn Ile Phe His Pro
            850                 855                 860

Tyr Phe Tyr Gly Asp Arg Met Asp Leu Ser Ser Ile Thr Asp Pro Leu
865                 870                 875                 880

Ile Lys Ser Thr Ile Leu Gly Phe Val Ser Asn Phe Gly Gln Val Pro
            885                 890                 895

Lys Gln Leu Phe Thr Lys Pro His Pro Ala Arg Thr Ala Ala Gly Lys
            900                 905                 910

Pro Leu Pro Gly Lys Asp Val Ser Thr Pro Val Ser Leu Pro Gly His
            915                 920                 925

Pro Gln Pro Phe Phe Tyr Ser Leu Gln Ser Leu Arg Pro Ser Gln Val
            930                 935                 940

Thr Val Lys Asp Met Tyr Leu Phe Ser Leu Gly Ser Glu Ser Pro Lys
945                 950                 955                 960

Gly Ala Ile Gly His Ile Val Ser Thr Glu Lys Thr Ile Leu Ala Val
            965                 970                 975

Glu Arg Asn Lys Val Leu Leu Pro Pro Leu Trp Asn Arg Thr Phe Ser
            980                 985                 990

Trp Gly Phe Asp Asp Phe Ser Cys Cys Leu Gly Ser Tyr Gly Ser Asp
            995                 1000                1005

Lys Val Leu Met Thr Phe Glu Asn Leu Ala Ala Trp Gly Arg Cys Leu
    1010                1015                1020

Cys Ala Val Cys Pro Ser Pro Thr Thr Ile Val Thr Ser Gly Thr Ser
1025                1030                1035                1040

Thr Val Val Cys Val Trp Glu Leu Ser Met Thr Lys Gly Arg Pro Arg
            1045                1050                1055

Gly Leu Arg Leu Arg Gln Ala Leu Tyr Gly His Thr Gln Ala Val Thr
            1060                1065                1070

Cys Leu Ala Ala Ser Val Thr Phe Ser Leu Leu Val Ser Gly Ser Gln
            1075                1080                1085

Asp Cys Thr Cys Ile Leu Trp Asp Leu Asp His Leu Thr His Val Thr
            1090                1095                1100

Arg Leu Pro Ala His Arg Glu Gly Ile Ser Ala Ile Thr Ile Ser Asp
1105                1110                1115                1120

Val Ser Gly Thr Ile Val Ser Cys Ala Gly Ala His Leu Ser Leu Trp
            1125                1130                1135

Asn Val Asn Gly Gln Pro Leu Ala Ser Ile Thr Thr Ala Trp Gly Pro
            1140                1145                1150
```

```
Glu Gly Ala Ile Thr Cys Cys Cys Leu Met Glu Gly Pro Ala Trp Asp
            1155                1160                1165

Thr Ser Gln Ile Ile Thr Gly Ser Gln Asp Gly Met Val Arg Val
        1170                1175                1180

Trp Lys Thr Glu Asp Val Lys Met Ser Val Pro Gly Arg Pro Ala Gly
1185                1190                1195                1200

Glu Glu Pro Leu Ala Gln Pro Pro Ser Pro Arg Gly His Lys Trp Glu
                1205                1210                1215

Lys Asn Leu Ala Leu Ser Arg Glu Leu Asp Val Ser Ile Ala Leu Thr
            1220                1225                1230

Gly Lys Pro Ser Lys Thr Ser Pro Ala Val Thr Ala Leu Ala Val Ser
        1235                1240                1245

Arg Asn His Thr Lys Leu Leu Val Gly Asp Glu Arg Gly Arg Ile Phe
    1250                1255                1260

Cys Trp Ser Ala Asp Gly
1265                1270

<210> SEQ ID NO 121
<211> LENGTH: 647
<212> TYPE: PRT
<213> ORGANISM: Homo sapiens

<400> SEQUENCE: 121

Met Leu Gln Lys Trp Gln Lys Arg Asp Ile Ser Asn Phe Glu Tyr Leu
1               5                   10                  15

Met Tyr Leu Asn Thr Ala Ala Gly Arg Thr Cys Asn Asp Tyr Met Gln
            20                  25                  30

Tyr Pro Val Phe Pro Trp Val Leu Ala Asp Tyr Thr Ser Glu Thr Leu
        35                  40                  45

Asn Leu Ala Asn Pro Lys Ile Phe Arg Asp Leu Ser Lys Pro Met Gly
    50                  55                  60

Ala Gln Thr Lys Glu Arg Lys Leu Lys Phe Ile Gln Arg Phe Lys Glu
65                  70                  75                  80

Val Glu Lys Thr Glu Gly Asp Met Thr Val Gln Cys His Tyr Tyr Thr
                85                  90                  95

His Tyr Ser Ser Ala Ile Ile Val Ala Ser Tyr Leu Val Arg Met Pro
            100                 105                 110

Pro Phe Thr Gln Ala Phe Cys Ala Leu Gln Gly Gly Ser Phe Asp Val
        115                 120                 125

Ala Asp Arg Met Phe His Ser Val Lys Ser Thr Trp Glu Ser Ala Ser
130                 135                 140

Arg Glu Asn Met Ser Asp Val Arg Glu Leu Thr Pro Glu Phe Phe Tyr
145                 150                 155                 160

Leu Pro Glu Phe Leu Thr Asn Cys Asn Gly Val Glu Phe Gly Cys Met
                165                 170                 175

Gln Asp Gly Thr Val Leu Gly Asp Val Gln Leu Pro Pro Trp Ala Asp
            180                 185                 190

Gly Asp Pro Arg Lys Phe Ile Ser Leu His Arg Lys Ala Leu Glu Ser
        195                 200                 205

Asp Phe Val Ser Ala Asn Leu His His Trp Ile Asp Leu Ile Phe Gly
    210                 215                 220

Tyr Lys Gln Gln Gly Pro Ala Ala Val Asp Ala Val Asn Ile Phe His
225                 230                 235                 240

Pro Tyr Phe Tyr Gly Asp Arg Met Asp Leu Ser Ser Ile Thr Asp Pro
                245                 250                 255
```

Leu Ile Lys Ser Thr Ile Leu Gly Phe Val Ser Asn Phe Gly Gln Val
            260                 265                 270

Pro Lys Gln Leu Phe Thr Lys Pro His Pro Ala Arg Thr Ala Ala Gly
            275                 280                 285

Lys Pro Leu Pro Gly Lys Asp Val Ser Thr Pro Val Ser Leu Pro Gly
            290                 295                 300

His Pro Gln Pro Phe Phe Tyr Ser Leu Gln Ser Leu Arg Pro Ser Gln
305                 310                 315                 320

Val Thr Val Lys Asp Met Tyr Leu Phe Ser Leu Gly Ser Glu Ser Pro
                325                 330                 335

Lys Gly Ala Ile Gly His Ile Val Ser Thr Glu Lys Thr Ile Leu Ala
            340                 345                 350

Val Glu Arg Asn Lys Val Leu Leu Pro Pro Leu Trp Asn Arg Thr Phe
            355                 360                 365

Ser Trp Gly Phe Asp Asp Phe Ser Cys Cys Leu Gly Ser Tyr Gly Ser
            370                 375                 380

Asp Lys Val Leu Met Thr Phe Glu Asn Leu Ala Ala Trp Gly Arg Cys
385                 390                 395                 400

Leu Cys Ala Val Cys Pro Ser Pro Thr Thr Ile Val Thr Ser Gly Thr
            405                 410                 415

Ser Thr Val Val Cys Val Trp Glu Leu Ser Met Thr Lys Gly Arg Pro
            420                 425                 430

Arg Gly Leu Arg Leu Arg Gln Ala Leu Tyr Gly His Thr Gln Ala Val
            435                 440                 445

Thr Cys Leu Ala Ala Ser Val Thr Phe Ser Leu Leu Val Ser Gly Ser
            450                 455                 460

Gln Asp Cys Thr Cys Ile Leu Trp Asp Leu Asp His Leu Thr His Val
465                 470                 475                 480

Thr Arg Leu Pro Ala His Arg Glu Gly Ile Ser Ala Ile Thr Ile Ser
                485                 490                 495

Asp Val Ser Gly Thr Ile Val Ser Cys Ala Gly Ala His Leu Ser Leu
            500                 505                 510

Trp Asn Val Asn Gly Gln Pro Leu Ala Ser Ile Thr Thr Ala Trp Gly
            515                 520                 525

Pro Glu Gly Ala Ile Thr Cys Cys Leu Met Glu Gly Pro Ala Trp
            530                 535                 540

Asp Thr Ser Gln Ile Ile Ile Thr Gly Ser Gln Asp Gly Met Val Arg
545                 550                 555                 560

Val Trp Lys Thr Glu Asp Val Lys Met Ser Val Pro Gly Arg Pro Ala
                565                 570                 575

Gly Glu Glu Pro Leu Ala Gln Pro Pro Ser Pro Arg Gly His Lys Trp
            580                 585                 590

Glu Lys Asn Leu Ala Leu Ser Arg Glu Leu Asp Val Ser Ile Ala Leu
            595                 600                 605

Thr Gly Lys Pro Ser Lys Thr Ser Pro Ala Val Thr Ala Leu Ala Val
            610                 615                 620

Ser Arg Asn His Thr Lys Leu Leu Val Gly Asp Glu Arg Gly Arg Ile
625                 630                 635                 640

Phe Cys Trp Ser Ala Asp Gly
                645

<210> SEQ ID NO 122
<211> LENGTH: 32

-continued

```
<212> TYPE: DNA
<213> ORGANISM: Artificial Sequence
<220> FEATURE:
<223> OTHER INFORMATION: Description of Artificial Sequence:PCR
      amplification primer PDM-797

<400> SEQUENCE: 122
gtgtcacaat ctacagtcag gcaggattct cc                                    32

<210> SEQ ID NO 123
<211> LENGTH: 35
<212> TYPE: DNA
<213> ORGANISM: Artificial Sequence
<220> FEATURE:
<223> OTHER INFORMATION: Description of Artificial Sequence:PCR
      amplification primer PDM-799

<400> SEQUENCE: 123
gttatgtagc ggccgcttat catgttgctg cagag                                 35

<210> SEQ ID NO 124
<211> LENGTH: 980
<212> TYPE: DNA
<213> ORGANISM: Homo sapiens

<400> SEQUENCE: 124
gccgctgccg ctccaggaga caggttccca tgcaggaatg aaagacatgg aagggaagag       60
gggggccagc tccctgagtc ctgtgtccac cagctgctgc taaatacctc tgagaaactc      120
tgcttctatc taaggggacc tacttctctc gggaatctca atacttggaa caagaacctc      180
ctagacggac cctttggcat aatgaattgg accaactgta ggttccagga ctagagagcc      240
agcaatgcct ccatgaacaa tctcacccaa ttactctgct caggaaacga ggtaactgat      300
ggacagccga ggcagcccct taggcggctt aggcctcccc tgtggagcat ccctgaggcg      360
gactccggcc agcccgagtg atgcgatcca aagagcactc ccgggtagga aattgccccg      420
gtggaatgcc tcaccagagc agcgtgtagc agttccctgt ggaggattaa cacagtggct      480
gaacaccggg aaggaactgg cacttggagt ccggacatct gaaacttgta gactgggagc      540
tgtacatgga tgggagcagc ttcaccaacc cctgcaaagt gactctgaag aagacgacaa      600
gccctgctcc agtcacaccc ggaagctgac tggtccacgc acagctgaag catgaggaaa      660
ctcatcgcgg gactaatttt ccttaaaatt tagacttgca cagtaaggac ttcaactgac      720
cttcctcaga ctgagaactg tttccagtat atacatcaag tcactgaggt aggacaaaag      780
attgctacat tcctattatt ttaaggttac attttgggg acccctcttt cttctgttct      840
agctattacc tttcttgtgt cacctagaaa aggaccagtc cttaattgta ttttaaaaac      900
tgtgatcatg ggaagcttta aattggttca ataacacgca tcaagttggt tatttcctgg      960
gctacatacc ttggatagat                                                  980
```